(12) United States Patent
Coverley

(10) Patent No.: US 7,833,702 B2
(45) Date of Patent: Nov. 16, 2010

(54) REPLICATION PROTEIN

(75) Inventor: Dawn Coverley, University of York (GB)

(73) Assignee: Cizzle Biotechnology Limited, Cambridge (GB)

( * ) Notice: Subject to any disclaimer, the term of this patent is extended or adjusted under 35 U.S.C. 154(b) by 1339 days.

(21) Appl. No.: 10/537,228

(22) PCT Filed: Dec. 5, 2003

(86) PCT No.: PCT/GB03/05334

§ 371 (c)(1),
(2), (4) Date: Jan. 13, 2006

(87) PCT Pub. No.: WO2004/051269

PCT Pub. Date: Jun. 17, 2004

(65) Prior Publication Data

US 2006/0155113 A1    Jul. 13, 2006

Related U.S. Application Data

(60) Provisional application No. 60/433,925, filed on Dec. 17, 2002.

(30) Foreign Application Priority Data

Dec. 5, 2002   (GB) ................................ 0228337.2

(51) Int. Cl.
*C12Q 1/68* (2006.01)

(52) U.S. Cl. ........................................ 435/6; 536/24.31

(58) Field of Classification Search ................ None
See application file for complete search history.

(56) References Cited

FOREIGN PATENT DOCUMENTS

| WO | WO 00/58473 | 10/2000 |
|---|---|---|
| WO | WO 01/53312 | 7/2001 |
| WO | WO 01/70979 | 9/2001 |
| WO | WO 01/72777 | 10/2001 |

OTHER PUBLICATIONS

Database EMBL EBI, Strausberg R.L. et al; "Mus musculus CDKN1A interacting zinc finger protein 1, mRNA (cDNA clone MGC: 27988 Image: 3597692), complete cds", Dec. 10, 2001, XP 002285021, Database accession No. BC018483, abstract, Hinxton, Cambridgeshire, UK.
Database GENESEQ EBI, Hillman, JL et al; Human transcription factor TRFX-47, Feb. 5, 2002, XP002285018, Database accession No. ABB50196, abstract, Hinxton, Cambridgeshire, UK.
Database GENESEQ EBI, Shimkets RA; Leach M: "Human ORFX ORF3109 polynucleotide sequence SEQ ID No. 6217" Feb. 8, 2001, XP002285019, Database accession No. AAC77554, abstract, Hinxton, Cambridgeshire, UK.
Database GENESEQ EBI, Tang YT. et al, "Human polypeptide SEQ ID No. 2772", Oct. 22, 2001, XP 002285017, Database accession No. AAM39627 abstract, Hinxton, Cambridgeshire, UK.
Database UNIPROT EBI, Mitsui K et al, Cipl-interacting zinc finger protein (Nuclear protein NP94) Oct. 16, 2001, XP002285016, Database accession No. Q9ULV3 abstract, Hinxton, Cambridgeshire, UK.
Database UNIPROT EBI, Strausberg R: "Hypothetical protein (CIZI)" Mar. 1, 2002, XP002285020, Database accession No. Q8VEH2, abstract, Hinxton, Cambridgeshire, UK.
Database UNIPROT EBI, The Fantom Consortium & The Riken Genome Exploration Research Group Phase I & II Team: "LSFR1 protein homolog", Mar. 1, 2003, XP-002285015, Database accession No. Q8BIT2 abstract, Hinxton, Cambridgeshire, UK &.
Mitsui Kaoru et al: "Cloning and characterization of a novel p21 Cipl/Wafl-interacting zinc finger protein, Cizl" Biochemiical and Biophysical Research Communications, vol. 264, No. 2, Oct. 22, 1999, pp. 457-464, XP002285057, ISSN: 006-291X.
The Fantom Consortium & The Riken Genome Exploration Research Group Phase I & II Team, "Analysis of the Mouse Transcriptome Based on a Functional Annotation of 60, 770 Full-Length CDNAS" Nature, MacMillan Journals Ltd, London, UK, vol. 420, No. 6915, Dec. 5, 2002, pp. 563-573, XP001165660, ISSN: 0028-0836.

*Primary Examiner*—James S Ketter
(74) *Attorney, Agent, or Firm*—Janet Sleath; Speckman Law Group PLLC

(57) ABSTRACT

This invention relates to a screening method for the identification of agents which modulate the activity of a DNA replication protein as a target for intervention in cancer therapy and includes agents which modulate said activity. The invention also relates to the use of the DNA replication protein, and its RNA transcripts in the prognosis and diagnosis of proliferative disease e.g., cancer.

6 Claims, 39 Drawing Sheets

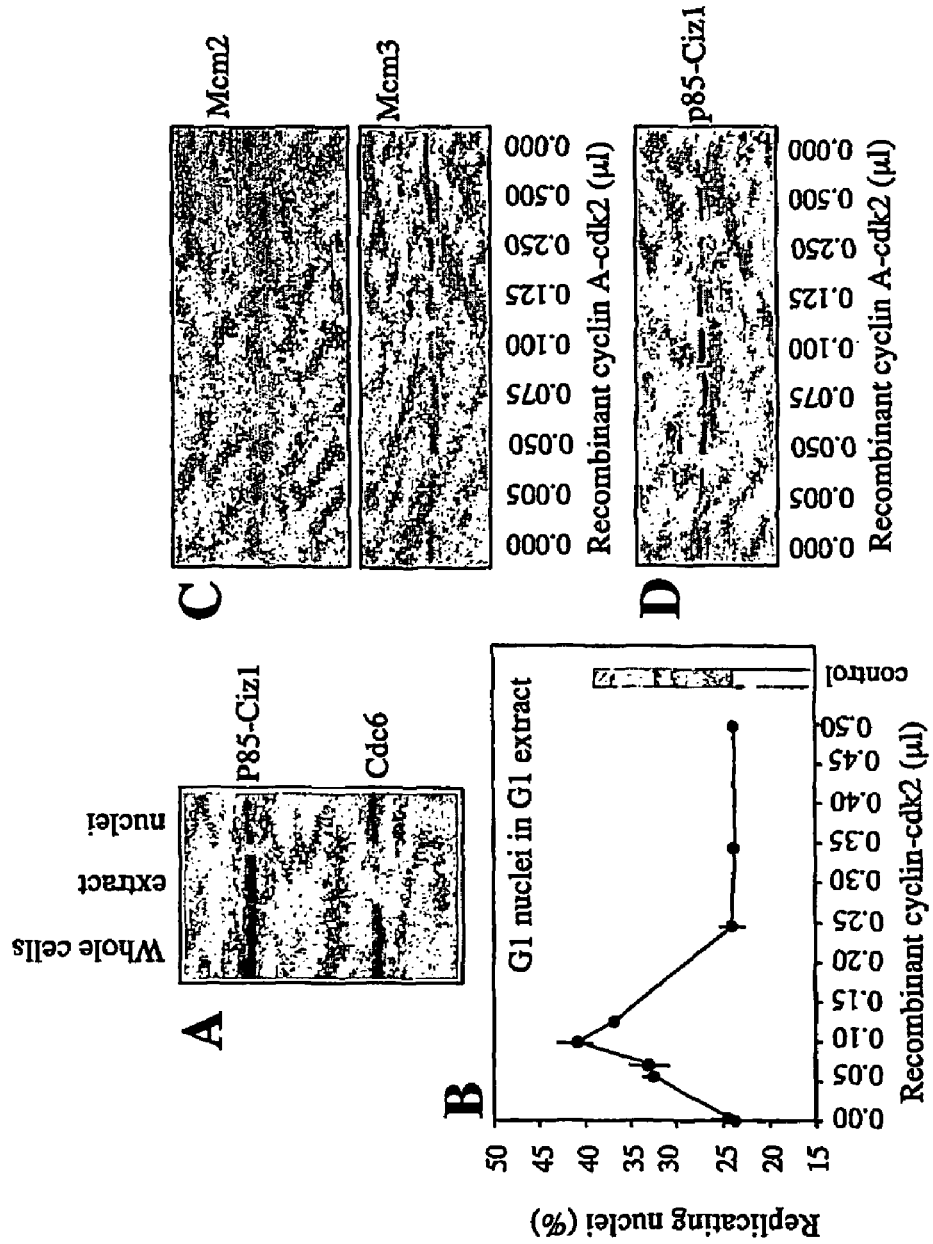
Figure 1A-D

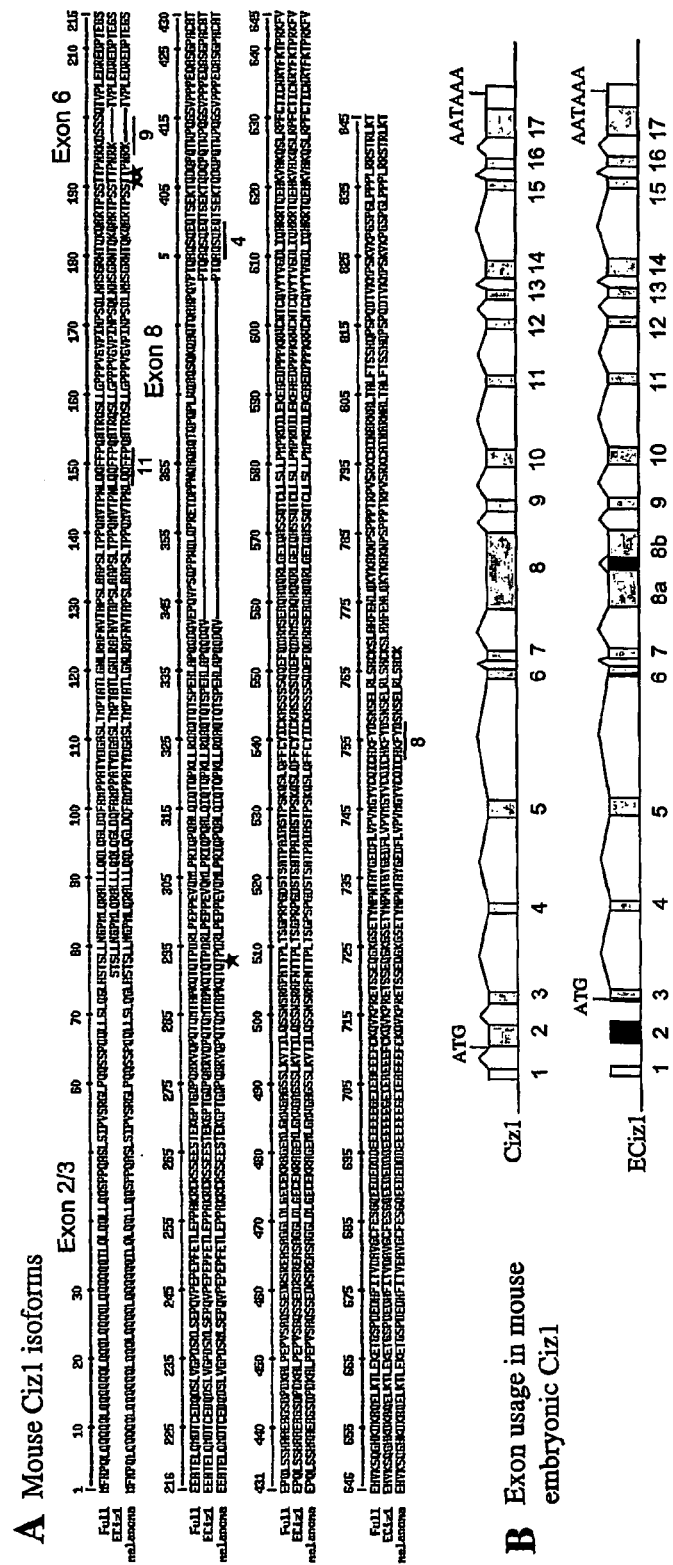
Figure 2A and B

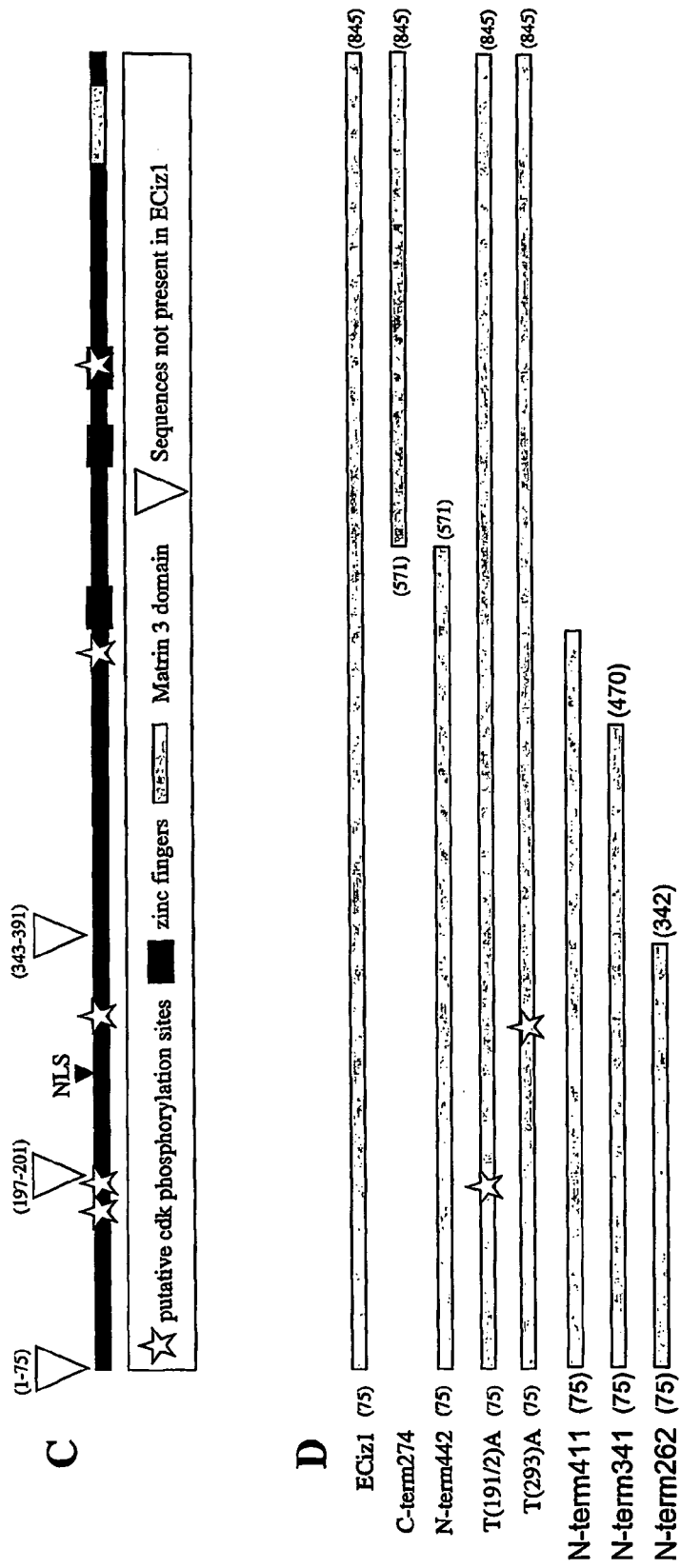
Figure 2C and D

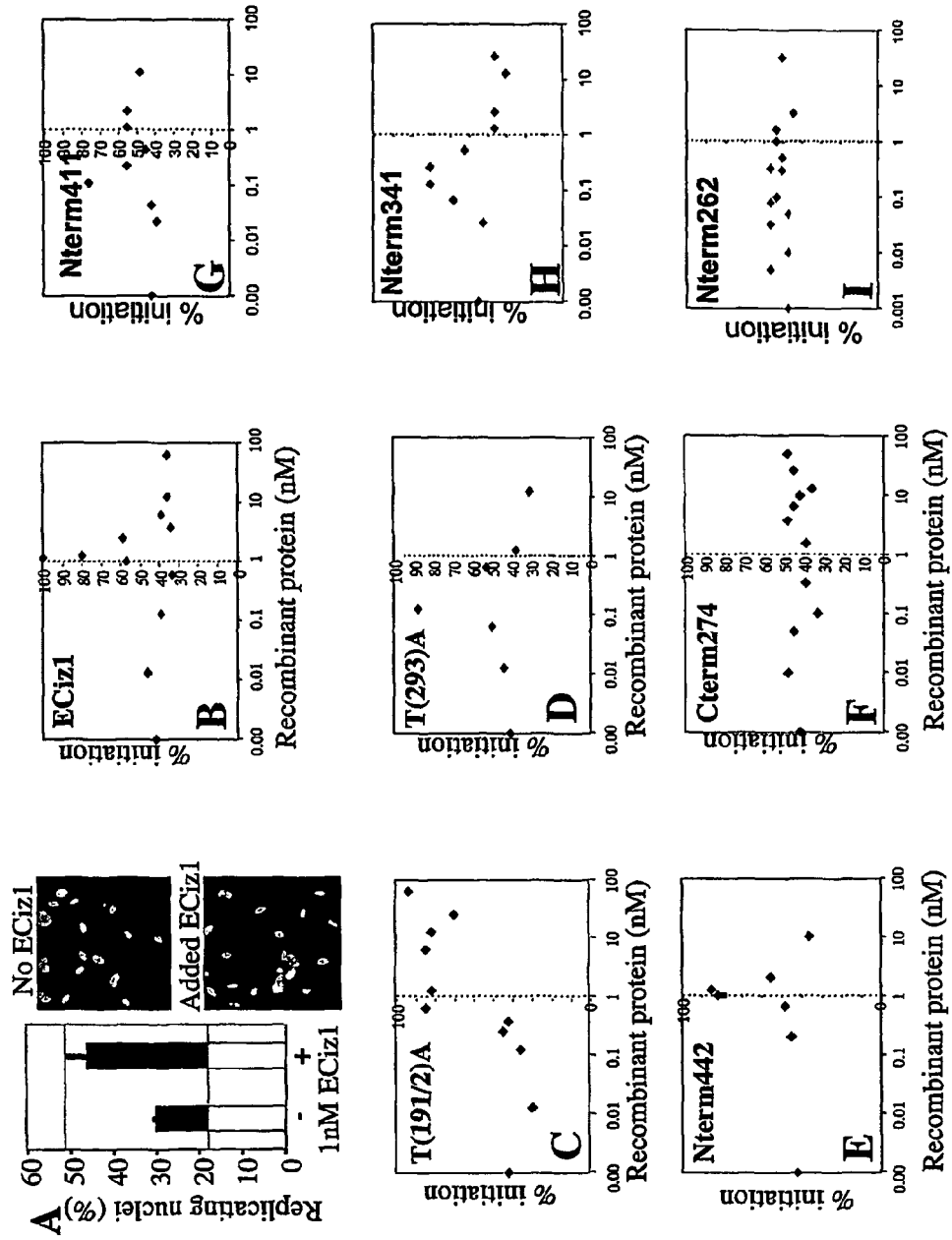
Figure 3A to I

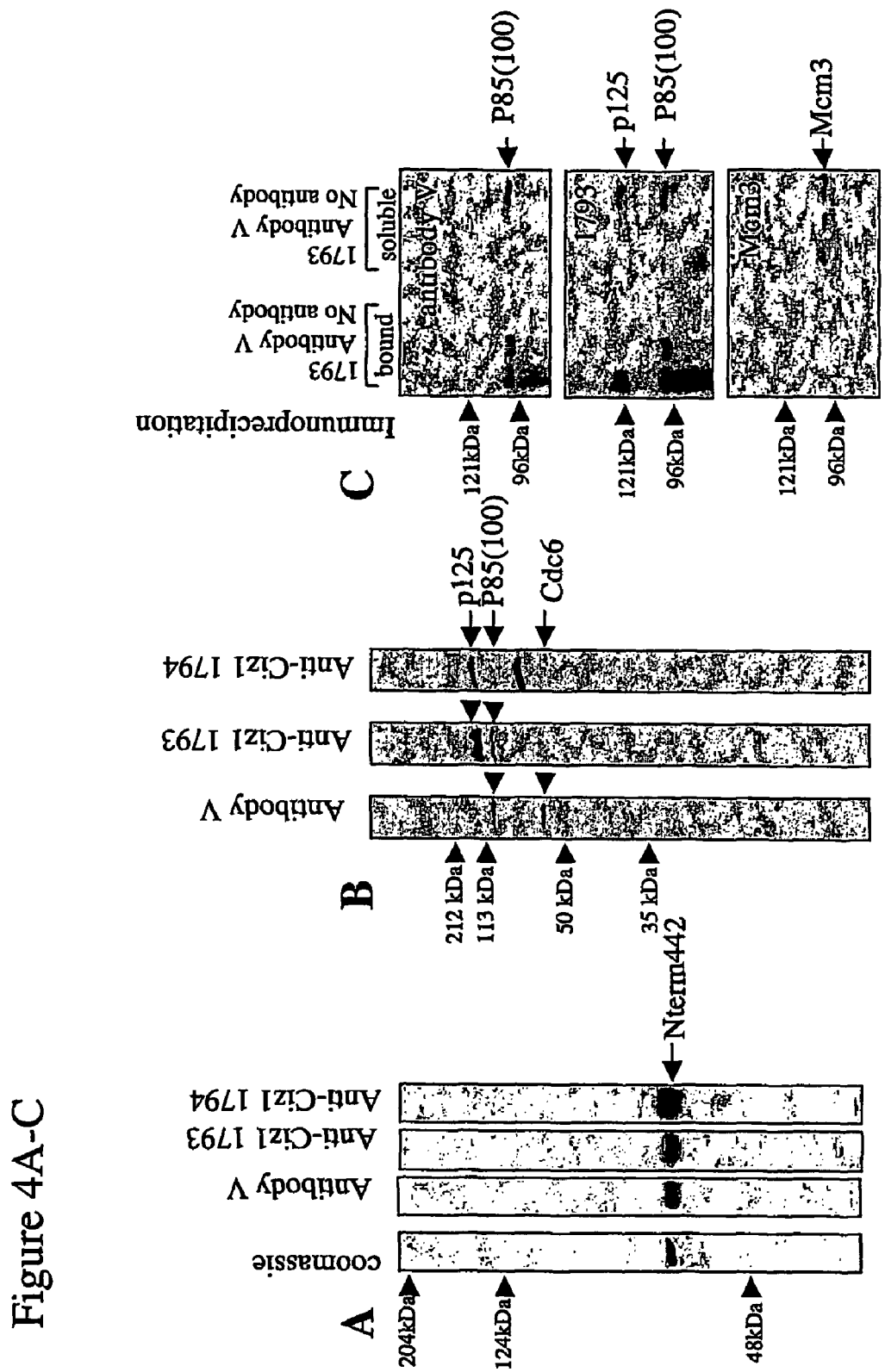
Figure 4A-C

Figure 5A-F
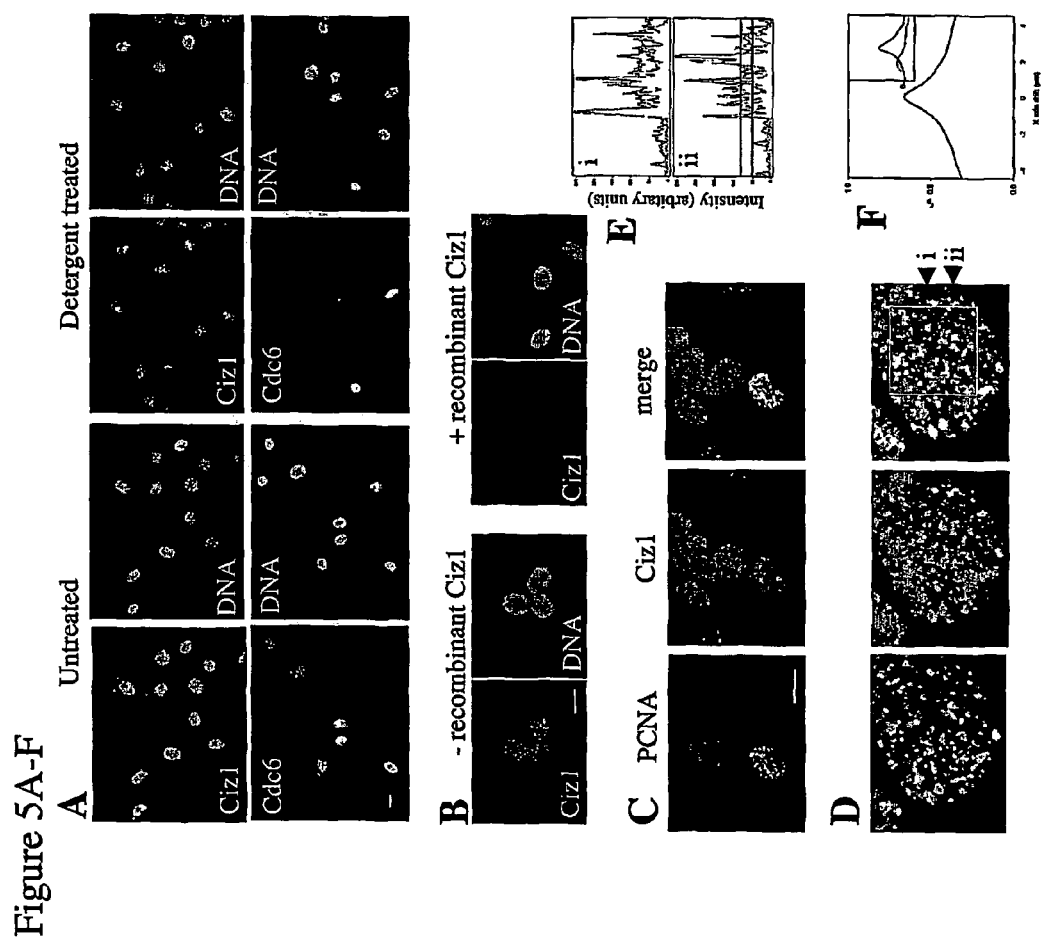

Figure 6A and B
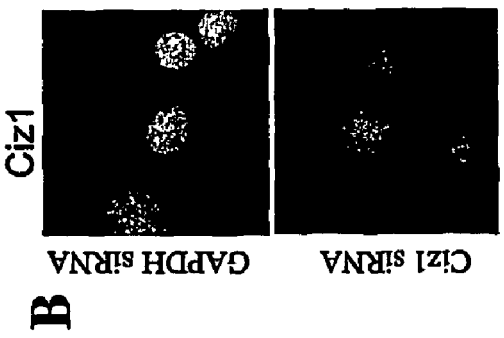
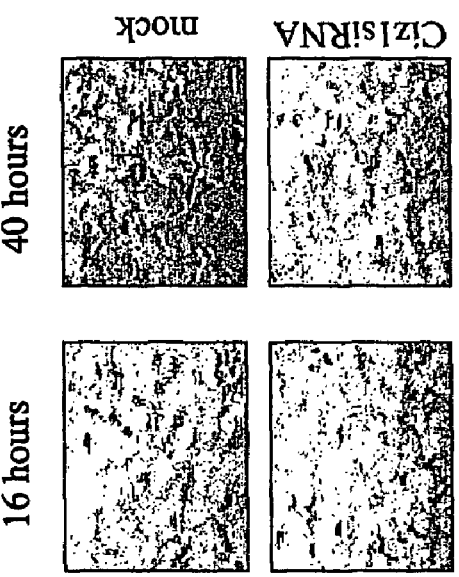
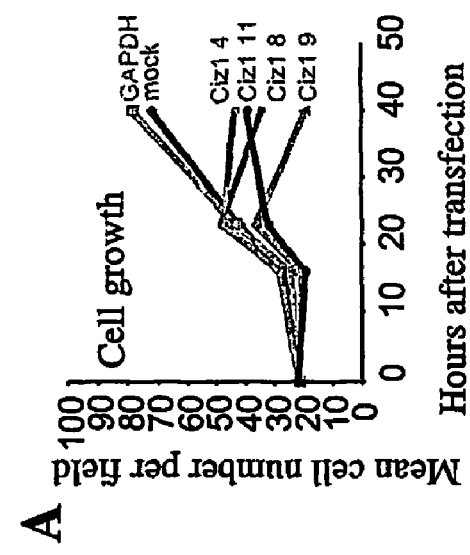

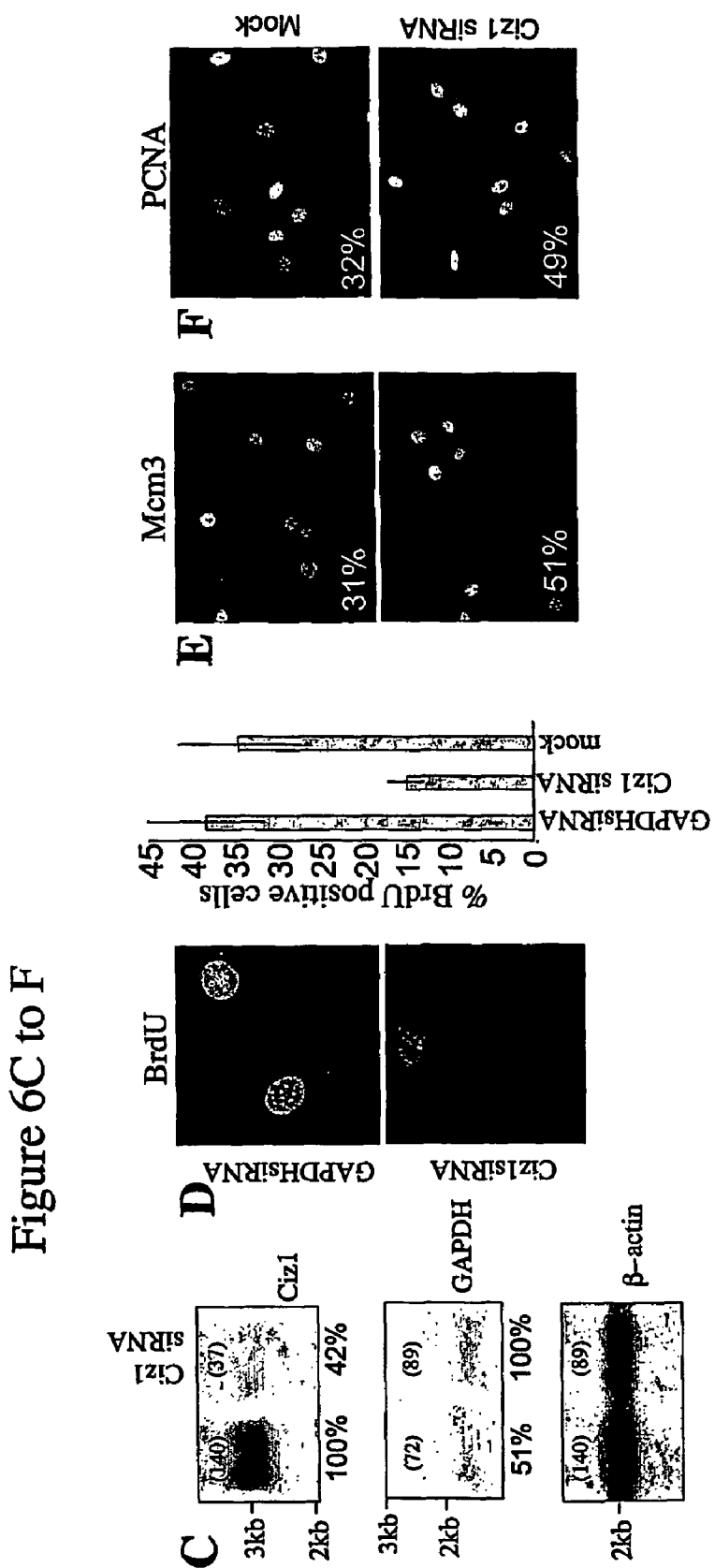
Figure 6C to F

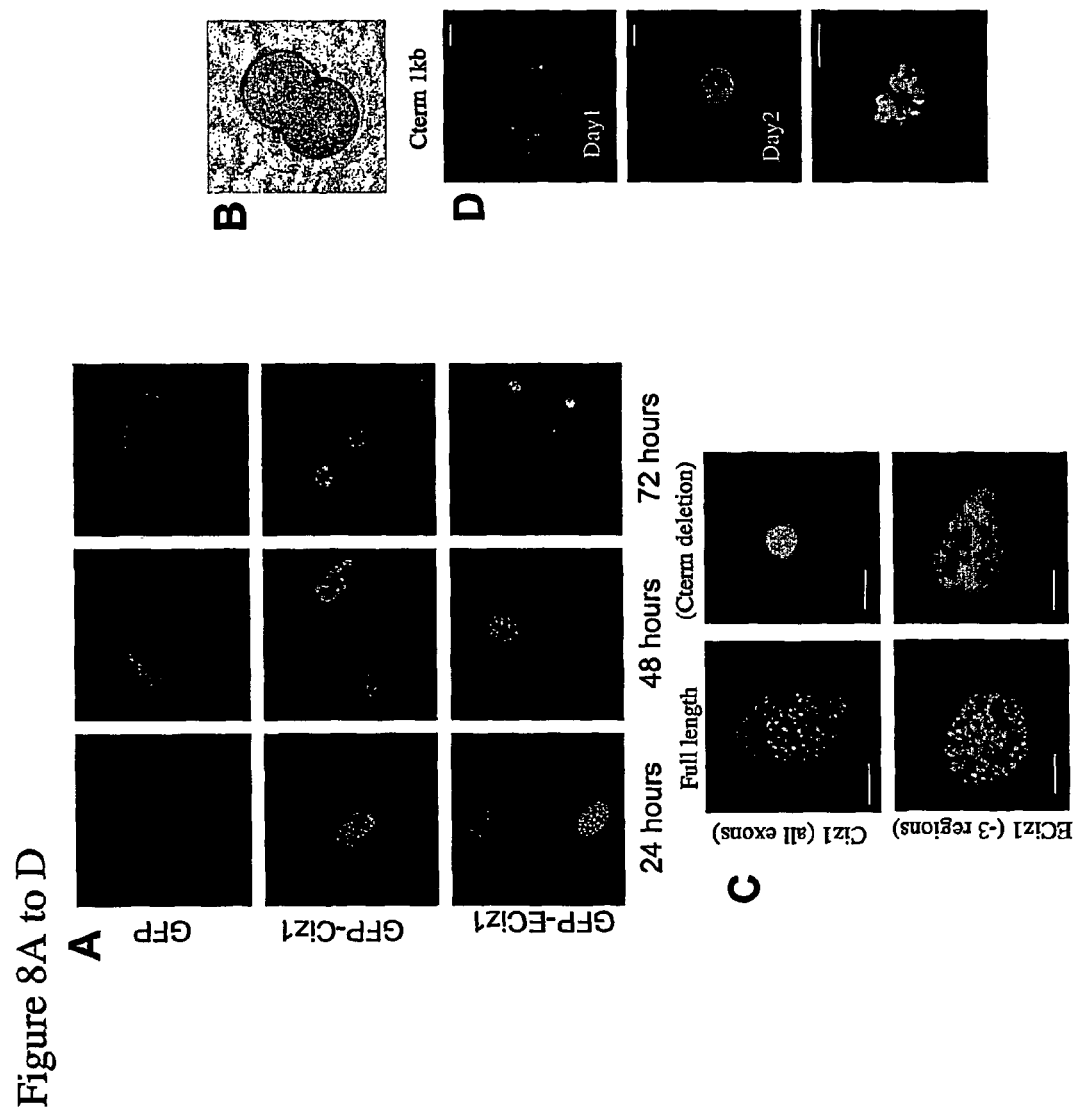
Figure 8A to D

Figure 12B

Summary of PCR products

|  | 1 | 2 | 3 | 4 | 5 | 6 | N1 | N2 | 293 |
|---|---|---|---|---|---|---|---|---|---|
| 'DSSSQ' | 0 | 0 | 0 | 0 | 2 | 0 | 1 | 2 | 0 |
| 'exon4' | 1* | 0 | 1* | 3 | 0 | 3 | 1 | 0 | 0 |
| 'FL' | 4 | 1 | 5 | 2 | 2 | 3 | 8 | 3 | 4 |
| other | 0 | 0 | 0 | 1 | 0 | 0 | 1 | 0 | 0 |

ESFTs            Neuroblastomas
DSSSQ 2/26       DSSSQ 3/16
Exon4 8/26       Exon4 1/16

Examples of PCR products

Ewings 6

Neuroblastoma 2

HEK293

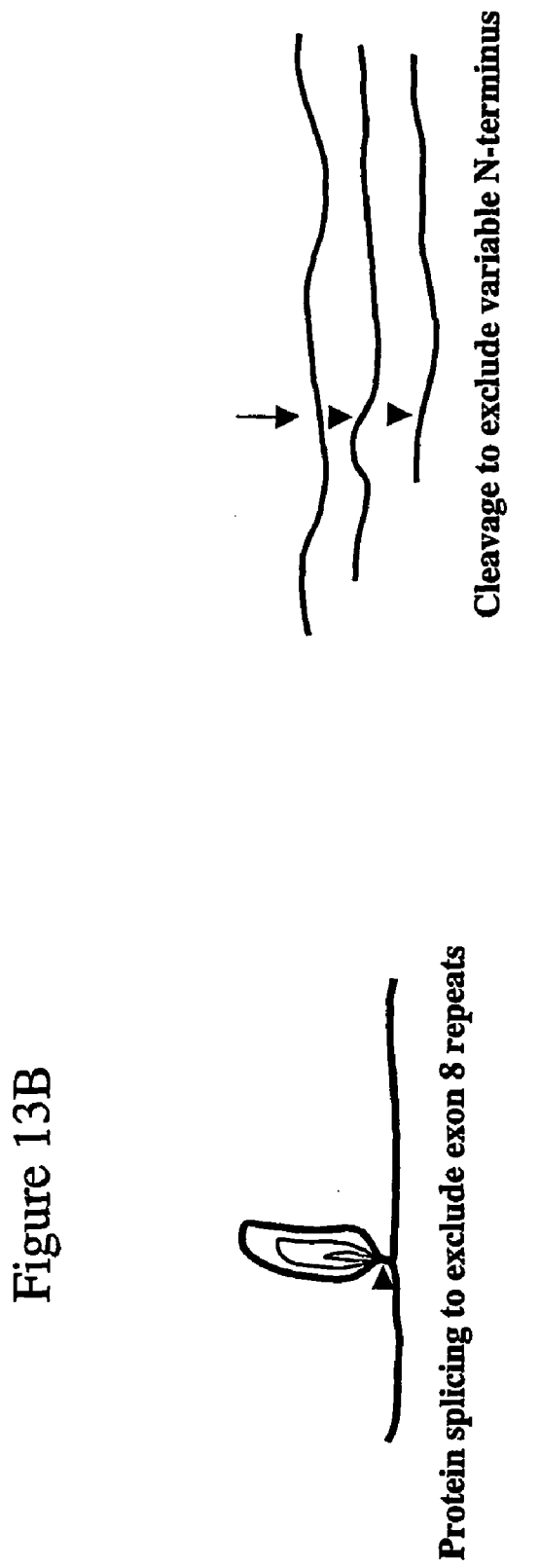

Figure 14

```
CATGTTCAAC CCGCAACTCC AGCAGCAGCA ACAGTTGCAG CAGCAGCAGC
AACAGTTGCA GCAGCAGCTC CAGCAGCAGC AGCTCCAGCA GCAGCAACAG
CAGATACTGC AGCTCCAACA GCTGCTGCAA CAGTCCCCAC CACAGGCCTC
CTTGTCCATT CCTGTCAGCC GGGGCCTCCC CCAGCAGTCA TCCCCGCAAC
AGCTTCTGAG TCTCCAGGGC CTCCACTCGA CCTCCCTGCT CAATGGCCCC
ATGCTGCAAA GAGCTTTGCT CCTACAGCAG TTGCAAGGAC TGGACCAGTT
TGCAATGCCA CCAGCCACGT ATGACGGTGC CAGCCTCACC ATGCCTACGG
CAACACTGGG TAACCTCCGT GCTTTCAATG TGACAGCCCC AAGCCTAGCA
GCTCCCAGCC TTACACCACC CCAGATGGTC ACCCCAAATC TGCAGCAGTT
CTTTCCCCAG GCTACTCGAC AGTCTCTGCT GGGGCCTCCT CCTGTTGGGG
TCCCAATAAA CCCTTCTCAG CTCAACCACT CAGGGAGGAA CACCCAGAAA
CAGGCCAGAA CCCCCTCTTC CACCACCCCC AATCGCAAGG ATTCTTCTTC
TCAGACGGTG CCTCTGGAAG ACAGGGAAGA CCCCACAGAG GGGTCTGAGG
AAGCCACGGA GCTCCAGATG GACACATGTG AAGACCAAGA TTCACTAGTC
GGTCCAGATA GCATGCTGAG TGAGCCCCAA GTGCCTGAGC CTGAGCCCTT
TGAGACATTG GAACCACCAG CCAAGAGGTG CAGGAGCTCA GAGGAGTCCA
CCGAGAAAGG CCCTACAGGG CAGCCACAAG CAAGGGTCCA GCCTCAGACC
CAGATGACAG CACCAAAGCA GACACAGACC CCGGATCGGC TGCCTGAGCC
ACCAGAAGTC CAAATGCTGC CGCGTATCCA GCCACAGGCA CTGCAGATCC
AGACCCAGCC AAAGCTGCTG AGGCAGGCAC AGACACAGAC CTCTCCAGAG
CACTTAGCGC CCCAGCAGGA TCAGGTAGAG CCACAGGTAC CATCACAGCC
CCCATGGCAG TTGCAGCCAC GGGAGACAGA CCCACCGAAC CAAGCTCAGG
CACAGACCCA GCCTCAGCCC CTCTGGCAGG CGCAGTCACA GAAGCAGGCC
CAGACACAGG CACATCCACA GGTACCCACC CAAGCACAGT CACAGGAGCA
GACATCAGAG AAGACCCAGG ACCAGCCTCA GACCTGGCCA CAGGGGTCAG
TACCCCCACC AGAACAAGCG TCAGGTCCAG CCTGTGCCAC GGAACCACAG
CTATCCTCTC ACGCTGCAGA AGCTGGGAGT GACCCAGACA AGGCCTTGCC
AGAACCAGTA AGTGCCCAGA GCAGTGAAGA CAGGAGCCGG GAGGCGTCCG
CTGGTGGCCT GGATTTGGGA GAATGTGAAA AGAGAGCGGG AGAGATGCTG
GGGATGTGGG GGGCTGGGAG CTCCCTGAAG GTCACCATCC TGCAGAGTAG
CAACAGCCGG GCCTTTAACA CCACACCCCT CACATCTGGA CCTCGCCCTG
GGGACTCTAC CTCTGCCACC CCTGCCATTG CCAGCACACC CTCCAAGCAA
AGCCTCCAGT TCTTCTGCTA CATCTGCAAG GCCAGCAGCA GCAGCCAGCA
GGAGTTCCAG GATCACATGT CAGAGGCTCA GCACCAACAG CGGCTTGGGG
AAATACAACA CTCGAGCCAG ACCTGCCTGC TGTCCCTGCT GCCCATGCCT
CGGGACATCC TGGAGAAAGA AGCGGAAGAT CCTCCGCCCA AACGCTGGTG
CAACACCTGC CAGGTGTACT ACGTGGGAGA CTTGATCCAG CACCGTAGGA
CACAGGAGCA CAAGGTTGCC AAACAATCCC TGAGGCCCTT CTGCACCATA
TGCAACCGTT ACTTCAAGAC CCCTCGAAAG TTTGTGGAGC ACGTGAAGTC
CCAGGGACAC AAGGACAAGG CCCAAGAGCT GAAGACACTTGAAAAGGAGA
CAGGCAGCCC AGATGAGGAC CACTTCATCA CTGTGGACGC CGTCGGTTGC
TTTGAGAGTG GTCAAGAAGA GGACGAGGAT GACGACGAGGAAGAAGAAGA
AGAAGGAGAG ATTGAGGCTG AGGAGGAATT CTGCAAGCAG GTGAAGCCGA
GAGAAACATC CTCAGAGCAA GGGAAGGGCT CTGAGACGTA CAACCCCAAC
ACAGCCTATG GTGAGGATTT CCTGGTGCCA GTGATGGGCT ATGTCTGTCA
AATCTGTCAC AAGTTCTACG ACAGCAACTC AGAATTGCGG CTTTCTCACT
GCAAGTCCCT GGCCCACTTT GAGAACCTGC AGAAATACAA AGCCAAGAAC
CCAAGCCCTC CTCCTACCCG GCCTGTGAGC CGCAAGTGTG CCATCAACGC
CCGCAACGCC CTGACTGCAC TGTTCACCTC TAGCCACCAG CCCAGCCCCC
AGGACACAGT GAAAATGCCC AGCAAGGTGA AGCCTGGATC CCCCGGACTC
CCTCCTCCCC TTCGGCGCTC AACACGCCTC AAAACCTGAT AGAGGGAGCT
CTGGCCACTC AGCCTGACTA AGGCTCAGTC TGCTAATGCT TCCTAGGTAT
CTGTGTAGAA ATGTTCAAGT GGTTGGTGTT TTTACTCAAA ATCCAATAAA
GAGTCAGTAG TTTGGCAAAA AAAAAAAAAA AAAAAAA
```

Figure 15

```
TGGGGGCTGC GGGGCCGGCC CATCCGTGGG GGCGACTTGA GCGTTGAGGG
CGCGCGGGGA GGCGAGCCAC CATGTTCAGC CAGCAGCAGC AGCAGCTCCA
GCAACAGCAG CAGCAGCTCC AGCAGTTACA GCAGCAGCAG CTCCAGCAGC
AGCAATTGCA GCAGCAGCAG TTACTGCAGC TCCAGCAGCT GCTCCAGCAG
TCCCCACCAC AGGCCCCGTT GCCCATGGCT GTCAGCCGGG GGCTCCCCCC
GCAGCAGCCA CAGCAGCCGC TTCTGAATCT CCAGGGCACC AACTCAGCCT
CCCTCCTCAA CGGCTCCATG CTGCAGAGAG CTTTGCTTTT ACAGCAGTTG
CAAGGACTGG ACCAGTTTGC AATGCCACCA GCCACGTATG ACACTGCCGG
TCTCACCATG CCCACAGCAA CACTGGGTAA CCTCCGAGGC TATGGCATGG
CATCCCCAGG CCTCGCAGCC CCCAGCCTCA CACCCCCACA ACTGGCCACT
CCAAATTTGC AACAGTTCTT TCCCCAGGCC ACTCGCCAGT CCTTGCTGGG
ACCTCCTCCT GTTGGGGTCC CCATGAACCC TTCCCAGTTC AACCTTTCAG
GACGGAACCC CCAGAAACAG GCCCGGACCT CCTCCTCTAC CACCCCCAAT
CGAAAGGATT CTTCTTCTCA GACAATGCCT GTGGAAGACA AGTCAGACCC
CCCAGAGGGG TCTGAGGAAG CCGCAGAGCC CCGGATGGAC ACACCAGAAG
ACCAAGATTT ACCGCCCTGC CAGAGGACA TCGCCAAGGA AAAACGCACT
CCAGCACCTG AGCCTGAGCC TTGTGAGGCG TCCGAGCTGC AGCAAAGAG
ATTGAGGAGC TCAGAAGAGC CCACAGAGAA GGAACCTCCA GGGCAGTTAC
AGGTGAAGGC CCAGCCGCAG GCCCGGATGA CAGTACCGAA ACAGACACAG
ACACCAGACC TGCTGCCTGA GGCCCTGGAA GCCCAAGTGC TGCCACGATT
CCAGCCACGG GTCCTGCAGG TCCAGGCCCA GGTGCAGTCA CAGACTCAGC
CGCGGATACC ATCCACAGAC ACCCAGGTGC AGCCAAAGCT GCAGAAGCAG
GCGCAAACAC AGACCTCTCC AGAGCACTTA GTGCTGCAAC AGAAGCAGGT
GCAGCCACAG CTGCAGCAGG AGGCAGAGCC ACAGAAGCAGG TGCAGCCAC
AGGTACAGCC ACAGGCACAT TCACAGGGCC CAAGGCAGGT GCAGCTGCAG
CAGGAGGCAG AGCCGCTGAA GCAGGTGCAG CCACAGGTGC AGCCCCAGGC
ACATTCACAG CCCCCAAGGC AGGTGCAGCT GCAGCTGCAG AAGCAGGTCC
AGACACAGAC ATATCCACAG GTCCACACAC AGGCACAGCC AAGCGTCCAG
CCACAGGAGC ATCCTCCAGC GCAGGTGTCA GTACAGCCAC CAGAGCAGAC
CCATGAGCAG CCTCACACCC AGCCGCAGGT GTCGTTGCTG GCTCCAGAGC
AAACACCAGT TGTGGTTCAT GTCTGCGGGC TGGAGATGCC ACCTGATGCA
GTAGAAGCTG GTGGAGGCAT GGAAAAGACC TTGCCAGAGC CTGTGGGCAC
CCAAGTCAGC ATGGAAGAGA TTCAGAATGA GTCGGCCTGT GGCCTAGATG
TGGGAGAATG TGAAAACAGA GCGAGAGAGA TGCCAGGGGTATGGGGCGCC
GGGGGCTCCC TGAAGGTCAC CATTCTGCAG AGCAGTGACA GCCGGGCCTT
TAGCACTGTA CCCCTGACAC CTGTCCCCCG CCCCAGTGAC TCCGTCTCCT
CCACCCCTGC GGCTACCAGC ACTCCCTCTA AGCAGGCCCT CCAGTTCTTC
TGCTACATCT GCAAGGCCAG CTGCTCCAGC CAGCAGGAGT TCCAGGACCA
CATGTCGGAG CCTCAGCACC AGCAGCGGCT AGGGGAGATC CAGCACATGA
GCCAAGCCTG CCTCCTGTCC CTGCTGCCCG TGCCCCGGGA CGTCCTGGAG
ACAGAGGATG AGGAGCCTCC ACCAAGGCGC TGGTGCAACA CCTGCCAGCT
CTACTACATG GGGGACCTGA TCCAACACCG CAGGACACAG GACCACAAGA
TTGCCAAACA ATCCTTGCGA CCCTTCTGCA CCGTTTGCAA CCGCTACTTC
AAAACCCCTC GCAAGTTTGT GGAGCACGTG AAGTCCCAGG GGCATAAGGA
CAAAGCCAAG GAGCTGAAGT CGCTTGAGAA AGAAATTGCT GGCCAAGATG
AGGACCACTT CATTACAGTG GACGCTGTGG GTTGCTTCGA GGGTGATGAA
GAAGAGGAAG AGGATGATGA GGATGAAGAA GAGATCGAGG TTGAGGAGGA
ACTCTGCAAG CAGGTGAGGT CCAGAGATAT ATCCAGAGAG GAGTGGAAGG
GCTCGGAGAC CTACAGCCCC AATACTGCAT ATGGTGTGGA CTTCCTGGTG
CCCGTGATGG GCTATATCTG CCGCATCTGC CACAAGTTCT ATCACAGCAA
CTCAGGGGCA CAGCTCTCCC ACTGCAAGTC CCTGGGCCAC TTTGAGAACC
TGCAGAAATA CAAGGCGGCC AAGAACCCCA GCCCCACCAC CCGACCTGTG
AGCCGCCGGT GCGCAATCAA CGCCCGGAAC GCTTTGACAG CCCTGTTCAC
CTCCAGCGGC CGCCCACCCT CCCAGCCCAA CACCCAGGAC AAAACACCCA
GCAAGGTGAC GGCTCGACCC TCCCAGCCCC CACTACCTCG GCGCTCAACC
CGCCTCAAAA CCTGATAGAG GGACCTCCCT GTCCCTGGCC TGCCTGGGTC
CAGATCTGCT AATGCTTTTT AGGAGTCTGC CTGGAAACTT TGACATGGTT
CATGTTTTTA CTCAAAATCC AATAAAACAA GGTAGTTTGG CTGTGCAAAA
AAAAAAAAAA AAAAAAAAAA AA
```

Figure 16

MFNPQLQQQQ QLQQQQQLQ QLQQQQLQQ QQQILQLQQ LLQQSPPQAS
LSIPVSRGLP QQSSPQQLLS LQGLHSTSLL NGPMLQRALL LQQLQGLDQF
AMPPATYDGA SLTMPTATLG NLRAFNVTAP SLAAPSLTPP QMVTPNLQQF
FPQATRQSLL GPPPVGVPIN PSQLNHSGRN TQKQARTPSS TTPNRKDSSS
QTVPLEDRED PTEGSEEATE LQMDTCEDQD SLVGPDSMLS EPQVPEPEPF
ETLEPPAKRC RSSEESTEKG PTGQPQARVQ PQTQMTAPKQ TQTPDRLPEP
PEVQMLPRIQ PQALQIQTQP KLLRQAQTQT SPEHLAPQQD QVEPQVPSQP
PWQLQPRETD PPNQAQAQTQ PQPLWQAQSQ KQAQTQAHPQ VPTQAQSQEQ
TSEKTQDQPQ TWPQGSVPPP EQASGPACAT EPQLSSHAAE AGSDPDKALP
EPVSAQSSED RSREASAGGL DLGECEKRAG EMLGMWGAGS SLKVTILQSS
NSRAFNTTPL TSGPRPGDST SATPAIASTP SKQSLQFFCY ICKASSSSQQ
EFQDHMSEAQ HQQRLGEIQH SSQTCLLSLL PMPRDILEKE AEDPPPKRWC
NTCQVYYVGD LIQHRRTQEH KVAKQSLRPF CTICNRYFKT PRKFVEHVKS
QGHKDKAQEL KTLEKETGSP DEDHFITVDA VGCFESGQEE DEDDDEEEEE
EGEIEAEEEF CKQVKPRETS SEQGKGSETY NPNTAYGEDF LVPVMGYVCQ
ICHKFYDSNS ELRLSHCKSL AHFENLQKYK AKNPSPPPTR PVSRKCAINA
RNALTALFTS SHQPSPQDTV KMPSKVKPGS PGLPPPLRRS TRLKT

Figure 17

MF SQQQQQLQQQ QQQLQQLQQQ QLQQQQLQQQ QLLQLQQLLQQQ QLLQLQQLLQQSPPQ APLPM AVSRGLPPQQ PQQPLLNLQG TNSASLLNGS M
LQRALLQQLQ GL DQFAMP PATYDTAGLT MPTATLGNLR GYGMASPGLA APSLTPPQLATPN LQQFFPQ ATRQSLLGPP PVGVPM
NPSQ FNLSGRNPQK QARTSSSTTPNRK DSSSQTM PVEDKSDPPE GSEEAAEPRM DTPEDQDLPP CPEDIAKEKRTPA PEPEPCE ASEL
PAKRLR SSEEPTEKEP PGQLQVKAQP QARMTVPKQTQTP DLLPEAL EAQVLPRFQP RVLQVQAQVQ SQTQPRIPST DTQVQPKLQK
QAQTQTSPEH LVLQQKQVQP QLQQEAEPQK QVQPQVQPQAHSQGPRQ VQLQQEAEPLKQV QPQVQPQAHS QPPRQVQLQL QKQV
QTQTYP QVHT QAQPSVQPQEHPPAQV SVQPPEQTHE QPHTQPQVSL LAPEQTPVVV HVC GLEMPPDAVEAGGGMEK TLPEPVGTQ
V SMEEIQNESA CGLDVGECEN RAREMPGVWGAGGSLKVTIL QSSDSRAFST VPLTPVPRPS DSVSSTPAAT STPSKQALQFFCYICKA
SCS SQQEFQDHMS EPQHQQRLGE IQHMSQACLL SLLPVPRDVLETEDEEPPR RWCNTCQLYY MGDLIQHRRT QDHKIAKQSL RPF
CTVCNRYFKTPRKFVEH VKSQGHKDKA KELKSLEKEI AGQDEDHFTT VDAVGCFEGDEEEEEDEDE EEIEVEEELC KQVRSRDISR E
EWKGSETYS PNTAYGVDFL VPVMGYICRI CHKFYHSNSG AQLSHCKSLG HFENLQKYKA AKNPSPTTRPVSRRCAINAR NALTALFTS
S GRPPSQPNTQ DKTPSKVTAR PSQPPLPRRSTRLKT

Figure 18

From exons 2/3 (at least two versions)
MFSQQQQQL QQQQQQLQQL QQQQLQQQQL QQQQLLQLQQ LLQQSPPQA

QQLQQL QQQQLQQQL QQQQLLQLQQ LLQQSPP

Exon 4
GLDQFAMPPATYDTAGLTMPTATL

From exon 6
DSSSQ

From exon 8 (at least three versions)
PQVQPQAHSQPPRQVQLQKQVQTQTY

PQVQPQAHSQGPRQVQLQQEAEPLKQVQPQVQPQAHSQPPRQVQLQLQKQVQTQTY

QVQSQTQPRIPSTDTQVQPKLQKQAQTQ
TSPEHLVLQQKQVQPQLQQEAEPQKQVQ
PQVQPQAHSQGPRQVQLQQEAEPLKQVQ
PQVQPQAHSQPPRQVQLQKQVQTQ TY

From exon 14
VEEELCKQ

The following sequence is inserted in one carcinoma derived library (MGC102) between the third and fourth zinc finger, altering the spacing between them.
PPTPRDVFAHVPVQGWSTARLVTDM

Figure 19

From exons 2/3 (at least two versions)
TGGGGGCTGC GGGGCCGGCC CATCCGTGGG GGCGACTTGA GCGTTGAGGG GCGCGCGGGA GGCGAGCCAC
CATGTTCAGC CAGCAGCAGC AGCAGCTCCA GCAACAGCAG CAGCAGCTCC AGCAGTTACA GCAGCAGCAG
CTCCAGCAGC AGCAATTGCA GCAGCAGCAG TTACTGCAGC TCCAGCAGCT GCTCCAGCAGTCCCCACCAC
AGGCC CAGCAG CTCCAGCAGT TACAGCAGCA GCAGCTCCAG CAGCAGCAATTGCAGCAGCA GCAGTTACTG CAGC
TCCAGC AGCTGCTCCA GCAGTCCCACCACA Exon 4
GGACTGGAC CAGTTTGCAA TGCCACCAGC CACGTATGAC ACTGCCGGTCTCACCATGCC CACAGCAACA CTG From exon 6
AGGATTCTCTTCTC From exon 8 (at least three versions)
CCACAGGTGC AGCCCCAGGC ACATTCACAG CCCCCAAGGC AGGTGCAGCTGCAGCTGCAG AAGCAGGTCC
AGACACAGAC ATATCC CCACAGGTAC AGCCACAGGC ACATTCACAG GGCCCAAGGC AGGTGCAGCTGCAGCAGGAG GCAGAGCCGC
TGAAGCAGGT GCAGCCACAG GTGCAGCCCCAGGCACATTC ACAGCCCCCA AGGCAGGTGC AGCTGCAGCT
GCAGAAGCAGGTCCAGACAC AGACATAT CAGGTGCAGT CACAGACTCA GCGCGGGATA CCATCCACAG ACACCCAGGTGCAGCCAAAG CTGCAGAAGC
AGGCGCAAAC ACAGACCTCT CCAGAGCACTTAGTGCTGCA ACAGAAGCAG GTGCAGCCAC AGCTGCAGCA
GGAGGCAGAGCCACAGAAGC AGGTGCAGCC ACAGGTACAG CCACAGGCAC ATTCACAGGGCCAAGGCAG
GTGCAGCTGC AGCAGGAGGC AGAGCCGCTG AAGCAGGTGCAGCCACAGGT GCAGCCCCAG GCACATTCAC
AGCCCCCAAG GCAGGTGCAGCTGCAGCTGC AGAAGCAGGT CCAGACACAG ACATAT From exon 14
GTTGAGGAGGAGAACTCTGCAAGCAG The following sequence is inserted in to Ciz1 transcripts in one carcinoma library (from Ciz1 intron 12)
GCCACCCACCACCACGAAGAGATGTGTTTGCCCACGTTCCAGTGCAGGGGTGGAGCACAGCCCGGCTTGTTACAGATAT

Figure 20A

Part of exons 2/3 absent
MF SQQQQLQQQ QQ APLPM AVSRGLPPQQ PQQPLLNLQG TNSASLLNGS MLQRALLLQQLQ GL DQFAMP PATYDTAGLT MPTATLGNLR GYGMASPGLA APSLTPQLATPN LQQFFPQ ATRQSLLGPP PVGVPMNPSQ FNLSGRNPQK QARTSSSTTPNRK DSSSQTM PVEDKSDPPE GSEEAAEPRM DTPEDQDLPP CPEDIAKEKRTPA PEPEPCE ASELPAKRLR SSEEPTEKEP PGQL QVKAQP QARMTVPKQTQTP DLLPEAL EAQVLPRFQP RVLQVQAQVQ SQTQPRIPST DTQVQPKLQKQAQTQTSPEH LVLQQKQVQP QLQQEAEPQK QVQPVQPQAHSQGPRQ VQLQQEA EPLKQV QPQVQPQAHS QPPRQVQLQL QKQVQTQTYP QVHT QAQPSVQPQEHPPAQV SVQPPEQTHE QPHTQPQVSL LAPEQTPVVV HVC GLEMPPDAVEAGGGMEK TLPEPVGTQV SME EIQNESA CGLDVGECEN RAREMPGVWGAGGSLKVTIL QSSDSRAFST VPLTPVPRFS DSVSSTPAAT STPSKQALQFFCYICKASCS SQQEFQDHMS EPQHQQRLGE IQHMSQALL SLLPVPRD VLETEDEEPPR RWCNTCQLYY MGDLIQHRRT QDHKIAKQSL RPFCTVCNRYFKTPRKFVEH VKSQGHKDKA KELKSLEKEI AGQDEDHFIT VDAVGCFEGDEEEEED EEIEVEEELC K QVRSRDISR EEWKGSETYS PNTAYGVDFLVPVMGYICRI CHKFYHSNSG AQLSHCKSLG HFENLQKYKA AKNPSPTTRPVSRRCAINAR NALTALFTSS GRPPSQPNTQ DKTPSKVTAR PSQPP LPRRSTRLKT

Exon 4 absent
MF SQQQQQLQQQ QQQLQQLQQQ QLQQQQLQQQ APLPM AVSRGLPPQQ PQQPLLNLQG TNSASLLNGS MLQRALLLQQLQG GYGMASPGLA APSLTPPQLA TPN LQQFFPQ ATRQSLLGPP PVGVPMNPSQ FNLSGRNPQK QARTSSSTTPNRK DSSSQTM PVEDKSDPPE GSEEAAEPRM DTPEDQDLPP CPEDIAKEKRTPA PEPEPCE ASELPAKRLR SSE EPTEKEP PGQLQVKAQP QARMTVPKQTQTP DLLPEAL EAQVLPRFQP RVLQVQAQVQ SQTQPRIPST DTQVQPKLQKQAQTQTSPEH LVLQQKQVQP QLQQEAEPQK QVQPVQPQAHSQ GPRQ VQLQQEAEPLKQV QPQVQPQAHS QPPRQVQLQL QKQVQTQTYP QVHT QAQPSVQPQEHPPAQV SVQPPEQTHE QPHTQPQVSL LAPEQTPVVV HVC GLEMPPDAVEAGGGMEK T LPEPVGTQV SMEEIQNESA CGLDVGECEN RAREMPGVWGAGGSLKVTIL QSSDSRAFST VPLTPVPRFS DSVSSTPAAT STPSKQALQFFCYICKASCS SQQEFQDHMS EPQHQQRLGE IQHM SQACLL SLLPVPRDVLETEDEEPPR RWCNTCQLYY MGDLIQHRRT QDHKIAKQSL RPFCTVCNRYFKTPRKFVEH VKSQGHKDKA KELKSLEKEI AGQDEDHFIT VDAVGCFEGDEEEEED DEDH EEIEVEEELC KQVRSRDISR EEWKGSETYS PNTAYGVDFLVPVMGYICRI CHKFYHSNSG AQLSHCKSLG HFENLQKYKA AKNPSPTTRPVSRRCAINAR NALTALFTSS GRPPSQPNTQ DKTPSKVTAR PSQPPLPRRSTRLKT

Part of exon 6 absent
MF SQQQQQLQQQ QQQLQQLQQQ QLQQQQLQQQ QLQLQLQQLLQQSPPQ APLPM AVSRGLPPQQ PQQPLLNLQG TNSASLLNGS MLQRALLLQQLQ GL DQFAMP PATYDTAGLT MPTAT LGNLR GYGMASPGLA APSLTPQLATPN LQQFFPQ ATRQSLLGPP PVGVPMNPSQ FNLSGRNPQK QARTSSSTTPNRK PVEDKSDPPE GSEEAAEPRM DTPEDQDLPP CPEDIAKEKRTPA PEPEPCE ASELPAKRLR SSEEPTEKEP PGQLQVKAQP QARMTVPKQTQTP DLLPEAL EAQVLPRFQP RVLQVQAQVQ SQTQPRIPST DTQVQPKLQKQAQTQTSPEH LVLQQKQVQP QLQQ EABPQK QVQPVQPQAHSQGPRQ VQLQQEABPLKQV QPQVQPQAHS QPPRQVQLQL QKQVQTQTYP QVHT QAQPSVQPQEHPAQV SVQPPEQTHE QPHTQPQVSL LAPEQTPVVV HVC GLEMPPDA VEAGGGMEK TLPEPVGTQV SMEEIQNESA CGLDVGECEN RAREMPGVWGAGGSLKVTIL QSSDSRAFST VPLTPVPRFS DSVSSTPAAT STPSKQALQFFCYICKASCS SQQEF QDHMS EPQHQQRLGE IQHMSQACLL SLLPVPRDVLETEDEEPPR RWCNTCQLYY MGDLIQHRRT QDHKIAKQSL RPFCTVCNRYFKTPRKFVEH VKSQGHKDKA KELKSLEKEI AGQDE DHFIT VDAVGCFEGDEEEEEDDEDH EEIEVEEELC KQVRSRDISR EEWKGSETYS PNTAYGVDFLVPVMGYICRI CHKFYHSNSG AQLSHCKSLG HFENLQKYKA AKNPSPTTRPVSRRCAIN AR NALTALFTSS GRPPSQPNTQ DKTPSKVTAR PSQPPLPRRSTRLKT

Exon 8 minus variant 1
MF SQQQQQLQQQ QQQLQQLQQQ QLQQQQLQQQ QLQLQLQQLLQQSPPQ APLPM AVSRGLPPQQ PQQPLLNLQG TNSASLLNGS MLQRALLLQQLQ GL DQFAMP PATYDTAGLT MPT ATLGNLR GYGMASPGLA AFSLTPQLATPN LQQFFPQ ATRQSLLGPP PVGVPMNPSQ FNLSGRNPQK QARTSSSTTPNRK DSSSQTM PVEDKSDPPE GSEEAAEPRM DTPEDQDLPP CPE DIAKEKRTPA PEPEPCE ASELPAKRLR SSEEPTEKEP PGQLQVKAQP QARMTVPKQTQTP DLLPEAL EAQVLPRFQP RVLQVQAQVQ SQTQPRIPST DTQVQPKLQKQAQTQTSPEH LVL QQKQVQP QLQQEAEPQK QVQPVQPQAHSQGPRQ VQLQQEABPLKQV Q QVHT QAQPSVQPQEHPPAQV SVQPPEQTHE QPHTQPQVSL LAPEQTPVVV HVC GLEMPPDAVEAGGG MEK TLPEPVGTQV SMEEIQNESA CGLDVGECEN RAREMPGVWGAGGSLKVTIL QSSDSRAFST VPLTPVPRFS DSVSSTPAAT STPSKQALQFFCYICKASCS SQQEFQDHMS EPQHQQR LGE IQHMSQACLL SLLPVPRDVLETEDEEPPR RWCNTCQLYY MGDLIQHRRT QDHKIAKQSL RPFCTVCNRYFKTPRKFVEH VKSQGHKDKA KELKSLEKEI AGQDEDHFIT VDAVGC FEGDEEEEEDDEDH EEIEVEEELC KQVRSRDISR EEWKGSETYS PNTAYGVDFLVPVMGYICRI CHKFYHSNSG AQLSHCKSLG HFENLQKYKA AKNPSPTTRPVSRRCAINAR NALTAL FTSS GRPPSQPNTQ DKTPSKVTAR PSQPPLPRRSTRLKT

Figure 20B

Exon 8 minus variant 2
MF SQQQQLQQQ QQQLQQLQQQ QLQQQQLQQQ QLQLQQLLQQSPPQ APLPM AVSRGLPPQQ PQQPLLNLQG TNSASLLNGS MLQRALLLQQLQ GL DQFAMP PATYDTAGLT MPTATLGNLR GYGMASPGLA APSLTPQLATPN LQQFFPQ ATRQSLLGPP PVGVPMNPSQ FNLSGRNPQK QARTSSSTTPNRK DSSSQTM PVEDKSDPPE GSEEAAEPRM DTPED QDLPP CPEDIAKEKRTPA PEPEPCE ASELPAKRLR SSEEPTEKEP PGQLQVKAQP QARMTVPKQTQTP DLLPEAL EAQVLPRFQP RVLQVQAQVQ SQTQRIPST DTQVQPKLQK QAQTQTSPEH LVLQQKQVQP QLQQEAEPQK QV Q P QVHT QAQPSVQPQEHPPAQV SVQPPEQTHE QPHTQPQVSL LAPEQTPVVV HVC GLEMPPDAVEAGGGMEK TLPEPVGTQ V SMEEIQNESA CGLDVGECEN RAREMPGVWGAGGSLKVTIL QSSDSRAFST VPLTPVPRS DSVSSTPAAT STPSKQALQFFCYICKASCS SQQEFQDHMS EPQHQQRLGE IQHMSQ ACLL SLLPVPRDVLETEDEEPPPR RWCNTCQLYY MGDLIQHRRT QDHKIAKQSL KELKSLEKEI AGQDEDHFIT VDAVGCFEGDEE EHEDDREDE EHEVEHELC KQVRSRDISR EEWKGSETYS PNTAYGVDFL VPVMGYICRI CHKFYHSNSG AQLSHCKSLG HFENLQKYKA AKNPSPTTRPVSRRCAINAR NALTALFTSS GRPPSQPNTQ DKTPSKVTAR PSQPPLPRRSTRLKT Exon 8 minus variant 3
MF SQQQQLQQQ QQQLQQLQQQ QLQQQQLQQQ QLQLQQLLQQSPPQ APLPM AVSRGLPPQQ PQQPLLNLQG TNSASLLNGS MLQRALLLQQLQ GL DQFAMP PATYDTAGLT MPTATLGNLR GYGMASPGLA APSLTPQLATPN LQQFFPQ ATRQSLLGPP PVGVPMNPSQ FNLSGRNPQK QARTSSSTTPNRK DSSSQTM PVEDKSDPPE GSEEAAEPRM DTPED QDLPP CPEDIAKEKRTPA PEPEPCE ASELPAKRLR SSEEPTEKEP PGQLQVKAQP QARMTVPKQTQTP DLLPEAL EAQVLPRFQP RVLQVQA P QVHT QAPSVQPQEHPPAQV SV QPPEQTHE QPHTQPQVSL LAPEQTPVV V HVC GLEMPPDAVEAGGGMEK TLPEPVGTQV SMEEIQNESA CGLDVGECEN RAREMPGVWGAGGSLKVTIL QSSDSRAFST VPLTPVP RPS DSVSSTPAAT STPSKQALQFFCYICKASCS SQQEFQDHMS EPQHQQRLGE IQHMSQACLL SLLPVPRDVLETEDEEPPR RWCNTCQLYY MGDLIQHRRT QDHKIAKQSL RPFC TVCNRYFKTPRKFVEH VKSQGHKDKA KELKSLEKEI AGQDEDHFIT VDAVGCFEGDEHEDEHEVEEELC KQVRSRDISR EEWKGSETYS PNTAYGVDFL VPVMGYICRI CHKFYHSNSG AQLSHCKSLG HFENLQKYKA AKNPSPTTRPVSRRCAINAR NALTALFTSS GRPPSQPNTQ DKTPSKVTAR PSQPPLPRRSTRLKT Exon 14 minus variant
MF SQQQQLQQQ QQQLQQLQQQ QLQQQQLQQQ QLQLQQLLQQSPPQ APLPM AVSRGLPPQQ PQQPLLNLQG TNSASLLNGS MLQRALLLQQLQ GL DQFAMP PATYDTAGLT MPTATLGNLR GYGMASPGLA APSLTPQLATPN LQQFFPQ ATRQSLLGPP PVGVPMNPSQ FNLSGRNPQK QARTSSSTTPNRK DSSSQTM PVEDKSDPPE GSEEAAEPRM DTPEDQ DLPP CPEDIAKEKRTPA PEPEPCE ASELPAKRLR SSEEPTEKEP PGQLQVKAQP QARMTVPKQTQTP DLLPEAL EAQVLPRFQP RVLQVQAQVQ QKQVQTQTYP QVHT QAPSVQPQEHPPAQV SVQ QAQTQTSPEH LVLQQKQVQP QLQQEAEPLKQV QPQVQPQAHSQGPRQ VQLQQEAEPLKQV QPQVQPQAHS QPPRQVQLQL OKQVQTQTYP QVHT QAPSVQPQEHPPAQV SVQ PPEQTHE QPHTQPQVSL LAPEQTPVVV HVC GLEMPPDAVEAGGGMEK TLPEPVGTQV SMEEIQNESA CGLDVGECEN RAREMPGVWGAGGSLKVTIL QSSDSRAFST VPLTPVPRP S DSVSSTPAAT STPSKQALQFFCYICKASCS SQQEFQDHMS EPQHQQRLGE IQHMSQACLL SLLPVPRDVLETEDEEPPR RWCNTCQLYY MGDLIQHRRT QDHKIAKQSL RPFCTV CNRYFKTPRKFVEH VKSQGHKDKA KELKSLEKEI AGQDEDHFIT VDAVGCFEGDEHEDEHE EHEVRSRDISR EEWKGSETYS PNTAYGVDFLVPVMGYICRI CHKFYHSNSG AQLSHCKSLG HFENLQKYKA AKNPSPTTRPVSRRCAINAR NALTALFTSS GRPPSQPNTQ DKTPSKVTAR PSQPPLPRRSTRLKT Also to be protected are transcripts which lack combinations of the variable exons. For example:-

Exon 4 and partial exon 6 minus variant
MF SQQQQLQQQ QQQLQQLQQQ QLQQQQLQQQ QLQLQQLLQQSPPQ APLPM AVSRGLPPQQ PQQPLLNLQG TNSASLLNGS MLQRALLLQQLQGNLR GYGMASPGLA APS LTPQLATPN LQQFFPQ ATRQSLLGPP PVGVPMNPSQ FNLSGRNPQK QARTSSSTTPNRK DSSSQTM PVEDKSDPPE GSEEAAEPRM DTPEDQDLPP CPEDIAKEKRTPA PEPEPCE ASELPAKRLR SSEEPTEKEP PGQLQVKAQP QARMTVPKQTQTP DLLPEAL EAQVLPRFQP RVLQVQAQVQ SQTQRIPST DTQVQPKLQKQAQTQTSPEH LVLQQKQVQP QLQQ EAEPQK QVQPQVQPQAHSQGPRQ VQLQQEAEPLKQV QPQVQPQAHS QPPRQVQLQL OKQVQTQTYP QVHT QAPSVQPQEHPPAQV SVQPPEQTHE QPHTQPQVSL LAPEQT PVVV HVC GLEMPPDAVEAGGGMEK TLPEPVGTQV SMEEIQNESA CGLDVGECEN RAREMPGVWGAGGSLKVTIL QSSDSRAFST VPLTPVRPS DSVSSTPAAT STPSKQALQF FCYICKASCS SQQEFQDHMS EPQHQQRLGE IQHMSQACLL SLLPVPRDVLETEDEEPPR RWCNTCQLYY MGDLIQHRRT QDHKIAKQSL RPFCTVCNRYFKTPRKFVEH VKSQG HKDKA KELKSLEKEI AGQDEDHFIT VDAVGCFEGDEHEDEHE EHEVEHELC KQVRSRDISR EEWKGSETYS PNTAYGVDFL VPVMGYICRI CHKFYHSNSG AQLSHCKSLG HFENLQKYKA AKNPSPTTRPVSRRCAINAR NALTALFTSS GRPPSQPNTQ DKTPSKVTAR PSQPPLPRRSTRLKT

Figure 21A

Part of exons 2/3 absent
TGGGGGCTGC GGGGCCGGCC CATCCGTGGG GGCGACTTGA GCGTTGAGGG
CGCGCGGGGA GGCGAGCCAC CATGTTCAGC CAGCAGCAGC AGCAGCTCCA
GCAACAGCAG GGCCCCGTT GCCCATGGCT GTCAGCCGGG GGCTCCCCCC
GCAGCAGCCA CAGCAGCCGC TTCTGAATCT CCAGGGCACC AACTCAGCCT
CCCTCCTCAA CGGCTCCATG CTGCAGAGAG CTTTGCTTTT ACAGCAGTTG
CAAGGACTGG ACCAGTTTGC AATGCCACCA GCCACGTATG ACACTGCCGG
TCTCACCATG CCCACAGCAA CACTGGGTAA CCTCCGAGGC TATGGCATGG
CATCCCCAGG CCTCGCAGCC CCCAGCCTCA CACCCCACA ACTGGCCACT
CCAAATTTGC AACAGTTCTT TCCCCAGGCC ACTCGCCAGT CCTTGCTGGG
ACCTCCTCCT GTTGGGGTCC CCATGAACCC TTCCCAGTTC AACCTTTCAG
GACGGAACCC CCAGAAACAG GCCCGGACCT CCTCCTCTAC CACCCCCAAT
CGAAAGGATT CTTCTTCTCA GACAATGCCT GTGGAAGACA AGTCAGACCC
CCCAGAGGGG TCTGAGGAAG CCGCAGAGCC CCGGATGGAC ACACCAGAAG
ACCAAGATTT ACCGCCCTGC CAGAGGACA TCGCCAAGGA AAAACGCACT
CCAGCACCTG AGCCTGAGCC TTGTGAGGCG TCCGAGCTGC AGCAAAGAG
ATTGAGGAGC TCAGAAGAGC CCACAGAGAA GGAACCTCCA GGGCAGTTAC
AGGTGAAGGC CCAGCCGCAG GCCCGGATGA CAGTACCGAA ACAGACACAG
ACACCAGACC TGCTGCCTGA GGCCCTGGAA GCCCAAGTGC TGCCACGATT
CCAGCCACGG GTCCTGCAGG TCCAGGCCCA GGTGCAGTCA CAGACTCAGC
CGCGGATACC ATCCACAGAC ACCCAGGTGC AGCCAAAGCT GCAGAAGCAG
GCGCAAACAC AGACCTCTCC AGAGCACTTA GTGCTGCAAC AGAAGCAGGT
GCAGCCACAG CTGCAGCAGG AGGCAGAGCC ACAGAAGCAG GTGCAGCCAC
AGGTACAGCC ACAGGCACAT TCACAGGGCC CAAGGCAGGT GCAGCTGCAG
CAGGAGGCAG AGCCGCTGAA GCAGGTGCAG CCACAGGTGC AGCCCCAGGC
ACATTCACAG CCCCCAAGGC AGGTGCAGCT GCAGCTGCAG AAGCAGGTCC
AGACACAGAC ATATCCACAG GTCCACACAC AGGCACAGCC AAGCGTCCAG
CCACAGGAGC ATCCTCCAGC GCAGGTGTCA GTACAGCCAC CAGAGCAGAC
CCATGAGCAG CCTCACACCC AGCCGCAGGT GTCGTTGCTG GCTCCAGAGC
AAACACCAGT TGTGGTTCAT GTCTGCGGGC TGGAGATGCC ACCTGATGCA
GTAGAAGCTG GTGGAGGCAT GGAAAAAGACC TTGCCAGAGC CTGTGGGCAC
CCAAGTCAGC ATGGAAGAGA TTCAGAATGA GTCGGCCTGT GGCCTAGATG
TGGGAGAATG TGAAAACAGA GCGAGAGAGA TGCCAGGGGT ATGGGGCGCC
GGGGGCTCCC TGAAGGTCAC CATTCTGCAG AGCAGTGACA GCCGGGCCTT
TAGCACTGTA CCCCTGACAC CTGTCCCCCG CCCCAGTGAC TCCGTCTCCT
CCACCCCTGC GGCTACCAGC ACTCCCTCTA AGCAGGCCCT CCAGTTCTTC
TGCTACATCT GCAAGGCCAG CTGCTCCAGC CAGCAGGAGT TCCAGGACCA
CATGTCGGAG CCTCAGCACC AGCAGCGGCT AGGGGAGATC CAGCACATGA
GCCAAGCCTG CCTCCTGTCC CTGCTGCCCG TGCCCCGGGA CGTCCTGGAG
ACAGAGGATG AGGAGCCTCC ACCAAGGGCG TGGTGCAACA CCTGCCAGCT
CTACTACATG GGGGACCTGA TCCAACACCG CAGGACACAG GACCACAAGA
TTGCCAAACA ATCCTTGCGA CCCTTCTGCA CCGTTTGCAA CCGCTACTTC
AAAACCCCTC GCAAGTTTGT GGAGCACGTG AAGTCCCAGG GGCATAAGGA
CAAAGCCAAG GAGCTGAAGT CGCTTGAGAA AGAAATTGCT GGCCAAGATG
AGGACCACTT CATTACAGTG GACGCTGTGG GTTGCTTCGA GGGTGATGAA
GAAGAGGAAG AGGATGATGA GGATGAAGAA GAGATCGAGG TTGAGGAGGA
ACTCTGCAAG CAGGTGAGGT CCAGAGATAT ATCCAGAGAG GAGTGGAAGG
GCTCGGAGAC CTACAGCCCC AATACTGCAT ATGGTGTGGA CTTCCTGGTG
CCCGTGATGG GCTATATCTG CCGCATCTGC CACAAGTTCT ATCACAGCAA
CTCAGGGGCA CAGCTCTCCC ACTGCAAGTC CCTGGGCCAC TTTGAGAACC
TGCAGAAATA CAAGGCGGCC AAGAACCCCA GCCCCACCAC CCGACCTGTG
AGCCGCCGGT GCGCAATCAA CGCCCGGAAC GCTTTGACAG CCCTGTTCAC
CTCCAGCGGC CGCCCACCCT CCCAGCCCAA CACCCAGGAC AAAACACCCA
GCAAGGTGAC GGCTCGACCC TCCCAGCCCC CACTACCTCG GCGCTCAACC
CGCCTCAAAA CCTGATAGAG GGACCTCCCT GTCCCTGGCC TGCCTGGGTC
CAGATCTGCT AATGCTTTTT AGGAGTCTGC CTGGAAACTT TGACATGGTT
CATGTTTTTA CTCAAAATCC AATAAAACAA GGTAGTTTGG CTGTGCAAAA
AAAAAAAAAA AAAAAAAAA AA

Figure 21B

Exon 4 absent
TGGGGGCTGC GGGGCCGGCC CATCCGTGGG GGCGACTTGA GCGTTGAGGG
CGCGCGGGGA GGCGAGCCAC CATGTTCAGC CAGCAGCAGC AGCAGCTCCA
GCAACAGCAG CAGCAGCTCC AGCAGTTACA GCAGCAGCAG CTCCAGCAGC
AGCAATTGCA GCAGCAGCAG TTACTGCAGC TCCAGCAGCT GCTCCAGCAG
TCCCCACCAC AGGCCCCGTT GCCCATGGCT GTCAGCCGGG GGCTCCCCCC
GCAGCAGCCA CAGCAGCCGC TTCTGAATCT CCAGGGCACC AACTCAGCCT
CCCTCCTCAA CGGCTCCATG CTGCAGAGAG CTTTGCTTTT ACAGCAGTTG
CAAGGTAACC TCCGAGGCTA TGGCATGGCA TCCCCAGGCC TCGCAGCCCC
CAGCCTCACA CCCCCACAAC TGGCCACTCC AAATTTGCAA CAGTTCTTTC
CCCAGGCCAC TCGCCAGTCC TTGCTGGGAC CTCCTCCTGT TGGGGTCCCC
ATGAACCCTT CCCAGTTCAA CCTTTCAGGA CGGAACCCCC AGAAACAGGC
CCGGACCTCC TCCTCTACCA CCCCCAATCG AAAGGATTCT TCTTCTCAGA
CAATGCCTGT GGAAGACAAG TCAGACCCCC AGAGGGGTC TGAGGAAGCC
GCAGAGCCCC GGATGGACAC ACCAGAAGAC CAAGATTTAC CGCCCTGCCC
AGAGGACATC GCCAAGGAAA AACGCACTCC AGCACCTGAG CCTGAGCCTT
GTGAGGCGTC CGAGCTGCCA GCAAAGAGAT TGAGGAGCTC AGAAGAGCCC
ACAGAGAAGG AACCTCCAGG GCAGTTACAG GTGAAGGCCC AGCCGCAGGC
CCGGATGACA GTACCGAAAC AGACACAGAC ACCAGACCTG CTGCCTGAGG
CCCTGGAAGC CCAAGTGCTG CCACGATTCC AGCCACGGGT CCTGCAGGTC
CAGGCCCAGG TGCAGTCACA GACTCAGCCG CGGATACCAT CCACAGACAC
CCAGGTGCAG CCAAAGCTGC AGAAGCAGGC GCAAACACAG ACCTCTCCAG
AGCACTTAGT GCTGCAACAG AAGCAGGTGC AGCCACAGCT GCAGCAGGAG
GCAGAGCCAC AGAAGCAGGT GCAGCCACAG GTACAGCCAC AGGCACATTC
ACAGGGCCCA AGGCAGGTGC AGCTGCAGCA GGAGGCAGAG CCGCTGAAGC
AGGTGCAGCC ACAGGTGCAG CCCCAGGCAC ATTCACAGCC CCAAGGCAG
GTGCAGCTGC AGCTGCAGAA GCAGGTCCAG ACACAGACAT ATCCACAGGT
CCACACACAG GCACAGCCAA GCGTCCAGCC ACAGGAGCAT CCTCCAGCGC
AGGTGTCAGT ACAGCCACCA GAGCAGACCC ATGAGCAGCC TCACACCCAG
CCGCAGGTGT CGTTGCTGGC TCCAGAGCAA ACACCAGTTG TGGTTCATGT
CTGCGGGCTG GAGATGCCAC CTGATGCAGT AGAAGCTGGT GGAGGCATGG
AAAAGACCTT GCCAGAGCCT GTGGGCACCC AAGTCAGCAT GGAAGAGATT
CAGAATGAGT CGGCCTGTGG CCTAGATGTG GGAGAATGTG AAAACAGAGC
GAGAGAGATG CCAGGGGTAT GGGGCGCCGG GGGCTCCCTG AAGGTCACCA
TTCTGCAGAG CAGTGACAGC CGGGCCTTTA GCACTGTACC CCTGACACCT
GTCCCCCGCC CCAGTGACTC CGTCTCCTCC ACCCCTGCGG CTACCAGCAC
TCCCTCTAAG CAGGCCCTCC AGTTCTTCTG CTACATCTGC AAGGCCAGCT
GCTCCAGCCA GCAGGAGTTC CAGGACCACA TGTCGGAGCC TCAGCACCAG
CAGCGGCTAG GGGAGATCCA GCACATGAGC CAAGCCTGCC TCCTGTCCCT
GCTGCCCGTG CCCCGGGACG TCCTGGAGAC AGAGGATGAG GAGCCTCCAC
CAAGGCGCTG GTGCAACACC TGCCAGCTCT ACTACATGGG GGACCTGATC
CAACACCGCA GGACACAGGA CCACAAGATT GCCAAACAAT CCTTGCGACC
CTTCTGCACC GTTTGCAACC GCTACTTCAA AACCCCTCGC AAGTTTGTGG
AGCACGTGAA GTCCCAGGGG CATAAGGACA AAGCCAAGGA GCTGAAGTCG
CTTGAGAAAG AAATTGCTGG CCAAGATGAG GACCACTTCA TTACAGTGGA
CGCTGTGGGT TGCTTCGAGG GTGATGAAGA AGAGGAAGAG GATGATGAGG
ATGAAGAAGA GATCGAGGTT GAGGAGGAAC TCTGCAAGCA GGTGAGGTCC
AGAGATATAT CCAGAGAGGA GTGGAAGGGC TCGGAGACCT ACAGCCCCAA
TACTGCATAT GGTGTGGACT TCCTGGTGCC CGTGATGGGC TATATCTGCC
GCATCTGCCA CAAGTTCTAT CACAGCAACT CAGGGGCACA GCTCTCCCAC
TGCAAGTCCC TGGGCCACTT TGAGAACCTG CAGAAATACA AGGCGGCCAA
GAACCCCAGC CCCACCACCC GACCTGTGAG CCGCCGGTGC GCAATCAACG
CCCGGAACGC TTTGACAGCC CTGTTCACCT CCAGCGGCCG CCCACCCTCC
CAGCCCAACA CCCAGGACAA AACACCCAGC AAGGTGACGG CTCGACCCTC
CCAGCCCCCA CTACCTCGGC GCTCAACCCG CCTCAAAACC TGATAGAGGG
ACCTCCCTGT CCCTGGCCTG CCTGGGTCCA GATCTGCTAA TGCTTTTTAG
GAGTCTGCCT GGAAACTTTG ACATGGTTCA TGTTTTTACT CAAAATCCAA
TAAAACAAGG TAGTTTGGCT GTGCAAAAAA AAAAAAAAAA AAAAAAAAAA

Figure 21C

Exon 6 minus transcript
TGGGGGCTGC GGGGCCGGCC CATCCGTGGG GGCGACTTGA GCGTTGAGGG
CGCGCGGGGA GGCGAGCCAC CATGTTCAGC CAGCAGCAGC AGCAGCTCCA
GCAACAGCAG CAGCAGCTCC AGCAGTTACA GCAGCAGCAG CTCCAGCAGC
AGCAATTGCA GCAGCAGCAG TTACTGCAGC TCCAGCAGCT GCTCCAGCAG
TCCCCACCAC AGGCCCCGTT GCCCATGGCT GTCAGCCGGG GGCTCCCCCC
GCAGCAGCCA CAGCAGCCGC TTCTGAATCT CCAGGGCACC AACTCAGCCT
CCCTCCTCAA CGGCTCCATG CTGCAGAGAG CTTTGCTTTT ACAGCAGTTG
CAAGGACTGG ACCAGTTTGC AATGCCACCA GCCACGTATG ACACTGCCGG
TCTCACCATG CCCACAGCAA CACTGGGTAA CCTCCGAGGC TATGGCATGG
CATCCCCAGG CCTCGCAGCC CCCAGCCTCA CACCCCACA ACTGGCCACT
CCAAATTTGC AACAGTTCTT TCCCCAGGCC ACTCGCCAGT CCTTGCTGGG
ACCTCCTCCT GTTGGGGTCC CCATGAACCC TTCCCAGTTC AACCTTTCAG
GACGGAACCC CCAGAAACAG GCCCGGACCT CCTCCTCTAC CACCCCCAAT
CGAAAGACAA TGCCTGTGGA AGACAAGTCA GACCCCCCAG AGGGGTCTGA
GGAAGCCGCA GAGCCCCGGA TGGACACACC AGAAGACCAA GATTTACCGC
CCTGCCCAGA GGACATCGCC AAGGAAAAAC GCACTCCAGC ACCTGAGCCT
GAGCCTTGTG AGGCGTCCGA GCTGCCAGCA AAGAGATTGA GGAGCTCAGA
AGAGCCCACA GAGAAGGAAC CTCCAGGGCA GTTACAGGTG AAGGCCCAGC
CGCAGGCCCG GATGACAGTA CCGAAACAGA CACAGACACC AGACCTGCTG
CCTGAGGCCC TGGAAGCCCA AGTGCTGCCA CGATTCCAGC CACGGGTCCT
GCAGGTCCAG GCCCAGGTGC AGTCACAGAC TCAGCCGCGG ATACCATCCA
CAGACACCCA GGTGCAGCCA AAGCTGCAGA AGCAGGCGCA AACACAGACC
TCTCCAGAGC ACTTAGTGCT GCAACAGAAG CAGGTGCAGC CACACGTGCA
GCAGGAGGCA GAGCCACAGA AGCAGGTGCA GCCACAGGTA CAGCCACAGG
CACATTCACA GGGCCCAAGG CAGGTGCAGC TGCAGCAGGA GGCAGAGCCG
CTGAAGCAGG TGCAGCCACA GGTGCAGCCC CAGGCACATT CACAGCCCCC
AAGGCAGGTG CAGCTGCAGC TGCAGAAGCA GGTCCAGACA CAGACATATC
CACAGGTCCA CACACAGGCA CAGCCAAGCG TCCAGCCACA GGAGCATCCT
CCAGCGCAGG TGTCAGTACA GCCACCAGAG CAGACCCATG AGCAGCCTCA
CACCCAGCCG CAGGTGTCGT TGCTGGCTCC AGAGCAAACA CCAGTTGTGG
TTCATGTCTG CGGGCTGGAG ATGCCACCTG ATGCAGTAGA AGCTGGTGGA
GGCATGGAAA AGACCTTGCC AGAGCCTGTG GGCACCCAAG TCAGCATGGA
AGAGATTCAG AATGAGTCGG CCTGTGGCCT AGATGTGGGA GAATGTGAAA
ACAGAGCGAG AGAGATGCCA GGGGTATGGG GCGCCGGGGG CTCCCTGAAG
GTCACCATTC TGCAGAGCAG TGACAGCCGG GCCTTTAGCA CTGTACCCCT
GACACCTGTC CCCCGCCCCA GTGACTCCGT CTCCTCCACC CCTGCGGCTA
CCAGCACTCC CTCTAAGCAG GCCCTCCAGT TCTTCTGCTA CATCTGCAAG
GCCAGCTGCT CCAGCCAGCA GGAGTTCCAG GACCACATGT CGGAGCCTCA
GCACCAGCAG CGGCTAGGGG AGATCCAGCA CATGAGCCAA GCCTGCCTCC
TGTCCCTGCT GCCCGTGCCC CGGGACGTCC TGGAGACAGA GGATGAGGAG
CCTCCACCAA GGCGCTGGTG CAACACCTGC CAGCTCTACT ACATGGGGGA
CCTGATCCAA CACCGCAGGA CACAGGACCA CAAGATTGCC AAACAATCCT
TGCGACCCTT CTGCACCGTT TGCAACCGCT ACTTCAAAAC CCCTCGCAAG
TTTGTGGAGC ACGTGAAGTC CCAGGGGCAT AAGGACAAAG CCAAGGAGCT
GAAGTCGCTT GAGAAAGAAA TTGCTGGCCA AGATGAGGAC CACTTCATTA
CAGTGGACGC TGTGGGTTGC TTCGAGGGTG ATGAAGAAGA GGAAGAGGAT
GATGAGGATG AAGAAGAGAT CGAGGTTGAG GAGGAACTCT GCAAGCAGGT
GAGGTCCAGA GATATATCCA GAGAGGAGTG GAAGGGCTCG AGACCTACA
GCCCCAATAC TGCATATGGT GTGGACTTCC TGGTGCCCGT GATGGGCTAT
ATCTGCCGCA TCTGCCACAA GTTCTATCAC AGCAACTCAG GGGCACAGCT
CTCCCACTGC AAGTCCCTGG GCCACTTTGA GAACCTGCAG AAATACAAGG
CGGCCAAGAA CCCCAGCCCC ACCACCCGAC CTGTGAGCCG CCGGTGCGCA
ATCAACGCCC GGAACGCTTT GACAGCCCTG TTCACCTCCA GCGGCCGCCC
ACCCTCCCAG CCCAACACCC AGGACAAAAC ACCCAGCAAG GTGACGGCTC
GACCCTCCCA GCCCCCACTA CCTCGGCGCT CAACCCGCCT CAAAACCTGA
TAGAGGGACC TCCCTGTCCC TGGCCTGCCT GGGTCCAGAT CTGCTAATGC
TTTTTAGGAG TCTGCCTGGA AACTTTGACA TGGTTCATGT TTTTACTCAA
AATCCAATAA AACAAGGTAG TTTGGCTGTG CAAAAAAAAA AAAAAAAAA
AAAAAAA

Figure 21D

Exon 8 minus variant 1
TGGGGGCTGC GGGGCCGGCC CATCCGTGGG GGCGACTTGA GCGTTGAGGG
CGCGCGGGGA GGCGAGCCAC CATGTTCAGC CAGCAGCAGC AGCAGCTCCA
GCAACAGCAG CAGCAGCTCC AGCAGTTACA GCAGCAGCAG CTCCAGCAGC
AGCAATTGCA GCAGCAGCAG TTACTGCAGC TCCAGCAGCT GCTCCAGCAG
TCCCCACCAC AGGCCCCGTT GCCCATGGCT GTCAGCCGGG GGCTCCCCCC
GCAGCAGCCA CAGCAGCCGC TTCTGAATCT CCAGGGCACC AACTCAGCCT
CCCTCCTCAA CGGCTCCATG CTGCAGAGAG CTTTGCTTTT ACAGCAGTTG
CAAGGACTGG ACCAGTTTGC AATGCCACCA GCCACGTATG ACACTGCCGG
TCTCACCATG CCCACAGCAA CACTGGGTAA CCTCCGAGGC TATGGCATGG
CATCCCCAGG CCTCGCAGCC CCAGCCTCA CACCCCACA ACTGGCCACT
CCAAATTTGC AACAGTTCTT TCCCCAGGCC ACTCGCCAGT CCTTGCTGGG
ACCTCCTCCT GTTGGGGTCC CCATGAACCC TTCCCAGTTC AACCTTTCAG
GACGGAACCC CCAGAAACAG GCCCGGACCT CCTCCTCTAC CACCCCCAAT
CGAAAGGATT CTTCTTCTCA GACAATGCCT GTGGAAGACA AGTCAGACCC
CCCAGAGGGG TCTGAGGAAG CCGCAGAGCC CCGGATGGAC ACACCAGAAG
ACCAAGATTT ACCGCCCTGC CAGAGGACA TCGCCAAGGA AAAACGCACT
CCAGCACCTG AGCCTGAGCC TTGTGAGGCG TCCGAGCTGC CAGCAAAGAG
ATTGAGGAGC TCAGAAGAGC CCACAGAGAA GGAACCTCCA GGGCAGTTAC
AGGTGAAGGC CCAGCCGCAG GCCCGGATGA CAGTACCGAA ACAGACACAG
ACACCAGACC TGCTGCCTGA GGCCCTGGAA GCCCAAGTGC TGCCACGATT
CCAGCCACGG GTCCTGCAGG TCCAGGCCCA GGTGCAGTCA CAGACTCAGC
CGCGGATACC ATCCACAGAC ACCCAGGTGC AGCCAAAGCT GCAGAAGCAG
GCGCAAACAC AGACCTCTCC AGAGCACTTA GTGCTGCAAC AGAAGCAGGT
GCAGCCACAG CTGCAGCAGG AGGCAGAGCC ACAGAAGCAG GTGCAGCCAC
AGGTACAGCC ACAGGCACAT TCACAGGGCC CAAGGCAGGT GCAGCTGCAG
CAGGAGGCAG AGCCGCTGAA GCAGGTGCAG ACAG GTCCACACAC AGGCA
CAGCC AAGCGTCCAG
CCACAGGAGC ATCCTCCAGC GCAGGTGTCA GTACAGCCAC CAGAGCAGAC
CCATGAGCAG CCTCACACCC AGCCGCAGGT GTCGTTGCTG GCTCCAGAGC
AAACACCAGT TGTGGTTCAT GTCTGCGGGC TGGAGATGCC ACCTGATGCA
GTAGAAGCTG GTGGAGGCAT GGAAAAGACC TTGCCAGAGC CTGTGGGCAC
CCAAGTCAGC ATGAAGAGA TTCAGAATGA GTCGGCCTGT GGCCTAGATG
TGGGAGAATG TGAAAACAGA GCGAGAGAGA TGCCAGGGGT ATGGGGCGCC
GGGGGCTCCC TGAAGGTCAC CATTCTGCAG AGCAGTGACA GCCGGGCCTT
TAGCACTGTA CCCCTGACAC CTGTCCCCCG CCCAGTGAC TCCGTCTCCT
CCACCCCTGC GGCTACCAGC ACTCCCTCTA AGCAGGCCCT CCAGTTCTTC
TGCTACATCT GCAAGGCCAG CTGCTCCAGC CAGCAGGAGT TCCAGGACCA
CATGTCGGAG CCTCAGCACC AGCAGCGGCT AGGGGAGATC CAGCACATGA
GCCAAGCCTG CCTCCTGTCC CTGCTGCCCG TGCCCCGGGA CGTCCTGGAG
ACAGAGGATG AGGAGCCTCC ACCAAGGCGC TGGTGCAACA CCTGCCAGCT
CTACTACATG GGGGACCTGA TCCAACACCG CAGGACACAG GACCACAAGA
TTGCCAAACA ATCCTTGCGA CCCTTCTGCA CCGTTTGCAA CCGCTACTTC
AAAACCCCTC GCAAGTTTGT GGAGCACGTG AAGTCCCAGG GGCATAAGGA
CAAAGCCAAG GAGCTGAAGT CGCTTGAGAA AGAAATTGCT GGCCAAGATG
AGGACCACTT CATTACAGTG GACGCTGTGG GTTGCTTCGA GGGTGATGAA
GAAGAGGAAG AGGATGATGA GGATGAAGAA GAGATCGAGG TTGAGGAGGA
ACTCTGCAAG CAGGTGAGGT CCAGAGATAT ATCCAGAGAG GAGTGGAAGG
GCTCGGAGAC CTACAGCCCC AATACTGCAT ATGGTGTGGA CTTCCTGGTG
CCCGTGATGG GCTATATCTG CCGCATCTGC CACAAGTTCT ATCACAGCAA
CTCAGGGGCA CAGCTCTCCC ACTGCAAGTC CCTGGGCCAC TTTGAGAACC
TGCAGAAATA CAAGGCGGCC AAGAACCCCA GCCCCACCAC CCGACCTGTG
AGCCGCCGGT GCGCAATCAA CGCCCGGAAC GCTTTGACAG CCCTGTTCAC
CTCCAGCGGC CGCCCACCCT CCCAGCCCAA CACCCAGGAC AAAACACCCA
GCAAGGTGAC GGCTCGACCC TCCCAGCCCC CACTACCTCG GCGCTCAACC
CGCCTCAAAA CCTGATAGAG GGACCTCCCT GTCCCTGGCC TGCCTGGGTC
CAGATCTGCT AATGCTTTTT AGGAGTCTGC CTGGAAACTT TGACATGGTT
CATGTTTTTA CTCAAAATCC AATAAAACAA GGTAGTTTGG CTGTGCAAAA
AAAAAAAAAA AAAAAAAAAA AA

Figure 21E

Exon 8 minus variant 2
TGGGGGCTGC GGGGCCGGCC CATCCGTGGG GGCGACTTGA GCGTTGAGGG
CGCGCGGGGA GGCGAGCCAC CATGTTCAGC CAGCAGCAGC AGCAGCTCCA
GCAACAGCAG CAGCAGCTCC AGCAGTTACA GCAGCAGCAG CTCCAGCAGC
AGCAATTGCA GCAGCAGCAG TTACTGCAGC TCCAGCAGCT GCTCCAGCAG
TCCCCACCAC AGGCCCCGTT GCCCATGGCT GTCAGCCGGG GGCTCCCCCC
GCAGCAGCCA CAGCAGCCGC TTCTGAATCT CCAGGGCACC AACTCAGCCT
CCCTCCTCAA CGGCTCCATG CTGCAGAGAG CTTTGCTTTT ACAGCAGTTG
CAAGGACTGG ACCAGTTTGC AATGCCACCA GCCACGTATG ACACTGCCGG
TCTCACCATG CCCACAGCAA CACTGGGTAA CCTCCGAGGC TATGGCATGG
CATCCCCAGG CCTCGCAGCC CCCAGCCTCA CACCCCCACA ACTGGCCACT
CCAAATTTGC AACAGTTCTT TCCCCAGGCC ACTCGCCAGT CCTTGCTGGG
ACCTCCTCCT GTTGGGGTCC CCATGAACCC TTCCCAGTTC AACCTTTCAG
GACGGAACCC CCAGAAACAG GCCCGGACCT CCTCCTCTAC CACCCCCAAT
CGAAAGGATT CTTCTTCTCA GACAATGCCT GTGGAAGACA AGTCAGACCC
CCCAGAGGGG TCTGAGGAAG CCGCAGAGCC CCGGATGGAC ACACCAGAAG
ACCAAGATTT ACCGCCCTGC CCAGAGGACA TCGCCAAGGA AAAACGCACT
CCAGCACCTG AGCCTGAGCC TTGTGAGGCG TCCGAGCTGC AGCAAAGAG
ATTGAGGAGC TCAGAAGAGC CCACAGAGAA GGAACCTCCA GGGCAGTTAC
AGGTGAAGGC CCAGCCGCAG GCCCGGATGA CAGTACCGAA ACAGACACAG
ACACCAGACC TGCTGCCTGA GGCCCTGGAA GCCCAAGTGC TGCCACGATT
CCAGCCACGG GTCCTGCAGG TCCAGGCCCA GGTGCAGTCA CAGACTCAGC
CGCGGATACC ATCCACAGAC ACCCAGGTGC AGCCAAAGCT GCAGAAGCAG
GCGCAAACAC AGACCTCTCC AGAGCACTTA GTGCTGCAAC AGAAGCAGGT
GCAGCCACAG CTGCAGCAGG AGGCAGAGCC ACAGAAGCAG GTGCAGCCAC
AGGTCCACAC ACAGGCACAG CCAAGCGTCC AGCCACAGGA GCATCCTCCA
GCGCAGGTGT CAGTACAGCC ACCAGAGCAG ACCCATGAGC AGCCTCACAC
CCAGCCGCAG GTGTCGTTGC TGGCTCCAGA GCAAACACCA GTTGTGGTTC
ATGTCTGCGG GCTGGAGATG CCACCTGATG CAGTAGAAGC TGGTGGAGGC
ATGGAAAAGA CCTTGCCAGA GCCTGTGGGC ACCCAAGTCA GCATGGAAGA
GATTCAGAAT GAGTCGGCCT GTGGCCTAGA TGTGGGAGAA TGTGAAAACA
GAGCGAGAGA GATGCCAGGG GTATGGGGCG CCGGGGGCTC CCTGAAGGTC
ACCATTCTGC AGAGCAGTGA CAGCCGGGCC TTTAGCACTG TACCCCTGAC
ACCTGTCCCC CGCCCCAGTG ACTCCGTCTC CTCCACCCCT GCGGCTACCA
GCACTCCCTC TAAGCAGGCC CTCCAGTTCT TCTGCTACAT CTGCAAGGCC
AGCTGCTCCA GCCAGCAGGA GTTCCAGGAC CACATGTCGG AGCCTCAGCA
CCAGCAGCGG CTAGGGGAGA TCCAGCACAT GAGCCAAGCC TGCCTCCTGT
CCCTGCTGCC CGTGCCCCGG GACGTCCTGG AGACAGAGGA TGAGGAGCCT
CCACCAAGGC GCTGGTGCAA CACCTGCCAG CTCTACTACA TGGGGGACCT
GATCCAACAC CGCAGGACAC AGGACCACAA GATTGCCAAA CAATCCTTGC
GACCCTTCTG CACCGTTTGC AACCGCTACT TCAAAACCCC TCGCAAGTTT
GTGGAGCACG TGAAGTCCCA GGGGCATAAG ACAAAGCCA AGGAGCTGAA
GTCGCTTGAG AAAGAAATTG CTGGCCAAGA TGAGGACCAC TTCATTACAG
TGGACGCTGT GGGTTGCTTC GAGGGTGATG AAGAAGAGGA AGAGGATGAT
GAGGATGAAG AAGAGATCGA GGTTGAGGAG GAACTCTGCA AGCAGGTGAG
GTCCAGAGAT ATATCCAGAG AGGAGTGGAA GGGCTCGGAG ACCTACAGCC
CCAATACTGC ATATGGTGTG GACTTCCTGG TGCCCGTGAT GGGCTATATC
TGCCGCATCT GCCACAAGTT CTATCACAGC AACTCAGGGG CACAGCTCTC
CCACTGCAAG TCCCTGGGCC ACTTTGAGAA CCTGCAGAAA TACAAGGCGG
CCAAGAACCC CAGCCCCACC ACCCGACCTG TGAGCCGCCG GTGCGCAATC
AACGCCCGGA ACGCTTTGAC AGCCCTGTTC ACCTCCAGCG GCCGCCCACC
CTCCCAGCCC AACACCCAGG ACAAAACACC CAGCAAGGTG ACGGCTCGAC
CCTCCCAGCC CCACTACCT CGGCGCTCAA CCCGCCTCAA AACCTGATAG
AGGGACCTCC CTGTCCCTGG CCTGCCTGGG TCCAGATCTG CTAATGCTTT
TTAGGAGTCT GCCTGGAAAC TTTGACATGG TTCATGTTTT TACTCAAAAT
CCAATAAAAC AAGGTAGTTT GGCTGTGCAA AAAAAAAAAA AAAAAAAAAAAA

Figure 21F

Exon 8 minus variant 3
TGGGGGCTGC GGGGCCGGCC CATCCGTGGG GGCGACTTGA GCGTTGAGGG
CGCGCGGGGA GGCGAGCCAC CATGTTCAGC CAGCAGCAGC AGCAGCTCCA
GCAACAGCAG CAGCAGCTCC AGCAGTTACA GCAGCAGCAG CTCCAGCAGC
AGCAATTGCA GCAGCAGCAG TTACTGCAGC TCCAGCAGCT GCTCCAGCAG
TCCCCACCAC AGGCCCCGTT GCCCATGGCT GTCAGCCGGG GGCTCCCCCC
GCAGCAGCCA CAGCAGCCGC TTCTGAATCT CCAGGGCACC AACTCAGCCT
CCCTCCTCAA CGGCTCCATG CTGCAGAGAG CTTTGCTTTT ACAGCAGTTG
CAAGGACTGG ACCAGTTTGC AATGCCACCA GCCACGTATG ACACTGCCGG
TCTCACCATG CCCACAGCAA CACTGGGTAA CCTCCGAGGC TATGGCATGG
CATCCCCAGG CCTCGCAGCC CCCAGCCTCA CACCCCCACA ACTGGCCACT
CCAAATTTGC AACAGTTCTT TCCCCAGGCC ACTCGCCAGT CCTTGCTGGG
ACCTCCTCCT GTTGGGGTCC CCATGAACCC TTCCCAGTTC AACCTTTCAG
GACGGAACCC CCAGAAACAG GCCCGGACCT CCTCCTCTAC CACCCCCAAT
CGAAAGGATT CTTCTTCTCA GACAATGCCT GTGGAAGACA AGTCAGACCC
CCCAGAGGGG TCTGAGGAAG CCGCAGAGCC CCGGATGGAC ACACCAGAAG
ACCAAGATTT ACCGCCCTGC CCAGAGGACA TCGCCAAGGA AAAACGCACT
CCAGCACCTG AGCCTGAGCC TTGTGAGGCG TCCGAGCTGC CAGCAAAGAG
ATTGAGGAGC TCAGAAGAGC CCACAGAGAA GGAACCTCCA GGGCAGTTAC
AGGTGAAGGC CCAGCCGCAG GCCCGGATGA CAGTACCGAA ACAGACACAG
ACACCAGACC TGCTGCCTGA GGCCCTGGAA GCCCAAGTGC TGCCACGATT
CCAGCCACGG GTCCTGCAGG TCCAGGCCTC CACAGGTCCA CACACAGGCA
CAGCCAAGCG TCCAGCCACA GGAGCATCCT CCAGCGCAGG TGTCAGTACA
GCCACCAGAG CAGACCCATG AGCAGCCTCA CACCCAGCCG CAGGTGTCGT
TGCTGGCTCC AGAGCAAACA CCAGTTGTGG TTCATGTCTG CGGGCTGGAG
ATGCCACCTG ATGCAGTAGA AGCTGGTGGA GGCATGGAAA AGACCTTGCC
AGAGCCTGTG GGCACCCAAG TCAGCATGGA AGAGATTCAG AATGAGTCGG
CCTGTGGCCT AGATGTGGGA GAATGTGAAA ACAGAGCGAG AGAGATGCCA
GGGGTATGGG GCGCCGGGGG CTCCCTGAAG GTCACCATTC TGCAGAGCAG
TGACAGCCGG GCCTTTAGCA CTGTACCCCT GACACCTGTC CCCCGCCCCA
GTGACTCCGT CTCCTCCACC CCTGCGGCTA CCAGCACTCC CTCTAAGCAG
GCCCTCCAGT TCTTCTGCTA CATCTGCAAG GCCAGCTGCT CCAGCCAGCA
GGAGTTCCAG GACCACATGT CGGAGCCTCA GCACCAGCAG CGGCTAGGGG
AGATCCAGCA CATGAGCCAA GCCTGCCTCC TGTCCCTGCT GCCCGTGCCC
CGGGACGTCC TGGAGACAGA GGATGAGGAG CCTCCACCAA GGCGCTGGTG
CAACACCTGC CAGCTCTACT ACATGGGGGA CCTGATCCAA CACCGCAGGA
CACAGGACCA CAAGATTGCC AAACAATCCT TGCGACCCTT CTGCACCGTT
TGCAACCGCT ACTTCAAAAC CCCTCGCAAG TTTGTGGAGC ACGTGAAGTC
CCAGGGGCAT AAGGACAAAG CCAAGGAGCT GAAGTCGCTT GAGAAAGAAA
TTGCTGGCCA AGATGAGGAC CACTTCATTA CAGTGGACGC TGTGGGTTGC
TTCGAGGGTG ATGAAGAAGA GGAAGAGGAT GATGAGGATG AAGAAGAGAT
CGAGGTTGAG GAGGAACTCT GCAAGCAGGT GAGGTCCAGA GATATATCCA
GAGAGGAGTG GAAGGGCTCG GAGACCTACA GCCCCAATAC TGCATATGGT
GTGGACTTCC TGGTGCCCGT GATGGGCTAT ATCTGCCGCA TCTGCCACAA
GTTCTATCAC AGCAACTCAG GGGCACAGCT CTCCCACTGC AAGTCCCTGG
GCCACTTTGA GAACCTGCAG AAATACAAGG CGGCCAAGAA CCCCAGCCCC
ACCACCCGAC CTGTGAGCCG CCGGTGCGCA ATCAACGCCC GGAACGCTTT
GACAGCCCTG TTCACCTCCA GCGGCCGCCC ACCCTCCCAG CCCAACACCC
AGGACAAAAC ACCCAGCAAG GTGACGGCTC GACCCTCCCA GCCCCCACTA
CCTCGGCGCT CAACCCGCCT CAAAACCTGA TAGAGGGACC TCCCTGTCCC
TGGCCTGCCT GGGTCCAGAT CTGCTAATGC TTTTTAGGAG TCTGCCTGGA
AACTTTGACA TGGTTCATGT TTTTACTCAA AATCCAATAA AACAAGGTAG
TTTGGCTGTG CAAAAAAAAA AAAAAAAAAA AAAAAAA

Figure 21G

Exon 14 minus transcript
TGGGGGCTGC GGGGCCGGCC CATCCGTGGG GGCGACTTGA GCGTTGAGGG
CGCGCGGGGA GGCGAGCCAC CATGTTCAGC CAGCAGCAGC AGCAGCTCCA
GCAACAGCAG CAGCAGCTCC AGCAGTTACA GCAGCAGCAG CTCCAGCAGC
AGCAATTGCA GCAGCAGCAG TTACTGCAGC TCCAGCAGCT GCTCCAGCAG
TCCCCACCAC AGGCCCCGTT GCCCATGGCT GTCAGCCGGG GGCTCCCCCC
GCAGCAGCCA CAGCAGCCGC TTCTGAATCT CCAGGGCACC AACTCAGCCT
CCCTCCTCAA CGGCTCCATG CTGCAGAGAG CTTTGCTTTT ACAGCAGTTG
CAAGGACTGG ACCAGTTTGC AATGCCACCA GCCACGTATG ACACTGCCGG
TCTCACCATG CCCACAGCAA CACTGGGTAA CCTCCGAGGC TATGGCATGG
CATCCCCAGG CCTCGCAGCC CCCAGCCTCA CACCCCACA ACTGGCCACT
CCAAATTTGC AACAGTTCTT TCCCCAGGCC ACTCGCCAGT CCTTGCTGGG
ACCTCCTCCT GTTGGGGTCC CCATGAACCC TTCCCAGTTC AACCTTTCAG
GACGGAACCC CCAGAAACAG GCCCGGACCT CCTCCTCTAC CACCCCCAAT
CGAAAGGATT CTTCTTCTCA GACAATGCCT GTGGAAGACA AGTCAGACCC
CCCAGAGGGG TCTGAGGAAG CCGCAGAGCC CCGGATGGAC ACACCAGAAG
ACCAAGATTT ACCGCCCTGC CCAGAGGACA TCGCCAAGGA AAAACGCACT
CCAGCACCTG AGCCTGAGCC TTGTGAGGCG TCCGAGCTGC CAGCAAAGAG
ATTGAGGAGC TCAGAAGAGC CCACAGAGAA GGAACCTCCA GGGCAGTTAC
AGGTGAAGGC CCAGCCGCAG GCCCGGATGA CAGTACCGAA ACAGACACAG
ACACCAGACC TGCTGCCTGA GGCCCTGGAA GCCCAAGTGC TGCCACGATT
CCAGCCACGG GTCCTGCAGG TCCAGGCCCA GGTGCAGTCA CAGACTCAGC
GGCGGATACC ATCCACAGAC ACCCAGGTGC AGCCAAAGCT GCAGAAGCAG
GCGCAAACAC AGACCTCTCC AGAGCACTTA GTGCTGCAAC AGAAGCAGGT
GCAGCCACAG CTGCAGCAGG AGGCAGAGCC ACAGAAGCAG GTGCAGCCAC
AGGTACAGCC ACAGGCACAT TCACAGGGCC CAAGGCAGGT GCAGCTGCAG
CAGGAGGCAG AGCCGCTGAA GCAGGTGCAG CCACAGGTGC AGCCCCAGGC
ACATTCACAG CCCCCAAGGC AGGTGCAGCT GCAGCTGCAG AAGCAGGTCC
AGACACAGAC ATATCCACAG GTCCACACAC AGGCACAGCC AAGCGTCCAG
CCACAGGAGC ATCCTCCAGC GCAGGTGTCA GTACAGCCAC CAGAGCAGAC
CCATGAGCAG CCTCACACCC AGCCGCAGGT GTCGTTGCTG GCTCCAGAGC
AAACACCAGT TGTGGTTCAT GTCTGCGGGC TGGAGATGCC ACCTGATGCA
GTAGAAGCTG GTGGAGGCAT GGAAAAGACC TTGCCAGAGC CTGTGGGCAC
CCAAGTCAGC ATGGAAGAGA TTCAGAATGA GTCGGCCTGT GGCCTAGATG
TGGGAGAATG TGAAAACAGA GCGAGAGAGA TGCCAGGGGT ATGGGGCGCC
GGGGGCTCCC TGAAGGTCAC CATTCTGCAG AGCAGTGACA GCCGGGCCTT
TAGCACTGTA CCCCTGACAC CTGTCCCCCG CCCCAGTGAC TCCGTCTCCT
CCACCCCTGC GGCTACCAGC ACTCCCTCTA GCAGGCCCT CCAGTTCTTC
TGCTACATCT GCAAGGCCAG CTGCTCCAGC CAGCAGGAGT TCCAGGACCA
CATGTCGGAG CCTCAGCACC AGCAGCGGCT AGGGGAGATC AGCAGCACATGA
GCCAAGCCTG CCTCCTGTCC CTGCTGCCCG TGCCCCGGGA CGTCCTGGAG
ACAGAGGATG AGGAGCCTCC ACCAAGGCGC TGGTGCAACA CCTGCCAGCT
CTACTACATG GGGGACCTGA TCCAACACCG CAGGACACAG GACCACAAGA
TTGCCAAACA ATCCTTGCGA CCCTTCTGCA CCGTTTGCAA CCGCTACTTC
AAAACCCCTC GCAAGTTTGT GGAGCACGTG AAGTCCCAGG GGCATAAGGA
CAAAGCCAAG GAGCTGAAGT CGCTTGAGAA AGAAATTGCT GGCCAAGATG
AGGACCACTT CATTACAGTG GACGCTGTGG GTTGCTTCGA GGGTGATGAA
GAAGAGGAAG AGGATGATGA GGATGAAGAA GAGATCGAGG TGAGGTCCAG
AGATATATCC AGAGAGGAGT GGAAGGGCTC GGAGACCTAC AGCCCCAATA
CTGCATATGG TGTGGACTTC CTGGTGCCCG TGATGGGCTA TATCTGCCGC
ATCTGCCACA AGTTCTATCA CAGCAACTCA GGGGCACAGC TCTCCCACTG
CAAGTCCCTG GGCCACTTTG AGAACCTGCA GAAATACAAG GCGGCCAAGA
ACCCCAGCCC CACCACCCGA CCTGTGAGCC CCGGTGCGC AATCAACGCC
CGGAACGCTT TGACAGCCCT GTTCACCTCC AGCGGCCGCC CACCCTCCCA
GCCCAACACC CAGGACAAAA CACCCAGCAA GGTGACGGCT CGACCCTCCC
AGCCCCCACT ACCTCGGCGC TCAACCCGCC TCAAAACCTG ATAGAGGGAC
CTCCCTGTCC CTGGCCTGCC TGGGTCCAGA TCTGCTAATG CTTTTTAGGA
GTCTGCCTGG AAACTTTGAC ATGGTTCATG TTTTTACTCA AAATCCAATA
AAACAAGGTA GTTTGGCTGT GCAAAAAAAA AAAAAAAAAA AAAAAAAA Also to be protected are transcripts which lack combinations of the variable exons. For example:-

Exon 14 and partial exon 6 minus variant
TGGGGGCTGC GGGGCCGGCC CATCCGTGGG GGCGACTTGA GCGTTGAGGG
CGCGCGGGGA GGCGAGCCAC CATGTTCAGC CAGCAGCAGC AGCAGCTCCA
GCAACAGCAG CAGCAGCTCC AGCAGTTACA GCAGCAGCAG CTCCAGCAGC
AGCAATTGCA GCAGCAGCAG TTACTGCAGC TCCAGCAGCT GCTCCAGCAG
TCCCCACCAC AGGCCCCGTT GCCCATGGCT GTCAGCCGGG GGCTCCCCCC
GCAGCAGCCA CAGCAGCCGC TTCTGAATCT CCAGGGCACC AACTCAGCCT
CCCTCCTCAA CGGCTCCATG CTGCAGAGAG CTTTGCTTTT ACAGCAGTTG
CAAGGACTGG ACCAGTTTGC AATGCCACCA GCCACGTATG ACACTGCCGG
TCTCACCATG CCCACAGCAA CACTGGGTAA CCTCCGAGGC TATGGCATGG
CATCCCCAGG CCTCGCAGCC CCCAGCCTCA CACCCCACA ACTGGCCACT
CCAAATTTGC AACAGTTCTT TCCCCAGGCC ACTCGCCAGT CCTTGCTGGG
ACCTCCTCCT GTTGGGGTCC CCATGAACCC TTCCCAGTTC AACCTTTCAG
GACGGAACCC CCAGAAACAG GCCCGGACCT CCTCCTCTAC CACCCCCAAT
CGAAAGACAA TGCCTGTGGA AGACAAGTCA GACCCCCCAG AGGGGTCTGA
GGAAGCCGCA GAGCCCCGGA TGGACACACC AGAAGACCAA GATTTACCGC
CCTGCCCAGA GGACATCGCC AAGGAAAAAC GCACTCCAGC ACCTGAGCCT
GAGCCTTGTG AGGCGTCCGA GCTGCCAGCA AAGAGATTGA GGAGCTCAGA
AGAGCCCACA GAGAAGGAAC CTCCAGGGCA GTTACAGGTG AAGGCCCAGC
CGCAGGCCCG GATGACAGTA CCGAAACAGA CACAGACACC AGACCTGCTG
CCTGAGGCCC TGGAAGCCCA AGTGCTGCCA CGATTCCAGC CACGGGTCCT
GCAGGTCCAG GCCCAGGTGC AGTCACAGAC TCAGCCGCGG ATACCATCCA
CAGACACCCA GGTGCAGCCA AAGCTGCAGA AGCAGGCGCA AACACAGACC
TCTCCAGAGC ACTTAGTGCT GCAACAGAAG CAGGTGCAGC CACAGCTGCA
GCAGGAGGCA GAGCCACAGA AGCAGGTGCA GCCACAGGTA CAGCCACAGG
CACATTCACA GGGCCCAAGG CAGGTGCAGC TGCAGCAGGA GGCAGAGCCG
CTGAAGCAGG TGCAGCCACA GGTGCAGCCC CAGGCACATT CACAGCCCCC
AAGGCAGGTG CAGCTGCAGC TGCAGAAGCA GGTCCAGACA CAGACATATC
CACAGGTCCA CACACAGGCA CAGCCAAGCG TCCAGCCACA GGAGCATCCT
CCAGCGCAGG TGTCAGTACA GCCACCAGAG CAGACCCATG AGCAGCCTCA
CACCCAGCCG CAGGTGTCGT TGCTGGCTCC AGAGCAAACA CCAGTTGTGG
TTCATGTCTG CGGGCTGGAA ATGCCACCTG ATGCAGTAGA AGCTGGTGGA
GGCATGGAAA AGACCTTGCC AGAGCCTGTG GGCACCCAAG TCAGCATGGA
AGAGATTCAG AATGAGTCGG CCTGTGGCCT AGATGTGGGA GAATGTGAAA
ACAGAGCGAG AGAGATGCCA GGGGTATGGG GCGCCGGGGG CTCCCTGAAG
GTCACCATTC TGCAGAGCAG TGACAGCCGG GCCTTTAGCA CTGTACCCCT
GACACCTGTC CCCCGCCCCA GTGACTCCGT CTCCTCCACC CCTGCGGCTA
CCAGCACTCC CTCTAAGCAG GCCCTCCAGT TCTTCTGCTA CATCTGCAAG
GCCAGCTGCT CCAGCCAGCA GGAGTTCCAG GACCACATGT CGGAGCCTCA
GCACCAGCAG CGGCTAGGGG AGATCCAGCA CATGAGCCAA GCCTGCCTCC
TGTCCCTGCT GCCCGTGCCC CGGGACGTCC TGGAGACAGA GGATGGAGGA
CCTCCACCAA GGCGCTGGTG CAACACCTGC CAGCTCTACT ACATGGGGGA
CCTGATCCAA CACCGCAGGA CACAGGACCA CAAGATTGCC AAACAATCCT
TGCGACCCTT CTGCACCGTT TGCAACCGCT ACTTCAAAAC CCCTCGCAAG
TTTGTGGAGC ACGTGAAGTC CCAGGGGCAT AAGGACAAAG CCAAGGAGCT
GAAGTCGCTT GAGAAAGAAA TTGCTGGCCA AGATGAGGAC CACTTCATTA
CAGTGGACGC TGTGGGTTGC TTCGAGGGTG ATGAAGAAGA GGAAGAGGAT
GATGAGGATG AAGAAGAGAT CGAGGTGAGG TCCAGAGATA TATCCAGAGA
GGAGTGGAAG GGCTCGGAGA CCTACAGCCC CAATACTGCA TATGGTGTGG
ACTTCCTGGT GCCCGTGATG GGCTATATCT GCCGCATCTG CCACAAGTTC
TATCACAGCA ACTCAGGGGC ACAGCTCTCC CACTGCAAGT CCCTGGGCCA
CTTTGAGAAC CTGCAGAAAT ACAAGGCGGC CAAGAACCCC AGCCCCACCA
CCCGACCTGT GAGCCGCCGG TGCGCAATCA ACGCCGGAA CGCTTTGACA
GCCCTGTTCA CCTCCAGCGG CCGCCCACCC TCCAGCCCA ACACCCAGGA
CAAAACACCC AGCAAGGTGA CGGCTCGACC CTCCCAGCCC CCACTACCTC
GGCGCTCAAC CCGCCTCAAA ACCTGATAGA GGGACCTCCC TGTCCCTGGC
CTGCCTGGGT CCAGATCTGC TAATGCTTTT TAGGAGTCTG CCTGGAAACT
TTGACATGGT TCATGTTTTT ACTCAAAATC CAATAAAACA AGGTAGTTTG
GCTGTGCAAA AAAAAAAAAA AAAAAAAAAA AAA

Figure 21H

SEQUENCE LISTING

```
<160> NUMBER OF SEQ ID NOS: 74

<210> SEQ ID NO 1
<211> LENGTH: 5
<212> TYPE: PRT
<213> ORGANISM: Homo sapiens

<400> SEQUENCE: 1

Asp Ser Ser Ser Gln
1               5

<210> SEQ ID NO 2
<211> LENGTH: 24
<212> TYPE: DNA
<213> ORGANISM: Homo sapiens

<400> SEQUENCE: 2
gttgaggagg aactctgcaa gcag                                          24

<210> SEQ ID NO 3
<211> LENGTH: 8
<212> TYPE: PRT
<213> ORGANISM: Homo sapiens

<400> SEQUENCE: 3

Val Glu Glu Glu Leu Cys Lys Gln
1               5

<210> SEQ ID NO 4
<211> LENGTH: 78
<212> TYPE: DNA
<213> ORGANISM: Homo sapiens

<400> SEQUENCE: 4
gccacccaca ccacgaagag atgtgtttgc ccacgttcca gtgcaggggt ggagcacagc    60
ccggcttgtt acagatat                                                  78

<210> SEQ ID NO 5
<211> LENGTH: 32
<212> TYPE: DNA
```

-continued

```
<213> ORGANISM: Artificial
<220> FEATURE:
<223> OTHER INFORMATION: Oligonucleotide primer

<400> SEQUENCE: 5
aaccccctct tccgccgccc ccaatcgcaa ga                                    32

<210> SEQ ID NO 6
<211> LENGTH: 32
<212> TYPE: DNA
<213> ORGANISM: Artificial
<220> FEATURE:
<223> OTHER INFORMATION: Oligonucleotide primer

<400> SEQUENCE: 6
tcttgcgatt gggggcggcg aagaggggg tt                                     32

<210> SEQ ID NO 7
<211> LENGTH: 30
<212> TYPE: DNA
<213> ORGANISM: Artificial
<220> FEATURE:
<223> OTHER INFORMATION: Oligonucleotide primer

<400> SEQUENCE: 7
aagcagacac aggccccgga tcggctgcct                                       30

<210> SEQ ID NO 8
<211> LENGTH: 30
<212> TYPE: DNA
<213> ORGANISM: Artificial
<220> FEATURE:
<223> OTHER INFORMATION: Oligonucleotide primer

<400> SEQUENCE: 8
aggcagccga tccggggcct gtgtctgctt                                       30

<210> SEQ ID NO 9
<211> LENGTH: 29
<212> TYPE: DNA
<213> ORGANISM: Artificial
<220> FEATURE:
<223> OTHER INFORMATION: Oligonucleotide primer

<400> SEQUENCE: 9
aagcacagtc acaggagcag acctgtctc                                        29

<210> SEQ ID NO 10
<211> LENGTH: 29
<212> TYPE: DNA
<213> ORGANISM: Artificial
<220> FEATURE:
<223> OTHER INFORMATION: Oligonucleotide primer

<400> SEQUENCE: 10
aatctgctcc tgtgactgtg ccctgtctc                                        29

<210> SEQ ID NO 11
<211> LENGTH: 29
<212> TYPE: DNA
<213> ORGANISM: Artificial
<220> FEATURE:
<223> OTHER INFORMATION: Oligonucleotide primer

<400> SEQUENCE: 11
aatctgtcac aagttctacg acctgtctc                                        29
```

<210> SEQ ID NO 12
<211> LENGTH: 29
<212> TYPE: DNA
<213> ORGANISM: Artificial
<220> FEATURE:
<223> OTHER INFORMATION: Oligonucleotide primer

<400> SEQUENCE: 12
aatcgtagaa cttgtgacag acctgtctc                              29

<210> SEQ ID NO 13
<211> LENGTH: 29
<212> TYPE: DNA
<213> ORGANISM: Artificial
<220> FEATURE:
<223> OTHER INFORMATION: Oligonucleotide primer

<400> SEQUENCE: 13
aatcgcaagg attcttcttc tcctgtctc                              29

<210> SEQ ID NO 14
<211> LENGTH: 29
<212> TYPE: DNA
<213> ORGANISM: Artificial
<220> FEATURE:
<223> OTHER INFORMATION: Oligonucleotide primer

<400> SEQUENCE: 14
aaagaagaag aatccttgcg acctgtctc                              29

<210> SEQ ID NO 15
<211> LENGTH: 29
<212> TYPE: DNA
<213> ORGANISM: Artificial
<220> FEATURE:
<223> OTHER INFORMATION: Oligonucleotide primer

<400> SEQUENCE: 15
aatctgcagc agttctttcc ccctgtctc                              29

<210> SEQ ID NO 16
<211> LENGTH: 29
<212> TYPE: DNA
<213> ORGANISM: Artificial
<220> FEATURE:
<223> OTHER INFORMATION: Oligonucleotide primer

<400> SEQUENCE: 16
aagggaaaga actgctgcag acctgtctc                              29

<210> SEQ ID NO 17
<211> LENGTH: 18
<212> TYPE: DNA
<213> ORGANISM: Artificial
<220> FEATURE:
<223> OTHER INFORMATION: Oligonucleotide primer

<400> SEQUENCE: 17
cagtccccac cacaggcc                                          18

<210> SEQ ID NO 18
<211> LENGTH: 20
<212> TYPE: DNA
<213> ORGANISM: Artificial
<220> FEATURE:

<223> OTHER INFORMATION: Oligonucleotide primer

<400> SEQUENCE: 18
ggcttcctca gacccctctg                                              20

<210> SEQ ID NO 19
<211> LENGTH: 25
<212> TYPE: DNA
<213> ORGANISM: Artificial
<220> FEATURE:
<223> OTHER INFORMATION: Oligonucleotide primer

<400> SEQUENCE: 19
acacagacct ctccagagca cttag                                        25

<210> SEQ ID NO 20
<211> LENGTH: 19
<212> TYPE: DNA
<213> ORGANISM: Artificial
<220> FEATURE:
<223> OTHER INFORMATION: Oligonucleotide primer

<400> SEQUENCE: 20
atggtgacct tcagggagc                                               19

<210> SEQ ID NO 21
<211> LENGTH: 25
<212> TYPE: DNA
<213> ORGANISM: Artificial
<220> FEATURE:
<223> OTHER INFORMATION: Oligonucleotide primer

<400> SEQUENCE: 21
tccttggcga tgtcctctgg gcagg                                        25

<210> SEQ ID NO 22
<211> LENGTH: 25
<212> TYPE: DNA
<213> ORGANISM: Artificial
<220> FEATURE:
<223> OTHER INFORMATION: Oligonucleotide primer

<400> SEQUENCE: 22
tccctcctca acggctccat gctgc                                        25

<210> SEQ ID NO 23
<211> LENGTH: 25
<212> TYPE: DNA
<213> ORGANISM: Artificial
<220> FEATURE:
<223> OTHER INFORMATION: Oligonucleotide primer

<400> SEQUENCE: 23
cgtgggggcg acttgagcgt tgagg                                        25

<210> SEQ ID NO 24
<211> LENGTH: 25
<212> TYPE: DNA
<213> ORGANISM: Artificial
<220> FEATURE:
<223> OTHER INFORMATION: Oligonucleotide primer

<400> SEQUENCE: 24
gatgccaggg gtatggggcg ccggg                                        25

-continued

```
<210> SEQ ID NO 25
<211> LENGTH: 25
<212> TYPE: DNA
<213> ORGANISM: Artificial
<220> FEATURE:
<223> OTHER INFORMATION: Oligonucleotide primer

<400> SEQUENCE: 25
tccgagccct tccactcctc tctgg                                              25

<210> SEQ ID NO 26
<211> LENGTH: 845
<212> TYPE: PRT
<213> ORGANISM: Mus musculus

<400> SEQUENCE: 26

Met Phe Asn Pro Gln Leu Gln Gln Gln Gln Leu Gln Gln Gln Gln
  1               5                  10                  15

Gln Gln Leu Gln Gln Leu Gln Gln Gln Leu Gln Gln Gln Gln
                 20                  25                  30

Gln Gln Ile Leu Gln Leu Gln Gln Leu Leu Gln Ser Pro Pro Gln
             35                  40                  45

Ala Ser Leu Ser Ile Pro Val Ser Arg Gly Leu Pro Gln Ser Ser
         50                  55                  60

Pro Gln Gln Leu Leu Ser Leu Gln Gly Leu His Ser Thr Ser Leu Leu
 65                  70                  75                  80

Asn Gly Pro Met Leu Gln Arg Ala Leu Leu Leu Gln Leu Gln Gly
                 85                  90                  95

Leu Asp Gln Phe Ala Met Pro Pro Ala Thr Tyr Asp Gly Ala Ser Leu
                100                 105                 110

Thr Met Pro Thr Ala Thr Leu Gly Asn Leu Arg Ala Phe Asn Val Thr
            115                 120                 125

Ala Pro Ser Leu Ala Ala Pro Ser Leu Thr Pro Pro Gln Met Val Thr
        130                 135                 140

Pro Asn Leu Gln Gln Phe Phe Pro Gln Ala Thr Arg Gln Ser Leu Leu
145                 150                 155                 160

Gly Pro Pro Pro Val Gly Val Pro Ile Asn Pro Ser Gln Leu Asn His
                165                 170                 175

Ser Gly Arg Asn Thr Gln Lys Gln Ala Arg Thr Pro Ser Ser Thr Thr
            180                 185                 190

Pro Asn Arg Lys Asp Ser Ser Ser Gln Thr Val Pro Leu Glu Asp Arg
        195                 200                 205

Glu Asp Pro Thr Glu Gly Ser Glu Ala Thr Glu Leu Gln Met Asp
    210                 215                 220

Thr Cys Glu Asp Gln Asp Ser Leu Val Gly Pro Asp Ser Met Leu Ser
225                 230                 235                 240

Glu Pro Gln Val Pro Glu Pro Glu Pro Phe Glu Thr Leu Glu Pro Pro
                245                 250                 255

Ala Lys Arg Cys Arg Ser Ser Glu Glu Ser Thr Glu Lys Gly Pro Thr
            260                 265                 270

Gly Gln Pro Gln Ala Arg Val Gln Pro Gln Thr Gln Met Thr Ala Pro
        275                 280                 285

Lys Gln Thr Gln Thr Pro Asp Arg Leu Pro Glu Pro Pro Glu Val Gln
    290                 295                 300

Met Leu Pro Arg Ile Gln Pro Gln Ala Leu Gln Ile Gln Thr Gln Pro
305                 310                 315                 320
```

-continued

```
Lys Leu Leu Arg Gln Ala Gln Thr Gln Thr Ser Pro Glu His Leu Ala
            325                 330                 335

Pro Gln Gln Asp Gln Val Glu Pro Gln Val Pro Ser Gln Pro Pro Trp
        340                 345                 350

Gln Leu Gln Pro Arg Glu Thr Asp Pro Pro Asn Gln Ala Gln Ala Gln
            355                 360                 365

Thr Gln Pro Gln Pro Leu Trp Gln Ala Gln Ser Gln Lys Gln Ala Gln
370                 375                 380

Thr Gln Ala His Pro Gln Val Pro Thr Gln Ala Gln Ser Gln Glu Gln
385                 390                 395                 400

Thr Ser Glu Lys Thr Gln Asp Gln Pro Gln Thr Trp Pro Gln Gly Ser
                405                 410                 415

Val Pro Pro Glu Gln Ala Ser Gly Pro Ala Cys Ala Thr Glu Pro
            420                 425                 430

Gln Leu Ser Ser His Ala Ala Glu Ala Gly Ser Asp Pro Asp Lys Ala
            435                 440                 445

Leu Pro Glu Pro Val Ser Ala Gln Ser Ser Glu Asp Arg Ser Arg Glu
        450                 455                 460

Ala Ser Ala Gly Gly Leu Asp Leu Gly Glu Cys Glu Lys Arg Ala Gly
465                 470                 475                 480

Glu Met Leu Gly Met Trp Gly Ala Gly Ser Ser Leu Lys Val Thr Ile
                485                 490                 495

Leu Gln Ser Ser Asn Ser Arg Ala Phe Asn Thr Thr Pro Leu Thr Ser
            500                 505                 510

Gly Pro Arg Pro Gly Asp Ser Thr Ser Ala Thr Pro Ala Ile Ala Ser
        515                 520                 525

Thr Pro Ser Lys Gln Ser Leu Gln Phe Phe Cys Tyr Ile Cys Lys Ala
    530                 535                 540

Ser Ser Ser Ser Gln Gln Glu Phe Gln Asp His Met Ser Glu Ala Gln
545                 550                 555                 560

His Gln Gln Arg Leu Gly Glu Ile Gln His Ser Ser Gln Thr Cys Leu
                565                 570                 575

Leu Ser Leu Leu Pro Met Pro Arg Asp Ile Leu Glu Lys Glu Ala Glu
            580                 585                 590

Asp Pro Pro Lys Arg Trp Cys Asn Thr Cys Gln Val Tyr Tyr Val
        595                 600                 605

Gly Asp Leu Ile Gln His Arg Arg Thr Gln Glu His Lys Val Ala Lys
    610                 615                 620

Gln Ser Leu Arg Pro Phe Cys Thr Ile Cys Asn Arg Tyr Phe Lys Thr
625                 630                 635                 640

Pro Arg Lys Phe Val Glu His Val Lys Ser Gln Gly His Lys Asp Lys
                645                 650                 655

Ala Gln Glu Leu Lys Thr Leu Glu Lys Glu Thr Gly Ser Pro Asp Glu
            660                 665                 670

Asp His Phe Ile Thr Val Asp Ala Val Gly Cys Phe Glu Ser Gly Gln
        675                 680                 685

Glu Glu Asp Glu Asp Asp Glu Glu Glu Glu Glu Gly Glu Ile
    690                 695                 700

Glu Ala Glu Glu Glu Phe Cys Lys Gln Val Lys Pro Arg Glu Thr Ser
705                 710                 715                 720

Ser Glu Gln Gly Lys Gly Ser Glu Thr Tyr Asn Pro Asn Thr Ala Tyr
                725                 730                 735

Gly Glu Asp Phe Leu Val Pro Val Met Gly Tyr Val Cys Gln Ile Cys
```

```
                      740                 745                 750
His Lys Phe Tyr Asp Ser Asn Ser Glu Leu Arg Leu Ser His Cys Lys
        755                 760                 765

Ser Leu Ala His Phe Glu Asn Leu Gln Lys Tyr Lys Ala Lys Asn Pro
        770                 775                 780

Ser Pro Pro Thr Arg Pro Val Ser Arg Lys Cys Ala Ile Asn Ala
785                 790                 795                 800

Arg Asn Ala Leu Thr Ala Leu Phe Thr Ser His Gln Pro Ser Pro
                805                 810                 815

Gln Asp Thr Val Lys Met Pro Ser Lys Val Lys Pro Gly Ser Pro Gly
        820                 825                 830

Leu Pro Pro Leu Arg Arg Ser Thr Arg Leu Lys Thr
        835                 840                 845

<210> SEQ ID NO 27
<211> LENGTH: 716
<212> TYPE: PRT
<213> ORGANISM: Mus musculus

<400> SEQUENCE: 27

Ser Thr Ser Leu Leu Asn Gly Pro Met Leu Gln Arg Ala Leu Leu Leu
1               5                   10                  15

Gln Gln Leu Gln Gly Leu Asp Gln Phe Ala Met Pro Pro Ala Thr Tyr
            20                  25                  30

Asp Gly Ala Ser Leu Thr Met Pro Thr Ala Thr Leu Gly Asn Leu Arg
        35                  40                  45

Ala Phe Asn Val Thr Ala Pro Ser Leu Ala Ala Pro Ser Leu Thr Pro
    50                  55                  60

Pro Gln Met Val Thr Pro Asn Leu Gln Gln Phe Phe Pro Gln Ala Thr
65                  70                  75                  80

Arg Gln Ser Leu Leu Gly Pro Pro Val Gly Val Pro Ile Asn Pro
                85                  90                  95

Ser Gln Leu Asn His Ser Gly Arg Asn Thr Gln Lys Gln Ala Arg Thr
            100                 105                 110

Pro Ser Ser Thr Thr Pro Asn Arg Lys Thr Val Pro Leu Glu Asp Arg
        115                 120                 125

Glu Asp Pro Thr Glu Gly Ser Glu Glu Ala Thr Glu Leu Gln Met Asp
    130                 135                 140

Thr Cys Glu Asp Gln Asp Ser Leu Val Gly Pro Asp Ser Met Leu Ser
145                 150                 155                 160

Glu Pro Gln Val Pro Glu Pro Glu Pro Phe Glu Thr Leu Glu Pro Pro
                165                 170                 175

Ala Lys Arg Cys Arg Ser Ser Glu Glu Ser Thr Glu Lys Gly Pro Thr
            180                 185                 190

Gly Gln Pro Gln Ala Arg Val Gln Pro Gln Thr Gln Met Thr Ala Pro
        195                 200                 205

Lys Gln Thr Gln Thr Pro Asp Arg Leu Pro Glu Pro Pro Glu Val Gln
    210                 215                 220

Met Leu Pro Arg Ile Gln Pro Gln Ala Leu Gln Ile Gln Thr Gln Pro
225                 230                 235                 240

Lys Leu Leu Arg Gln Ala Gln Thr Gln Thr Ser Pro Glu His Leu Ala
                245                 250                 255

Pro Gln Gln Asp Gln Val Pro Thr Gln Ala Gln Ser Gln Glu Gln Thr
            260                 265                 270
```

-continued

```
Ser Glu Lys Thr Gln Asp Gln Pro Gln Thr Trp Pro Gln Gly Ser Val
        275                 280                 285

Pro Pro Pro Glu Gln Ala Ser Gly Pro Ala Cys Ala Thr Glu Pro Gln
290                 295                 300

Leu Ser Ser His Ala Ala Glu Ala Gly Ser Asp Pro Asp Lys Ala Leu
305                 310                 315                 320

Pro Glu Pro Val Ser Ala Gln Ser Ser Glu Asp Arg Ser Arg Glu Ala
                325                 330                 335

Ser Ala Gly Gly Leu Asp Leu Gly Glu Cys Glu Lys Arg Ala Gly Glu
            340                 345                 350

Met Leu Gly Met Trp Gly Ala Gly Ser Ser Leu Lys Val Thr Ile Leu
        355                 360                 365

Gln Ser Ser Asn Ser Arg Ala Phe Asn Thr Thr Pro Leu Thr Ser Gly
    370                 375                 380

Pro Arg Pro Gly Asp Ser Thr Ser Ala Thr Pro Ala Ile Ala Ser Thr
385                 390                 395                 400

Pro Ser Lys Gln Ser Leu Gln Phe Phe Cys Tyr Ile Cys Lys Ala Ser
                405                 410                 415

Ser Ser Ser Gln Gln Glu Phe Gln Asp His Met Ser Glu Ala His His
            420                 425                 430

Gln Gln Arg Leu Gly Glu Ile Gln His Ser Ser Gln Thr Cys Leu Leu
        435                 440                 445

Ser Leu Leu Pro Met Pro Arg Asp Ile Leu Glu Lys Glu Ala Glu Asp
    450                 455                 460

Pro Pro Pro Lys Arg Trp Cys Asn Thr Cys Gln Val Tyr Tyr Val Gly
465                 470                 475                 480

Asp Leu Ile Gln His Arg Arg Thr Gln Glu His Lys Val Ala Lys Gln
                485                 490                 495

Ser Leu Arg Pro Phe Cys Thr Ile Cys Asn Arg Tyr Phe Lys Thr Pro
            500                 505                 510

Arg Lys Phe Val Glu His Val Lys Ser Gln Gly His Lys Asp Lys Ala
        515                 520                 525

Gln Glu Leu Lys Thr Leu Lys Glu Thr Gly Ser Pro Asp Glu Asp
    530                 535                 540

His Phe Ile Thr Val Asp Ala Val Gly Cys Phe Glu Ser Gly Gln Glu
545                 550                 555                 560

Glu Asp Glu Asp Asp Asp Glu Glu Glu Glu Gly Glu Ile Glu
                565                 570                 575

Ala Glu Glu Glu Phe Cys Lys Gln Val Lys Pro Arg Glu Thr Ser Ser
            580                 585                 590

Glu Gln Gly Lys Gly Ser Glu Thr Tyr Asn Pro Asn Thr Ala Tyr Gly
        595                 600                 605

Glu Asp Phe Leu Val Pro Val Met Gly Tyr Val Cys Gln Ile Cys His
    610                 615                 620

Lys Phe Tyr Asp Ser Asn Ser Glu Leu Arg Leu Ser His Cys Lys Ser
625                 630                 635                 640

Leu Ala His Phe Glu Asn Leu Gln Lys Tyr Lys Ala Lys Asn Pro Ser
                645                 650                 655

Pro Pro Pro Thr Arg Pro Val Ser Arg Lys Cys Ala Ile Asn Ala Arg
            660                 665                 670

Asn Ala Leu Thr Ala Leu Phe Thr Ser Ser His Gln Pro Ser Pro Gln
        675                 680                 685

Asp Thr Val Lys Met Pro Ser Lys Val Lys Pro Gly Ser Pro Gly Leu
```

```
                    690                 695                 700
Pro Pro Pro Leu Arg Arg Ser Thr Arg Leu Lys Thr
705                 710                 715

<210> SEQ ID NO 28
<211> LENGTH: 714
<212> TYPE: PRT
<213> ORGANISM: Mus musculus

<400> SEQUENCE: 28

Met Phe Asn Pro Gln Leu Gln Gln Gln Gln Leu Gln Gln Gln Gln
1               5                   10                  15

Gln Gln Leu Gln Gln Leu Gln Gln Gln Leu Gln Gln Gln Gln
            20                  25                  30

Gln Gln Ile Leu Gln Leu Gln Leu Leu Gln Gln Ser Pro Gln
            35                  40                  45

Ala Ser Leu Ser Ile Pro Val Ser Arg Gly Leu Pro Gln Gln Ser Ser
50                  55                  60

Pro Gln Gln Leu Leu Ser Leu Gln Gly Leu His Ser Thr Ser Leu Leu
65                  70                  75                  80

Asn Gly Pro Met Leu Gln Arg Ala Leu Leu Leu Gln Leu Gln Gly
            85                  90                  95

Leu Asp Gln Phe Ala Met Pro Pro Ala Thr Tyr Asp Gly Ala Ser Leu
                100                 105                 110

Thr Met Pro Thr Ala Thr Leu Gly Asn Leu Arg Ala Phe Asn Val Thr
            115                 120                 125

Ala Pro Ser Leu Ala Ala Pro Ser Leu Thr Pro Pro Gln Met Val Thr
130                 135                 140

Pro Asn Leu Gln Gln Phe Phe Pro Gln Ala Thr Arg Gln Ser Leu Leu
145                 150                 155                 160

Gly Pro Pro Pro Val Gly Val Pro Ile Asn Pro Ser Gln Leu Asn His
                165                 170                 175

Ser Gly Arg Asn Thr Gln Lys Gln Ala Arg Thr Pro Ser Ser Thr Thr
            180                 185                 190

Pro Asn Arg Lys Thr Val Pro Leu Glu Asp Arg Glu Asp Pro Thr Glu
        195                 200                 205

Gly Ser Glu Glu Ala Thr Glu Leu Gln Met Asp Thr Cys Glu Asp Gln
    210                 215                 220

Asp Ser Leu Val Gly Pro Asp Ser Met Leu Ser Glu Pro Gln Val Pro
225                 230                 235                 240

Glu Pro Glu Pro Phe Glu Thr Leu Glu Pro Pro Ala Lys Arg Cys Arg
                245                 250                 255

Ser Ser Glu Glu Ser Thr Glu Lys Gly Pro Thr Gly Gln Pro Gln Ala
            260                 265                 270

Arg Val Gln Pro Gln Thr Gln Met Thr Ala Pro Lys Gln Thr Gln Thr
        275                 280                 285

Pro Asp Arg Leu Pro Glu Pro Pro Glu Val Gln Met Leu Pro Arg Ile
290                 295                 300

Gln Pro Gln Ala Leu Gln Ile Gln Thr Gln Pro Lys Leu Leu Arg Gln
305                 310                 315                 320

Ala Gln Thr Gln Thr Ser Pro Glu His Leu Ala Pro Gln Gln Asp Gln
                325                 330                 335

Val Pro Thr Gln Ala Gln Ser Gln Glu Gln Thr Ser Glu Lys Thr Gln
            340                 345                 350
```

Asp Gln Pro Gln Thr Trp Pro Gln Gly Ser Val Pro Pro Glu Gln
            355                 360                 365

Ala Ser Gly Pro Ala Cys Ala Thr Glu Pro Gln Leu Ser Ser His Ala
        370                 375                 380

Ala Glu Ala Gly Ser Asp Pro Asp Lys Ala Leu Pro Glu Pro Val Ser
385                 390                 395                 400

Ala Gln Ser Ser Glu Asp Arg Ser Arg Glu Ala Ser Ala Gly Gly Leu
                405                 410                 415

Asp Leu Gly Glu Cys Glu Lys Arg Ala Gly Glu Met Leu Gly Met Trp
            420                 425                 430

Gly Ala Gly Ser Ser Leu Lys Val Thr Ile Leu Gln Ser Ser Asn Ser
        435                 440                 445

Arg Ala Phe Asn Thr Thr Pro Leu Thr Ser Gly Pro Ser Pro Gly Asp
    450                 455                 460

Ser Thr Ser Ala Thr Pro Ala Ile Ala Ser Thr Pro Ser Lys Gln Ser
465                 470                 475                 480

Leu Gln Phe Phe Cys Tyr Ile Cys Lys Ala Ser Ser Ser Ser Gln Gln
                485                 490                 495

Glu Phe Gln Asp His Met Ser Glu Ala His Gln Gln Arg Leu Gly
            500                 505                 510

Glu Ile Gln His Ser Ser Gln Thr Cys Leu Leu Ser Leu Leu Pro Met
        515                 520                 525

Pro Arg Asp Ile Leu Glu Lys Glu Ala Glu Asp Pro Pro Lys Arg
    530                 535                 540

Trp Cys Asn Thr Cys Gln Val Tyr Tyr Val Gly Asp Leu Ile Gln His
545                 550                 555                 560

Arg Arg Thr Gln Glu His Lys Val Ala Lys Gln Ser Leu Arg Pro Phe
                565                 570                 575

Cys Thr Ile Cys Asn Arg Tyr Phe Lys Thr Pro Arg Lys Phe Val Glu
            580                 585                 590

His Val Lys Ser Gln Gly His Lys Asp Lys Ala Gln Glu Leu Lys Thr
        595                 600                 605

Leu Glu Lys Glu Thr Gly Ser Pro Asp Glu Asp His Phe Ile Thr Val
    610                 615                 620

Glu Ala Val Gly Cys Phe Glu Ser Gly Gln Glu Glu Asp Glu Asp
625                 630                 635                 640

Asp Glu Glu Glu Glu Glu Gly Glu Ile Glu Ala Glu Glu Glu Phe
                645                 650                 655

Cys Lys Gln Val Lys Pro Arg Glu Thr Ser Ser Glu Gln Gly Lys Gly
            660                 665                 670

Ser Glu Thr Tyr Asn Pro Asn Thr Ala Tyr Gly Glu Asp Phe Leu Val
        675                 680                 685

Pro Val Met Gly Tyr Val Cys Gln Ile Cys His Lys Phe Tyr Asp Ser
    690                 695                 700

Asn Ser Glu Leu Arg Leu Ser His Cys Lys
705                 710

<210> SEQ ID NO 29
<211> LENGTH: 898
<212> TYPE: PRT
<213> ORGANISM: Homo sapiens

<400> SEQUENCE: 29

Met Phe Ser Gln Gln Gln Gln Gln Leu Gln Gln Gln Gln Gln
1               5                   10                  15

```
Leu Gln Gln Leu Gln Gln Gln Leu Gln Gln Gln Leu Gln Gln
            20                  25                  30
Gln Gln Leu Leu Gln Leu Gln Leu Leu Gln Ser Pro Pro Gln
            35                  40                  45
Ala Pro Leu Pro Met Ala Val Ser Arg Gly Leu Pro Gln Gln Pro
50                  55                  60
Gln Gln Pro Leu Leu Asn Leu Gln Gly Thr Asn Ser Ala Ser Leu Leu
65                  70                  75                  80
Asn Gly Ser Met Leu Gln Arg Ala Leu Leu Leu Gln Gln Leu Gln Gly
                85                  90                  95
Leu Asp Gln Phe Ala Met Pro Pro Ala Thr Tyr Asp Thr Ala Gly Leu
            100                 105                 110
Thr Met Pro Thr Ala Thr Leu Gly Asn Leu Arg Gly Tyr Gly Met Ala
            115                 120                 125
Ser Pro Gly Leu Ala Ala Pro Ser Leu Thr Pro Pro Gln Leu Ala Thr
            130                 135                 140
Pro Asn Leu Gln Gln Phe Phe Pro Gln Ala Thr Arg Gln Ser Leu Leu
145                 150                 155                 160
Gly Pro Pro Pro Val Gly Val Pro Met Asn Pro Ser Gln Phe Asn Leu
                165                 170                 175
Ser Gly Arg Asn Pro Gln Lys Gln Ala Arg Thr Ser Ser Thr Thr
            180                 185                 190
Pro Asn Arg Lys Asp Ser Ser Ser Gln Thr Met Pro Val Glu Asp Lys
            195                 200                 205
Ser Asp Pro Pro Glu Gly Ser Glu Glu Ala Ala Glu Pro Arg Met Asp
210                 215                 220
Thr Pro Glu Asp Gln Asp Leu Pro Pro Cys Pro Glu Asp Ile Ala Lys
225                 230                 235                 240
Glu Lys Arg Thr Pro Ala Pro Glu Pro Glu Pro Cys Glu Ala Ser Glu
                245                 250                 255
Leu Pro Ala Lys Arg Leu Arg Ser Ser Glu Glu Pro Thr Glu Lys Glu
            260                 265                 270
Pro Pro Gly Gln Leu Gln Val Lys Ala Gln Pro Gln Ala Arg Met Thr
            275                 280                 285
Val Pro Lys Gln Thr Gln Thr Pro Asp Leu Leu Pro Glu Ala Leu Glu
            290                 295                 300
Ala Gln Val Leu Pro Arg Phe Gln Pro Arg Val Leu Gln Val Gln Ala
305                 310                 315                 320
Gln Val Gln Ser Gln Thr Gln Pro Arg Ile Pro Ser Thr Asp Thr Gln
                325                 330                 335
Val Gln Pro Lys Leu Gln Lys Gln Ala Gln Thr Gln Thr Ser Pro Glu
            340                 345                 350
His Leu Val Leu Gln Gln Lys Gln Val Gln Pro Gln Leu Gln Gln Glu
            355                 360                 365
Ala Glu Pro Gln Lys Gln Val Gln Pro Gln Val Gln Pro Gln Ala His
            370                 375                 380
Ser Gln Gly Pro Arg Gln Val Gln Leu Gln Gln Glu Ala Glu Pro Leu
385                 390                 395                 400
Lys Gln Val Gln Pro Gln Val Gln Pro Gln Ala His Ser Gln Pro Pro
                405                 410                 415
Arg Gln Val Gln Leu Gln Leu Gln Lys Gln Val Gln Thr Gln Thr Tyr
            420                 425                 430
```

```
Pro Gln Val His Thr Gln Ala Gln Pro Ser Val Gln Pro Gln Glu His
        435                 440                 445

Pro Pro Ala Gln Val Ser Val Gln Pro Glu Gln Thr His Glu Gln
450                 455                 460

Pro His Thr Gln Pro Gln Val Ser Leu Leu Ala Pro Glu Gln Thr Pro
465                 470                 475                 480

Val Val Val His Val Cys Gly Leu Glu Met Pro Pro Asp Ala Val Glu
            485                 490                 495

Ala Gly Gly Gly Met Glu Lys Thr Leu Pro Glu Pro Val Gly Thr Gln
            500                 505                 510

Val Ser Met Glu Glu Ile Gln Asn Glu Ser Ala Cys Gly Leu Asp Val
        515                 520                 525

Gly Glu Cys Glu Asn Arg Ala Arg Glu Met Pro Gly Val Trp Gly Ala
        530                 535                 540

Gly Gly Ser Leu Lys Val Thr Ile Leu Gln Ser Ser Asp Ser Arg Ala
545                 550                 555                 560

Phe Ser Thr Val Pro Leu Thr Pro Val Pro Arg Pro Ser Asp Ser Val
            565                 570                 575

Ser Ser Thr Pro Ala Ala Thr Ser Thr Pro Ser Lys Gln Ala Leu Gln
            580                 585                 590

Phe Phe Cys Tyr Ile Cys Lys Ala Ser Cys Ser Ser Gln Gln Glu Phe
            595                 600                 605

Gln Asp His Met Ser Glu Pro Gln His Gln Gln Arg Leu Gly Glu Ile
        610                 615                 620

Gln His Met Ser Gln Ala Cys Leu Leu Ser Leu Leu Pro Val Pro Arg
625                 630                 635                 640

Asp Val Leu Glu Thr Glu Asp Glu Glu Pro Pro Arg Arg Trp Cys
            645                 650                 655

Asn Thr Cys Gln Leu Tyr Tyr Met Gly Asp Leu Ile Gln His Arg Arg
            660                 665                 670

Thr Gln Asp His Lys Ile Ala Lys Gln Ser Leu Arg Pro Phe Cys Thr
        675                 680                 685

Val Cys Asn Arg Tyr Phe Lys Thr Pro Arg Lys Phe Val Glu His Val
690                 695                 700

Lys Ser Gln Gly His His Lys Asp Lys Ala Lys Glu Leu Lys Ser Leu Glu
705                 710                 715                 720

Lys Glu Ile Ala Gly Gln Asp Glu Asp His Phe Ile Thr Val Asp Ala
            725                 730                 735

Val Gly Cys Phe Glu Gly Asp Glu Glu Glu Asp Asp Glu Asp
            740                 745                 750

Glu Glu Glu Ile Glu Val Glu Glu Leu Cys Lys Gln Val Arg Ser
        755                 760                 765

Arg Asp Ile Ser Arg Glu Glu Trp Lys Gly Ser Glu Thr Tyr Ser Pro
770                 775                 780

Asn Thr Ala Tyr Gly Val Asp Phe Leu Val Pro Val Met Gly Tyr Ile
785                 790                 795                 800

Cys Arg Ile Cys His Lys Phe Tyr His Ser Asn Ser Gly Ala Gln Leu
            805                 810                 815

Ser His Cys Lys Ser Leu Gly His Phe Glu Asn Leu Gln Lys Tyr Lys
        820                 825                 830

Ala Ala Lys Asn Pro Ser Pro Thr Thr Arg Pro Val Ser Arg Arg Cys
        835                 840                 845

Ala Ile Asn Ala Arg Asn Ala Leu Thr Ala Leu Phe Thr Ser Ser Gly
```

```
                850                 855                 860
Arg Pro Pro Ser Gln Pro Asn Thr Gln Asp Lys Thr Pro Ser Lys Val
865                 870                 875                 880

Thr Ala Arg Pro Ser Gln Pro Pro Leu Pro Arg Arg Ser Thr Arg Leu
                885                 890                 895

Lys Thr

<210> SEQ ID NO 30
<211> LENGTH: 898
<212> TYPE: PRT
<213> ORGANISM: Homo sapiens

<400> SEQUENCE: 30

Met Phe Ser Gln Gln Gln Gln Gln Leu Gln Gln Gln Gln Gln Gln Gln
1               5                   10                  15

Leu Gln Gln Leu Gln Gln Gln Leu Gln Gln Gln Leu Gln Gln Gln Gln
                20                  25                  30

Gln Gln Leu Leu Gln Leu Gln Leu Leu Gln Ser Pro Pro Gln
            35                  40                  45

Ala Pro Leu Pro Met Ala Val Ser Arg Gly Leu Pro Pro Gln Gln Pro
    50                  55                  60

Gln Gln Pro Leu Leu Asn Leu Gln Gly Thr Asn Ser Ala Ser Leu Leu
65                  70                  75                  80

Asn Gly Ser Met Leu Gln Arg Ala Leu Leu Leu Gln Leu Gln Gly
                85                  90                  95

Leu Asp Gln Phe Ala Met Pro Pro Ala Thr Tyr Asp Thr Ala Gly Leu
                100                 105                 110

Thr Met Pro Thr Ala Thr Leu Gly Asn Leu Arg Gly Tyr Gly Met Ala
                115                 120                 125

Ser Pro Gly Leu Ala Ala Pro Ser Leu Thr Pro Pro Gln Leu Ala Thr
            130                 135                 140

Pro Asn Leu Gln Gln Phe Phe Pro Gln Ala Thr Arg Gln Ser Leu Leu
145                 150                 155                 160

Gly Pro Pro Val Gly Val Pro Met Asn Pro Ser Gln Phe Asn Leu
                165                 170                 175

Ser Gly Arg Asn Pro Gln Lys Gln Ala Arg Thr Ser Ser Ser Thr Thr
                180                 185                 190

Pro Asn Arg Lys Asp Ser Ser Ser Gln Thr Met Pro Val Glu Asp Lys
            195                 200                 205

Ser Asp Pro Pro Glu Gly Ser Glu Glu Ala Ala Glu Pro Arg Met Asp
    210                 215                 220

Thr Pro Glu Asp Gln Asp Leu Leu Pro Cys Pro Glu Asp Ile Ala Lys
225                 230                 235                 240

Glu Lys Arg Thr Pro Ala Pro Glu Pro Glu Pro Cys Glu Ala Ser Glu
                245                 250                 255

Leu Pro Ala Lys Arg Leu Arg Ser Ser Glu Glu Pro Thr Glu Lys Glu
                260                 265                 270

Pro Pro Gly Gln Leu Gln Val Lys Ala Gln Pro Gln Ala Arg Met Thr
            275                 280                 285

Val Pro Lys Gln Thr Gln Thr Pro Asp Leu Leu Pro Glu Ala Leu Glu
    290                 295                 300

Ala Gln Val Leu Pro Arg Phe Gln Pro Arg Val Leu Gln Val Gln Ala
305                 310                 315                 320

Gln Val Gln Ser Gln Thr Gln Pro Arg Ile Pro Ser Thr Asp Thr Gln
```

```
                325                 330                 335
Val Gln Pro Lys Leu Gln Lys Gln Ala Gln Thr Gln Thr Ser Pro Glu
            340                 345                 350
His Leu Val Leu Gln Gln Lys Gln Val Gln Pro Gln Leu Gln Gln Glu
            355                 360                 365
Ala Glu Pro Gln Lys Gln Val Gln Pro Gln Val Gln Pro Gln Ala His
            370                 375                 380
Ser Gln Gly Pro Arg Gln Val Gln Leu Gln Gln Ala Glu Pro Leu
385                 390                 395                 400
Lys Gln Val Gln Pro Gln Val Gln Pro Gln Ala His Ser Gln Pro Pro
                405                 410                 415
Arg Gln Val Gln Leu Gln Leu Gln Lys Gln Val Gln Thr Gln Thr Tyr
            420                 425                 430
Pro Gln Val His Thr Gln Ala Gln Pro Ser Val Gln Pro Gln Glu His
            435                 440                 445
Pro Pro Ala Gln Val Ser Gln Pro Pro Glu Gln Thr His Glu Gln
            450                 455                 460
Pro His Thr Gln Pro Gln Val Ser Leu Leu Ala Pro Glu Gln Thr Pro
465                 470                 475                 480
Val Val Val His Val Cys Gly Leu Glu Met Pro Pro Asp Ala Val Glu
                485                 490                 495
Ala Gly Gly Gly Met Glu Lys Thr Leu Pro Glu Pro Val Gly Thr Gln
                500                 505                 510
Val Ser Met Glu Glu Ile Gln Asn Glu Ser Ala Cys Gly Leu Asp Val
            515                 520                 525
Gly Glu Cys Glu Asn Arg Ala Arg Glu Met Pro Gly Val Trp Gly Ala
            530                 535                 540
Gly Gly Ser Leu Lys Val Thr Ile Leu Gln Gly Ser Asp Ser Arg Ala
545                 550                 555                 560
Phe Ser Thr Val Pro Leu Thr Pro Val Pro Arg Pro Ser Asp Ser Val
                565                 570                 575
Ser Ser Thr Pro Ala Ala Thr Ser Thr Pro Ser Lys Gln Ala Leu Gln
            580                 585                 590
Phe Phe Cys Tyr Ile Cys Lys Ala Ser Cys Ser Ser Gln Gln Glu Phe
            595                 600                 605
Gln Asp His Met Ser Glu Pro Gln His Gln Gln Arg Leu Gly Glu Ile
            610                 615                 620
Gln His Met Ser Gln Ala Cys Leu Leu Ser Leu Pro Val Pro Arg
625                 630                 635                 640
Asp Val Leu Glu Thr Glu Asp Glu Glu Pro Pro Pro Arg Arg Trp Cys
                645                 650                 655
Asn Thr Cys Gln Leu Tyr Tyr Met Gly Asp Leu Ile Gln His Arg Arg
            660                 665                 670
Thr Gln Asp His Lys Ile Ala Lys Gln Ser Leu Arg Pro Phe Cys Thr
            675                 680                 685
Val Cys Asn Arg Tyr Phe Lys Thr Pro Arg Lys Phe Val Glu His Val
            690                 695                 700
Lys Ser Gln Gly His Lys Asp Lys Ala Lys Glu Leu Lys Ser Leu Glu
705                 710                 715                 720
Lys Glu Ile Ala Gly Gln Asp Glu Asp His Phe Ile Thr Val Asp Ala
                725                 730                 735
Val Gly Cys Phe Glu Gly Asp Glu Glu Glu Glu Asp Asp Glu Asp
                740                 745                 750
```

```
Glu Glu Glu Ile Glu Val Glu Glu Leu Cys Lys Gln Val Arg Ser
            755                 760                 765
Arg Asp Ile Ser Arg Glu Glu Trp Lys Gly Ser Glu Thr Tyr Ser Pro
        770                 775                 780
Asn Thr Ala Tyr Gly Val Asp Phe Leu Val Pro Val Met Gly Tyr Ile
785                 790                 795                 800
Cys Arg Ile Cys His Lys Phe Tyr His Ser Asn Ser Gly Ala Gln Leu
            805                 810                 815
Ser His Cys Lys Ser Leu Gly His Phe Glu Asn Leu Gln Lys Tyr Lys
        820                 825                 830
Ala Ala Lys Asn Pro Ser Pro Thr Thr Arg Pro Val Ser Arg Arg Cys
            835                 840                 845
Ala Ile Asn Ala Arg Asn Ala Leu Thr Ala Leu Phe Thr Ser Ser Gly
        850                 855                 860
Arg Pro Pro Ser Gln Pro Asn Thr Gln Asp Lys Thr Pro Ser Lys Val
865                 870                 875                 880
Thr Ala Arg Pro Ser Gln Pro Leu Pro Arg Arg Ser Thr Arg Leu
            885                 890                 895
Lys Thr

<210> SEQ ID NO 31
<211> LENGTH: 896
<212> TYPE: PRT
<213> ORGANISM: Homo sapiens

<400> SEQUENCE: 31

Phe Ser Gln Gln Gln Gln Leu Gln Gln Gln Gln Gln Gln Gln Leu Gln
1               5                   10                  15
Gln Leu Gln Gln Gln Gln Leu Gln Gln Gln Leu Gln Gln Gln Gln
            20                  25                  30
Ser Leu Gln Leu Gln Leu Leu Gln Gln Ser Pro Pro Gln Ala Pro
        35                  40                  45
Leu Pro Met Ala Val Ser Arg Gly Leu Pro Pro Gln Gln Pro Gln Gln
50                  55                  60
Pro Leu Asn Leu Gln Gly Thr Asn Ser Ala Ser Leu Leu Asn Gly
65                  70                  75                  80
Ser Met Leu Gln Arg Ala Leu Leu Leu Gln Gln Leu Gln Gly Leu Asp
            85                  90                  95
Gln Phe Ala Met Pro Pro Ala Thr Tyr Asp Thr Ala Gly Leu Thr Met
            100                 105                 110
Pro Thr Ala Thr Leu Gly Asn Leu Arg Gly Tyr Gly Met Ala Ser Pro
        115                 120                 125
Gly Leu Ala Ala Pro Ser Leu Thr Pro Pro Gln Leu Ala Thr Pro Asn
    130                 135                 140
Leu Gln Gln Phe Phe Pro Gln Ala Thr Arg Gln Ser Leu Leu Gly Pro
145                 150                 155                 160
Pro Pro Val Gly Val Pro Met Asn Pro Ser Gln Phe Asn Leu Ser Gly
                165                 170                 175
Arg Asn Pro Gln Lys Gln Ala Arg Thr Ser Ser Ser Thr Pro Asn
            180                 185                 190
Arg Lys Asp Ser Ser Ser Gln Thr Met Pro Val Glu Asp Lys Ser Asp
        195                 200                 205
Pro Pro Glu Gly Ser Glu Glu Ala Ala Glu Pro Arg Met Asp Thr Pro
    210                 215                 220
```

-continued

```
Glu Asp Gln Asp Leu Pro Pro Cys Pro Glu Asp Ile Ala Lys Glu Lys
225                 230                 235                 240

Arg Thr Pro Ala Pro Glu Pro Glu Pro Cys Glu Ala Ser Glu Leu Pro
                245                 250                 255

Ala Lys Arg Leu Arg Ser Ser Glu Glu Pro Thr Glu Lys Glu Pro Pro
            260                 265                 270

Gly Gln Leu Gln Val Lys Ala Gln Pro Gln Ala Arg Met Thr Val Pro
                275                 280                 285

Lys Gln Thr Gln Thr Pro Asp Leu Leu Pro Glu Ala Leu Glu Ala Gln
290                 295                 300

Val Leu Pro Arg Phe Gln Pro Arg Val Leu Gln Val Gln Ala Gln Val
305                 310                 315                 320

Gln Ser Gln Thr Gln Pro Arg Ile Pro Ser Thr Asp Thr Gln Val Gln
                325                 330                 335

Pro Lys Leu Gln Lys Gln Ala Gln Thr Gln Thr Ser Pro Glu His Leu
                340                 345                 350

Val Leu Gln Gln Lys Gln Val Gln Pro Gln Leu Gln Gln Glu Ala Glu
                355                 360                 365

Pro Gln Lys Gln Val Gln Pro Gln Val Gln Pro Gln Ala His Ser Gln
                370                 375                 380

Gly Pro Arg Gln Val Gln Leu Gln Gln Glu Ala Glu Pro Leu Lys Gln
385                 390                 395                 400

Val Gln Pro Gln Val Gln Pro Gln Ala His Ser Gln Pro Pro Arg Gln
                405                 410                 415

Val Gln Leu Gln Leu Gln Lys Gln Val Gln Thr Gln Thr Tyr Pro Gln
                420                 425                 430

Val His Thr Gln Ala Gln Pro Ser Val Gln Pro Gln Glu His Pro Pro
                435                 440                 445

Ala Gln Val Ser Val Gln Pro Pro Glu Gln Thr His Glu Gln Pro His
450                 455                 460

Thr Gln Pro Gln Val Ser Leu Leu Ala Pro Glu Gln Thr Pro Val Val
465                 470                 475                 480

Val His Val Cys Gly Leu Glu Met Pro Pro Asp Ala Val Glu Ala Gly
                485                 490                 495

Gly Gly Met Glu Lys Thr Leu Pro Glu Pro Val Gly Thr Gln Val Ser
                500                 505                 510

Met Glu Glu Ile Gln Asn Glu Ser Ala Cys Gly Leu Asp Val Gly Glu
                515                 520                 525

Cys Glu Asn Arg Ala Arg Glu Met Pro Gly Val Trp Gly Ala Gly Gly
                530                 535                 540

Ser Leu Lys Val Thr Ile Leu Gln Ser Ser Asp Ser Arg Ala Phe Ser
545                 550                 555                 560

Thr Val Pro Leu Thr Leu Val Pro Arg Pro Ser Asp Ser Val Ser Ser
                565                 570                 575

Thr Pro Ala Ala Thr Ser Thr Pro Ser Lys Gln Ala Leu Gln Phe Phe
                580                 585                 590

Cys Tyr Ile Cys Lys Ala Ser Cys Ser Ser Gln Gln Glu Phe Gln Asp
                595                 600                 605

His Met Ser Glu Pro Gln His Gln Gln Arg Leu Gly Glu Ile Gln His
                610                 615                 620

Met Ser Gln Ala Cys Leu Leu Pro Leu Leu Pro Val Pro Arg Asp Val
625                 630                 635                 640
```

```
Leu Glu Thr Glu Asp Glu Pro Pro Arg Arg Trp Cys Asn Thr
            645                 650                 655

Cys Gln Leu Tyr Tyr Met Gly Asp Leu Ile Gln His Arg Thr Gln
            660                 665                 670

Asp His Lys Ile Ala Lys Gln Ser Leu Arg Pro Phe Cys Thr Val Cys
            675                 680                 685

Asn Arg Tyr Phe Lys Thr Pro Arg Lys Phe Val Glu His Val Lys Ser
            690                 695                 700

Gln Gly His Lys Asp Lys Ala Lys Glu Leu Lys Ser Leu Glu Lys Glu
705                 710                 715                 720

Ile Ala Gly Gln Asp Glu His Phe Ile Thr Val Gly Ala Val Gly
            725                 730                 735

Cys Phe Glu Gly Asp Glu Glu Glu Asp Asp Glu Asp Glu Glu
            740                 745                 750

Glu Ile Glu Val Glu Glu Glu Leu Cys Lys Gln Val Arg Ser Arg Asp
            755                 760                 765

Ile Ser Arg Glu Glu Trp Lys Gly Ser Glu Thr Tyr Ser Pro Asn Thr
770                 775                 780

Ala Tyr Gly Val Asp Phe Leu Val Pro Val Met Gly Tyr Ile Cys Arg
785                 790                 795                 800

Ile Cys His Lys Phe Tyr His Ser Asn Ser Gly Ala Gln Leu Ser His
            805                 810                 815

Cys Lys Ser Leu Gly His Phe Glu Asn Leu Gln Lys Tyr Lys Ala Ala
            820                 825                 830

Lys Asn Pro Ser Pro Thr Thr Arg Pro Val Ser Arg Cys Ala Ile
            835                 840                 845

Asn Ala Arg Asn Ala Leu Thr Ala Leu Phe Thr Ser Ser Gly Arg Pro
850                 855                 860

Pro Ser Gln Pro Asn Thr Gln Asp Lys Thr Pro Ser Lys Val Thr Ala
865                 870                 875                 880

Arg Pro Ser Gln Pro Pro Leu Pro Arg Arg Ser Thr Arg Leu Lys Thr
            885                 890                 895

<210> SEQ ID NO 32
<211> LENGTH: 842
<212> TYPE: PRT
<213> ORGANISM: Homo sapiens

<400> SEQUENCE: 32

Met Phe Ser Gln Gln Gln Gln Gln Leu Gln Gln Gln Gln Gln
1               5                   10                  15

Leu Gln Gln Leu Gln Gln Gln Leu Gln Gln Gln Leu Gln Gln
                20                  25                  30

Gln Gln Leu Leu Gln Leu Gln Gln Leu Leu Gln Ser Pro Pro Gln
                35                  40                  45

Ala Pro Leu Pro Met Ala Val Ser Arg Gly Leu Pro Gln Gln Pro
            50                  55                  60

Gln Gln Pro Leu Asn Leu Gln Gly Thr Asn Ser Ala Ser Leu Leu
65                  70                  75                  80

Asn Gly Ser Met Leu Gln Arg Ala Leu Leu Leu Gln Leu Gln Gly
                85                  90                  95

Leu Asp Gln Phe Val Met Pro Pro Ala Thr Tyr Asp Thr Ala Gly Leu
                100                 105                 110

Thr Met Pro Thr Ala Thr Leu Gly Asn Leu Arg Gly Tyr Gly Met Ala
                115                 120                 125
```

```
Ser Pro Gly Leu Ala Ala Pro Ser Leu Thr Pro Gln Leu Ala Thr
    130                 135                 140

Pro Asn Leu Gln Gln Phe Phe Pro Gln Ala Thr Arg Gln Ser Leu Leu
145                 150                 155                 160

Gly Pro Pro Pro Val Gly Val Pro Met Asn Pro Ser Gln Phe Asn Leu
                165                 170                 175

Ser Gly Arg Asn Pro Gln Lys Gln Ala Arg Thr Ser Ser Thr Thr
                180                 185                 190

Pro Asn Arg Lys Asp Ser Ser Gln Thr Met Pro Val Glu Asp Lys
                195                 200                 205

Ser Asp Pro Pro Glu Gly Ser Glu Ala Ala Glu Pro Arg Met Asp
    210                 215                 220

Thr Pro Glu Asp Gln Asp Leu Pro Pro Cys Pro Glu Asp Ile Ala Lys
225                 230                 235                 240

Glu Lys Arg Thr Pro Ala Pro Glu Pro Glu Pro Cys Glu Ala Ser Glu
                245                 250                 255

Leu Pro Ala Lys Arg Leu Arg Ser Ser Glu Glu Pro Thr Glu Lys Glu
                260                 265                 270

Pro Pro Gly Gln Leu Gln Val Lys Ala Gln Pro Gln Ala Arg Met Thr
    275                 280                 285

Val Pro Lys Gln Thr Gln Thr Pro Asp Leu Leu Pro Glu Ala Leu Glu
    290                 295                 300

Ala Gln Val Leu Pro Arg Phe Gln Pro Arg Val Leu Gln Val Gln Ala
305                 310                 315                 320

Gln Val Gln Ser Gln Thr Gln Pro Arg Ile Pro Ser Thr Asp Thr Gln
                325                 330                 335

Val Gln Pro Lys Leu Gln Lys Gln Ala Gln Thr Gln Thr Ser Pro Glu
                340                 345                 350

His Leu Val Leu Gln Gln Lys Gln Val Gln Pro Gln Leu Gln Gln Glu
    355                 360                 365

Ala Glu Pro Gln Lys Gln Val Gln Pro Gln Val His Thr Gln Ala Gln
    370                 375                 380

Pro Ser Val Gln Pro Gln Glu His Pro Pro Ala Gln Val Ser Val Gln
385                 390                 395                 400

Pro Pro Glu Gln Thr His Glu Gln Pro His Thr Gln Pro Gln Val Ser
                405                 410                 415

Leu Leu Ala Pro Glu Gln Thr Pro Val Val His Val Cys Gly Leu
                420                 425                 430

Glu Met Pro Pro Asp Ala Val Glu Ala Gly Gly Met Glu Lys Thr
    435                 440                 445

Leu Pro Glu Pro Val Gly Thr Gln Val Ser Met Glu Glu Ile Gln Asn
    450                 455                 460

Glu Ser Ala Cys Gly Leu Asp Val Gly Glu Cys Glu Asn Arg Ala Arg
465                 470                 475                 480

Glu Met Pro Gly Val Trp Gly Ala Gly Gly Ser Leu Lys Val Thr Ile
                485                 490                 495

Leu Gln Ser Ser Asp Ser Arg Ala Phe Ser Thr Val Pro Leu Thr Pro
                500                 505                 510

Val Pro Arg Pro Ser Asp Ser Val Ser Ser Thr Pro Ala Ala Thr Ser
    515                 520                 525

Thr Pro Ser Lys Gln Ala Leu Gln Phe Phe Cys Tyr Ile Cys Lys Ala
    530                 535                 540
```

-continued

```
Ser Cys Ser Ser Gln Gln Glu Phe Gln Asp His Met Ser Glu Pro Gln
545                 550                 555                 560

His Gln Gln Arg Leu Gly Glu Ile Gln His Met Ser Gln Ala Cys Leu
                565                 570                 575

Leu Ser Leu Leu Pro Met Pro Arg Asp Val Leu Glu Thr Glu Asp Glu
            580                 585                 590

Glu Pro Pro Arg Arg Trp Cys Asn Thr Cys Gln Leu Tyr Tyr Met
        595                 600                 605

Gly Asp Leu Ile Gln His Arg Arg Thr Gln Asp His Lys Val Ala Lys
610                 615                 620

Gln Pro Leu Arg Pro Phe Cys Thr Val Cys Asn Arg Tyr Phe Lys Thr
625                 630                 635                 640

Pro Arg Lys Phe Val Glu His Val Lys Ser Gln Gly His Lys Asp Lys
                645                 650                 655

Ala Lys Glu Leu Lys Ser Leu Glu Lys Glu Ile Ala Gly Gln Asp Glu
            660                 665                 670

Asp His Phe Ile Thr Val Asp Ala Val Gly Cys Phe Glu Gly Asp Glu
        675                 680                 685

Glu Glu Glu Glu Asp Asp Glu Asp Glu Glu Ile Lys Val Glu Glu
690                 695                 700

Glu Leu Cys Lys Gln Val Arg Ser Arg Asp Ile Ser Arg Glu Glu Trp
705                 710                 715                 720

Lys Gly Ser Glu Thr Tyr Ser Pro Asn Thr Ala Tyr Gly Val Asp Phe
                725                 730                 735

Leu Val Pro Val Met Gly Tyr Ile Cys Arg Ile Cys His Lys Phe Tyr
            740                 745                 750

His Ser Asn Ser Gly Ala Gln Leu Ser His Cys Lys Ser Leu Gly His
        755                 760                 765

Phe Glu Asn Leu Gln Lys Tyr Lys Ala Ala Lys Asn Pro Ser Pro Thr
770                 775                 780

Thr Arg Pro Val Ser Arg Arg Cys Ala Ile Asn Ala Arg Asn Ala Leu
785                 790                 795                 800

Thr Ala Leu Phe Thr Ser Ser Gly Arg Pro Pro Ser Gln Pro Asn Thr
                805                 810                 815

Gln Asp Lys Thr Pro Ser Lys Val Thr Ala Arg Pro Ser Gln Pro Pro
            820                 825                 830

Leu Pro Arg Arg Ser Thr Arg Leu Lys Thr
        835                 840

<210> SEQ ID NO 33
<211> LENGTH: 837
<212> TYPE: PRT
<213> ORGANISM: Homo sapiens

<400> SEQUENCE: 33

Met Phe Ser Gln Gln Gln Gln Gln Leu Gln Gln Gln Gln Gln Gln Ala
1               5                   10                  15

Pro Leu Pro Met Ala Val Ser Arg Gly Leu Pro Pro Gln Gln Pro Gln
                20                  25                  30

Gln Pro Leu Leu Asn Leu Gln Gly Thr Asn Ser Ala Ser Leu Leu Asn
            35                  40                  45

Gly Ser Met Leu Gln Arg Ala Leu Leu Leu Gln Leu Gln Gly Leu
        50                  55                  60

Asp Gln Phe Ala Met Pro Pro Thr Tyr Asp Thr Ala Gly Leu Thr
65                  70                  75                  80
```

-continued

```
Met Pro Thr Ala Thr Leu Gly Asn Leu Arg Gly Tyr Gly Met Ala Ser
                 85                  90                  95

Pro Gly Leu Ala Ala Pro Ser Leu Thr Pro Pro Gln Leu Ala Thr Pro
            100                 105                 110

Asn Leu Gln Gln Phe Phe Pro Gln Ala Thr Arg Gln Ser Leu Leu Gly
        115                 120                 125

Pro Pro Pro Val Gly Val Pro Met Asn Pro Ser Gln Phe Asn Leu Ser
    130                 135                 140

Gly Arg Asn Pro Gln Lys Gln Ala Arg Thr Ser Ser Ser Thr Thr Pro
145                 150                 155                 160

Asn Arg Lys Asp Ser Ser Gln Thr Met Pro Val Glu Asp Lys Ser
                165                 170                 175

Asp Pro Pro Glu Gly Ser Glu Glu Ala Glu Pro Arg Met Asp Thr
            180                 185                 190

Pro Glu Asp Gln Asp Leu Pro Pro Cys Pro Glu Asp Ile Ala Lys Glu
        195                 200                 205

Lys Arg Thr Pro Ala Pro Glu Pro Glu Pro Cys Glu Ala Ser Glu Leu
    210                 215                 220

Pro Ala Lys Arg Leu Arg Ser Ser Glu Glu Pro Thr Glu Lys Glu Pro
225                 230                 235                 240

Pro Gly Gln Leu Gln Val Lys Ala Gln Pro Gln Ala Arg Met Thr Val
                245                 250                 255

Pro Lys Gln Thr Gln Thr Pro Asp Leu Leu Pro Glu Ala Leu Glu Ala
            260                 265                 270

Gln Val Leu Pro Arg Phe Gln Pro Arg Val Leu Gln Val Gln Ala Gln
        275                 280                 285

Val Gln Ser Gln Thr Gln Pro Arg Ile Pro Ser Thr Asp Thr Gln Val
    290                 295                 300

Gln Pro Lys Leu Gln Lys Gln Ala Gln Thr Gln Thr Ser Pro Glu His
305                 310                 315                 320

Leu Val Leu Gln Gln Lys Gln Val Gln Pro Gln Leu Gln Gln Glu Ala
                325                 330                 335

Glu Pro Gln Lys Gln Val Gln Pro Gln Val Gln Pro Gln Ala His Ser
            340                 345                 350

Gln Gly Pro Arg Gln Val Gln Leu Gln Gln Glu Ala Glu Pro Leu Lys
        355                 360                 365

Gln Val Gln Pro Gln Val His Thr Gln Ala Gln Pro Ser Val Gln Pro
    370                 375                 380

Gln Glu His Pro Pro Ala Gln Val Ser Val Gln Pro Pro Glu Gln Thr
385                 390                 395                 400

His Glu Gln Pro His Thr Gln Pro Gln Val Ser Leu Leu Ala Pro Glu
                405                 410                 415

Gln Thr Pro Val Val His Val Cys Gly Leu Glu Met Pro Pro Asp
            420                 425                 430

Ala Val Glu Ala Gly Gly Met Glu Lys Thr Leu Pro Glu Pro Val
        435                 440                 445

Gly Thr Gln Val Ser Met Glu Glu Ile Gln Asn Glu Ser Ala Cys Gly
    450                 455                 460

Leu Asp Val Gly Glu Cys Glu Asn Arg Ala Arg Glu Met Pro Gly Val
465                 470                 475                 480

Trp Gly Ala Gly Gly Ser Leu Lys Val Thr Ile Leu Gln Ser Ser Asp
                485                 490                 495
```

```
Ser Arg Ala Phe Ser Thr Val Pro Leu Thr Pro Val Pro Arg Pro Ser
            500                 505                 510

Asp Ser Val Ser Ser Thr Pro Ala Ala Thr Ser Thr Pro Ser Lys Gln
            515                 520                 525

Ala Leu Gln Phe Phe Cys Tyr Ile Cys Lys Ala Ser Cys Ser Ser Gln
        530                 535                 540

Gln Glu Phe Gln Asp His Met Ser Glu Pro Gln His Gln Gln Arg Leu
545                 550                 555                 560

Gly Glu Ile Gln His Met Ser Gln Ala Cys Leu Leu Ser Leu Leu Pro
                565                 570                 575

Val Pro Arg Asp Val Leu Glu Thr Glu Asp Glu Pro Pro Pro Arg
            580                 585                 590

Arg Trp Cys Asn Thr Cys Gln Leu Tyr Tyr Met Gly Asp Leu Ile Gln
            595                 600                 605

His Arg Arg Thr Gln Asp His Lys Ile Ala Lys Gln Ser Leu Arg Pro
    610                 615                 620

Phe Cys Thr Val Cys Asn Arg Tyr Phe Lys Thr Pro Arg Lys Phe Val
625                 630                 635                 640

Glu His Val Lys Ser Gln Gly His Lys Asp Lys Ala Lys Glu Leu Lys
                645                 650                 655

Ser Leu Glu Lys Glu Ile Ala Gly Gln Asp Glu Asp His Phe Ile Thr
            660                 665                 670

Val Asp Ala Val Gly Cys Phe Glu Gly Asp Glu Glu Glu Glu Asp
            675                 680                 685

Asp Glu Asp Glu Glu Ile Glu Val Glu Glu Glu Leu Cys Lys Gln
            690                 695                 700

Val Arg Ser Arg Asp Ile Ser Arg Glu Glu Trp Lys Gly Ser Glu Thr
705                 710                 715                 720

Tyr Ser Pro Asn Thr Ala Tyr Gly Val Asp Phe Leu Val Pro Val Met
                725                 730                 735

Gly Tyr Ile Cys Arg Ile Cys His Lys Phe Tyr His Ser Asn Ser Gly
            740                 745                 750

Ala Gln Leu Ser His Cys Lys Ser Leu Gly His Phe Glu Asn Leu Gln
        755                 760                 765

Lys Tyr Lys Ala Ala Lys Asn Pro Ser Pro Thr Thr Arg Pro Val Ser
    770                 775                 780

Arg Arg Cys Ala Ile Asn Ala Arg Asn Ala Leu Thr Ala Leu Phe Thr
785                 790                 795                 800

Ser Ser Gly Arg Pro Pro Ser Gln Pro Asn Thr Gln Asp Lys Thr Pro
                805                 810                 815

Ser Lys Val Thr Ala Arg Pro Ser Gln Pro Pro Leu Pro Arg Arg Ser
            820                 825                 830

Thr Arg Leu Lys Thr
        835

<210> SEQ ID NO 34
<211> LENGTH: 818
<212> TYPE: PRT
<213> ORGANISM: Homo sapiens

<400> SEQUENCE: 34

Met Phe Ser Gln Gln Gln Gln Gln Leu Gln Gln Gln Gln Gln Gln Gln
1               5                   10                  15

Leu Gln Gln Leu Gln Gln Gln Gln Leu Gln Gln Gln Gln Leu Gln Gln
                20                  25                  30
```

-continued

```
Gln Gln Leu Leu Gln Leu Gln Gln Leu Leu Gln Ser Pro Pro Gln
         35                  40                  45

Ala Pro Leu Pro Met Ala Val Ser Arg Gly Leu Pro Pro Gln Gln Pro
 50                  55                  60

Gln Gln Pro Leu Leu Asn Leu Gln Gly Thr Asn Ser Ala Ser Leu Leu
65                  70                  75                  80

Asn Gly Ser Met Leu Gln Arg Ala Leu Leu Gln Gln Leu Gln Gly
             85                  90                  95

Asn Leu Arg Gly Tyr Gly Met Ala Ser Pro Gly Leu Ala Ala Pro Ser
             100                 105                 110

Leu Thr Pro Pro Gln Leu Ala Thr Pro Asn Leu Gln Gln Phe Phe Pro
             115                 120                 125

Gln Ala Thr Arg Gln Ser Leu Leu Gly Pro Pro Val Gly Val Pro
         130                 135                 140

Met Asn Pro Ser Gln Phe Asn Leu Ser Gly Arg Asn Pro Gln Lys Gln
145                 150                 155                 160

Ala Arg Thr Ser Ser Ser Thr Thr Pro Asn Arg Lys Asp Ser Ser Ser
             165                 170                 175

Gln Thr Met Pro Val Glu Asp Lys Ser Asp Pro Pro Glu Gly Ser Glu
             180                 185                 190

Glu Ala Ala Glu Pro Arg Met Asp Thr Pro Glu Asp Gln Asp Leu Pro
         195                 200                 205

Pro Cys Pro Glu Asp Ile Ala Lys Glu Lys Arg Thr Pro Ala Pro Glu
         210                 215                 220

Pro Glu Pro Cys Glu Ala Ser Glu Leu Pro Ala Lys Arg Leu Arg Ser
225                 230                 235                 240

Ser Glu Glu Pro Thr Glu Lys Glu Pro Pro Gly Gln Leu Gln Val Lys
             245                 250                 255

Ala Gln Pro Gln Ala Arg Met Thr Val Pro Lys Gln Thr Gln Thr Pro
         260                 265                 270

Asp Leu Leu Pro Glu Ala Leu Glu Ala Gln Val Leu Pro Arg Phe Gln
         275                 280                 285

Pro Arg Val Leu Gln Val Gln Ala Gln Val Gln Ser Gln Thr Gln Pro
         290                 295                 300

Arg Ile Pro Ser Thr Asp Thr Gln Val Gln Pro Lys Leu Gln Lys Gln
305                 310                 315                 320

Ala Gln Thr Gln Thr Ser Pro Glu His Leu Val Leu Gln Gln Lys Gln
             325                 330                 335

Val Gln Pro Gln Leu Gln Gln Glu Ala Glu Pro Gln Lys Gln Val Gln
         340                 345                 350

Pro Gln Val His Thr Gln Ala Gln Pro Ser Val Gln Pro Gln Glu His
         355                 360                 365

Pro Pro Ala Gln Val Ser Val Gln Pro Glu Gln Thr His Glu Gln
         370                 375                 380

Pro His Thr Gln Pro Gln Val Ser Leu Leu Ala Pro Glu Gln Thr Pro
385                 390                 395                 400

Val Val Val His Val Cys Gly Leu Glu Met Pro Pro Asp Ala Val Glu
             405                 410                 415

Ala Gly Gly Gly Met Glu Lys Thr Leu Pro Glu Pro Val Gly Thr Gln
             420                 425                 430

Val Ser Met Glu Glu Ile Gln Asn Glu Ser Ala Cys Gly Leu Asp Val
             435                 440                 445
```

```
Gly Glu Cys Glu Asn Arg Ala Arg Glu Met Pro Gly Val Trp Gly Ala
    450                 455                 460

Gly Gly Ser Leu Lys Val Thr Ile Leu Gln Ser Ser Asp Ser Arg Ala
465                 470                 475                 480

Phe Ser Thr Val Pro Leu Thr Pro Val Pro Arg Pro Ser Asp Ser Val
                485                 490                 495

Ser Ser Thr Pro Ala Ala Thr Ser Thr Pro Ser Lys Gln Ala Leu Gln
            500                 505                 510

Phe Phe Cys Tyr Ile Cys Lys Ala Ser Cys Ser Ser Gln Gln Glu Phe
        515                 520                 525

Gln Asp His Met Ser Glu Pro Gln His Gln Gln Arg Leu Gly Glu Ile
    530                 535                 540

Gln His Met Ser Gln Ala Cys Leu Leu Ser Leu Leu Pro Val Pro Arg
545                 550                 555                 560

Asp Val Leu Glu Thr Glu Asp Glu Glu Pro Pro Arg Arg Trp Cys
                565                 570                 575

Asn Thr Cys Gln Leu Tyr Tyr Met Gly Asp Leu Ile Gln His Arg Arg
            580                 585                 590

Thr Gln Asp His Lys Ile Ala Lys Gln Ser Leu Arg Pro Phe Cys Thr
    595                 600                 605

Val Cys Asn Arg Tyr Phe Lys Thr Pro Arg Lys Phe Val Glu His Val
610                 615                 620

Lys Ser Gln Gly His His Lys Asp Lys Ala Lys Glu Leu Lys Ser Leu Glu
625                 630                 635                 640

Lys Glu Ile Ala Gly Gln Asp Glu Asp His Phe Ile Thr Val Asp Ala
                645                 650                 655

Val Gly Cys Phe Glu Gly Asp Glu Glu Glu Glu Asp Asp Glu Asp
            660                 665                 670

Glu Glu Glu Ile Glu Val Glu Glu Glu Leu Cys Lys Gln Val Arg Ser
    675                 680                 685

Arg Asp Ile Ser Arg Glu Glu Trp Lys Gly Ser Glu Thr Tyr Ser Pro
    690                 695                 700

Asn Thr Ala Tyr Gly Val Asp Phe Leu Val Pro Val Met Gly Tyr Ile
705                 710                 715                 720

Cys Arg Ile Cys His Lys Phe Tyr His Ser Asn Ser Gly Ala Gln Leu
                725                 730                 735

Ser His Cys Lys Ser Leu Gly His Phe Glu Asn Leu Gln Lys Tyr Lys
            740                 745                 750

Ala Ala Lys Asn Pro Ser Pro Thr Thr Arg Pro Val Ser Arg Arg Cys
        755                 760                 765

Ala Ile Asn Ala Arg Asn Ala Leu Thr Ala Leu Phe Thr Ser Ser Gly
    770                 775                 780

Arg Pro Pro Ser Gln Pro Asn Thr Gln Asp Lys Thr Pro Ser Lys Val
785                 790                 795                 800

Thr Ala Arg Pro Ser Gln Pro Pro Leu Pro Arg Arg Ser Thr Arg Leu
                805                 810                 815

Lys Thr

<210> SEQ ID NO 35
<211> LENGTH: 820
<212> TYPE: PRT
<213> ORGANISM: Homo sapiens

<400> SEQUENCE: 35
```

```
Pro Leu Pro Met Ala Val Ser Arg Gly Leu Pro Pro Gln Gln Pro Gln
1               5                   10                  15

Gln Pro Leu Leu Asn Leu Gln Gly Thr Asn Ser Ala Ser Leu Leu Asn
            20                  25                  30

Gly Ser Met Leu Gln Arg Ala Leu Leu Gln Leu Gln Gly Asn
        35                  40                  45

Leu Arg Gly Tyr Gly Met Ala Ser Pro Gly Leu Ala Ala Pro Ser Leu
    50                  55                  60

Thr Pro Pro Gln Leu Ala Thr Pro Asn Leu Gln Gln Phe Phe Pro Gln
65                  70                  75                  80

Ala Thr Arg Gln Ser Leu Leu Gly Pro Pro Val Gly Val Pro Met
                85                  90                  95

Asn Pro Ser Gln Phe Asn Leu Ser Gly Arg Asn Pro Gln Lys Gln Ala
                100                 105                 110

Arg Thr Ser Ser Ser Thr Thr Pro Asn Arg Lys Thr Met Pro Val Glu
            115                 120                 125

Asp Lys Ser Asp Pro Pro Glu Gly Ser Glu Glu Ala Ala Glu Pro Arg
    130                 135                 140

Met Asp Thr Pro Glu Asp Gln Asp Leu Pro Pro Cys Pro Glu Asp Ile
145                 150                 155                 160

Ala Lys Glu Lys Arg Thr Pro Ala Pro Glu Pro Glu Pro Cys Glu Ala
                165                 170                 175

Ser Glu Leu Pro Ala Lys Arg Leu Arg Ser Glu Glu Pro Thr Glu
            180                 185                 190

Lys Glu Pro Pro Gly Gln Leu Gln Val Lys Ala Gln Pro Gln Ala Arg
        195                 200                 205

Met Thr Val Pro Lys Gln Thr Gln Thr Pro Asp Leu Leu Pro Glu Ala
    210                 215                 220

Leu Glu Ala Gln Val Leu Pro Arg Phe Gln Pro Arg Val Leu Gln Val
225                 230                 235                 240

Gln Ala Gln Val Gln Ser Gln Thr Gln Pro Arg Ile Pro Ser Thr Asp
                245                 250                 255

Thr Gln Val Gln Pro Lys Leu Gln Lys Gln Ala Gln Thr Gln Thr Ser
            260                 265                 270

Pro Glu His Leu Val Leu Gln Gln Lys Gln Val Gln Pro Gln Leu Gln
        275                 280                 285

Gln Glu Ala Glu Pro Gln Lys Gln Val Gln Pro Gln Val Gln Pro Gln
290                 295                 300

Ala His Ser Gln Gly Pro Arg Gln Val Gln Leu Gln Gln Glu Ala Glu
305                 310                 315                 320

Pro Leu Lys Gln Val Gln Pro Gln Val Gln Pro Gln Ala His Ser Gln
                325                 330                 335

Pro Pro Arg Gln Val Gln Leu Gln Leu Gln Lys Gln Val Gln Thr Gln
            340                 345                 350

Thr Tyr Pro Gln Val His Thr Gln Ala Gln Pro Ser Val Gln Pro Gln
        355                 360                 365

Glu His Pro Pro Ala Gln Val Ser Val Gln Pro Glu Gln Thr His
370                 375                 380

Glu Gln Pro His Thr Gln Pro Gln Val Ser Leu Leu Ala Pro Glu Gln
385                 390                 395                 400

Thr Pro Val Val Val His Val Cys Gly Leu Glu Met Pro Pro Asp Ala
                405                 410                 415

Val Glu Ala Gly Gly Ser Met Glu Lys Thr Leu Pro Glu Pro Val Gly
```

```
                420             425             430
Thr Gln Val Ser Met Glu Ile Gln Asn Glu Ser Ala Cys Gly Leu
            435             440             445
Asp Val Gly Glu Cys Glu Asn Arg Ala Arg Glu Met Pro Gly Val Trp
450             455             460
Gly Ala Gly Gly Ser Leu Lys Val Thr Ile Leu Gln Ser Ser Asp Ser
465             470             475             480
Arg Ala Phe Ser Thr Val Pro Leu Thr Pro Val Arg Pro Ser Asp
            485             490             495
Ser Val Ser Ser Thr Pro Ala Thr Ser Thr Pro Ser Lys Gln Ala
500             505             510
Leu Gln Phe Phe Cys Tyr Ile Cys Lys Ala Ser Cys Ser Ser Gln Gln
            515             520             525
Glu Phe Gln Asp His Met Ser Glu Pro Gln His Gln Gln Arg Leu Gly
            530             535             540
Glu Ile Gln His Met Ser Gln Ala Cys Leu Leu Ser Leu Leu Pro Val
545             550             555             560
Pro Arg Asp Val Leu Glu Thr Glu Asp Glu Pro Pro Arg Arg
            565             570             575
Trp Cys Asn Thr Cys Gln Leu Tyr Tyr Met Gly Asp Leu Ile Gln His
            580             585             590
Arg Arg Thr Gln Asp His Arg Ile Ala Lys Gln Ser Leu Arg Pro Phe
            595             600             605
Cys Thr Val Cys Asn Arg Tyr Phe Lys Thr Pro Arg Lys Phe Val Glu
            610             615             620
His Val Lys Ser Gln Gly His Lys Asp Lys Ala Lys Glu Leu Lys Ser
625             630             635             640
Leu Glu Lys Glu Ile Ala Gly Gln Asp Glu Asp His Phe Ile Thr Val
            645             650             655
Asp Ala Val Gly Cys Phe Glu Gly Glu Glu Glu Glu Asp Asp
            660             665             670
Glu Asp Glu Glu Glu Ile Glu Val Glu Glu Leu Cys Lys Gln Val
            675             680             685
Arg Ser Arg Asp Ile Ser Arg Glu Glu Trp Lys Gly Ser Glu Thr Tyr
690             695             700
Ser Pro Asn Thr Ala Tyr Gly Val Asp Phe Leu Val Pro Val Met Gly
705             710             715             720
Tyr Ile Cys Arg Ile Cys His Lys Phe Tyr His Asn Asn Ser Gly Ala
            725             730             735
Gln Leu Ser His Cys Lys Ser Leu Gly His Phe Glu Asn Leu Gln Lys
            740             745             750
Tyr Lys Ala Ala Lys Asn Pro Ser Pro Thr Thr Arg Pro Val Ser Arg
            755             760             765
Arg Cys Ala Ile Asn Ala Arg Asn Ala Leu Thr Ala Leu Phe Thr Ser
            770             775             780
Ser Gly Arg Pro Pro Ser Gln Pro Asn Thr Gln Asp Lys Thr Pro Ser
785             790             795             800
Lys Val Thr Ala Arg Pro Ser Gln Pro Pro Leu Pro Arg Arg Ser Thr
            805             810             815
Arg Leu Lys Thr
            820

<210> SEQ ID NO 36
```

<211> LENGTH: 391
<212> TYPE: PRT
<213> ORGANISM: Homo sapiens

<400> SEQUENCE: 36

Met Phe Ser Gln Gln Gln Gln Gln Leu Gln Gln Gln Gln Gln
1               5                   10                  15

Leu Gln Gln Leu Gln Gln Gln Leu Gln Gln Gln Leu Gln Gln
            20                  25                  30

Gln Gln Leu Leu Gln Leu Gln Leu Leu Gln Ser Pro Pro Gln
        35                  40                  45

Ala Pro Leu Pro Met Ala Val Ser Arg Gly Leu Pro Gln Gln Pro
50                  55                  60

Gln Gln Pro Leu Leu Asn Leu Gln Gly Thr Asn Ser Ala Ser Leu Leu
65                  70                  75                  80

Asn Gly Ser Met Leu Gln Arg Ala Leu Leu Leu Gln Leu Gln Gly
                85                  90                  95

Asn Leu Arg Gly Tyr Gly Met Ala Ser Pro Gly Leu Ala Ala Pro Ser
            100                 105                 110

Leu Thr Pro Pro Gln Leu Ala Thr Pro Asn Leu Gln Gln Phe Phe Pro
        115                 120                 125

Gln Ala Thr Arg Gln Ser Leu Leu Gly Pro Pro Val Gly Val Pro
130                 135                 140

Met Asn Pro Ser Gln Phe Asn Leu Ser Gly Arg Asn Pro Gln Lys Gln
145                 150                 155                 160

Ala Arg Thr Ser Ser Ser Thr Thr Pro Asn Arg Lys Asp Ser Ser
                165                 170                 175

Gln Thr Met Pro Val Glu Asp Lys Ser Asp Pro Glu Gly Ser Glu
            180                 185                 190

Glu Ala Ala Glu Pro Arg Met Asp Thr Pro Glu Asp Gln Asp Leu Pro
        195                 200                 205

Pro Cys Pro Glu Asp Ile Ala Lys Glu Lys Arg Thr Pro Ala Pro Glu
210                 215                 220

Pro Glu Pro Cys Glu Ala Ser Glu Leu Pro Ala Lys Arg Leu Arg Ser
225                 230                 235                 240

Ser Glu Glu Pro Thr Glu Lys Glu Pro Pro Gly Gln Leu Gln Val Lys
                245                 250                 255

Ala Gln Pro Gln Ala Arg Met Thr Val Pro Lys Gln Thr Gln Thr Pro
            260                 265                 270

Asp Leu Leu Pro Glu Ala Leu Glu Ala Gln Val Leu Pro Arg Phe Gln
        275                 280                 285

Pro Arg Val Leu Gln Val Gln Ala Gln Val Ser Gln Thr Gln Pro
290                 295                 300

Arg Ile Pro Ser Thr Asp Thr Gln Val Gln Pro Lys Leu Gln Lys Gln
305                 310                 315                 320

Ala Gln Thr Gln Thr Ser Pro Glu His Leu Val Leu Gln Lys Gln
                325                 330                 335

Val Gln Pro Gln Leu Gln Gln Glu Ala Glu Pro Gln Lys Gln Val Gln
            340                 345                 350

Pro Gln Val Gln Pro Gln Ala His Ser Gln Gly Pro Arg Gln Val Gln
        355                 360                 365

Leu Gln Gln Glu Ala Glu Pro Leu Lys Gln Val Gln Pro Gln Val Gln
370                 375                 380

Pro Gln Ala His Ser Gln Pro

```
385                 390

<210> SEQ ID NO 37
<211> LENGTH: 75
<212> TYPE: PRT
<213> ORGANISM: Homo sapiens

<400> SEQUENCE: 37

Leu Gln Gln Gln Gln Gln Gln Leu Gln Gln Leu Gln Gln Gln Gln Leu
1               5                   10                  15

Gln Gln Gln Gln Leu Gln Gln Gln Leu Leu Gln Leu Gln Gln Leu
            20                  25                  30

Leu Gln Gln Ser Pro Pro Gln Ala Pro Leu Pro Met Ala Val Ser Arg
        35                  40                  45

Gly Leu Pro Pro Gln Gln Pro Gln Gln Pro Leu Leu Asn Leu Gln Gly
    50                  55                  60

Thr Asn Ser Ala Ser Leu Leu Asn Gly Ser Met
65                  70                  75

<210> SEQ ID NO 38
<211> LENGTH: 33
<212> TYPE: PRT
<213> ORGANISM: Homo sapiens

<400> SEQUENCE: 38

Gln Gln Leu Gln Gln Leu Gln Gln Gln Leu Gln Gln Gln Gln Gln Leu
1               5                   10                  15

Gln Gln Gln Gln Leu Leu Gln Leu Gln Gln Leu Leu Gln Gln Ser Pro
            20                  25                  30

Pro

<210> SEQ ID NO 39
<211> LENGTH: 52
<212> TYPE: PRT
<213> ORGANISM: Homo sapiens

<400> SEQUENCE: 39

Met Phe Ser Gln Gln Gln Gln Gln Leu Gln Gln Gln Gln Gln
1               5                   10                  15

Leu Gln Gln Leu Gln Gln Gln Gln Leu Gln Gln Gln Gln Leu Gln Gln
            20                  25                  30

Gln Gln Leu Leu Gln Leu Gln Gln Leu Leu Gln Gln Ser Pro Pro Gln
        35                  40                  45

Ala Pro Leu Pro
    50

<210> SEQ ID NO 40
<211> LENGTH: 26
<212> TYPE: PRT
<213> ORGANISM: Homo sapiens

<400> SEQUENCE: 40

Pro Pro Thr Pro Arg Arg Asp Val Phe Ala His Val Pro Val Gln Gly
1               5                   10                  15

Trp Ser Thr Ala Arg Leu Val Thr Asp Met
            20                  25

<210> SEQ ID NO 41
<211> LENGTH: 24
<212> TYPE: PRT
```

-continued

<213> ORGANISM: Homo sapiens

<400> SEQUENCE: 41

Gly Leu Asp Gln Phe Ala Met Pro Pro Ala Thr Tyr Asp Thr Ala Gly
1               5                   10                  15

Leu Thr Met Pro Thr Ala Thr Leu
            20

<210> SEQ ID NO 42
<211> LENGTH: 56
<212> TYPE: PRT
<213> ORGANISM: Homo sapiens

<400> SEQUENCE: 42

Pro Gln Val Gln Pro Gln Ala His Ser Gln Gly Pro Arg Gln Val Gln
1               5                   10                  15

Leu Gln Gln Glu Ala Glu Pro Leu Lys Gln Val Gln Pro Gln Val Gln
            20                  25                  30

Pro Gln Ala His Ser Gln Pro Pro Arg Gln Val Gln Leu Gln Leu Gln
        35                  40                  45

Lys Gln Val Gln Thr Gln Thr Tyr
    50                  55

<210> SEQ ID NO 43
<211> LENGTH: 28
<212> TYPE: PRT
<213> ORGANISM: Homo sapiens

<400> SEQUENCE: 43

Pro Gln Val Gln Pro Gln Ala His Ser Gln Pro Pro Arg Gln Val Gln
1               5                   10                  15

Leu Gln Leu Gln Lys Gln Val Gln Thr Gln Thr Tyr
            20                  25

<210> SEQ ID NO 44
<211> LENGTH: 112
<212> TYPE: PRT
<213> ORGANISM: Homo sapiens

<400> SEQUENCE: 44

Gln Val Gln Ser Gln Thr Gln Pro Arg Ile Pro Ser Thr Asp Thr Gln
1               5                   10                  15

Val Gln Pro Lys Leu Gln Lys Gln Ala Gln Thr Gln Thr Ser Pro Glu
            20                  25                  30

His Leu Val Leu Gln Gln Lys Gln Val Gln Pro Gln Leu Gln Gln Glu
        35                  40                  45

Ala Glu Pro Gln Lys Gln Val Gln Pro Val Gln Pro Gln Ala His
    50                  55                  60

Ser Gln Gly Pro Arg Gln Val Gln Leu Gln Gln Glu Ala Glu Pro Leu
65                  70                  75                  80

Lys Gln Val Gln Pro Gln Val Gln Pro Gln Ala His Ser Gln Pro Pro
                85                  90                  95

Arg Gln Val Gln Leu Gln Leu Gln Lys Gln Val Gln Thr Gln Thr Tyr
            100                 105                 110

<210> SEQ ID NO 45
<211> LENGTH: 2687
<212> TYPE: DNA
<213> ORGANISM: Mus musculus

<400> SEQUENCE: 45

```
catgttcaac ccgcaactcc agcagcagca acagttgcag cagcagcagc aacagttgca        60
gcagcagctc cagcagcagc agctccagca gcagcaacag cagatactgc agctccaaca       120
gctgctgcaa cagtccccac cacaggcctc cttgtccatt cctgtcagcc ggggcctccc       180
ccagcagtca tccccgcaac agcttctgag tctccagggc tccactcga cctccctgct        240
caatggcccc atgctgcaaa gagctttgct cctacacag ttgcaaggac tggaccagtt        300
tgcaatgcca ccagccacgt atgacggtgc cagcctcacc atgcctacgg caacactggg       360
taacctccgt gctttcaatg tgacagcccc aagcctagca gctcccagcc ttacaccacc       420
ccagatggtc accccaaatc tgcagcagtt cttcccccag gctactcgac agtctctgct       480
ggggcctcct cctgttgggg tcccaataaa cccttctcag ctcaaccact cagggaggaa       540
cacccagaaa caggccagaa cccctcttc caccacccc aatcgcaagg attcttcttc         600
tcagacggtg cctctggaag acagggaaga ccccacagag gggtctgagg aagccacgga       660
gctccagatg gacacatgtg aagaccaaga ttcactagtc ggtccagata gcatgctgag       720
tgagccccaa gtgcctgagc ctgagccctt tgagacattg gaaccaccag ccaagaggtg       780
caggagctca gaggagtcca ccgagaaagg ccctacaggg cagccacaag caagggtcca       840
gcctcagacc cagatgacag caccaaagca gacacagacc ccggatcggc tgcctgagcc       900
accagaagtc caaatgctgc cgcgtatcca gccacaggca ctgcagatcc agacccagcc       960
aaagctgctg aggcaggcac agacacagac ctctccagag cacttagcgc cccagcagga      1020
tcaggtagag ccacaggtac catcacagcc cccatggcag ttgcagccac gggagacaga      1080
cccaccgaac caagctcagg cacagaccca gcctcagccc ctctggcagg cgcagtcaca      1140
gaagcaggcc cagacacagg cacatccaca ggtacccacc caagcacagt cacaggagca      1200
gacatcagag aagacccagg accagcctca gacctggcca caggggtcag tacccccacc      1260
agaacaagcg tcaggtccag cctgtgccac ggaaccacag ctatcctctc acgctgcaga      1320
agctgggagt gacccagaca aggccttgcc agaaccagta agtgcccaga gcagtgaaga      1380
caggagccgg gaggcgtccg ctggtggcct ggatttggga gaatgtgaaa agagagcggg      1440
agagatgctg gggatgtggg gggctgggag ctccctgaag gtcaccatcc tgcagagtag      1500
caacagccgg gcctttaaca ccacacccct cacatctgga cctcgccctg gggactctac      1560
ctctgccacc cctgccattg ccagcacacc ctccaagcaa agcctccagt tcttctgcta      1620
catctgcaag gccagcagca gcagccagca ggagttccag gatcacatgt cagaggctca      1680
gcaccaacag cggcttgggg aaatacaaca ctcgagccag acctgcctgc tgtccctgct      1740
gcccatgcct cgggacatcc tggagaaaga agcggaagat cctccgccca aacgctggtg      1800
caacacctgc caggtgtact acgtgggaga cttgatccag caccgtagga cacaggagca      1860
caaggttgcc aaacaatccc tgaggccctt ctgcaccata tgcaaccgtt acttcaagac      1920
ccctcgaaag tttgtggagc acgtgaagtc ccagggacac aaggacaagg cccaagagct      1980
gaagacactt gaaaaggaga caggcagccc agatgaggac cacttcatca ctgtggacgc      2040
cgtcggttgc tttgagagtg gtcaagaaga ggacgaggat gacgacgagg aagaagaaga      2100
agaaggagag attgaggctg aggaggaatt ctgcaagcag gtgaagccga gagaaacatc      2160
ctcagagcaa gggaagggct ctgagacgta caaccccaac acagcctatg gtgaggattt      2220
cctggtgcca gtgatgggct atgtctgtca aatctgtcac aagttctacg acagcaactc      2280
agaattgcgg ctttctcact gcaagtccct ggcccacttt gagaacctgc agaaatacaa      2340
```

| | | |
|---|---|---|
| agccaagaac ccaagccctc ctcctacccg gcctgtgagc cgcaagtgtg ccatcaacgc | 2400 |
| ccgcaacgcc ctgactgcac tgttcacctc tagccaccag cccagccccc aggacacagt | 2460 |
| gaaaatgccc agcaaggtga agcctggatc ccccggactc cctcctcccc ttcggcgctc | 2520 |
| aacacgcctc aaaacctgat agagggagct ctggccactc agcctgacta aggctcagtc | 2580 |
| tgctaatgct tcctaggtat ctgtgtagaa atgttcaagt ggttggtgtt tttactcaaa | 2640 |
| atccaataaa gagtcagtag tttggcaaaa aaaaaaaaaa aaaaaaa | 2687 |

<210> SEQ ID NO 46
<211> LENGTH: 2922
<212> TYPE: DNA
<213> ORGANISM: Homo sapiens

<400> SEQUENCE: 46

| | |
|---|---|
| tgggggctgc ggggccggcc catccgtggg ggcgacttga gcgttgaggg cgcgcgggga | 60 |
| ggcgagccac catgttcagc cagcagcagc agcagctcca gcaacagcag cagcagctcc | 120 |
| agcagttaca gcagcagcag ctccagcagc agcaattgca gcagcagcag ttactgcagc | 180 |
| tccagcagct gctccagcag tccccaccac aggccccgtt gcccatggct gtcagccggg | 240 |
| ggctcccccc gcagcagcca cagcagccgc ttctgaatct ccagggcacc aactcagcct | 300 |
| ccctcctcaa cggctccatg ctgcagagag cttgctttt acagcagttg caaggactgg | 360 |
| accagtttgc aatgccacca gccacgtatg acactgccgg tctcaccatg cccacagcaa | 420 |
| cactgggtaa cctccgaggc tatggcatgg catcccagg cctcgcagcc cccagcctca | 480 |
| caccccaca actggccact ccaaatttgc aacagttctt tccccaggcc actcgccagt | 540 |
| ccttgctggg acctcctcct gttggggtcc ccatgaaccc ttcccagttc aacctttcag | 600 |
| gacggaaccc ccagaaacag gcccggacct cctcctctac caccccaat cgaaaggatt | 660 |
| cttcttctca gacaatgcct gtggaagaca agtcagaccc cccagagggg tctgaggaag | 720 |
| ccgcagagcc ccggatggac acaccagaag accaagattt accgccctgc cagaggaca | 780 |
| tcgccaagga aaaacgcact ccagcacctg agcctgagcc ttgtgaggcg tccgagctgc | 840 |
| cagcaaagag attgaggagc tcagaagagc ccacagagaa ggaacctcca gggcagttac | 900 |
| aggtgaaggc ccagccgcag gcccggatga cagtaccgaa acagacacag acaccagacc | 960 |
| tgctgcctga ggccctggaa gcccaagtgc tgccacgatt ccagccacgg gtcctgcagg | 1020 |
| tccaggccca ggtgcagtca cagactcagc gcggataccc atccacagac cccaggtgc | 1080 |
| agccaaagct gcagaagcag gcgcaaacac agacctctcc agagcactta gtgctgcaac | 1140 |
| agaagcaggt gcagccacag ctgcagcagg aggcagagcc acagaagcag gtgcagccac | 1200 |
| aggtacagcc acaggcacat tcacagggcc caaggcaggt gcagctgcag caggaggcag | 1260 |
| agccgctgaa gcaggtgcag ccacaggtgc agccccaggc acattcacag cccccaaggc | 1320 |
| aggtgcagct gcagctgcag aagcaggtcc agacacagac atatccacag gtccacacac | 1380 |
| aggcacagcc aagcgtccag ccacaggagc atcctccagc gcaggtgtca gtacagccac | 1440 |
| cagagcagac ccatgagcag cctcacaccc agccgcaggt gtcgttgctg gctccagagc | 1500 |
| aaacaccagt tgtggttcat gtctgcgggc tggagatgcc acctgatgca gtagaagctg | 1560 |
| gtggaggcat ggaaaagacc ttgccagagc ctgtgggcac ccaagtcagc atggaagaga | 1620 |
| ttcagaatga gtcggcctgt ggcctagatg tgggagaatg tgaaaacaga gcagagagag | 1680 |
| tgccaggggt atggggcgcc ggggggctccc tgaaggtcac cattctgcag agcagtgaca | 1740 |

-continued

```
gccgggcctt tagcactgta cccctgacac ctgtccccg ccccagtgac tccgtctcct    1800
ccaccctgc ggctaccagc actccctcta agcaggccct ccagttcttc tgctacatct    1860
gcaaggccag ctgctccagc cagcaggagt tccaggacca catgtcggag cctcagcacc    1920
agcagcggct aggggagatc cagcacatga gccaagcctg cctcctgtcc ctgctgcccg    1980
tgccccggga cgtcctggag acagaggatg aggagcctcc accaaggcgc tggtgcaaca    2040
cctgccagct ctactacatg ggggacctga tccaacaccg caggacacag gaccacaaga    2100
ttgccaaaca atccttgcga cccttctgca ccgtttgcaa ccgctacttc aaaacccctc    2160
gcaagtttgt ggagcacgtg aagtcccagg gcataagga caaagccaag gagctgaagt    2220
cgcttgagaa agaaattgct ggccaagatg aggaccactt cattacagtg gacgctgtgg    2280
gttgcttcga gggtgatgaa gagaggaag aggatgatga ggatgaagaa gagatcgagg    2340
ttgaggagga actctgcaag caggtgaggt ccagagatat atccagagag gagtggaagg    2400
gctcggagac ctacagcccc aatactgcat atggtgtgga cttcctggtg cccgtgatgg    2460
gctatatctg ccgcatctgc cacaagttct atcacagcaa ctcaggggca cagctctccc    2520
actgcaagtc cctgggccac tttgagaacc tgcagaaata caaggcggcc aagaacccca    2580
gccccaccac ccgacctgtg agccgccggt gcgcaatcaa cgcccggaac gctttgacag    2640
ccctgttcac ctccagcggc cgcccaccct cccagcccaa cacccaggac aaaacaccca    2700
gcaaggtgac ggctcgaccc tcccagcccc cactacctcg gcgctcaacc cgcctcaaaa    2760
cctgatagag ggacctccct gtccctggcc tgcctgggtc cagatctgct aatgcttttt    2820
aggagtctgc ctggaaactt tgacatggtt catgttttta ctcaaaatcc aataaaacaa    2880
ggtagtttgg ctgtgcaaaa aaaaaaaaaa aaaaaaaaa aa                        2922
```

<210> SEQ ID NO 47
<211> LENGTH: 897
<212> TYPE: PRT
<213> ORGANISM: Homo sapiens

<400> SEQUENCE: 47

```
Met Phe Ser Gln Gln Gln Gln Leu Gln Gln Gln Gln Gln Gln Gln Leu
1               5                   10                  15

Gln Gln Leu Gln Gln Gln Gln Leu Gln Gln Gln Gln Leu Gln Gln Gln
            20                  25                  30

Gln Leu Leu Gln Leu Gln Gln Leu Leu Gln Gln Ser Pro Pro Gln Ala
        35                  40                  45

Pro Leu Pro Met Ala Val Ser Arg Gly Leu Pro Pro Gln Gln Pro Gln
    50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Gln Leu Gln Gly Leu
                85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
        115                 120                 125

Pro Gly Leu Ala Ala Pro Ser Leu Thr Pro Gln Leu Ala Thr Pro
    130                 135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
```

-continued

```
                165                 170                 175
Gly Arg Asn Pro Gln Lys Gln Ala Arg Thr Ser Ser Thr Thr Pro
            180                 185                 190

Asn Arg Lys Asp Ser Ser Gln Thr Met Pro Val Glu Asp Lys Ser
            195                 200                 205

Asp Pro Pro Glu Gly Ser Glu Glu Ala Ala Glu Pro Arg Met Asp Thr
            210                 215                 220

Pro Glu Asp Gln Asp Leu Pro Pro Cys Pro Glu Asp Ile Ala Lys Glu
225                 230                 235                 240

Lys Arg Thr Pro Ala Pro Glu Pro Glu Pro Cys Glu Ala Ser Glu Leu
                245                 250                 255

Pro Ala Lys Arg Leu Arg Ser Ser Glu Glu Pro Thr Glu Lys Glu Pro
            260                 265                 270

Pro Gly Gln Leu Gln Val Lys Ala Gln Pro Gln Ala Arg Met Thr Val
            275                 280                 285

Pro Lys Gln Thr Gln Thr Pro Asp Leu Leu Pro Glu Ala Leu Glu Ala
            290                 295                 300

Gln Val Leu Pro Arg Phe Gln Pro Arg Val Leu Gln Val Gln Ala Gln
305                 310                 315                 320

Val Gln Ser Gln Thr Gln Pro Arg Ile Pro Ser Thr Asp Thr Gln Val
                325                 330                 335

Gln Pro Lys Leu Gln Lys Ala Gln Thr Gln Thr Ser Pro Glu His
            340                 345                 350

Leu Val Leu Gln Gln Lys Gln Val Gln Pro Gln Leu Gln Gln Glu Ala
            355                 360                 365

Glu Pro Gln Lys Gln Val Gln Pro Gln Val Pro Gln Ala His Ser
370                 375                 380

Gln Gly Pro Arg Gln Val Gln Leu Gln Glu Ala Glu Pro Leu Lys
385                 390                 395                 400

Gln Val Gln Pro Gln Val Pro Gln Ala His Ser Gln Pro Pro Arg
                405                 410                 415

Gln Val Gln Leu Gln Leu Gln Lys Gln Val Gln Thr Gln Thr Tyr Pro
            420                 425                 430

Gln Val His Thr Gln Ala Gln Pro Ser Val Gln Pro Gln Glu His Pro
            435                 440                 445

Pro Ala Gln Val Ser Val Gln Pro Glu Gln Thr His Glu Gln Pro
450                 455                 460

His Thr Gln Pro Gln Val Ser Leu Leu Ala Pro Glu Gln Thr Pro Val
465                 470                 475                 480

Val Val His Val Cys Gly Leu Glu Met Pro Pro Asp Ala Val Glu Ala
                485                 490                 495

Gly Gly Gly Met Glu Lys Thr Leu Pro Glu Pro Val Gly Thr Gln Val
            500                 505                 510

Ser Met Glu Glu Ile Gln Asn Glu Ser Ala Cys Gly Leu Asp Val Gly
            515                 520                 525

Glu Cys Glu Asn Arg Ala Arg Glu Met Pro Gly Val Trp Gly Ala Gly
            530                 535                 540

Gly Ser Leu Lys Val Thr Ile Leu Gln Ser Ser Asp Ser Arg Ala Phe
545                 550                 555                 560

Ser Thr Val Pro Leu Thr Pro Val Pro Arg Pro Ser Asp Ser Val Ser
                565                 570                 575

Ser Thr Pro Ala Ala Thr Ser Pro Ser Lys Gln Ala Leu Gln Phe
            580                 585                 590
```

```
Phe Cys Tyr Ile Cys Lys Ala Ser Cys Ser Gln Gln Glu Phe Gln
            595                 600                 605

Asp His Met Ser Glu Pro Gln His Gln Gln Arg Leu Gly Glu Ile Gln
610                 615                 620

His Met Ser Gln Ala Cys Leu Leu Ser Leu Leu Pro Val Pro Arg Asp
625                 630                 635                 640

Val Leu Glu Thr Glu Asp Glu Glu Pro Pro Arg Arg Trp Cys Asn
                    645                 650                 655

Thr Cys Gln Leu Tyr Tyr Met Gly Asp Leu Ile Gln His Arg Arg Thr
            660                 665                 670

Gln Asp His Lys Ile Ala Lys Gln Ser Leu Arg Pro Phe Cys Thr Val
        675                 680                 685

Cys Asn Arg Tyr Phe Lys Thr Pro Arg Lys Phe Val Glu His Val Lys
    690                 695                 700

Ser Gln Gly His His Lys Asp Lys Ala Lys Glu Leu Lys Ser Leu Glu Lys
705                 710                 715                 720

Glu Ile Ala Gly Gln Asp Glu Asp His Phe Ile Thr Val Asp Ala Val
                725                 730                 735

Gly Cys Phe Glu Gly Asp Glu Glu Glu Asp Glu Asp Glu
                740                 745                 750

Glu Glu Ile Glu Val Glu Glu Leu Cys Lys Gln Val Arg Ser Arg
            755                 760                 765

Asp Ile Ser Arg Glu Glu Trp Lys Gly Ser Glu Thr Tyr Ser Pro Asn
770                 775                 780

Thr Ala Tyr Gly Val Asp Phe Leu Val Pro Val Met Gly Tyr Ile Cys
785                 790                 795                 800

Arg Ile Cys His Lys Phe Tyr His Ser Asn Ser Gly Ala Gln Leu Ser
                805                 810                 815

His Cys Lys Ser Leu Gly His Phe Glu Asn Leu Gln Lys Tyr Lys Ala
            820                 825                 830

Ala Lys Asn Pro Ser Pro Thr Thr Arg Pro Val Ser Arg Arg Cys Ala
        835                 840                 845

Ile Asn Ala Arg Asn Ala Leu Thr Ala Leu Phe Thr Ser Ser Gly Arg
    850                 855                 860

Pro Pro Ser Gln Pro Asn Thr Gln Asp Lys Thr Pro Ser Lys Val Thr
865                 870                 875                 880

Ala Arg Pro Ser Gln Pro Pro Leu Pro Arg Arg Ser Thr Arg Leu Lys
                885                 890                 895

Thr

<210> SEQ ID NO 48
<211> LENGTH: 49
<212> TYPE: PRT
<213> ORGANISM: Homo sapiens

<400> SEQUENCE: 48

Met Phe Ser Gln Gln Gln Gln Gln Leu Gln Gln Gln Gln Gln
1               5                   10                  15

Leu Gln Gln Leu Gln Gln Gln Gln Leu Gln Gln Gln Leu Gln Gln
                20                  25                  30

Gln Gln Leu Leu Gln Leu Gln Leu Leu Gln Gln Ser Pro Pro Gln
            35                  40                  45

Ala
```

<210> SEQ ID NO 49
<211> LENGTH: 215
<212> TYPE: DNA
<213> ORGANISM: Homo sapiens

<400> SEQUENCE: 49

```
tgggggctgc ggggccggcc catccgtggg ggcgacttga gcgttgaggg cgcgcgggga      60
ggcgagccac catgttcagc cagcagcagc agcagctcca gcaacagcag cagcagctcc     120
agcagttaca gcagcagcag ctccagcagc agcaattgca gcagcagcag ttactgcagc     180
tccagcagct gctccagcag tccccaccac aggcc                                215
```

<210> SEQ ID NO 50
<211> LENGTH: 101
<212> TYPE: DNA
<213> ORGANISM: Homo sapiens

<400> SEQUENCE: 50

```
cagcagctcc agcagttaca gcagcagcag ctccagcagc agcaattgca gcagcagcag      60
ttactgcagc tccagcagct gctccagcag tccccaccac a                         101
```

<210> SEQ ID NO 51
<211> LENGTH: 72
<212> TYPE: DNA
<213> ORGANISM: Homo sapiens

<400> SEQUENCE: 51

```
ggactggacc agtttgcaat gccaccagcc acgtatgaca ctgccggtct caccatgccc      60
acagcaacac tg                                                          72
```

<210> SEQ ID NO 52
<211> LENGTH: 15
<212> TYPE: DNA
<213> ORGANISM: Homo sapiens

<400> SEQUENCE: 52

```
aggattcttc ttctc                                                       15
```

<210> SEQ ID NO 53
<211> LENGTH: 86
<212> TYPE: DNA
<213> ORGANISM: Homo sapiens

<400> SEQUENCE: 53

```
ccacaggtgc agccccaggc acattcacag cccccaaggc aggtgcagct gcagctgcag      60
aagcaggtcc agacacagac atatcc                                           86
```

<210> SEQ ID NO 54
<211> LENGTH: 168
<212> TYPE: DNA
<213> ORGANISM: Homo sapiens

<400> SEQUENCE: 54

```
ccacaggtac agccacaggc acattcacag ggcccaaggc aggtgcagct gcagcaggag      60
gcagagccgc tgaagcaggt gcagccacag gtgcagcccc aggcacattc acagccccca     120
aggcaggtgc agctgcagct gcagaagcag gtccagacac agacatat                  168
```

<210> SEQ ID NO 55
<211> LENGTH: 336

<210> SEQ ID NO 56
<211> LENGTH: 24
<212> TYPE: DNA
<213> ORGANISM: Homo sapiens

<400> SEQUENCE: 55

```
caggtgcagt cacagactca gccgcggata ccatccacag acacccaggt gcagccaaag      60
ctgcagaagc aggcgcaaac acagacctct ccagagcact tagtgctgca acagaagcag     120
gtgcagccac agctgcagca ggaggcagag ccacagaagc aggtgcagcc acaggtacag     180
ccacaggcac attcacaggg cccaaggcag gtgcagctgc agcaggaggc agagccgctg     240
aagcaggtgc agccacaggt gcagccccag gcacattcac agcccccaag gcaggtgcag     300
ctgcagctgc agaagcaggt ccagacacag acatat                              336
```

<210> SEQ ID NO 56
<211> LENGTH: 24
<212> TYPE: DNA
<213> ORGANISM: Homo sapiens

<400> SEQUENCE: 56

```
gttgaggagg aactctgcaa gcag                                            24
```

<210> SEQ ID NO 57
<211> LENGTH: 78
<212> TYPE: DNA
<213> ORGANISM: Homo sapiens

<400> SEQUENCE: 57

```
gccacccaca ccacgaagag atgtgtttgc ccacgttcca gtgcaggggt ggagcacagc      60
ccggcttgtt acagatat                                                   78
```

<210> SEQ ID NO 58
<211> LENGTH: 863
<212> TYPE: PRT
<213> ORGANISM: Homo sapiens

<400> SEQUENCE: 58

```
Met Phe Ser Gln Gln Gln Gln Leu Gln Gln Gln Gln Gln Ala Pro
1               5                   10                  15

Leu Pro Met Ala Val Ser Arg Gly Leu Pro Gln Gln Pro Gln Gln
                20                  25                  30

Pro Leu Leu Asn Leu Gln Gly Thr Asn Ser Ala Ser Leu Leu Asn Gly
                35                  40                  45

Ser Met Leu Gln Arg Ala Leu Leu Gln Gln Leu Gln Gly Leu Asp
    50                  55                  60

Gln Phe Ala Met Pro Pro Ala Thr Tyr Asp Thr Ala Gly Leu Thr Met
65                  70                  75                  80

Pro Thr Ala Thr Leu Gly Asn Leu Arg Gly Tyr Gly Met Ala Ser Pro
                85                  90                  95

Gly Leu Ala Ala Pro Ser Leu Thr Pro Pro Gln Leu Ala Thr Pro Asn
                100                 105                 110

Leu Gln Gln Phe Phe Pro Gln Ala Thr Arg Gln Ser Leu Leu Gly Pro
                115                 120                 125

Pro Pro Val Gly Val Pro Met Asn Pro Ser Gln Phe Asn Leu Ser Gly
                130                 135                 140

Arg Asn Pro Gln Lys Gln Ala Arg Thr Ser Ser Ser Thr Pro Asn
145                 150                 155                 160

Arg Lys Asp Ser Ser Ser Gln Thr Met Pro Val Glu Asp Lys Ser Asp
                165                 170                 175
```

```
Pro Pro Glu Gly Ser Glu Glu Ala Ala Glu Pro Arg Met Asp Thr Pro
            180                 185                 190

Glu Asp Gln Asp Leu Pro Pro Cys Pro Glu Asp Ile Ala Lys Glu Lys
        195                 200                 205

Arg Thr Pro Ala Pro Glu Pro Glu Pro Cys Glu Ala Ser Glu Leu Pro
        210                 215                 220

Ala Lys Arg Leu Arg Ser Ser Glu Glu Pro Thr Glu Lys Glu Pro Pro
225                 230                 235                 240

Gly Gln Leu Gln Val Lys Ala Gln Pro Gln Ala Arg Met Thr Val Pro
            245                 250                 255

Lys Gln Thr Gln Thr Pro Asp Leu Leu Pro Glu Ala Leu Glu Ala Gln
            260                 265                 270

Val Leu Pro Arg Phe Gln Pro Arg Val Leu Gln Val Gln Ala Gln Val
            275                 280                 285

Gln Ser Gln Thr Gln Pro Arg Ile Pro Ser Thr Asp Thr Gln Val Gln
            290                 295                 300

Pro Lys Leu Gln Lys Gln Ala Gln Thr Gln Thr Ser Pro Glu His Leu
305                 310                 315                 320

Val Leu Gln Gln Lys Gln Val Gln Pro Gln Leu Gln Gln Glu Ala Glu
            325                 330                 335

Pro Gln Lys Gln Val Gln Pro Val Gln Pro Gln Ala His Ser Gln
            340                 345                 350

Gly Pro Arg Gln Val Gln Leu Gln Gln Glu Ala Glu Pro Leu Lys Gln
            355                 360                 365

Val Gln Pro Gln Val Gln Pro Gln Ala His Ser Gln Pro Pro Arg Gln
            370                 375                 380

Val Gln Leu Gln Leu Gln Lys Gln Val Gln Thr Gln Thr Tyr Pro Gln
385                 390                 395                 400

Val His Thr Gln Ala Gln Pro Ser Val Gln Pro Gln Glu His Pro Pro
            405                 410                 415

Ala Gln Val Ser Val Gln Pro Glu Gln Thr His Glu Gln Pro His
            420                 425                 430

Thr Gln Pro Gln Val Ser Leu Leu Ala Pro Glu Gln Thr Pro Val Val
            435                 440                 445

Val His Val Cys Gly Leu Glu Met Pro Pro Asp Ala Val Glu Ala Gly
            450                 455                 460

Gly Gly Met Glu Lys Thr Leu Pro Glu Pro Val Gly Thr Gln Val Ser
465                 470                 475                 480

Met Glu Glu Ile Gln Asn Glu Ser Ala Cys Gly Leu Asp Val Gly Glu
            485                 490                 495

Cys Glu Asn Arg Ala Arg Glu Met Pro Gly Val Trp Gly Ala Gly Gly
            500                 505                 510

Ser Leu Lys Val Thr Ile Leu Gln Ser Asp Ser Arg Ala Phe Ser
            515                 520                 525

Thr Val Pro Leu Thr Pro Val Pro Arg Pro Ser Asp Ser Val Ser Ser
            530                 535                 540

Thr Pro Ala Ala Thr Ser Thr Pro Ser Lys Gln Ala Leu Gln Phe Phe
545                 550                 555                 560

Cys Tyr Ile Cys Lys Ala Ser Cys Ser Ser Gln Glu Phe Gln Asp
            565                 570                 575

His Met Ser Glu Pro Gln His Gln Gln Arg Leu Gly Glu Ile Gln His
            580                 585                 590
```

```
Met Ser Gln Ala Leu Leu Ser Leu Leu Pro Val Pro Arg Asp Val Leu
            595                 600                 605

Glu Thr Glu Asp Glu Glu Pro Pro Arg Arg Trp Cys Asn Thr Cys
        610                 615                 620

Gln Leu Tyr Tyr Met Gly Asp Leu Ile Gln His Arg Arg Thr Gln Asp
625                 630                 635                 640

His Lys Ile Ala Lys Gln Ser Leu Arg Pro Phe Cys Thr Val Cys Asn
                645                 650                 655

Arg Tyr Phe Lys Thr Pro Arg Lys Phe Val Glu His Val Lys Ser Gln
                660                 665                 670

Gly His Lys Asp Lys Ala Lys Glu Leu Lys Ser Leu Glu Lys Glu Ile
            675                 680                 685

Ala Gly Gln Asp Glu Asp His Phe Ile Thr Val Asp Ala Val Gly Cys
        690                 695                 700

Phe Glu Gly Asp Glu Glu Glu Asp Asp Glu Asp Glu Glu
705                 710                 715                 720

Ile Glu Val Glu Glu Leu Cys Lys Gln Val Arg Ser Arg Asp Ile
                725                 730                 735

Ser Arg Glu Glu Trp Lys Gly Ser Glu Thr Tyr Ser Pro Asn Thr Ala
            740                 745                 750

Tyr Gly Val Asp Phe Leu Val Pro Val Met Gly Tyr Ile Cys Arg Ile
        755                 760                 765

Cys His Lys Phe Tyr His Ser Asn Ser Gly Ala Gln Leu Ser His Cys
    770                 775                 780

Lys Ser Leu Gly His Phe Glu Asn Leu Gln Lys Tyr Lys Ala Ala Lys
785                 790                 795                 800

Asn Pro Ser Pro Thr Thr Arg Pro Val Ser Arg Cys Ala Ile Asn
                805                 810                 815

Ala Arg Asn Ala Leu Thr Ala Leu Phe Thr Ser Ser Gly Arg Pro Pro
                820                 825                 830

Ser Gln Pro Asn Thr Gln Asp Lys Thr Pro Ser Lys Val Thr Ala Arg
            835                 840                 845

Pro Ser Gln Pro Pro Leu Pro Arg Arg Ser Thr Arg Leu Lys Thr
        850                 855                 860

<210> SEQ ID NO 59
<211> LENGTH: 873
<212> TYPE: PRT
<213> ORGANISM: Homo sapiens

<400> SEQUENCE: 59

Met Phe Ser Gln Gln Gln Gln Leu Gln Gln Gln Gln Gln Leu
1               5                   10                  15

Gln Gln Leu Gln Gln Gln Leu Gln Gln Gln Leu Gln Gln
            20                  25                  30

Gln Leu Leu Gln Leu Gln Leu Gln Gln Ser Pro Gln Ala
        35                  40                  45

Pro Leu Pro Met Ala Val Ser Arg Gly Leu Pro Pro Gln Gln Pro Gln
50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Gln Leu Gln Gly Asn
                85                  90                  95

Leu Arg Gly Tyr Gly Met Ala Ser Pro Gly Leu Ala Ala Pro Ser Leu
                100                 105                 110
```

-continued

```
Thr Pro Pro Gln Leu Ala Thr Pro Asn Leu Gln Gln Phe Phe Pro Gln
            115                 120                 125
Ala Thr Arg Gln Ser Leu Leu Gly Pro Pro Val Gly Val Pro Met
    130                 135                 140
Asn Pro Ser Gln Phe Asn Leu Ser Gly Arg Asn Pro Gln Lys Gln Ala
145                 150                 155                 160
Arg Thr Ser Ser Ser Thr Thr Pro Asn Arg Lys Asp Ser Ser Gln
            165                 170                 175
Thr Met Pro Val Glu Asp Lys Ser Asp Pro Glu Gly Ser Glu Glu
            180                 185                 190
Ala Ala Glu Pro Arg Met Asp Thr Pro Glu Asp Gln Asp Leu Pro Pro
        195                 200                 205
Cys Pro Glu Asp Ile Ala Lys Glu Lys Arg Thr Pro Ala Pro Glu Pro
        210                 215                 220
Glu Pro Cys Glu Ala Ser Glu Leu Pro Ala Lys Arg Leu Arg Ser Ser
225                 230                 235                 240
Glu Glu Pro Thr Glu Lys Glu Pro Pro Gly Gln Leu Gln Val Lys Ala
            245                 250                 255
Gln Pro Gln Ala Arg Met Thr Val Pro Lys Gln Thr Gln Thr Pro Asp
            260                 265                 270
Leu Leu Pro Glu Ala Leu Glu Ala Gln Val Leu Pro Arg Phe Gln Pro
        275                 280                 285
Arg Val Leu Gln Val Gln Ala Gln Val Gln Ser Gln Thr Gln Pro Arg
    290                 295                 300
Ile Pro Ser Thr Asp Thr Gln Val Gln Pro Lys Leu Gln Lys Gln Ala
305                 310                 315                 320
Gln Thr Gln Thr Ser Pro Glu His Leu Val Leu Gln Gln Lys Gln Val
            325                 330                 335
Gln Pro Gln Leu Gln Gln Glu Ala Glu Pro Gln Lys Gln Val Gln Pro
        340                 345                 350
Gln Val Gln Pro Gln Ala His Ser Gln Gly Pro Arg Gln Val Gln Leu
    355                 360                 365
Gln Gln Glu Ala Glu Pro Leu Lys Gln Val Gln Pro Gln Val Gln Pro
370                 375                 380
Gln Ala His Ser Gln Pro Pro Arg Gln Val Gln Leu Gln Leu Gln Lys
385                 390                 395                 400
Gln Val Gln Thr Gln Thr Tyr Pro Gln Val His Thr Gln Ala Gln Pro
            405                 410                 415
Ser Val Gln Pro Gln Glu His Pro Pro Ala Gln Val Ser Val Gln Pro
            420                 425                 430
Pro Glu Gln Thr His Glu Gln Pro His Thr Gln Pro Gln Val Ser Leu
        435                 440                 445
Leu Ala Pro Glu Gln Thr Pro Val Val His Val Cys Gly Leu Glu
        450                 455                 460
Met Pro Pro Asp Ala Val Glu Ala Gly Gly Gly Met Glu Lys Thr Leu
465                 470                 475                 480
Pro Glu Pro Val Gly Thr Gln Val Ser Met Glu Glu Ile Gln Asn Glu
            485                 490                 495
Ser Ala Cys Gly Leu Asp Val Gly Glu Cys Glu Asn Arg Ala Arg Glu
            500                 505                 510
Met Pro Gly Val Trp Gly Ala Gly Gly Ser Leu Lys Val Thr Ile Leu
        515                 520                 525
```

-continued

```
Gln Ser Ser Asp Ser Arg Ala Phe Ser Thr Val Pro Leu Thr Pro Val
    530                 535                 540

Pro Arg Pro Ser Asp Ser Val Ser Ser Thr Pro Ala Ala Thr Ser Thr
545                 550                 555                 560

Pro Ser Lys Gln Ala Leu Gln Phe Phe Cys Tyr Ile Cys Lys Ala Ser
                565                 570                 575

Cys Ser Ser Gln Gln Glu Phe Gln Asp His Met Ser Glu Pro Gln His
            580                 585                 590

Gln Gln Arg Leu Gly Glu Ile Gln His Met Ser Gln Ala Cys Leu Leu
        595                 600                 605

Ser Leu Leu Pro Val Pro Arg Asp Val Leu Glu Thr Glu Asp Glu Glu
    610                 615                 620

Pro Pro Arg Arg Trp Cys Asn Thr Cys Gln Leu Tyr Tyr Met Gly
625                 630                 635                 640

Asp Leu Ile Gln His Arg Arg Thr Gln Asp His Lys Ile Ala Lys Gln
                645                 650                 655

Ser Leu Arg Pro Phe Cys Thr Val Cys Asn Arg Tyr Phe Lys Thr Pro
            660                 665                 670

Arg Lys Phe Val Glu His Val Lys Ser Gln Gly His Lys Asp Lys Ala
        675                 680                 685

Lys Glu Leu Lys Ser Leu Glu Lys Glu Ile Ala Gly Gln Asp Glu Asp
    690                 695                 700

His Phe Ile Thr Val Asp Ala Val Gly Cys Phe Glu Gly Asp Glu Glu
705                 710                 715                 720

Glu Glu Glu Asp Asp Glu Asp Glu Glu Ile Glu Val Glu Glu Glu
                725                 730                 735

Leu Cys Lys Gln Val Arg Ser Arg Asp Ile Ser Arg Glu Glu Trp Lys
        740                 745                 750

Gly Ser Glu Thr Tyr Ser Pro Asn Thr Ala Tyr Gly Val Asp Phe Leu
    755                 760                 765

Val Pro Val Met Gly Tyr Ile Cys Arg Ile Cys His Lys Phe Tyr His
770                 775                 780

Ser Asn Ser Gly Ala Gln Leu Ser His Cys Lys Ser Leu Gly His Phe
785                 790                 795                 800

Glu Asn Leu Gln Lys Tyr Lys Ala Ala Lys Asn Pro Ser Pro Thr Thr
                805                 810                 815

Arg Pro Val Ser Arg Arg Cys Ala Ile Asn Ala Arg Asn Ala Leu Thr
            820                 825                 830

Ala Leu Phe Thr Ser Ser Gly Arg Pro Pro Ser Gln Pro Asn Thr Gln
        835                 840                 845

Asp Lys Thr Pro Ser Lys Val Thr Ala Arg Pro Ser Gln Pro Pro Leu
    850                 855                 860

Pro Arg Arg Ser Thr Arg Leu Lys Thr
865                 870

<210> SEQ ID NO 60
<211> LENGTH: 892
<212> TYPE: PRT
<213> ORGANISM: Homo sapiens

<400> SEQUENCE: 60

Met Phe Ser Gln Gln Gln Gln Leu Gln Gln Gln Gln Gln Gln Gln Leu
1               5                   10                  15

Gln Gln Leu Gln Gln Gln Gln Leu Gln Gln Gln Leu Gln Gln Gln
            20                  25                  30
```

```
Gln Leu Leu Gln Leu Gln Gln Leu Leu Gln Ser Pro Pro Gln Ala
        35                  40                  45
Pro Leu Pro Met Ala Val Ser Arg Gly Leu Pro Pro Gln Gln Pro Gln
    50                  55                  60
Gln Pro Leu Leu Asn Leu Gln Gly Thr Asn Ser Ala Ser Leu Leu Asn
65                  70                  75                  80
Gly Ser Met Leu Gln Arg Ala Leu Leu Leu Gln Leu Gln Gly Leu
                85                  90                  95
Asp Gln Phe Ala Met Pro Ala Thr Tyr Asp Thr Ala Gly Leu Thr
            100                 105                 110
Met Pro Thr Ala Thr Leu Gly Asn Leu Arg Gly Tyr Gly Met Ala Ser
        115                 120                 125
Pro Gly Leu Ala Ala Pro Ser Leu Thr Pro Pro Gln Leu Ala Thr Pro
    130                 135                 140
Asn Leu Gln Gln Phe Phe Pro Gln Ala Thr Arg Gln Ser Leu Leu Gly
145                 150                 155                 160
Pro Pro Pro Val Gly Val Pro Met Asn Pro Ser Gln Phe Asn Leu Ser
                165                 170                 175
Gly Arg Asn Pro Gln Lys Gln Ala Arg Thr Ser Ser Ser Thr Thr Pro
            180                 185                 190
Asn Arg Lys Thr Met Pro Val Glu Asp Lys Ser Asp Pro Pro Glu Gly
        195                 200                 205
Ser Glu Glu Ala Ala Glu Pro Arg Met Asp Thr Pro Glu Asp Gln Asp
    210                 215                 220
Leu Pro Pro Cys Pro Glu Asp Ile Ala Lys Glu Lys Arg Thr Pro Ala
225                 230                 235                 240
Pro Glu Pro Glu Pro Cys Glu Ala Ser Glu Leu Pro Ala Lys Arg Leu
                245                 250                 255
Arg Ser Ser Glu Glu Pro Thr Glu Lys Glu Pro Pro Gly Gln Leu Gln
            260                 265                 270
Val Lys Ala Gln Pro Gln Ala Arg Met Thr Val Pro Lys Gln Thr Gln
        275                 280                 285
Thr Pro Asp Leu Leu Pro Glu Ala Leu Glu Ala Gln Val Leu Pro Arg
    290                 295                 300
Phe Gln Pro Arg Val Leu Gln Val Gln Ala Gly Val Gln Ser Gln Thr
305                 310                 315                 320
Gln Pro Arg Ile Pro Ser Thr Asp Thr Gln Val Gln Pro Lys Leu Gln
                325                 330                 335
Lys Gln Ala Gln Thr Gln Thr Ser Pro Glu His Leu Val Leu Gln Gln
            340                 345                 350
Lys Gln Val Gln Pro Gln Leu Gln Gln Glu Ala Glu Pro Gln Lys Gln
        355                 360                 365
Val Gln Pro Gln Val Gln Pro Ala His Ser Gln Gly Pro Arg Gln
    370                 375                 380
Val Gln Leu Gln Gln Glu Ala Glu Pro Leu Lys Gln Val Gln Pro Gln
385                 390                 395                 400
Val Gln Pro Gln Ala His Ser Gln Pro Arg Gln Val Gln Leu Gln
                405                 410                 415
Leu Gln Lys Gln Val Gln Thr Gln Thr Tyr Pro Gln Val His Thr Gln
            420                 425                 430
Ala Gln Pro Ser Val Gln Pro Gln Glu His Pro Pro Ala Gln Val Ser
        435                 440                 445
```

```
Val Gln Pro Pro Glu Gln Thr His Glu Gln Pro His Thr Gln Pro Gln
    450                 455                 460
Val Ser Leu Leu Ala Pro Glu Gln Thr Pro Val Val His Val Cys
465                 470                 475                 480
Gly Leu Glu Met Pro Pro Asp Ala Val Glu Ala Gly Gly Met Glu
                485                 490                 495
Lys Thr Leu Pro Glu Pro Val Gly Thr Gln Val Ser Met Glu Glu Ile
                500                 505                 510
Gln Asn Glu Ser Ala Cys Gly Leu Asp Val Gly Glu Cys Glu Asn Arg
            515                 520                 525
Ala Arg Glu Met Pro Gly Val Trp Gly Ala Gly Gly Ser Leu Lys Val
    530                 535                 540
Thr Ile Leu Gln Ser Ser Asp Ser Arg Ala Phe Ser Thr Val Pro Leu
545                 550                 555                 560
Thr Pro Val Pro Arg Pro Ser Asp Ser Val Ser Ser Thr Pro Ala Ala
                565                 570                 575
Thr Ser Thr Pro Ser Lys Gln Ala Leu Gln Phe Phe Cys Tyr Ile Cys
                580                 585                 590
Lys Ala Ser Cys Ser Ser Gln Gln Glu Phe Gln Asp His Met Ser Glu
            595                 600                 605
Pro Gln His Gln Gln Arg Leu Gly Glu Ile Gln His Met Ser Gln Ala
    610                 615                 620
Cys Leu Leu Ser Leu Leu Pro Val Pro Arg Asp Val Leu Glu Thr Glu
625                 630                 635                 640
Asp Glu Glu Pro Pro Arg Arg Trp Cys Asn Thr Cys Gln Leu Tyr
                645                 650                 655
Tyr Met Gly Asp Leu Ile Gln His Arg Arg Thr Gln Asp His Lys Ile
                660                 665                 670
Ala Lys Gln Ser Leu Arg Pro Phe Cys Thr Val Cys Asn Arg Tyr Phe
            675                 680                 685
Lys Thr Pro Arg Lys Phe Val Glu His Val Lys Ser Gln Gly His Lys
    690                 695                 700
Asp Lys Ala Lys Glu Leu Lys Ser Leu Glu Lys Glu Ile Ala Gly Gln
705                 710                 715                 720
Asp Glu Asp His Phe Ile Thr Val Asp Ala Val Gly Cys Phe Glu Gly
                725                 730                 735
Asp Glu Glu Glu Glu Asp Glu Asp Glu Glu Ile Glu Val
                740                 745                 750
Glu Glu Glu Leu Cys Lys Gln Val Arg Ser Arg Asp Ile Ser Arg Glu
        755                 760                 765
Glu Trp Lys Gly Ser Glu Thr Tyr Ser Pro Asn Thr Ala Tyr Gly Val
    770                 775                 780
Asp Phe Leu Val Pro Val Met Gly Tyr Ile Cys Arg Ile Cys His Lys
785                 790                 795                 800
Phe Tyr His Ser Asn Ser Gly Ala Gln Leu Ser His Cys Lys Ser Leu
                805                 810                 815
Gly His Phe Glu Asn Leu Gln Lys Tyr Lys Ala Ala Lys Asn Pro Ser
            820                 825                 830
Pro Thr Thr Arg Pro Val Ser Arg Arg Cys Ala Ile Asn Ala Arg Asn
    835                 840                 845
Ala Leu Thr Ala Leu Phe Thr Ser Ser Gly Arg Pro Pro Ser Gln Pro
850                 855                 860
Asn Thr Gln Asp Lys Thr Pro Ser Lys Val Thr Ala Arg Pro Ser Gln
```

```
                  865                 870                 875                 880
Pro Pro Leu Pro Arg Arg Ser Thr Arg Leu Lys Thr
                885                 890

<210> SEQ ID NO 61
<211> LENGTH: 868
<212> TYPE: PRT
<213> ORGANISM: Homo sapiens

<400> SEQUENCE: 61

Met Phe Ser Gln Gln Gln Gln Leu Gln Gln Gln Gln Gln Leu
1               5                   10                  15

Gln Gln Leu Gln Gln Gln Gln Leu Gln Gln Gln Leu Gln Gln Gln
                20                  25                  30

Gln Leu Leu Gln Leu Gln Gln Leu Gln Gln Ser Pro Pro Gln Ala
            35                  40                  45

Pro Leu Pro Met Ala Val Ser Arg Gly Leu Pro Pro Gln Gln Pro Gln
    50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Gln Leu Gln Gly Leu
                85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
            115                 120                 125

Pro Gly Leu Ala Ala Pro Ser Leu Thr Pro Gln Leu Ala Thr Pro
    130                 135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
            180                 185                 190

Asn Arg Lys Asp Ser Ser Gln Thr Met Pro Val Glu Asp Lys Ser
            195                 200                 205

Asp Pro Pro Glu Gly Ser Glu Glu Ala Ala Glu Pro Arg Met Asp Thr
    210                 215                 220

Pro Glu Asp Gln Asp Leu Pro Pro Cys Pro Glu Asp Ile Ala Lys Glu
225                 230                 235                 240

Lys Arg Thr Pro Ala Pro Glu Pro Glu Pro Cys Glu Ala Ser Glu Leu
                245                 250                 255

Pro Ala Lys Arg Leu Arg Ser Ser Glu Glu Pro Thr Glu Lys Glu Pro
            260                 265                 270

Pro Gly Gln Leu Gln Val Lys Ala Gln Pro Gln Ala Arg Met Thr Val
            275                 280                 285

Pro Lys Gln Thr Gln Thr Pro Asp Leu Leu Pro Glu Ala Leu Glu Ala
    290                 295                 300

Gln Val Leu Pro Arg Phe Gln Pro Arg Val Leu Gln Val Gln Ala Gln
305                 310                 315                 320

Val Gln Ser Gln Thr Gln Pro Arg Ile Pro Ser Thr Asp Thr Gln Val
                325                 330                 335

Gln Pro Lys Leu Gln Lys Gln Ala Gln Thr Gln Thr Ser Pro Glu His
            340                 345                 350
```

-continued

```
Leu Val Leu Gln Gln Lys Gln Val Gln Pro Gln Leu Gln Gln Glu Ala
            355                 360                 365
Glu Pro Gln Lys Gln Val Gln Pro Val Gln Pro Gln Ala His Ser
        370                 375                 380
Gln Gly Pro Arg Gln Val Gln Leu Gln Gln Ala Glu Pro Leu Lys
385                 390                 395                 400
Gln Val Gln Gln Val His Thr Gln Ala Gln Pro Ser Val Gln Pro Gln
                405                 410                 415
Glu His Pro Pro Ala Gln Val Ser Val Gln Pro Glu Gln Thr His
            420                 425                 430
Glu Gln Pro His Thr Gln Pro Gln Val Ser Leu Leu Ala Pro Glu Gln
                435                 440                 445
Thr Pro Val Val Val His Val Cys Gly Leu Glu Met Pro Pro Asp Ala
    450                 455                 460
Val Glu Ala Gly Gly Gly Met Glu Lys Thr Leu Pro Glu Pro Val Gly
465                 470                 475                 480
Thr Gln Val Ser Met Glu Glu Ile Gln Asn Glu Ser Ala Cys Gly Leu
                485                 490                 495
Asp Val Gly Glu Cys Glu Asn Arg Ala Arg Glu Met Pro Gly Val Trp
            500                 505                 510
Gly Ala Gly Gly Ser Leu Lys Val Thr Ile Leu Gln Ser Ser Asp Ser
        515                 520                 525
Arg Ala Phe Ser Thr Val Pro Leu Thr Pro Val Pro Arg Pro Ser Asp
    530                 535                 540
Ser Val Ser Ser Thr Pro Ala Ala Thr Ser Thr Pro Ser Lys Gln Ala
545                 550                 555                 560
Leu Gln Phe Phe Cys Tyr Ile Cys Lys Ala Ser Cys Ser Ser Gln Gln
                565                 570                 575
Glu Phe Gln Asp His Met Ser Glu Pro Gln His Gln Gln Arg Leu Gly
            580                 585                 590
Glu Ile Gln His Met Ser Gln Ala Cys Leu Leu Ser Leu Leu Pro Val
        595                 600                 605
Pro Arg Asp Val Leu Glu Thr Glu Asp Glu Glu Pro Pro Arg Arg
    610                 615                 620
Trp Cys Asn Thr Cys Gln Leu Tyr Tyr Met Gly Asp Leu Ile Gln His
625                 630                 635                 640
Arg Arg Thr Gln Asp His Lys Ile Ala Lys Gln Ser Leu Arg Pro Phe
                645                 650                 655
Cys Thr Val Cys Asn Arg Tyr Phe Lys Thr Pro Arg Lys Phe Val Glu
            660                 665                 670
His Val Lys Ser Gln Gly His Lys Asp Lys Ala Lys Glu Leu Lys Ser
        675                 680                 685
Leu Glu Lys Glu Ile Ala Gly Gln Asp Glu His Phe Ile Thr Val
    690                 695                 700
Asp Ala Val Gly Cys Phe Glu Gly Asp Glu Glu Glu Glu Asp Asp
705                 710                 715                 720
Glu Asp Glu Glu Glu Ile Glu Val Glu Glu Leu Cys Lys Gln Val
                725                 730                 735
Arg Ser Arg Asp Ile Ser Arg Glu Glu Trp Lys Gly Ser Glu Thr Tyr
            740                 745                 750
Ser Pro Asn Thr Ala Tyr Gly Val Asp Phe Leu Val Pro Val Met Gly
        755                 760                 765
Tyr Ile Cys Arg Ile Cys His Lys Phe Tyr His Ser Asn Ser Gly Ala
```

```
                    770                 775                 780
Gln Leu Ser His Cys Lys Ser Leu Gly His Phe Glu Asn Leu Gln Lys
785                 790                 795                 800

Tyr Lys Ala Ala Lys Asn Pro Ser Pro Thr Thr Arg Pro Val Ser Arg
                805                 810                 815

Arg Cys Ala Ile Asn Ala Arg Asn Ala Leu Thr Ala Leu Phe Thr Ser
            820                 825                 830

Ser Gly Arg Pro Pro Ser Gln Pro Asn Thr Gln Asp Lys Thr Pro Ser
        835                 840                 845

Lys Val Thr Ala Arg Pro Ser Gln Pro Pro Leu Pro Arg Arg Ser Thr
850                 855                 860

Arg Leu Lys Thr
865

<210> SEQ ID NO 62
<211> LENGTH: 841
<212> TYPE: PRT
<213> ORGANISM: Homo sapiens

<400> SEQUENCE: 62

Met Phe Ser Gln Gln Gln Gln Leu Gln Gln Gln Gln Gln Gln Gln Leu
1               5                   10                  15

Gln Gln Leu Gln Gln Gln Leu Gln Gln Gln Leu Gln Gln Gln Gln Gln
            20                  25                  30

Gln Leu Leu Gln Leu Gln Gln Leu Leu Gln Gln Ser Pro Pro Gln Ala
        35                  40                  45

Pro Leu Pro Met Ala Val Ser Arg Gly Leu Pro Pro Gln Gln Pro Gln
    50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Gln Leu Gln Gly Leu
                85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
        115                 120                 125

Pro Gly Leu Ala Ala Pro Ser Leu Thr Pro Pro Gln Leu Ala Thr Pro
    130                 135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
            180                 185                 190

Asn Arg Lys Asp Ser Ser Ser Gln Thr Met Pro Val Glu Asp Lys Ser
        195                 200                 205

Asp Pro Pro Glu Gly Ser Glu Glu Ala Ala Glu Pro Arg Met Asp Thr
    210                 215                 220

Pro Glu Asp Gln Asp Leu Pro Pro Cys Pro Glu Asp Ile Ala Lys Glu
225                 230                 235                 240

Lys Arg Thr Pro Ala Pro Glu Pro Glu Pro Cys Glu Ala Ser Glu Leu
                245                 250                 255

Pro Ala Lys Arg Leu Arg Ser Ser Glu Glu Pro Thr Glu Lys Glu Pro
            260                 265                 270
```

-continued

```
Pro Gly Gln Leu Gln Val Lys Ala Gln Pro Gln Ala Arg Met Thr Val
        275                 280                 285
Pro Lys Gln Thr Gln Thr Pro Asp Leu Leu Pro Glu Ala Leu Glu Ala
    290                 295                 300
Gln Val Leu Pro Arg Phe Gln Pro Arg Val Leu Gln Val Gln Ala Gln
305                 310                 315                 320
Val Gln Ser Gln Thr Gln Pro Arg Ile Pro Ser Thr Asp Thr Gln Val
            325                 330                 335
Gln Pro Lys Leu Gln Lys Gln Ala Gln Thr Gln Thr Ser Pro Glu His
            340                 345                 350
Leu Val Leu Gln Gln Lys Gln Val Gln Pro Gln Leu Gln Gln Glu Ala
            355                 360                 365
Glu Pro Gln Lys Gln Val Gln Pro Gln Val His Thr Gln Ala Gln Pro
    370                 375                 380
Ser Val Gln Pro Gln Glu His Pro Pro Ala Gln Val Ser Val Gln Pro
385                 390                 395                 400
Pro Glu Gln Thr His Glu Gln Pro His Thr Gln Pro Gln Val Ser Leu
            405                 410                 415
Leu Ala Pro Glu Gln Thr Pro Val Val His Val Cys Gly Leu Glu
            420                 425                 430
Met Pro Pro Asp Ala Val Glu Ala Gly Gly Gly Met Glu Lys Thr Leu
    435                 440                 445
Pro Glu Pro Val Gly Thr Gln Val Ser Met Glu Glu Ile Gln Asn Glu
    450                 455                 460
Ser Ala Cys Gly Leu Asp Val Gly Glu Cys Glu Asn Arg Ala Arg Glu
465                 470                 475                 480
Met Pro Gly Val Trp Gly Ala Gly Gly Ser Leu Lys Val Thr Ile Leu
            485                 490                 495
Gln Ser Ser Asp Ser Arg Ala Phe Ser Thr Val Pro Leu Thr Pro Val
            500                 505                 510
Pro Arg Pro Ser Asp Ser Val Ser Ser Thr Pro Ala Ala Thr Ser Thr
    515                 520                 525
Pro Ser Lys Gln Ala Leu Gln Phe Phe Cys Tyr Ile Cys Lys Ala Ser
    530                 535                 540
Cys Ser Ser Gln Gln Glu Phe Gln Asp His Met Ser Glu Pro Gln His
545                 550                 555                 560
Gln Gln Arg Leu Gly Glu Ile Gln His Met Ser Gln Ala Cys Leu Leu
            565                 570                 575
Ser Leu Leu Pro Val Pro Arg Asp Val Leu Glu Thr Glu Asp Glu Glu
            580                 585                 590
Pro Pro Pro Arg Arg Trp Cys Asn Thr Cys Gln Leu Tyr Tyr Met Gly
    595                 600                 605
Asp Leu Ile Gln His Arg Arg Thr Gln Asp His Lys Ile Ala Lys Gln
    610                 615                 620
Ser Leu Arg Pro Phe Cys Thr Val Cys Asn Arg Tyr Phe Lys Thr Pro
625                 630                 635                 640
Arg Lys Phe Val Glu His Val Lys Ser Gln Gly His Lys Asp Lys Ala
            645                 650                 655
Lys Glu Leu Lys Ser Leu Glu Lys Glu Ile Ala Gly Gln Asp Glu Asp
            660                 665                 670
His Phe Ile Thr Val Asp Ala Val Gly Cys Phe Glu Gly Asp Glu Glu
            675                 680                 685
Glu Glu Glu Asp Asp Glu Asp Glu Glu Glu Ile Glu Val Glu Glu Glu
```

```
                  690                 695                 700
Leu Cys Lys Gln Val Arg Ser Arg Asp Ile Ser Arg Glu Glu Trp Lys
705                 710                 715                 720

Gly Ser Glu Thr Tyr Ser Pro Asn Thr Ala Tyr Gly Val Asp Phe Leu
                725                 730                 735

Val Pro Val Met Gly Tyr Ile Cys Arg Ile Cys His Lys Phe Tyr His
                740                 745                 750

Ser Asn Ser Gly Ala Gln Leu Ser His Cys Lys Ser Leu Gly His Phe
                755                 760                 765

Glu Asn Leu Gln Lys Tyr Lys Ala Ala Lys Asn Pro Ser Pro Thr Thr
770                 775                 780

Arg Pro Val Ser Arg Cys Ala Ile Asn Ala Arg Asn Ala Leu Thr
785                 790                 795                 800

Ala Leu Phe Thr Ser Ser Gly Arg Pro Pro Ser Gln Pro Asn Thr Gln
                805                 810                 815

Asp Lys Thr Pro Ser Lys Val Thr Ala Arg Pro Ser Gln Pro Pro Leu
                820                 825                 830

Pro Arg Arg Ser Thr Arg Leu Lys Thr
                835                 840

<210> SEQ ID NO 63
<211> LENGTH: 785
<212> TYPE: PRT
<213> ORGANISM: Homo sapiens

<400> SEQUENCE: 63

Met Phe Ser Gln Gln Gln Gln Leu Gln Gln Gln Gln Gln Gln Gln Leu
1               5                   10                  15

Gln Gln Leu Gln Gln Gln Leu Gln Gln Gln Leu Gln Gln Gln Gln Gln
                20                  25                  30

Gln Leu Leu Gln Leu Gln Leu Leu Gln Gln Ser Pro Pro Gln Ala
            35                  40                  45

Pro Leu Pro Met Ala Val Ser Arg Gly Leu Pro Pro Gln Gln Pro Gln
        50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Leu Gln Gly Leu
                85                  90                  95

Asp Gln Phe Ala Met Pro Pro Ala Thr Tyr Asp Thr Ala Gly Leu Thr
                100                 105                 110

Met Pro Thr Ala Thr Leu Gly Asn Leu Arg Gly Tyr Gly Met Ala Ser
                115                 120                 125

Pro Gly Leu Ala Ala Pro Ser Leu Thr Pro Gln Leu Ala Thr Pro
            130                 135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
                180                 185                 190

Asn Arg Lys Asp Ser Ser Ser Gln Thr Met Pro Val Glu Asp Lys Ser
                195                 200                 205

Asp Pro Pro Glu Gly Ser Glu Glu Ala Ala Glu Pro Arg Met Asp Thr
    210                 215                 220
```

-continued

```
Pro Glu Asp Gln Asp Leu Pro Pro Cys Pro Glu Asp Ile Ala Lys Glu
225                 230                 235                 240

Lys Arg Thr Pro Ala Pro Glu Pro Glu Pro Cys Glu Ala Ser Glu Leu
            245                 250                 255

Pro Ala Lys Arg Leu Arg Ser Ser Glu Pro Thr Glu Lys Glu Pro
        260                 265                 270

Pro Gly Gln Leu Gln Val Lys Ala Gln Pro Gln Ala Arg Met Thr Val
    275                 280                 285

Pro Lys Gln Thr Gln Thr Pro Asp Leu Leu Pro Glu Ala Leu Glu Ala
    290                 295                 300

Gln Val Leu Pro Arg Phe Gln Pro Arg Val Leu Gln Val Gln Ala Pro
305                 310                 315                 320

Gln Val His Thr Gln Ala Gln Pro Ser Val Gln Pro Gln Glu His Pro
            325                 330                 335

Pro Ala Gln Val Ser Val Gln Pro Glu Gln Thr His Glu Gln Pro
        340                 345                 350

His Thr Gln Pro Gln Val Ser Leu Leu Ala Pro Glu Gln Thr Pro Val
        355                 360                 365

Val Val His Val Cys Gly Leu Glu Met Pro Pro Asp Ala Val Glu Ala
370                 375                 380

Gly Gly Gly Met Glu Lys Thr Leu Pro Glu Pro Val Gly Thr Gln Val
385                 390                 395                 400

Ser Met Glu Glu Ile Gln Asn Glu Ser Ala Cys Gly Leu Asp Val Gly
            405                 410                 415

Glu Cys Glu Asn Arg Ala Arg Glu Met Pro Gly Val Trp Gly Ala Gly
            420                 425                 430

Gly Ser Leu Lys Val Thr Ile Leu Gln Ser Ser Asp Ser Arg Ala Phe
        435                 440                 445

Ser Thr Val Pro Leu Thr Pro Val Pro Arg Pro Ser Asp Ser Val Ser
    450                 455                 460

Ser Thr Pro Ala Ala Thr Ser Thr Pro Ser Lys Gln Ala Leu Gln Phe
465                 470                 475                 480

Phe Cys Tyr Ile Cys Lys Ala Ser Cys Ser Ser Gln Gln Glu Phe Gln
            485                 490                 495

Asp His Met Ser Glu Pro Gln His Gln Gln Arg Leu Gly Glu Ile Gln
            500                 505                 510

His Met Ser Gln Ala Cys Leu Leu Ser Leu Leu Pro Val Pro Arg Asp
        515                 520                 525

Val Leu Glu Thr Glu Asp Glu Glu Pro Pro Arg Arg Trp Cys Asn
530                 535                 540

Thr Cys Gln Leu Tyr Tyr Met Gly Asp Leu Ile Gln His Arg Arg Thr
545                 550                 555                 560

Gln Asp His Lys Ile Ala Lys Gln Ser Leu Arg Pro Phe Cys Thr Val
            565                 570                 575

Cys Asn Arg Tyr Phe Lys Thr Pro Arg Lys Phe Val Glu His Val Lys
            580                 585                 590

Ser Gln Gly His His Lys Asp Lys Ala Lys Glu Leu Lys Ser Leu Lys
        595                 600                 605

Glu Ile Ala Gly Gln Asp Glu His Phe Ile Thr Val Asp Ala Val
        610                 615                 620

Gly Cys Phe Glu Gly Asp Glu Glu Glu Asp Glu Asp Glu
625                 630                 635                 640

Glu Glu Ile Glu Val Glu Glu Glu Leu Cys Lys Gln Val Arg Ser Arg
```

-continued

```
                645                 650                 655
Asp Ile Ser Arg Glu Glu Trp Lys Gly Ser Glu Thr Tyr Ser Pro Asn
            660                 665                 670

Thr Ala Tyr Gly Val Asp Phe Leu Val Pro Val Met Gly Tyr Ile Cys
        675                 680                 685

Arg Ile Cys His Lys Phe Tyr His Ser Asn Ser Gly Ala Gln Leu Ser
    690                 695                 700

His Cys Lys Ser Leu Gly His Phe Glu Asn Leu Gln Lys Tyr Lys Ala
705                 710                 715                 720

Ala Lys Asn Pro Ser Pro Thr Thr Arg Pro Val Ser Arg Arg Cys Ala
                725                 730                 735

Ile Asn Ala Arg Asn Ala Leu Thr Ala Leu Phe Thr Ser Ser Gly Arg
            740                 745                 750

Pro Pro Ser Gln Pro Asn Thr Gln Asp Lys Thr Pro Ser Lys Val Thr
        755                 760                 765

Ala Arg Pro Ser Gln Pro Leu Pro Arg Arg Ser Thr Arg Leu Lys
    770                 775                 780

Thr
785

<210> SEQ ID NO 64
<211> LENGTH: 889
<212> TYPE: PRT
<213> ORGANISM: Homo sapiens

<400> SEQUENCE: 64

Met Phe Ser Gln Gln Gln Gln Leu Gln Gln Gln Gln Gln Gln Gln Leu
1               5                   10                  15

Gln Gln Leu Gln Gln Gln Leu Gln Gln Gln Leu Gln Gln Gln Gln Gln
            20                  25                  30

Gln Leu Leu Gln Leu Gln Leu Leu Gln Gln Ser Pro Pro Gln Ala
        35                  40                  45

Pro Leu Pro Met Ala Val Ser Arg Gly Leu Pro Pro Gln Gln Pro Gln
    50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Gln Leu Gln Gly Leu
                85                  90                  95

Asp Gln Phe Ala Met Pro Pro Ala Thr Tyr Asp Thr Ala Gly Leu Thr
            100                 105                 110

Met Pro Thr Ala Thr Leu Gly Asn Leu Arg Gly Tyr Gly Met Ala Ser
        115                 120                 125

Pro Gly Leu Ala Ala Pro Ser Leu Thr Pro Pro Gln Leu Ala Thr Pro
    130                 135                 140

Asn Leu Gln Gln Phe Phe Pro Gln Ala Thr Arg Gln Ser Leu Leu Gly
145                 150                 155                 160

Pro Pro Pro Val Gly Val Pro Met Asn Pro Ser Gln Phe Asn Leu Ser
                165                 170                 175

Gly Arg Asn Pro Gln Lys Gln Ala Arg Thr Ser Ser Ser Thr Thr Pro
            180                 185                 190

Asn Arg Lys Asp Ser Ser Ser Gln Thr Met Pro Val Glu Asp Lys Ser
        195                 200                 205

Asp Pro Pro Glu Gly Ser Glu Glu Ala Ala Glu Pro Arg Met Asp Thr
    210                 215                 220
```

-continued

```
Pro Glu Asp Gln Asp Leu Pro Pro Cys Pro Glu Asp Ile Ala Lys Glu
225                 230                 235                 240

Lys Arg Thr Pro Ala Pro Glu Pro Glu Pro Cys Glu Ala Ser Glu Leu
            245                 250                 255

Pro Ala Lys Arg Leu Arg Ser Ser Glu Glu Pro Thr Glu Lys Glu Pro
        260                 265                 270

Pro Gly Gln Leu Gln Val Lys Ala Gln Pro Gln Ala Arg Met Thr Val
    275                 280                 285

Pro Lys Gln Thr Gln Thr Pro Asp Leu Leu Pro Glu Ala Leu Glu Ala
    290                 295                 300

Gln Val Leu Pro Arg Phe Gln Pro Arg Val Leu Gln Val Gln Ala Gln
305                 310                 315                 320

Val Gln Ser Gln Thr Gln Pro Arg Ile Pro Ser Thr Asp Thr Gln Val
            325                 330                 335

Gln Pro Lys Leu Gln Lys Gln Ala Gln Thr Gln Thr Ser Pro Glu His
        340                 345                 350

Leu Val Leu Gln Gln Lys Gln Val Gln Pro Gln Leu Gln Gln Glu Ala
        355                 360                 365

Glu Pro Gln Lys Gln Val Pro Gln Val Gln Pro Gln Ala His Ser
370                 375                 380

Gln Gly Pro Arg Gln Val Gln Leu Gln Gln Glu Ala Glu Pro Leu Lys
385                 390                 395                 400

Gln Val Gln Pro Gln Val Gln Pro Gln Ala His Ser Gln Pro Pro Arg
            405                 410                 415

Gln Val Gln Leu Gln Leu Gln Lys Gln Val Gln Thr Gln Thr Tyr Pro
        420                 425                 430

Gln Val His Thr Gln Ala Gln Pro Ser Val Gln Pro Gln Glu His Pro
        435                 440                 445

Pro Ala Gln Val Ser Val Gln Pro Glu Gln Thr His Glu Gln Pro
450                 455                 460

His Thr Gln Pro Gln Val Ser Leu Leu Ala Pro Glu Gln Thr Pro Val
465                 470                 475                 480

Val Val His Val Cys Gly Leu Glu Met Pro Pro Asp Ala Val Glu Ala
            485                 490                 495

Gly Gly Gly Met Glu Lys Thr Leu Pro Glu Pro Val Gly Thr Gln Val
        500                 505                 510

Ser Met Glu Glu Ile Gln Asn Glu Ser Ala Cys Gly Leu Asp Val Gly
        515                 520                 525

Glu Cys Glu Asn Arg Ala Arg Glu Met Pro Gly Val Trp Gly Ala Gly
530                 535                 540

Gly Ser Leu Lys Val Thr Ile Leu Gln Ser Ser Asp Ser Arg Ala Phe
545                 550                 555                 560

Ser Thr Val Pro Leu Thr Pro Val Pro Arg Pro Ser Asp Ser Val Ser
            565                 570                 575

Ser Thr Pro Ala Ala Thr Ser Thr Pro Ser Lys Gln Ala Leu Gln Phe
        580                 585                 590

Phe Cys Tyr Ile Cys Lys Ala Ser Cys Ser Ser Gln Glu Phe Gln
        595                 600                 605

Asp His Met Ser Glu Pro Gln His Gln Arg Leu Gly Glu Ile Gln
610                 615                 620

His Met Ser Gln Ala Cys Leu Leu Ser Leu Leu Pro Val Pro Arg Asp
625                 630                 635                 640

Val Leu Glu Thr Glu Asp Glu Glu Pro Pro Pro Arg Arg Trp Cys Asn
```

```
                    645                 650                 655
Thr Cys Gln Leu Tyr Tyr Met Gly Asp Leu Ile Gln His Arg Arg Thr
                660                 665                 670

Gln Asp His Lys Ile Ala Lys Gln Ser Leu Arg Pro Phe Cys Thr Val
            675                 680                 685

Cys Asn Arg Tyr Phe Lys Thr Pro Arg Lys Phe Val Glu His Val Lys
        690                 695                 700

Ser Gln Gly His Lys Asp Lys Ala Lys Glu Leu Lys Ser Leu Glu Lys
705                 710                 715                 720

Glu Ile Ala Gly Gln Asp Glu His Phe Ile Thr Val Asp Ala Val
                725                 730                 735

Gly Cys Phe Glu Gly Asp Glu Glu Glu Glu Asp Asp Glu Asp Glu
                740                 745                 750

Glu Glu Ile Glu Val Arg Ser Arg Asp Ile Ser Arg Glu Glu Trp Lys
                755                 760                 765

Gly Ser Glu Thr Tyr Ser Pro Asn Thr Ala Tyr Gly Val Asp Phe Leu
                770                 775                 780

Val Pro Val Met Gly Tyr Ile Cys Arg Ile Cys His Lys Phe Tyr His
785                 790                 795                 800

Ser Asn Ser Gly Ala Gln Leu Ser His Cys Lys Ser Leu Gly His Phe
                805                 810                 815

Glu Asn Leu Gln Lys Tyr Lys Ala Ala Lys Asn Pro Ser Pro Thr Thr
                820                 825                 830

Arg Pro Val Ser Arg Arg Cys Ala Ile Asn Ala Arg Asn Ala Leu Thr
                835                 840                 845

Ala Leu Phe Thr Ser Ser Gly Arg Pro Pro Ser Gln Pro Asn Thr Gln
                850                 855                 860

Asp Lys Thr Pro Ser Lys Val Thr Ala Arg Pro Ser Gln Pro Pro Leu
865                 870                 875                 880

Pro Arg Arg Ser Thr Arg Leu Lys Thr
                885

<210> SEQ ID NO 65
<211> LENGTH: 873
<212> TYPE: PRT
<213> ORGANISM: Homo sapiens

<400> SEQUENCE: 65

Met Phe Ser Gln Gln Gln Gln Leu Gln Gln Gln Gln Gln Gln Gln Leu
1               5                   10                  15

Gln Gln Leu Gln Gln Gln Gln Leu Gln Gln Gln Gln Leu Gln Gln Gln
                20                  25                  30

Gln Leu Leu Gln Leu Gln Gln Leu Leu Gln Ser Pro Pro Gln Ala
            35                  40                  45

Pro Leu Pro Met Ala Val Ser Arg Gly Leu Pro Pro Gln Gln Pro Gln
        50                  55                  60

Gln Pro Leu Leu Asn Leu Gln Gly Thr Asn Ser Ala Ser Leu Leu Asn
65                  70                  75                  80

Gly Ser Met Leu Gln Arg Ala Leu Leu Leu Gln Gln Leu Gln Gly Asn
                85                  90                  95

Leu Arg Gly Tyr Gly Met Ala Ser Pro Gly Leu Ala Ala Pro Ser Leu
                100                 105                 110

Thr Pro Pro Gln Leu Ala Thr Pro Asn Leu Gln Gln Phe Phe Pro Gln
                115                 120                 125
```

-continued

```
Ala Thr Arg Gln Ser Leu Leu Gly Pro Pro Val Gly Val Pro Met
        130                 135                 140

Asn Pro Ser Gln Phe Asn Leu Ser Gly Arg Asn Pro Gln Lys Gln Ala
145                 150                 155                 160

Arg Thr Ser Ser Ser Thr Thr Pro Asn Arg Lys Asp Ser Ser Gln
            165                 170                 175

Thr Met Pro Val Glu Asp Lys Ser Asp Pro Pro Glu Gly Ser Glu Glu
                180                 185                 190

Ala Ala Glu Pro Arg Met Asp Thr Pro Glu Asp Gln Asp Leu Pro Pro
            195                 200                 205

Cys Pro Glu Asp Ile Ala Lys Glu Lys Arg Thr Pro Ala Pro Glu Pro
    210                 215                 220

Glu Pro Cys Glu Ala Ser Glu Leu Pro Ala Lys Arg Leu Arg Ser Ser
225                 230                 235                 240

Glu Glu Pro Thr Glu Lys Glu Pro Pro Gly Gln Leu Gln Val Lys Ala
            245                 250                 255

Gln Pro Gln Ala Arg Met Thr Val Pro Lys Gln Thr Gln Thr Pro Asp
                260                 265                 270

Leu Leu Pro Glu Ala Leu Glu Ala Gln Val Leu Pro Arg Phe Gln Pro
            275                 280                 285

Arg Val Leu Gln Val Gln Ala Gln Val Gln Ser Gln Thr Gln Pro Arg
    290                 295                 300

Ile Pro Ser Thr Asp Thr Gln Val Gln Pro Lys Leu Gln Lys Gln Ala
305                 310                 315                 320

Gln Thr Gln Thr Ser Pro Glu His Leu Val Leu Gln Gln Lys Gln Val
            325                 330                 335

Gln Pro Gln Leu Gln Gln Glu Ala Glu Pro Gln Lys Val Gln Pro
                340                 345                 350

Gln Val Gln Pro Gln Ala His Ser Gln Gly Pro Arg Gln Val Gln Leu
            355                 360                 365

Gln Gln Glu Ala Glu Pro Leu Lys Gln Val Gln Pro Gln Val Gln Pro
370                 375                 380

Gln Ala His Ser Gln Pro Arg Gln Val Leu Gln Leu Gln Lys
385                 390                 395                 400

Gln Val Gln Thr Gln Thr Tyr Pro Gln Val His Thr Gln Ala Gln Pro
            405                 410                 415

Ser Val Gln Pro Gln Glu His Pro Pro Ala Gln Val Ser Val Gln Pro
                420                 425                 430

Pro Glu Gln Thr His Glu Gln Pro His Thr Gln Pro Gln Val Ser Leu
        435                 440                 445

Leu Ala Pro Glu Gln Thr Pro Val Val Val His Val Cys Gly Leu Glu
    450                 455                 460

Met Pro Pro Asp Ala Val Glu Ala Gly Gly Met Glu Lys Thr Leu
465                 470                 475                 480

Pro Glu Pro Val Gly Thr Gln Val Ser Met Glu Glu Ile Gln Asn Glu
            485                 490                 495

Ser Ala Cys Gly Leu Asp Val Gly Glu Cys Glu Asn Arg Ala Arg Glu
                500                 505                 510

Met Pro Gly Val Trp Gly Ala Gly Gly Ser Leu Lys Val Thr Ile Leu
        515                 520                 525

Gln Ser Ser Asp Ser Arg Ala Phe Ser Thr Val Pro Leu Thr Pro Val
    530                 535                 540

Pro Arg Pro Ser Asp Ser Val Ser Ser Thr Pro Ala Ala Thr Ser Thr
```

```
                545                 550                 555                 560
Pro Ser Lys Gln Ala Leu Gln Phe Phe Cys Tyr Ile Cys Lys Ala Ser
                565                 570                 575
Cys Ser Ser Gln Gln Glu Phe Gln Asp His Met Ser Glu Pro Gln His
                580                 585                 590
Gln Gln Arg Leu Gly Glu Ile Gln His Met Ser Gln Ala Cys Leu Leu
                595                 600                 605
Ser Leu Leu Pro Val Pro Arg Asp Val Leu Glu Thr Glu Asp Glu Glu
                610                 615                 620
Pro Pro Pro Arg Arg Trp Cys Asn Thr Cys Gln Leu Tyr Tyr Met Gly
625                 630                 635                 640
Asp Leu Ile Gln His Arg Arg Thr Gln Asp His Lys Ile Ala Lys Gln
                645                 650                 655
Ser Leu Arg Pro Phe Cys Thr Val Cys Asn Arg Tyr Phe Lys Thr Pro
                660                 665                 670
Arg Lys Phe Val Glu His Val Lys Ser Gln Gly His Lys Asp Lys Ala
                675                 680                 685
Lys Glu Leu Lys Ser Leu Glu Lys Glu Ile Ala Gly Gln Asp Glu Asp
                690                 695                 700
His Phe Ile Thr Val Asp Ala Val Gly Cys Phe Glu Gly Asp Glu Glu
705                 710                 715                 720
Glu Glu Glu Asp Asp Glu Asp Glu Glu Ile Glu Val Glu Glu Glu
                725                 730                 735
Leu Cys Lys Gln Val Arg Ser Arg Asp Ile Ser Arg Glu Glu Trp Lys
                740                 745                 750
Gly Ser Glu Thr Tyr Ser Pro Asn Thr Ala Tyr Gly Val Asp Phe Leu
                755                 760                 765
Val Pro Val Met Gly Tyr Ile Cys Arg Ile Cys His Lys Phe Tyr His
                770                 775                 780
Ser Asn Ser Gly Ala Gln Leu Ser His Cys Lys Ser Leu Gly His Phe
785                 790                 795                 800
Glu Asn Leu Gln Lys Tyr Lys Ala Ala Lys Asn Pro Ser Pro Thr Thr
                805                 810                 815
Arg Pro Val Ser Arg Arg Cys Ala Ile Asn Ala Arg Asn Ala Leu Thr
                820                 825                 830
Ala Leu Phe Thr Ser Ser Gly Arg Pro Pro Ser Gln Pro Asn Thr Gln
                835                 840                 845
Asp Lys Thr Pro Ser Lys Val Thr Ala Arg Pro Ser Gln Pro Pro Leu
                850                 855                 860
Pro Arg Arg Ser Thr Arg Leu Lys Thr
865                 870

<210> SEQ ID NO 66
<211> LENGTH: 2821
<212> TYPE: DNA
<213> ORGANISM: Homo sapiens

<400> SEQUENCE: 66 tggggctgc gggccggcc catccgtggg ggcgacttga gcgttgaggg cgcgcgggga      60
ggcgagccac catgttcagc cagcagcagc agcagctcca gcaacagcag ggccccgttg     120
cccatggctg tcagccgggg gctcccccg cagcagccac agcagccgct tctgaatctc     180
cagggcacca actcagcctc cctcctcaac ggctccatgc tgcagagagc tttgcttta     240 cagcagttgc aaggactgga ccagtttgca atgccaccag ccacgtatga cactgccggt     300
```

```
ctcaccatgc ccacagcaac actgggtaac ctccgaggct atggcatggc atccccaggc   360
ctcgcagccc ccagcctcac accccacaa ctggccactc caaatttgca acagttcttt    420
ccccaggcca ctcgccagtc cttgctggga cctcctcctg ttggggtccc catgaaccct   480
tcccagttca acctttcagg acggaacccc cagaaacagg cccggacctc ctcctctacc   540
accccaatc gaaaggattc ttcttctcag acaatgcctg tggaagacaa gtcgacccc     600
ccagaggggt ctgaggaagc cgcagagccc cggatggaca caccagaaga ccaagattta   660
ccgccctgcc cagaggacat cgccaaggaa aaacgcactc cagcacctga gcctgagcct   720
tgtgaggcgt ccgagctgcc agcaaagaga ttgaggagct cagaagagcc cacagagaag   780
gaacctccag ggcagttaca ggtgaaggcc cagccgcagg cccggatgac agtaccgaaa   840
cagacacaga caccagacct gctgcctgag gccctggaag cccaagtgct gccacgattc   900
cagccacggg tcctgcaggt ccaggcccag gtgcagtcac agactcagcc gcggatacca   960
tccacagaca cccaggtgca gccaaagctg cagaagcagg cgcaaacaca gacctctcca  1020
gagcacttag tgctgcaaca gaagcaggtg cagccacagc tgcagcagga ggcagagcca  1080
cagaagcagg tgcagccaca ggtacagcca caggcacatt cacagggccc aaggcaggtg  1140
cagctgcagc aggaggcaga gccgctgaag caggtgcagc cacaggtgca gccccaggca  1200
cattcacagc ccccaaggca ggtgcagctg cagctgcaga gcaggtcca gacacagaca  1260
tatccacagg tccacacaca ggcacagcca agcgtccagc cacaggagca tcctccagcg  1320
caggtgtcag tacagccacc agagcagacc catgagcagc tcacacccca gccgcaggtg  1380
tcgttgctgg ctccagagca aacaccagtt gtggttcatg tctgcgggct ggagatgcca  1440
cctgatgcag tagaagctgg tggaggcatg gaaaagacct tgccagagcc tgtgggcacc  1500
caagtcagca tggaagagat tcagaatgag tcggcctgtg gcctagatgt gggagaatgt  1560
gaaaacagag cgagagagat gccaggggta tggggcgccg ggggctccct gaaggtcacc  1620
attctgcaga gcagtgacag ccgggccttt agcactgtac ccctgacacc tgtccccgc   1680
cccagtgact ccgtctcctc caccctgcg gctaccagca ctccctctaa gcaggccctc   1740
cagttcttct gctacatctg caaggccagc tgctccagcc agcaggagtt ccaggaccac   1800
atgtcggagc tcagcacca gcagcggcta ggggagatcc agcacatgag ccaagcctgc   1860
ctcctgtccc tgctgcccgt gccccgggac gtcctggaga cagaggatga ggagcctcca   1920
ccaaggcgct ggtgcaacac ctgccagctc tactacatgg gggacctgat ccaacaccgc   1980
aggacacagg accacaagat tgccaaacaa tccttgcgac ccttctgcac cgtttgcaac   2040
cgctacttca aaaccctcg caagtttgtg gagcacgtga gtcccaggg gcataaggac   2100
aaagccaagg agctgaagtc gcttgagaaa gaaattgctg gccaagatga ggaccacttc   2160
attacagtgg acgctgtggg ttgcttcgag ggtgatgaag aagaggaaga ggatgatgag   2220
gatgaagaag agatcgaggt tgaggaggaa ctctgcaagc aggtgaggtc cagagatata   2280
tccagagagg agtggaaggg ctcggagacc tacagcccca atactgcata tggtgtggac   2340
ttcctggtgc ccgtgatggg ctatatctgc cgcatctgcc acaagttcta tcacagcaac   2400
tcaggggcac agctctccca ctgcaagtcc ctgggcacte ttgagaacct gcagaaatac   2460
aaggcggcca agaaccccag ccccaccacc cgacctgtga gccgccggtg cgcaatcaac   2520
gcccggaacg ctttgacagc cctgttcacc tccagcggcc gcccaccctc ccagcccaac   2580
acccaggaca aacacccag caaggtgacg gctcgaccct cccagcccc actacctcgg   2640
```

```
cgctcaaccc gcctcaaaac ctgatagagg gacctccctg tccctggcct gcctgggtcc    2700
agatctgcta atgcttttta ggagtctgcc tggaaacttt gacatggttc atgtttttac    2760
tcaaaatcca ataaaacaag gtagtttggc tgtgcaaaaa aaaaaaaaaa aaaaaaaaa     2820 a                                                                    2821

<210> SEQ ID NO 67
<211> LENGTH: 2850
<212> TYPE: DNA
<213> ORGANISM: Homo sapiens

<400> SEQUENCE: 67
tgggggctgc ggggccggcc catccgtggg ggcgacttga gcgttgaggg cgcgcgggga     60
ggcgagccac catgttcagc cagcagcagc agcagctcca gcaacagcag cagcagctcc    120
agcagttaca gcagcagcag ctccagcagc agcaattgca gcagcagcag ttactgcagc    180
tccagcagct gctccagcag tccccaccac aggccccgtt gcccatggct gtcagccggg    240
ggctcccccc gcagcagcca cagcagccgc ttctgaatct ccagggcacc aactcagcct    300
ccctcctcaa cggctccatg ctgcagagag ctttgctttt acagcagttg caaggtaacc    360
tccgaggcta tggcatggca tccccaggcc tcgcagcccc cagcctcaca cccccacaac    420
tggccactcc aaatttgcaa cagttctttc cccaggccac tcgccagtcc ttgctgggac    480
ctcctcctgt tggggtcccc atgaacccctt cccagttcaa cctttcagga cggaaccccc    540
agaaacaggc ccggacctcc tcctctacca cccccaatcg aaaggattct tcttctcaga    600
caatgcctgt ggaagacaag tcagaccccc cagaggggtc tgaggaagcc gcagagcccc    660
ggatggacac accagaagac caagatttac cgccctgccc agaggacatc gccaaggaaa    720
aacgcactcc agcacctgag cctgagcctt gtgaggcgtc cgagctgcca gcaaagagat    780
tgaggagctc agaagagccc acagagaagg aacctccagg gcagttacag gtgaaggccc    840
agccgcaggc ccggatgaca gtaccgaaac agacacagac accagacctg ctgcctgagg    900
ccctggaagc ccaagtgctg ccacgattcc agccacgggt cctgcaggtc caggcccagg    960
tgcagtcaca gactcagccg cggataccat ccacagacac ccaggtgcag ccaaagctgc    1020
agaagcaggc gcaaacacag acctctccag agcacttagt gctgcaacag aagcaggtgc    1080
agccacagct gcagcaggag gcagagccac agaagcaggt gcagccacag gtacagccac    1140
aggcacattc acagggccca aggcaggtgc agctgcagca ggaggcagag ccgctgaagc    1200
aggtgcagcc acaggtgcag ccccaggcac attcacagcc cccaaggcag gtgcagctgc    1260
agctgcagaa gcaggtccag acacagacat atccacaggt ccacacacag gcacagccaa    1320
gcgtccagcc acaggagcat cctccagcgc aggtgtcagt acagccacca gagcagaccc    1380
atgagcagcc tcacacccag ccgcaggtgt cgttgctggc tccagagcaa acaccagttg    1440
tggttcatgt ctgcgggctg gagatgccac ctgatgcagt agaagctggt ggaggcatgg    1500
aaaagacctt gccagagcct gtgggcaccc aagtcagcat ggaagagatt cagaatgagt    1560
cggcctgtgg cctagatgtg ggagaatgtg aaaacagagc gagagagatg ccaggggtat    1620
ggggcgccgg gggctcccctg aaggtcacca ttctgcagag cagtgacagc cgggcctttα    1680 gcactgtacc cctgacacct gtcccccgcc ccagtgactc cgtctcctcc acccctgcgg    1740
ctaccagcac tccctctaag caggccctcc agttcttctg ctacatctgc aaggccagct    1800
gctccagcca gcaggagttc caggaccaca tgtcggagcc tcagcaccag cagcggctag    1860
gggagatcca gcacatgagc caagcctgcc tcctgtccct gctgccgtg ccccgggacg    1920
```

```
tcctggagac agaggatgag gagcctccac caaggcgctg gtgcaacacc tgccagctct    1980
actacatggg ggacctgatc caacaccgca ggacacagga ccacaagatt gccaaacaat    2040
ccttgcgacc cttctgcacc gtttgcaacc gctacttcaa accccctcgc aagtttgtgg    2100
agcacgtgaa gtcccagggg cataaggaca aagccaagga gctgaagtcg cttgagaaag    2160
aaattgctgg ccaagatgag gaccacttca ttacagtgga cgctgtgggt tgcttcgagg    2220
gtgatgaaga agaggaagag gatgatgagg atgaagaaga gatcgaggtt gaggaggaac    2280
tctgcaagca ggtgaggtcc agagatatat ccagagagga gtggaagggc tcggagacct    2340
acagccccaa tactgcatat ggtgtggact tcctggtgcc cgtgatgggc tatatctgcc    2400
gcatctgcca caagttctat cacagcaact caggggcaca gctctcccac tgcaagtccc    2460
tgggccactt tgagaacctg cagaaataca aggcggccaa gaaccccagc cccaccaccc    2520
gacctgtgag ccgccggtgc gcaatcaacg cccggaacgc tttgacagcc ctgttcacct    2580
ccagcggccg cccacccctcc cagcccaaca cccaggacaa acacccagc aaggtgacgg    2640 ctcgaccctc ccagccccca ctacctcggc gctcaacccg cctcaaaacc tgatagaggg    2700
acctccctgt ccctggcctg cctgggtcca gatctgctaa tgcttttttag gagtctgcct    2760 ggaaactttg acatggttca tgtttttact caaaatccaa taaaacaagg tagtttggct    2820
gtgcaaaaaa aaaaaaaaa aaaaaaaaa                                       2850

<210> SEQ ID NO 68
<211> LENGTH: 2907
<212> TYPE: DNA
<213> ORGANISM: Homo sapiens

<400> SEQUENCE: 68
tgggggctgc ggggccggcc catccgtggg ggcgacttga gcgttgaggg cgcgcgggga      60
ggcgagccac catgttcagc cagcagcagc agcagctcca gcaacagcag cagcagctcc     120
agcagttaca gcagcagcag ctccagcagc agcaattgca gcagcagcag ttactgcagc     180
tccagcagct gctccagcag tccccaccac aggccccgtt gcccatggct gtcagccggg     240
ggctcccccc gcagcagcca cagcagccgc ttctgaatct ccagggcacc aactcagcct     300
ccctcctcaa cggctccatg ctgcagagag ctttgctttt acagcagttg caaggactgg     360
accagtttgc aatgccacca gccacgtatg acactgccgg tctcaccatg cccacagcaa     420
cactgggtaa cctccgaggc tatggcatgg catcccagg cctcgcagcc cccagcctca     480 caccccccaca actggccact ccaaatttgc aacagttctt tccccaggcc actcgccagt     540
ccttgctggg acctcctcct gttggggtcc ccatgaaccc ttcccagttc aacctttcag     600
gacggaaccc ccagaaacag gcccggacct cctcctctac cacccccaat cgaaagacaa     660
tgcctgtgga agacaagtca gaccccccag aggggtctga ggaagccgca gagcccggga     720
tggacacacc agaagaccaa gatttaccgc cctgcccaga ggacatcgcc aaggaaaaac     780
gcactccagc acctgagcct gagccttgtg aggcgtccga gctgccagca aagagattga     840
ggagctcaga agagcccaca gagaaggaac ctccagggca gttacaggtg aaggcccagc     900
cgcaggcccg gatgacagta ccgaaacaga cacagacacc agacctgctg cctgaggccc     960
tggaagccca agtgctgcca cgattccagc cacgggtcct gcaggtccag gcccaggtgc    1020
agtcacagac tcagccgcgg ataccatcca cagacaccca ggtgcagcca agctgcagca    1080
agcaggcgca aacacagacc tctccagagc acttagtgct gcaacagaag caggtgcagc    1140
```

```
cacagctgca gcaggaggca gagccacaga agcaggtgca gccacaggta cagccacagg    1200
cacattcaca gggcccaagg caggtgcagc tgcagcagga ggcagagccg ctgaagcagg    1260
tgcagccaca ggtgcagccc caggcacatt cacagccccc aaggcaggtg cagctgcagc    1320
tgcagaagca ggtccagaca cagacatatc cacaggtcca cacacaggca cagccaagcg    1380
tccagccaca ggagcatcct ccagcgcagg tgtcagtaca gccaccagag cagacccatg    1440
agcagcctca cacccagccg caggtgtcgt tgctggctcc agagcaaaca ccagttgtgg    1500
ttcatgtctg cgggctggag atgccacctg atgcagtaga agctggtgga ggcatggaaa    1560
agaccttgcc agagcctgtg ggcacccaag tcagcatgga agagattcag aatgagtcgg    1620
cctgtggcct agatgtggga gaatgtgaaa acagagcgag agatgccagg ggtatggg     1680 gcgccggggg ctccctgaag gtcaccattc tgcagagcag tgacagccgg gcctttagca    1740
ctgtacccct gacacctgtc ccccgcccca gtgactccgt ctcctccacc cctgcggcta    1800
ccagcactcc ctctaagcag gccctccagt tcttctgcta catctgcaag gccagctgct    1860
ccagccagca ggagttccag gaccacatgt cggagcctca gcaccagcag cggctagggg    1920
agatccagca catgagccaa gcctgcctcc tgtccctgct gcccgtgccc cgggacgtcc    1980
tggagacaga ggatgaggag cctccaccaa ggcgctggtg caacacctgc cagctctact    2040
acatggggga cctgatccaa cacccgcagga cacaggacca caagattgcc aaacaatcct    2100
tgcgacccct ctgcaccgtt tgcaaccgct acttcaaaac ccctcgcaag tttgtggagc    2160
acgtgaagtc ccaggggcat aaggacaaag ccaaggagct gaagtcgctt gagaaagaaa    2220
ttgctggcca agatgaggac cacttcatta cagtggacgc tgtgggttgc ttcgagggtg    2280
atgaagaaga ggaagaggat gatgaggatg aagaagagat cgaggttgag gaggaactct    2340
gcaagcaggt gaggtccaga gatatatcca gagaggagtg aagggctcg gagacctaca     2400 gccccaatac tgcatatggt gtggacttcc tggtgcccgt gatgggctat atctgccgca    2460
tctgccacaa gttctatcac agcaactcag ggcacagct ctcccactgc aagtccctgg     2520
gccactttga gaacctgcag aaatacaagg cggccaagaa ccccagcccc accacccgac    2580
ctgtgagccg ccggtgcgca atcaacgccc ggaacgcttt gacagccctg ttcacctcca    2640
gcggccgccc accctcccag cccaacaccc aggacaaaac acccagcaag gtgacggctc    2700
gaccctccca gccccactac cctcggcgct caacccgcct caaaacctga tagagggacc    2760
tccctgtccc tggcctgcct gggtccagat ctgctaatgc ttttttaggag tctgcctgga    2820 aactttgaca tggttcatgt ttttactcaa aatccaataa aacaaggtag tttggctgtg    2880
caaaaaaaaa aaaaaaaaaa aaaaaaa                                         2907
```

<210> SEQ ID NO 69
<211> LENGTH: 2836
<212> TYPE: DNA
<213> ORGANISM: Homo sapiens

<400> SEQUENCE: 69

```
tgggggctgc ggggccggcc catccgtggg ggcgacttga gcgttgaggg cgcgcgggga      60
ggcgagccac catgttcagc cagcagcagc agcagctcca gcaacagcag cagcagctcc     120
agcagttaca gcagcagcag ctccagcagc agcaattgca gcagcagcag ttactgcagc     180
tccagcagct gctccagcag tccccaccac aggcccgtt gcccatggct gtcagccggg     240
ggctcccccc gcagcagcca cagcagccgc ttctgaatct ccaggcacc aactcagcct     300 ccctcctcaa cggctccatg ctgcagagag ctttgctttt acagcagttg caaggactgg     360
```

```
accagtttgc aatgccacca gccacgtatg acactgccgg tctcaccatg cccacagcaa    420
cactgggtaa cctccgaggc tatggcatgg catccccagg cctcgcagcc cccagcctca    480
cacccccaca actggccact ccaaatttgc aacagttctt tccccaggcc actcgccagt    540
ccttgctggg acctcctcct gttggggtcc ccatgaaccc ttcccagttc aacctttcag    600
gacgaaccc ccagaaacag gcccggacct cctcctctac cacccccaat cgaaaggatt    660
cttcttctca gacaatgcct gtggaagaca agtcagaccc ccagaggggt ctgaggaag    720
ccgcagagcc ccggatggac acaccagaag accaagattt accgccctgc cagaggaca    780
tcgccaagga aaaacgcact ccagcacctg agcctgagcc ttgtgaggcg tccgagctgc    840
cagcaaagag attgaggagc tcagaagagc ccacagagaa ggaacctcca gggcagttac    900
aggtgaaggc ccagccgcag gcccggatga cagtaccgaa acagacacag acaccagacc    960
tgctgcctga ggccctggaa gcccaagtgc tgccacgatt ccagccacgg gtcctgcagg   1020
tccaggccca ggtgcagtca cagactcagc cgcggatacc atccacagac acccaggtgc   1080
agccaaagct gcagaagcag gcgcaaacac agacctctcc agagcactta gtgctgcaac   1140
agaagcaggt gcagccacag ctgcagcagg aggcagagcc acagaagcag gtgcagccac   1200
aggtacagcc acaggcacat tcacagggcc caaggcaggt gcagctgcag caggaggcag   1260
agccgctgaa gcaggtgcag acaggtccac acacaggcac agccaagcgt ccagccacag   1320
gagcatcctc cagcgcaggt gtcagtacag ccaccagagc agacccatga gcagcctcac   1380
acccagccgc aggtgtcgtt gctggctcca gagcaaacac cagttgtggt tcatgtctgc   1440
gggctggaga tgccacctga tgcagtagaa gctggtggag gcatggaaaa gaccttgcca   1500
gagcctgtgg gcacccaagt cagcatgaaa gagattcaga atgagtcggc ctgtggccta   1560
gatgtgggag aatgtgaaaa cagagcgaga gagatgccag gggtatgggg cgccggggggc   1620
tccctgaagg tcaccattct gcagagcagt gacagccggg cctttagcac tgtacccctg   1680
acacctgtcc cccgccccag tgactccgtc tcctccaccc ctgcggctac cagcactccc   1740
tctaagcagg ccctccagtt cttctgctac atctgcaagg ccagctgctc cagccagcag   1800
gagttccagg accacatgtc ggagcctcag caccagcagc ggctagggga gatccagcac   1860
atgagccaag cctgcctcct gtccctgctg cccgtgcccc gggacgtcct ggagacagag   1920
gatgaggagc ctccaccaag gcgctggtgc aacacctgcc agctctacta catgggggac   1980
ctgatccaac accgcaggac acaggaccac aagattgcca acaatccttg cgacccttc   2040
tgcaccgttt gcaaccgcta cttcaaaacc cctcgcaagt tgtggagca cgtgaagtcc   2100
caggggcata aggacaaagc caaggagctg aagtcgcttg agaaagaaat tgctggccaa   2160
gatgaggacc acttcattac agtggacgct gtgggttgct tcgagggtga tgaagaagag   2220
gaagaggatg atgaggatga agaagagatc gaggttgagg aggaactctg caagcaggtg   2280
aggtccagag atatatccag agaggagtgg aagggctcgg agacctacag ccccaatact   2340
gcatatggtc tggacttcct ggtgcccgtg atgggctata tctgccgcat ctgccacaag   2400
ttctatcaca gcaactcagg ggcacagctc tcccactgca agtccctggg ccactttgag   2460
aacctgcaga aatacaaggc ggccaagaac cccagcccca ccccgacc tgtgagccgc   2520
cggtgcgcaa tcaacgcccg gaacgctttg acagccctgt tcacctccag cggccgccca   2580
ccctcccagc ccaacaccca ggacaaaaca cccagcaagg tgacggctcg accctcccag   2640
ccccactac ctcggcgctc aacccgcctc aaaacctgat agagggacct ccctgtccct   2700
```

```
ggcctgcctg gtccagatc tgctaatgct ttttaggagt ctgcctggaa actttgacat    2760
ggttcatgtt tttactcaaa atccaataaa acaaggtagt ttggctgtgc aaaaaaaaaa    2820
aaaaaaaaaa aaaaa                                                      2836

<210> SEQ ID NO 70
<211> LENGTH: 2754
<212> TYPE: DNA
<213> ORGANISM: Homo sapiens

<400> SEQUENCE: 70
tgggggctgc ggggccggcc catccgtggg ggcgacttga gcgttgaggg cgcgcgggga      60
ggcgagccac catgttcagc cagcagcagc agcagctcca gcaacagcag cagcagctcc     120
agcagttaca gcagcagcag ctccagcagc agcaattgca gcagcagcag ttactgcagc     180
tccagcagct gctccagcag tccccaccac aggccccgtt gcccatggct gtcagccggg     240
ggctcccccc gcagcagcca cagcagccgc ttctgaatct ccagggcacc aactcagcct     300
ccctcctcaa cggctccatg ctgcagagag cttTgctttt acagcagttg caaggactgg     360
accagtttgc aatgccacca gccacgtatg acactgccgg tctcaccatg cccacagcaa     420
cactgggtaa cctccgaggc tatggcatgg catccccagg cctcgcagcc ccagcctca     480 cacccccaca actggccact ccaaatttgc aacagttctt tccccaggcc actcgccagt     540
ccttgctggg acctcctcct gttggggtcc ccatgaaccc ttcccagttc aacctttcag     600
gacggaaccc ccagaaacag gcccggacct cctcctctac cacccccaat cgaaaggatt     660
cttcttctca gacaatgcct gtggaagaca agtcagaccc cccagagggg tctgaggaag     720
ccgcagagcc ccggatggac acaccagaag accaagattt accgccctgc cagaggaca      780 tcgccaagga aaaacgcact ccagcacctg agcctgagcc ttgtgaggcg tccgagctgc     840
cagcaaagag attgaggagc tcagaagagc ccacagagaa ggaacctcca gggcagttac     900
aggtgaaggc ccagccgcag gcccggatga cagtaccgaa acagacacag acaccagacc     960
tgctgcctga ggccctggaa gcccaagtgc tgccacgatt ccagccacgg gtcctgcagg    1020
tccaggccca ggtgcagtca cagactcagc cgcggatacc atccacagac acccaggtgc    1080
agccaaagct gcagaagcag gcgcaaacac agacctctcc agagcactta gtgctgcaac    1140
agaagcaggt gcagccacag ctgcagcagg aggcagagcc acagaagcag gtgcagccac    1200
aggtccacac acaggcacag ccaagcgtcc agccacagga gcatcctcca gcgcaggtgt    1260
cagtacagcc accagagcag acccatgagc agcctcacac ccagccgcag gtgtcgttgc    1320
tggctccaga gcaaacacca gttgtggttc atgtctgcgg gctggagatg ccacctgatg    1380
cagtagaagc tggtggaggc atggaaaaga ccttgccaga gcctgtgggc acccaagtca    1440
gcatggaaga gattcagaat gagtcggcct gtggcctaga tgtgggagaa tgtgaaaaca    1500
gagcgagaga gatgccaggg gtatgggcg ccggggctc cctgaaggtc accattctgc    1560
agagcagtga cagccgggcc tttagcactg taccctgac acctgtcccc cgccccagtg    1620
actccgtctc ctccacccct gcggctacca gcactcctc taagcaggcc ctccagttct    1680
tctgctacat ctgcaaggcc agctgctcca gccagcagga gttccaggac acatgtcgg    1740 agcctcagca ccagcagcgg ctaggggaga tccagcacat gagccaagcc tgcctcctgt    1800
ccctgctgcc cgtgcccgg gacgtcctgg agacagagga tgaggagcct ccaccaaggc    1860
gctggtgcaa cacctgccag ctctactaca tgggggaccct gatccaacac cgcaggacac    1920
aggaccacaa gattgccaaa caatccttgc gaccttctg caccgtttgc aaccgctact    1980
```

| | |
|---|---|
| tcaaaacccc tcgcaagttt gtggagcacg tgaagtccca ggggcataag gacaaagcca | 2040 |
| aggagctgaa gtcgcttgag aaagaaattg ctggccaaga tgaggaccac ttcattacag | 2100 |
| tggacgctgt gggttgcttc gagggtgatg aagaagagga gaggatgat gaggatgaag | 2160 |
| aagagatcga ggttgaggag gaactctgca agcaggtgag gtccagagat atatccagag | 2220 |
| aggagtggaa gggctcggag acctacagcc ccaatactgc atatggtgtg gacttcctgg | 2280 |
| tgcccgtgat gggctatatc tgccgcatct gccacaagtt ctatcacagc aactcagggg | 2340 |
| cacagctctc ccactgcaag tccctgggcc actttgagaa cctgcagaaa tacaaggcgg | 2400 |
| ccaagaaccc cagccccacc acccgacctg tgagccgccg gtgcgcaatc aacgcccgga | 2460 |
| acgctttgac agccctgttc acctccagcg gccgcccacc ctcccagccc aacacccagg | 2520 |
| acaaaacacc cagcaaggtg acggctcgac cctcccagcc cccactacct cggcgctcaa | 2580 |
| cccgcctcaa aacctgatag agggacctcc ctgtccctgg cctgcctggg tccagatctg | 2640 |
| ctaatgcttt ttaggagtct gcctggaaac tttgacatgg ttcatgtttt tactcaaaat | 2700 |
| ccaataaaac aaggtagttt ggctgtgcaa aaaaaaaaa aaaaaaaaa aaaa | 2754 |

<210> SEQ ID NO 71
<211> LENGTH: 2587
<212> TYPE: DNA
<213> ORGANISM: Homo sapiens

<400> SEQUENCE: 71

| | |
|---|---|
| tgggggctgc ggggccggcc catccgtggg ggcgacttga gcgttgaggg cgcgcgggga | 60 |
| ggcgagccac catgttcagc cagcagcagc agcagctcca gcaacagcag cagcagctcc | 120 |
| agcagttaca gcagcagcag ctccagcagc agcaattgca gcagcagcag ttactgcagc | 180 |
| tccagcagct gctccagcag tccccaccac aggccccgtt gcccatggct gtcagccggg | 240 |
| ggctcccccc gcagcagcca cagcagccgc ttctgaatct ccagggcacc aactcagcct | 300 |
| ccctcctcaa cggctccatg ctgcagagag ctttgctttt acagcagttg caaggactgg | 360 |
| accagtttgc aatgccacca gccacgtatg acactgccgg tctcaccatg cccacagcaa | 420 |
| cactgggtaa cctccgaggc tatggcatgg catccccagg cctcgcagcc cccagcctca | 480 |
| cacccccaca actggccact ccaaatttgc aacagttctt tccccaggcc actcgccagt | 540 |
| ccttgctggg acctcctcct gttggggtcc ccatgaaccc ttcccagttc aaccttttcag | 600 |
| gacggaaccc ccagaaacag gcccggacct cctcctctac cacccccaat cgaaaggatt | 660 |
| cttcttctca gacaatgcct gtggaagaca gtcagaccc cccagagggg tctgaggaag | 720 |
| ccgcagagcc ccggatggac acaccagaag accaagattt accgccctgc ccagaggaca | 780 |
| tcgccaagga aaaacgcact ccagcacctg agcctgagcc ttgtgaggcg tccgagctgc | 840 |
| cagcaaagag attgaggagc tcagaagagc ccacagagaa ggaacctcca gggcagttac | 900 |
| aggtgaaggc ccagccgcag gccgggatga cagtaccgaa acagacacag acaccagacc | 960 |
| tgctgcctga ggcctggaa gcccaagtgc tgccacgatt ccagccacgg gtcctgcagg | 1020 |
| tccaggcctc cacaggtcca cacacaggca cagccaagcg tccagccaca ggagcatcct | 1080 |
| ccagcgcagt tgtcagtaca gccaccgag cagacccatg agcagcctca cacccagccg | 1140 |
| caggtgtcgt tgctggctcc agagcaaaca ccagttgtgg ttcatgtctg cgggctggag | 1200 |
| atgccacctg atgcagtaga agctggtgga ggcatggaaa agaccttgcc agagcctgtg | 1260 |
| ggcacccaag tcagcatgga agagattcag aatgagtcgg cctgtggcct agatgtggga | 1320 |

| | | |
|---|---|---|
| gaatgtgaaa acagagcgag agagatgcca ggggtatggg gcgccggggg ctccctgaag | 1380 | |
| gtcaccattc tgcagagcag tgacagccgg gcctttagca ctgtacccct gacacctgtc | 1440 | |
| ccccgcccca gtgactccgt ctcctccacc cctgcggcta ccagcactcc ctctaagcag | 1500 | |
| gccctccagt tcttctgcta catctgcaag gccagctgct ccagccagca ggagttccag | 1560 | |
| gaccacatgt cggagcctca gcaccagcag cggctagggg agatccagca catgagccaa | 1620 | |
| gcctgcctcc tgtccctgct gcccgtgccc cgggacgtcc tggagacaga ggatgaggag | 1680 | |
| cctccaccaa ggcgctggtg caacacctgc cagctctact acatggggga cctgatccaa | 1740 | |
| cacccgcagga cacaggacca caagattgcc aaacaatcct tgcgacccct ctgcaccgtt | 1800 | |
| tgcaaccgct acttcaaaac ccctcgcaag tttgtggagc acgtgaagtc ccaggggcat | 1860 | |
| aaggacaaag ccaaggagct gaagtcgctt gagaaagaaa ttgctggcca agatgaggac | 1920 | |
| cacttcatta cagtggacgc tgtgggttgc ttcgagggtg atgaagaaga ggaagaggat | 1980 | |
| gatgaggatg aagaagagat cgaggttgag gaggaactct gcaagcaggt gaggtccaga | 2040 | |
| gatatatcca gagaggagtg gaagggctcg gagacctaca gccccaatac tgcatatggt | 2100 | |
| gtggacttcc tggtgcccgt gatgggctat atctgccgca tctgccacaa gttctatcac | 2160 | |
| agcaactcag gggcacagct ctcccactgc aagtccctgg ccactttga gaacctgcag | 2220 | |
| aaatacaagg cggccaagaa ccccagcccc accaccgac ctgtgagccg ccggtgcgca | 2280 | |
| atcaacgccc ggaacgcttt gacagccctg ttcacctcca gcggccgccc accctcccag | 2340 | |
| cccaacaccc aggacaaaac acccagcaag gtgacggctc gaccctccca gcccccacta | 2400 | |
| cctcggcgct caacccgcct caaaacctga tagagggacc tccctgtccc tggcctgcct | 2460 | |
| gggtccagat ctgctaatgc ttttttaggag tctgcctgga aactttgaca tggttcatgt | 2520 | |
| ttttactcaa aatccaataa aacaaggtag tttggctgtg caaaaaaaaa aaaaaaaaa | 2580 | |
| aaaaaaa | 2587 | |

<210> SEQ ID NO 72
<211> LENGTH: 2898
<212> TYPE: DNA
<213> ORGANISM: Homo sapiens

<400> SEQUENCE: 72

| | | |
|---|---|---|
| tgggggctgc ggggccggcc catccgtggg ggcgacttga gcgttgaggg cgcgcgggga | 60 | |
| ggcgagccac catgttcagc cagcagcagc agcagctcca gcaacagcag cagcagctcc | 120 | |
| agcagttaca gcagcagcag ctccagcagc agcaattgca gcagcagcag ttactgcagc | 180 | |
| tccagcagct gctccagcag tccccaccac aggcccgtt gcccatggct gtcagccggg | 240 | |
| ggctcccccc gcagcagcca cagcagccgc ttctgaatct ccagggcacc aactcagcct | 300 | |
| ccctcctcaa cggctccatg ctgcagagag ctttgctttt acagcagttg caaggactgg | 360 | |
| accagtttgc aatgccacca gccacgtatg acactgccgg tctcaccatg cccacagcaa | 420 | |
| cactgggtaa cctccgaggc tatggcatgg catccccagg cctcgcagcc cccagcctca | 480 | |
| cacccccaca actggccact ccaaatttgc aacagttctt tccccaggcc actcgccagt | 540 | |
| ccttgctggg acctcctcct gttggggtcc ccatgaaccc ttcccagttc aacctttcag | 600 | |
| gacggaaccc ccagaaacag gcccggacct cctcctctac cacccccaat cgaaaggatt | 660 | |
| cttcttctca gacaatgcct gtggaagaca gtcagaccc ccagaggggg tctgaggaag | 720 | |
| ccgcagagcc ccgatggac acaccagaag accaagattt accgcccctgc ccagaggaca | 780 | |
| tcgccaagga aaaacgcact ccagcacctg agcctgagcc ttgtgaggcg tccgagctgc | 840 | |

| | | |
|---|---|---|
| cagcaaagag attgaggagc tcagaagagc ccacagagaa ggaacctcca gggcagttac | 900 |
| aggtgaaggc ccagccgcag gcccggatga cagtaccgaa acagacacag acaccagacc | 960 |
| tgctgcctga ggccctggaa gcccaagtgc tgccacgatt ccagccacgg gtcctgcagg | 1020 |
| tccaggccca ggtgcagtca cagactcagc cgcggatacc atccacagac acccaggtgc | 1080 |
| agccaaagct gcagaagcag gcgcaaacac agacctctcc agagcactta gtgctgcaac | 1140 |
| agaagcaggt gcagccacag ctgcagcagg aggcagagcc acagaagcag gtgcagccac | 1200 |
| aggtacagcc acaggcacat tcacagggcc caaggcaggt gcagctgcag caggaggcag | 1260 |
| agccgctgaa gcaggtgcag ccacaggtgc agccccaggc acattcacag cccccaaggc | 1320 |
| aggtgcagct gcagctgcag aagcaggtcc agacacagac atatccacag gtccacacac | 1380 |
| aggcacagcc aagcgtccag ccacaggagc atcctccagc gcaggtgtca gtacagccac | 1440 |
| cagagcagac ccatgagcag cctcacaccc agccgcaggt gtcgttgctg gctccagagc | 1500 |
| aaacaccagt tgtggttcat gtctgcgggc tggagatgcc acctgatgca gtagaagctg | 1560 |
| gtggaggcat ggaaaagacc ttgccagagc ctgtgggcac ccaagtcagc atggaagaga | 1620 |
| ttcagaatga gtcggcctgt ggcctagatg tgggagaatg tgaaaacaga gcgagagaga | 1680 |
| tgccaggggt atgggcgcc gggggctccc tgaaggtcac cattctgcag agcagtgaca | 1740 |
| gccgggcctt tagcactgta ccctgacac ctgtcccccg ccccagtgac tccgtctcct | 1800 |
| ccaccctgc ggctaccagc actccctcta agcaggccct ccagttcttc tgctacatct | 1860 |
| gcaaggccag ctgctccagc cagcaggagt tccaggacca catgtcggag cctcagcacc | 1920 |
| agcagcggct aggggagatc cagcacatga gccaagcctg cctcctgtcc ctgctgcccg | 1980 |
| tgccccggga cgtcctggag acagaggatg aggagcctcc accaaggcgc tggtgcaaca | 2040 |
| cctgccagct ctactacatg ggggacctga tccaacaccg caggacacag gaccacaaga | 2100 |
| ttgccaaaca atccttgcga cccttctgca ccgtttgcaa ccgctacttc aaaacccctc | 2160 |
| gcaagtttgt ggagcacgtg aagtcccagg ggcataagga caaagccaag gagctgaagt | 2220 |
| cgcttgagaa agaaattgct ggccaagatg aggaccactt cattacagtg gacgctgtgg | 2280 |
| gttgcttcga gggtgatgaa gaagaggaag aggatgatga ggatgaagaa gagatcgagg | 2340 |
| tgaggtccag agatatatcc agagaggagt ggaagggctc ggagacctac agccccaata | 2400 |
| ctgcatatgg tgtggacttc ctggtgcccg tgatgggcta tatctgccgc atctgccaca | 2460 |
| agttctatca cagcaactca ggggcacagc tctcccactg caagtccctg ggccactttg | 2520 |
| agaacctgca gaaatacaag gcggccaaga accccagccc caccaccga cctgtgagcc | 2580 |
| gccggtgcgc aatcaacgcc cggaacgctt tgacagccct gttcacctcc agcggccgcc | 2640 |
| caccctccca gcccaacacc caggacaaaa cacccagcaa ggtgacggct cgaccctccc | 2700 |
| agcccccact acctcggcgc tcaacccgcc tcaaaacctg atagagggac ctccctgtcc | 2760 |
| ctggcctgcc tgggtccaga tctgctaatg cttttaggaa gtctgcctgg aaactttgac | 2820 |
| atggttcatg tttttactca aaatccaata aaacaaggta gtttggctgt gcaaaaaaaa | 2880 |
| aaaaaaaaaa aaaaaaaa | 2898 |

<210> SEQ ID NO 73
<211> LENGTH: 2883
<212> TYPE: DNA
<213> ORGANISM: Homo sapiens

<400> SEQUENCE: 73

-continued

```
tgggggctgc ggggccggcc catccgtggg ggcgacttga gcgttgaggg cgcgcgggga      60
ggcgagccac catgttcagc cagcagcagc agcagctcca gcaacagcag cagcagctcc     120
agcagttaca gcagcagcag ctccagcagc agcaattgca gcagcagcag ttactgcagc     180
tccagcagct gctccagcag tccccaccac aggccccgtt gcccatggct gtcagccggg     240
ggctccccc gcagcagcca cagcagccgc ttctgaatct ccagggcacc aactcagcct      300
ccctcctcaa cggctccatg ctgcagagag ctttgctttt acagcagttg caaggactgg     360
accagtttgc aatgccacca gccacgtatg acactgccgg tctcaccatg cccacagcaa     420
cactgggtaa cctccgaggc tatggcatgg catcccagg cctcgcagcc cccagcctca      480
cacccccaca actggccact ccaaatttgc aacagttctt tccccaggcc actcgccagt     540
ccttgctggg acctcctcct gttggggtcc ccatgaaccc ttcccagttc aacctttcag     600
gacggaaccc ccagaaacag gcccggacct cctcctctac cacccccaat cgaaagacaa     660
tgcctgtgga agacaagtca dacccccccag agggtctga ggaagccgca gagcccggaa     720
tggacacacc agaagaccaa gatttaccgc cctgcccaga ggacatcgcc aaggaaaaac     780
gcactccagc acctgagcct gagccttgtg aggcgtccga gctgccagca aagagattga     840
ggagctcaga agagcccaca gagaaggaac ctccagggca gttacaggtg aaggcccagc     900
cgcaggcccg gatgacagta ccgaaacaga cacagacacc agacctgctg cctgaggccc     960
tggaagccca agtgctgcca cgattccagc cacgggtcct gcaggtccag gcccaggtgc    1020
agtcacagac tcagccgcgg ataccatcca cagacaccca ggtgcagcca agctgcaga    1080
agcaggcgca aacacagacc tctccagagc acttagtgct gcaacagaag caggtgcagc    1140
cacagctgca gcaggaggca gagccacaga agcaggtgca gccacaggta cagccacagg    1200
cacattcaca gggcccaagg caggtgcagc tgcagcagga ggcagagccg ctgaagcagg    1260
tgcagccaca ggtgcagccc caggcacatt cacagccccc aaggcaggtg cagctgcagc    1320
tgcagaagca ggtccagaca cagacatatc cacaggtcca cacacaggca cagccaagcg    1380
tccagccaca ggagcatcct ccagcgcagg tgtcagtaca gccaccagag cagacccatg    1440
agcagcctca cacccagccg caggtgtcgt tgctggctcc agagcaaaca ccagttgtgg    1500
ttcatgtctg cgggctggag atgccacctg atgcagtaga agctggtgga ggcatggaaa    1560
agaccttgcc agagcctgtg ggcacccaag tcagcatgga agagattcag aatgagtcgg    1620
cctgtggcct agatgtggga gaatgtgaaa acagagcgag agagatgcca ggggtatggg    1680
gcgccggggg ctccctgaag gtcaccattc tgcagagcag tgacagccgg gcctttagca    1740
ctgtacccct gacacctgtc ccccgcccca gtgactccgt ctcctccacc cctgcggcta    1800
ccagcactcc ctctaagcag gccctccagt tcttctgcta catctgcaag gccagctgct    1860
ccagccagca ggagttccag gaccacatgt cggagcctca gcaccagcag cggctagggg    1920
agatccagca catgagccaa gcctgcctcc tgtccctgct gccgtgcc cgggacgtcc      1980
tggagacaga ggatgaggag cctccaccaa ggcgctggtg caacacctgc cagctctact    2040
acatggggga cctgatccaa caccgcagga cacaggacca caagattgcc aaacaatcct    2100
tgcgaccctt ctgcaccgtt tgcaaccgct acttcaaaac ccctcgcaag tttgtggagc    2160
acgtgaagtc ccaggggcat aaggacaaag ccaaggagct gaagtcgctt gagaaagaaa    2220
ttgctggcca agatgaggac cacttcatta cagtggacgc tgtgggttgc ttcgagggtg    2280
atgaagaaga ggaagaggat gatgaggatg aagaagagat cgaggtgagg tccagagata    2340
tatccagaga ggagtggaag ggctcggaga cctacagccc caatactgca tatggtgtgg    2400
```

```
                                                    -continued acttcctggt gcccgtgatg ggctatatct gccgcatctg ccacaagttc tatcacagca    2460
actcaggggc acagctctcc cactgcaagt ccctgggcca ctttgagaac ctgcagaaat    2520
acaaggcggc caagaacccc agccccacca cccgacctgt gagccgccgg tgcgcaatca    2580
acgcccggaa cgctttgaca gccctgttca cctccagcgg ccgcccaccc tcccagccca    2640
acacccagga caaaacaccc agcaaggtga cggctcgacc ctcccagccc ccactacctc    2700
ggcgctcaac ccgcctcaaa acctgataga gggacctccc tgtccctggc ctgcctgggt    2760
ccagatctgc taatgctttt taggagtctg cctggaaact ttgacatggt tcatgttttt    2820
actcaaaatc caataaaaca aggtagtttg gctgtgcaaa aaaaaaaaaa aaaaaaaaa    2880 aaa                                                                 2883

<210> SEQ ID NO 74
<211> LENGTH: 33
<212> TYPE: PRT
<213> ORGANISM: Homo sapiens

<400> SEQUENCE: 74

Gln Gln Leu Gln Gln Leu Gln Gln Gln Gln Leu Gln Gln Gln Gln Leu
1               5                   10                  15

Gln Gln Gln Gln Leu Leu Gln Leu Gln Gln Leu Leu Gln Gln Ser Pro
            20                  25                  30

Pro
```

REPLICATION PROTEIN

RELATED APPLICATION INFORMATION

This application claims the benefit under 35 U.S.C. §371 of PCT Application Serial No. PCT/GB2003/005334, filed Dec. 5, 2003, the disclosure of which is incorporated by reference herein in its entirety, which claims the benefit of Great Britain Application Serial No. 0228337.2, filed Dec. 5, 2002 and Untied States Provisional Application Ser. No. 60/433,925, filed Dec. 17, 2002, the disclosure of which are incorporated by reference herein in their entireties.

FIELD OF THE INVENTION

This invention relates to a screening method for the identification of agents which modulate the activity of a DNA replication protein as a target for intervention in cancer therapy and includes agents which modulate said activity.

The invention also relates to the use of the DNA replication protein, and its RNA transcripts in the prognosis and diagnosis of proliferative disease e.g., cancer.

BACKGROUND

Initiation of DNA replication is a major control point in the mammalian cell cycle, and the point of action of many gene products that are mis-regulated in cancer (Hanahan and Weinberg, 2000). The initiation process involves assembly of pre-replication complex proteins, which include the origin recognition complex (ORC), Cdc6, Cdt1 and Mcm proteins, at replication origins during G1 phase of the cell cycle. This is followed by the action of a second group of proteins, which facilitate loading of DNA polymerases and their accessory factors including PCNA, and the transition to S phase. The initiation process is regulated by cyclin-dependent protein kinase 2 (Cdk2), Cdc7-dbf4 and the Cdt1 inhibitor geminin (for review see Bell and Dutta, 2002). In the nucleus of S phase cells, replication forks cluster together to form hundreds of replication 'foci' or factories (Cook, 1999). Replication factories appear to be linked to a structural framework within the nucleus, however the nature of the molecules that form the link and their role in replication fork activity remains unclear.

Identification of proteins involved in eukaryotic DNA replication and analysis of the basic pathways that regulate their activity during the cell cycle has been driven largely by yeast genetics. These proteins and pathways are generally conserved from yeast to man. However, in multi-cellular organisms that differentiate down diverse developmental pathways, additional layers of complexity are being uncovered. For example, in vertebrates several proteins involved in neuronal differentiation also regulate the G1-S phase transition (Ohnuma et al., 2001). These include the cdk inhibitor $p21^{CIP1/WAF1/SDI1}$ which has been implicated in oligodendrocyte differentiation following growth arrest (Zezula et al., 2001), and in the terminal differentiation of other cell types (Parker et al., 1995).

Initiation of DNA replication can be reconstituted in vitro with isolated nuclei and cytosolic extracts from mammalian cells (Krude, 2000; Krude et al., 1997; Laman et al., 2001; Stoeber et al., 1998). Furthermore, using recombinant Cdk2 complexed with either cyclins E or A, replication complex assembly and activation of DNA synthesis can be reconstituted independently (Coverley et al., 2002). We have studied the activation step, catalysed in vitro by cyclin A-cdk2, and shown that a relatively unstudied protein, p21-Cip 1 interacting zinc-finger protein (Ciz 1) functions during this stage of the initiation process. Human Ciz 1 was previously identified using a modified yeast two-hybrid screen with cyclin E-p21, and biochemical analysis supported an interaction with p21 (Mitsui et al., 1999). A potential role in transcription was proposed but not demonstrated, and no other function was assigned to Ciz1. More recently the Ciz1 gene was isolated from a human medulloblastoma derived cDNA library using an in vivo tumorigenesis model (Warder and Keherly, 2003). Our analysis shows for the first time that Ciz1 plays a positive role in initiation of DNA replication.

A number of changes to chromatin bound proteins occur when DNA synthesis is activated in vitro by recombinant cyclin A-cdk2. The present invention relates to the finding that a cdc6-related antigen, p85, correlates with the initiation of DNA replication and is regulated by cyclin A-cdk2. The protein was cloned from a mouse embryo library and identified as mouse Ciz1.

In vitro analysis has shown that Ciz1 protein positively regulates initiation of DNA replication and that its activity is modulated by cdk phosphorylation at threonine 191/2, linking it to the cdk-dependent pathways that control initiation. The Embryonic form mouse Ciz1 is alternately spliced, compared to predicted and somatic forms. Human Ciz1 is also alternately spliced, with variability in the same exons as mouse Ciz1. It has been found that recombinant embryonic form Ciz1 promotes initiation of mammalian DNA replication and that pediatric cancers express 'embryonic-like' forms of Ciz1. Without wishing to be held to one theory, the inventors propose that Ciz1 mis-splicing produces embryonic-like forms of Ciz1 at inappropriate times in development. This promotes inappropriately regulated DNA replication and contributes to formation or progression of cancer cell lineages.

A number of techniques have been developed in recent years which purport to specifically ablate genes and/or gene products. For example, the use of anti-sense nucleic acid molecules to bind to and thereby block or inactivate target mRNA molecules is an effective means to inhibit the production of gene products.

A much more recent technique to specifically ablate gene function is through the introduction of double stranded RNA, also referred to as inhibitory RNA (RNAi), into a cell which results in the destruction of mRNA complementary to the sequence included in the RNAi molecule. The RNAi molecule comprises two complementary strands of RNA (a sense strand and an antisense strand) annealed to each other to form a double stranded RNA molecule. The RNAi molecule is typically derived from the exonic or coding sequence of the gene which is to be ablated.

Nucleic acids and proteins have both a linear sequence structure, as defined by their base or amino acid sequence, and also a three dimensional structure which in part is determined by the linear sequence and also the environment in which these molecules are located. Conventional therapeutic molecules are small molecules, for example, peptides, polypeptides, or antibodies, which bind target molecules to produce an agonistic or antagonistic effect. It has become apparent that nucleic acid molecules also have potential with respect to providing agents with the requisite binding properties which may have therapeutic utility. These nucleic acid molecules are typically referred to as aptamers. Aptamers are small, usually stabilised, nucleic acid molecules which comprise a binding domain for a target molecule.

Aptamers may comprise at least one modified nucleotide base. The term "modified nucleotide base" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include by example and not by way of limitation; alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N-6-methyladenine; 4-acetylcytosine, 5-(carboxyhydroxylmethyl)uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N-6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6-diaminopurine; methylpsuedouracil; 1-methylguanine; 1-methylcytosine;

Aptamers may be synthesized using conventional phosphodiester linked nucleotides using standard solid or solution phase synthesis techniques which are known in the art. Linkages between nucleotides may use alternative linking molecules. For example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

Other techniques which purport to specifically ablate genes and/or gene products focus on modulating the function or interfering with the activity of protein molecules. Proteins can be targeted by chemical inhibitors drawn, for example, from existing small molecule libraries.

Antibodies, preferably monoclonal, can be raised for example in mice or rats against different protein isoforms. Antibodies, also known as immunoglobulins, are protein molecules which have specificity for foreign molecules (antigens). Immunoglobulins (Ig) are a class of structurally related proteins consisting of two pairs of polypeptide chains, one pair of light (L) (low molecular weight) chain (κ or λ), and one pair of heavy (H) chains (γ, α, μ, δ and ε), all four linked together by disulphide bonds. Both H and L chains have regions that contribute to the binding of antigen and that are highly variable from one Ig molecule to another. In addition, H and L chains contain regions that are non-variable or constant.

The L chains consist of two domains. The carboxy-terminal domain is essentially identical among L chains of a given type and is referred to as the "constant" (C) region. The amino terminal domain varies from one L chain to anther and contributes to the binding site of the antibody. Because of its variability, it is referred to as the "variable" (V) region.

The H chains of Ig molecules are of several classes, α, μ, σ, α, and γ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the H chains, i.e., IgG1, IgG2, IgG3 and IgG4). Further detail regarding antibody structure and their various functions can be found in, Using Antibodies: A laboratory manual, Cold Spring Harbour Laboratory Press.

Chimeric antibodies are recombinant antibodies in which all of the V-regions of a mouse or rat antibody are combined with human antibody C-regions. Humanised antibodies are recombinant hybrid antibodies which fuse the complimentarity determining regions from a rodent antibody V-region with the framework regions from the human antibody V-regions. The C-regions from the human antibody are also used. The complimentarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not illicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

Other techniques for targetting at the protein level include the use of randomly generated peptides that specifically bind to proteins, and any other molecules which bind to proteins or protein variants and modify the function thereof.

Understanding the DNA replication process is of prime concern in the field of cancer therapy. It is known that cancer cells can become resistant to chemotherapeutic agents and can evade detection by the immune system. There is an on going need to identify targets for cancer therapy so that new agents can be identified. The DNA replication process represents a prime target for drug intervention in cancer therapy. There is a need to identify gene products which modulate DNA replication and which contribute to formation or progression of cancer cell lineages, and to develop agents that affect their function.

SUMMARY OF THE INVENTION

According to one aspect of the present invention there is provided the use of a Ciz1 nucleotide or polypeptide sequence, or any fragment or variant thereof, as a target for the identification of agents which modulate DNA replication.

As used herein the term 'fragment' or 'variant' is used to refer to any nucleic or amino acid sequence which is derived from the full length nucleotide or amino acid sequence of Ciz1 or derived from a splice variant thereof. In one embodiment of the invention the fragment is of sufficient length and/or of sufficient homology to full length Ciz1 to retain the DNA replication activity of Ciz1. In an alternative embodiment inactive Ciz1 fragments are used. The term 'fragment' or 'variant' also relates to the Ciz1 RNA transcripts described herein and protein isoforms (or parts thereof).

As used herein the term 'modulate' is used to refer to either increasing or decreasing DNA replication, above and below the levels which would normally be observed in the absence of the specific agent (i.e., any alterations in DNA replication activity which are either directly or indirectly linked to the use of the agent). The term 'modulate' also includes reference to a change of spacial or temporal organisation of DNA replication.

According to an alternative aspect of the invention there is provided a screening method for the identification of agents which modulate DNA replication wherein the screening method comprises the use of Ciz1 nucleotide or polypeptide sequence or fragments or variants thereof.

Preferably the screening method comprises detecting or measuring the effect of an agent on a nucleic acid molecule selected from the groups consisting of:
a) a nucleic acid molecule comprising a nucleic acid sequence represented in any of FIG. 14, 15, or 21 (SEQ ID NO: 45, 46, 66, 67, 68, 69, 70, 71, 72 or 73);
b) a nucleic acid molecule which hybridises to the nucleic acid sequence in (a) and which has Ciz1 activity or activity of a variant thereof;
c) a nucleic acid molecule which has a nucleic acid sequence which is degenerate because of the genetic code to the sequences in a) and b); and
d) a nucleic acid molecule derived from the genomic sequence at the Ciz1 locus or a nucleic acid molecule that hybridises to the genomic sequence.

In one embodiment of the invention, the nucleic acid molecule is modified by deletion, substitution or addition of at least one nucleic acid residue of the nucleic acid sequence.

Alternatively the screening method comprises the steps of:
(i) forming a preparation comprising a polypeptide molecule, or an active fragment thereof, encoded by a nucleic acid molecule selected from the group consisting of:
a) a nucleic acid molecule comprising a nucleic acid sequence represented in FIG. 14, 15 or 21 (SEQ ID NO: 45, 46, 66, 67, 68, 69, 70, 71, 72 or 73);
b) a nucleic acid molecule which hybridises to the nucleic acid sequence in (a) and which has Ciz1 activity or activity of a variant thereof;
c) a nucleic acid molecule which has a nucleic acid sequence which is degenerate because of the genetic code to the sequences in a) and b) and a candidate agent to be tested;
d) a nucleic acid molecule derived from the genomic sequence at the Ciz1 locus or a nucleic acid molecule that hybridises to the genomic sequence; and
ii) detecting or measuring the effect of the agent on the activity of said polypeptide.

Assays for the detection of DNA replication are known in the art. Activity residing in Ciz1, or derived peptide fragments, and the effect of potential therapeutic agents on that activity would be assayed in vitro or in vivo.

In vitro assays for Ciz1 protein activity would comprise synchronised isolated G1 phase nuclei and either S phase extract or G1 phase extract supplemented with cyclin-dependent kinases. Inclusion of Ciz1 or derived peptide fragments stimulates initiation of DNA replication in these circumstances and can be monitored visually (by scoring nuclei that have incorporated fluorescent nucleotides during in vitro reactions) or by measuring incorporation of radioactive nucleotides. The assay for therapeutic reagents that interfere with Ciz1 protein function would involve looking for inhibition of DNA replication in these assays. The effect of agents on Ciz1 nuclear localisation, chromatin binding, stability, modification and protein-protein interactions could also be monitored in these assays.

In vivo assays will include creation of cell and mouse models that over-express or under-express Ciz1, or derived fragments, resulting in altered cell proliferation. The preparation of transgenic animals is generally known in the art and within the ambit of the skilled person. The assay for therapeutic reagents would involve analysis of cell-cycle time, initiation of DNA replication and cancer incidence in the presence and absence of drugs that either impinge on Ciz1 protein activity, or interfere with Ciz1 production by targeting Ciz1 and its variants at the RNA level.

In a preferred method of the invention said hybridisation conditions are stringent.

Stringent hybridisation/washing conditions are well known in the art. For example, nucleic acid hybrids that are stable after washing in 0.1×SSC, 0.1% SDS at 60° C. It is well known in the art that optimal hybridisation conditions can be calculated if the sequence of the nucleic acid is known. Typically, hybridisation conditions uses 4–6×SSPE (20×SSPE contains 175.3 g NaCl, 88.2 g $NaH_2PO_4H_2O$ and 7.4 g EDTA dissolved to 1 liter and the pH adjusted to 7.4); 5-10×Denhardts solution (50×Denhardts solution contains 5 g Ficoll (Type 400, Pharmacia), 5 g polyvinylpyrrolidone abd 5 g bovine serum albumen; 100 μg-1.0 mg/ml sonicated salmon/herring DNA; 0.1-1.0% sodium dodecyl sulphate; optionally 40-60% deionised formamide. Hybridisation temperature will vary depending on the GC content of the nucleic acid target sequence but will typically be between 42°-65° C.

In a preferred method of the invention said polypeptide is modified by deletion, substitution or addition of at least one amino acid residue of the polypeptide sequence.

A modified or variant, i.e. a fragment polypeptide and reference polypeptide, may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and asparatic acid; c) asparagine and glutamine d) arginine and lysine; e) isoleucine, leucine, methionine and valine and f) phenylalanine, tyrosine and tryptophan. Preferred are variants which retain the same biological function and activity as the reference polypeptide from which it varies. Alternatively, variants include those with an altered biological function, for example variants which act as antagonists, so called "dominant negative" variants.

Alternatively or in addition, non-conservative substitutions may give the desired biological activity see Cain S A, Williams D M, Harris V, Monk P N. Selection of novel ligands from a whole-molecule randomly mutated C5a library. Protein Eng. 2001 March; 14(3):189-93, which is incorporated by reference.

A functionally equivalent polypeptide sequence according to the invention is a variant wherein one or more amino acid residues are substituted with conserved or non-conserved amino acid residues, or one in which one or more amino acid residues includes a substituent group. Conservative substitutions are the replacements, one for another, among the aliphatic amino acids Ala, Val, Leu and Ile; interchange of the hydroxl residues Ser and Thr; exchange of the acidic residues Asp and Glu; substitution between amide residues Asn and Gln; exchange of the basic residues Lys and Arg; and replacements among aromatic residues Phe and Tyr.

In addition, the invention features nucleotide or polypeptide sequences having at least 50% identity with the nucleotide or polypeptide sequences as herein disclosed, or fragments and functionally equivalent polypeptides thereof. In one embodiment, the nucleotide or polypeptide sequences have at least 75% to 85% identity, more preferably at least 90% identity, even more preferably at least 95% identity, still more preferably at least 97% identity, and most preferably at least 99% identity with the nucleotide and amino acid sequences illustrated herein.

In a preferred method of the invention said nucleic acid molecule comprises the nucleic acid sequence encoding the amino acid sequence Ciz1 in FIG. 16 (SEQ ID NO: 26) or FIG. 17 (SEQ ID NO: 47) or any variants thereof, including those described in FIGS. 20A (SEQ ID NO: 58-61) and 20B (SEQ ID NO: 62-65). In a further preferred method of the invention said nucleic acid molecule consists of the nucleic acid sequence which encodes the amino acid sequence Ciz1 in FIG. 16 (SEQ ID NO: 26) or FIG. 17 (SEQ ID NO: 47) or variants thereof, including those described in FIGS. 20A (SEQ ID NO: 58-61) and 20B (SEQ ID NO: 62-65).

In a further preferred method of the invention said polypeptide molecule comprises the amino acid sequence Ciz1 in FIG. 16 (SEQ ID NO: 26) or 17 (SEQ ID NO: 47) or variants thereof, including those described in FIGS. 20A (SEQ ID NO: 58-61) and 20B (SEQ ID NO: 62-65). In a further preferred method of the invention said polypeptide molecule consists of the amino acid sequence Ciz1 in FIG. 16 (SEQ ID NO: 26) or 17 (SEQ ID NO: 47) or variants thereof, including those described in FIGS. 20A (SEQ ID NO: 58-61) and 20B (SEQ ID NO: 62-65).

In a further preferred method of the invention said polypeptide is expressed by a cell, preferably a mammalian cell, or animal and said screening method is a cell-based screening method.

Preferably said cell naturally expresses the Ciz 1 polypeptide. Alternatively said cell is transfected with a nucleic acid molecule encoding a Ciz 1 polypeptide (or a variant molecule thereof, found, for example in cancer cell lineages).

According to a further aspect of the invention there is provided an agent obtainable by the method according to the invention.

Preferably said agent is an antagonist of Ciz1 mediated DNA replication. Alternatively said agent is an agonist of Ciz1 mediated DNA replication.

In a further preferred method of the invention said agent is selected from the group consisting of: polypeptide; peptide; aptamer; chemical; antibody; nucleic acid; or polypeptide or nucleotide probe.

Preferably the agent comprises a sequence that is complimentary or of sufficient homology to give specific binding to the target and can be used to detect the level of nucleic acid or protein for diagnostic purposes.

Alternatively the agent identified by the method of the invention is a therapeutic agent and can be used for the treatment of disease.

In one embodiment of the invention the agent is an antibody molecule and binds to any of the sequences represented by FIGS. 16 (SEQ ID NO: 26), 17 (SEQ ID NO: 47) or 20 (SEQ ID NO: 58-65).

Preferably said antibody is a monoclonal antibody.

Alternatively said agent is an anti-sense nucleic acid molecule which binds to and thereby blocks or inactivates the mRNA encoded by any of the nucleic acid sequences described above.

In an alternative embodiment, said agent is an RNAi molecule and comprises two complementary strands of RNA (a sense strand and an antisense strand) annealed to each other to form a double stranded RNA molecule. Preferably the RNAi molecule is derived from the exonic sequence of the Ciz1 gene or from another over-lapping gene.

In one embodiment unspliced mRNA is targetted with RNAi to inhibit production of the spliced variant. In another the spliced variant mRNA is ablated without affecting the non-variant mRNA.

In a preferred method of the invention said peptide is an oligopeptide. Preferably, said oligopeptide is at least 10 amino acids long. Preferably said oligopeptide is at least 20, 30, 40, 50 amino acids in length.

In a further preferred method of the invention said peptide is a modified peptide.

It will be apparent to one skilled in the art that modified amino acids include, by way of example and not by way of limitation, 4-hydroxyproline, 5-hydroxylysine, $N^6$-acetyl-ysine, $N^6$-methyllysine, $N^6,N^6$-dimethyllysine, $N^6,N^6,N^6$-trimethyllysine, cyclohexyalanine, D-amino acids, ornithine. Other modifications include amino acids with a $C_2$, $C_3$ or $C_4$ alkyl R group optionally substituted by 1, 2 or 3 substituents selected from halo (eg F, Br, I), hydroxy or $C_1$-$C_4$ alkoxy.

Alternatively said peptide is modified by acetylation and/or amidation.

In a preferred method of the invention the polypeptides or peptides are modified by cyclisation. Cyclisation is known in the art, (see Scott et al Chem Biol (2001), 8:801-815; Gellerman et al J. Peptide Res (2001), 57: 277-291; Dutta et al J. Peptide Res (2000), 8: 398-412; Ngoka and Gross J Amer Soc Mass Spec (1999), 10:360-363).

According to a further aspect of the invention there is provided a vector as a delivery means for, for example, an antisense or an RNAi molecule which inhibits Ciz1 or variants thereof and thereby allows the targetting of cells expressing the protein to be targeted.

In one embodiment of the invention a viral vector is used as delivery means.

Preferably the vector includes an expression cassette comprising the nucleotide sequence selected from the group consisting of;

a) the nucleic acid sequence which encodes Ciz1 amino acid sequence as shown in FIGS. 14, 15 and 21 (SEQ ID NO: 45, 46, 66, 67, 68, 69, 70, 71, 72 or 73);

b) a nucleic acid molecule which hybridizes to the nucleic acid sequence of (a);

c) a nucleic acid molecule which has a nucleic acid sequence which is degenerate because of the genetic code to the sequences in a) and b) and any sequence which is complimentary to any of the above sequences;

d) a nucleic acid sequence that encodes Ciz1 pre-mRNA (i.e., the genomic sequence), wherein the expression cassette is transcriptionally linked to a promoter sequence.

Preferably the vectors including the expression cassette is adapted for eukaryotic gene expression. Typically said adaptation includes, by example and not by way of limitation, the provision of transcription control sequences (promoter sequences) which mediate cell/tissue specific expression. These promoter sequences may be cell/tissue specific, inducible or constitutive.

Promoter elements typically also include so called TATA box and RNA polymerase initiation selection sequences which function to select a site of transcription initiation.

These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors which are maintained autonomously are referred to as episomal vectors. Further adaptations which facilitate the expression of vector encoded genes include the provision of transcription termination sequences.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

According to the present invention there is provided a diagnostic method for the identification of proliferative disorders comprising detecting the presence or expression of the Ciz1 gene, Ciz1 splice variants and mutations in the genomic or protein sequence thererof.

Preferably said diagnostic method comprises one of more of the following steps:
(i) contacting a sample isolated from a subject to be tested with an agent which specifically binds a polypeptide with Ciz 1 activity or a nucleic acid molecule encoding a polypeptide with Ciz 1 activity; and
(ii) detecting or measuring the binding of the agent on said polypeptide or nucleic acid in said sample;
(iii) use of reverse-transcribed PCR or real-time PCR to monitor Ciz1 isoform expression and to measure expression levels.
(iv) measuring the presence of nucleic acid or amino-acid mutations based on altered conformational properties of the molecule.

In one embodiment, the diagnostic method of the present invention is carried out in-vivo.

In an alternative embodiment, the diagnostic method of the present invention is carried out ex-vivo or in-vitro.

Preferably the diagnostic method provides for a quantitative measure of Ciz1 RNA or protein variants in a sample.

In one embodiment of the invention there is provided the use of an agent which modulates Ciz1 RNA or protein, or variants thereof, as a pharmaceutical.

Preferably said pharmaceutical comprises an agent identified by the screening method of the present invention in combination or association with a pharmaceutically acceptable carrier, excipient or diluent.

Preferably said pharmaceutical is for oral or topical administration or for administration by injection. In alternative embodiment of the invention the pharmaceutical is administered as an aerosol.

In a further preferred embodiment of the invention there is provided the use of an agent according to the invention for the manufacture of a medicament for use in the treatment of proliferative disease. Preferably said proliferative disease is cancer.

Preferably said cancer is a paediatric cancer and is selected from the group consisting of; retinoblastoma, neuroblastoma, Burkitt lymphoma, medulloblastoma, and Ewings Sarcoma family tumours (ESFTs).

In an alternative embodiment the cancer is a carcinoma, adenocarcinoma, lymphoma or leukemia.

In an alternate embodiment the disease is liver, lung or skin cancer or metastasis.

According to a further aspect of the invention there is provided a method to treat a proliferative disease comprising administering to an animal, preferably a human, an agent obtainable by the method according to the invention.

According to an alternate aspect of the invention, there is provided the use of an agent according to the invention for the manufacture of a medicament to slow cell division or growth.

The invention also includes the use of the Ciz1 amino acid sequence and protein structure in rational drug design and the use of Ciz1 nucleotide and amino acid sequences thereof or variants thereof for screening chemical libraries for agents that specifically bind to Ciz1.

The invention also includes a kit comprising a diagnostic, prognostic or therapeutic agent identified by the method of the invention.

In an alternative embodiment of the invention, an array based sequencing chip is used for the detection of altered Ciz1.

BRIEF DESCRIPTION OF THE FIGURES

An embodiment of the invention is described below by example only and with reference to the following figures:

FIG. 1 Illustrates the effect of cyclin A-cdk2 on late G1 nuclei. A) Anti-Cdc6 antibody V1 detects mouse Cdc6 and a second antigen in western blots of 3T3 whole cell extract, which migrates with approximate Mr of 100 kDa (based on the mobility of the Mcm3 protein this was previously estimated at nearer 85 kDa so the antigen was named p85—we have kept the same name here for clarity). P85 is present in both the soluble fraction and insoluble nuclear fraction (prepared under in vitro replication conditions). B) Initiation of DNA synthesis in 'replication competent' late G1 phase nuclei by G1 phase extract supplemented with recombinant cyclin A-cdk2. Control bar shows the proportion of nuclei already in S phase (unshaded), and those that initiated replication in extract from S phase cells (shaded). C) After 15 minutes under cell-free replication conditions nuclei were washed and the chromatin fraction was re-isolated and separated by SDS-Page and blotted for Mcm2 and Mcm3. D) The same nuclei blotted with antibody V1. p85 antigen is more abundant in nuclei exposed to initiation-inducing concentrations of cyclin A-cdk2. Antibody V1 was used to clone the gene for p85 from a mouse embryo expression library which was identified as Ciz1.

FIG. 2A) Alignment of mouse Ciz1 variants. The predicted full-length Ciz1 amino-acid sequence ('Full') is identical to a mouse mammary tumour cDNA clone (BC018483), while embryonic Ciz1 ('ECiz1', AJ575057), and a melanoma-derived clone (AK089986) lack two discrete internal sequences. In addition, the first available methionine in ECiz1 is in the middle of exon 3 (Met84), which excludes a polyglutamine rich region from the N-terminus. Melanoma derived AK089986 may be incomplete as it ends 77 codons before the C-terminus of all other mouse and human clones. Stars indicate amino-acids changed by site-directed mutagenesis in the constructs shown in D. Amino-acids that correspond to codons targeted by siRNAs are underlined. B) Mouse Ciz1 is encoded by at least 17 exons. Coding exons are shown in grey, alternatively spliced regions are black, untranslated regions are white. Two alternative exon 1 sequences are included in some Ciz1 transcripts (not shown) but an alternative translational start site upstream of the two depicted here has not yet been found. C) Sequence features and putative domains in ECiz1. Predicted nuclear localisation sequence (NLS), putative cyclin-dependent kinase phosphorylation sites, C2H2 type zinc-fingers and a C terminal domain with homology to the nuclear matrix protein matrin 3 (Nakayasu and Berezney, 1991) are shown. The positions of sequences absent from ECiz1 are indicated by triangles. D) ECiz1 and derived truncations and point mutants used in cell-free DNA replication experiments. Numbers in parentheses relate to amino-acid positions in the full-length form of mouse Ciz1, shown in A. Stars indicate putative phosphorylation sites ablated by site-directed mutagenesis.

FIG. 3 Shows the effect of Ciz1 protein and derived fragments in cell-free DNA replication experiments and illustrates that ECiz1 promotes initiation of mammalian DNA replication A) Recombinant ECiz1 stimulates initiation of DNA replication in 'replication competent' late G1 phase nuclei, during incubation in S phase extract. Histogram shows the average number of nuclei that incorporated biotinylated nucleotides in vitro (black), in the presence or absence of ectopic ECiz1, with standard deviations calculated from four independent experiments. The 17% of nuclei that were already in S phase when the nuclear preparation was made are shown in white. Images show nuclei replicating in vitro, with or without 1 nM ECiz1. Total nuclei are counterstained with propidium iodode (red). B) The response to recombinant ECiz1 is concentration dependent with a sharp optimum in the nM range. In this experiment, and all those shown in B-I, results are expressed as % initiation rather than % replication. This is calculated from the number of nuclei that initiate in vitro and the number of nuclei that are 'competent' to initiate in vitro (see methods). C) Threonines 191/2 are involved in regulating Ciz1 DNA replication activity as ECiz1 cdk site mutant T(191/2)A escapes suppression at high concentrations. D) Cdk site mutant T(293)A stimulates initiation with a similar profile to ECiz1 but at lower concentrations. E) Truncated ECiz1 (Nterm 442) lacks C-terminal sequences, but stimulates in vitro initiation to a similar extent as ECiz1. F) Cterm 274 retains no DNA replication activity in this assay. G, H, I) Further deletion analysis in the N-terminal two thirds of the ECiz1 protein show that a short region 3' of exon 8 is required for Ciz1 function when assayed in vitro.

FIG. 4 Characterisation of anti-Ciz1 polyclonal antibodies and identification of 125 kDa Ciz1-related bands A) Coomassie stained SDS-polyacrylamide gel showing purified recombinant ECiz1 fragment Nterm442, and western blots of recombinant Nterm442 using anti-Cdc6 antibody V1, and anti-Ciz1 antibodies 1793 and 1794. B) Western blot of 3T3 whole cell extract. Of the two bands detected by anti-Ciz1 antibody 1793 one has the same mobility as p85-Ciz1 (100 kDa) recognized by antibody V1 and the other has an apparent Mr of 125 kDa. Anti-Ciz1 antibody 1794 recognizes only the 125 kDa form of Ciz1 (and a second antigen of around 80 kDa). C) Immuno-precipitation from 3T3 nuclear extract, using antibody V1 or anti-Ciz1 1793. Both antibodies precipitate p85, which is recognized by the reciprocal antibody in western blots. P125 is precipitated by antibody 1793, and to a lesser extent by antibody V1 and these are recognized by 1793 in western blots. Mcm3 is shown as a control.

FIG. 5 Immunofluorescence analysis of endogenous Ciz1. Ciz1 resides in sub-nuclear foci that overlap with sites of DNA replication A) Endogenous Ciz1 (red) in 3T3 cells fixed before (untreated) or after (detergent treated) exposure to TritonX100, detected with anti-Ciz1 antibody 1793. Nuclei are counterstained with Hoescht 33258 (blue). Cdc6 (green), detected with a Cdc6-specific monoclonal antibody is shown for comparison. B) Inclusion of recombinant Ciz1 blocks reactivity of antibody 1793 with detergent treated nuclei. C) Detergent-resistant Ciz1 (red) is present in all nuclei in cycling populations, while detergent resistant PCNA (green) persists only in S phase nuclei. D) High magnification confocal sections of detergent resistant Ciz1 and PCNA, and merged image showing co-localising foci (yellow). E) Line plots of red and green fluorescence across the merged image in D, at the positions indicated (i and ii). F) Cross-correlation plot (Rubbi and Milner, 2000; van Steensel et al., 1996) for green foci compared to red over the whole merged image in D, and (inset) for the marked section after thresh-holding fluorescence at the levels shown in Eii. The red line in the inset to F shows loss of correlation when the Ciz1 image is rotated 90° with respect to PCNA. Bar is 10 µM.

FIG. 6 RNA interference. Ciz 1 depletion inhibits S phase A) siRNAs that target Ciz1 transcripts at four sites (see FIG. 2A) were individually applied to cycling 3T3 cells as a single 3 nM dose and cell number was monitored at the indicated times. Images of cell populations at 16 and 40 hours after transfection with siRNA 8 (red outline) or mock treated cells (blue outline) are shown. B) Ciz1 protein detected with anti-Ciz1 1793 (green) 48 hours after exposure to Ciz1 siRNAs (4 and 8), or control GAPDH siRNA. C) Ciz1, GAPDH and β-actin transcript levels in cells exposed to Ciz1 siRNAs (4 and 8), or control GAPDH siRNA for 24 hours. Numbers in parentheses reflect band intensity in arbitrary units, and the overall reduction in Ciz1 and GAPDH transcripts (normalised against β-actin) is expressed as a percentage. D) The proportion of cells that incorporated BrdU into DNA (green) is significantly decreased in Ciz1 depleted cells, 48 hours after treatment with Ciz1 siRNA. Histogram shows average results from four independent experiments. E) The number of nuclei with detergent resistant Mcm3 (green) increases in populations treated with Ciz1 siRNA. F) The proportion of nuclei with detergent resistant PCNA (green) also increases under these conditions. All nuclei are counterstained and shown in pseudo-colour (red).

Figure 7:
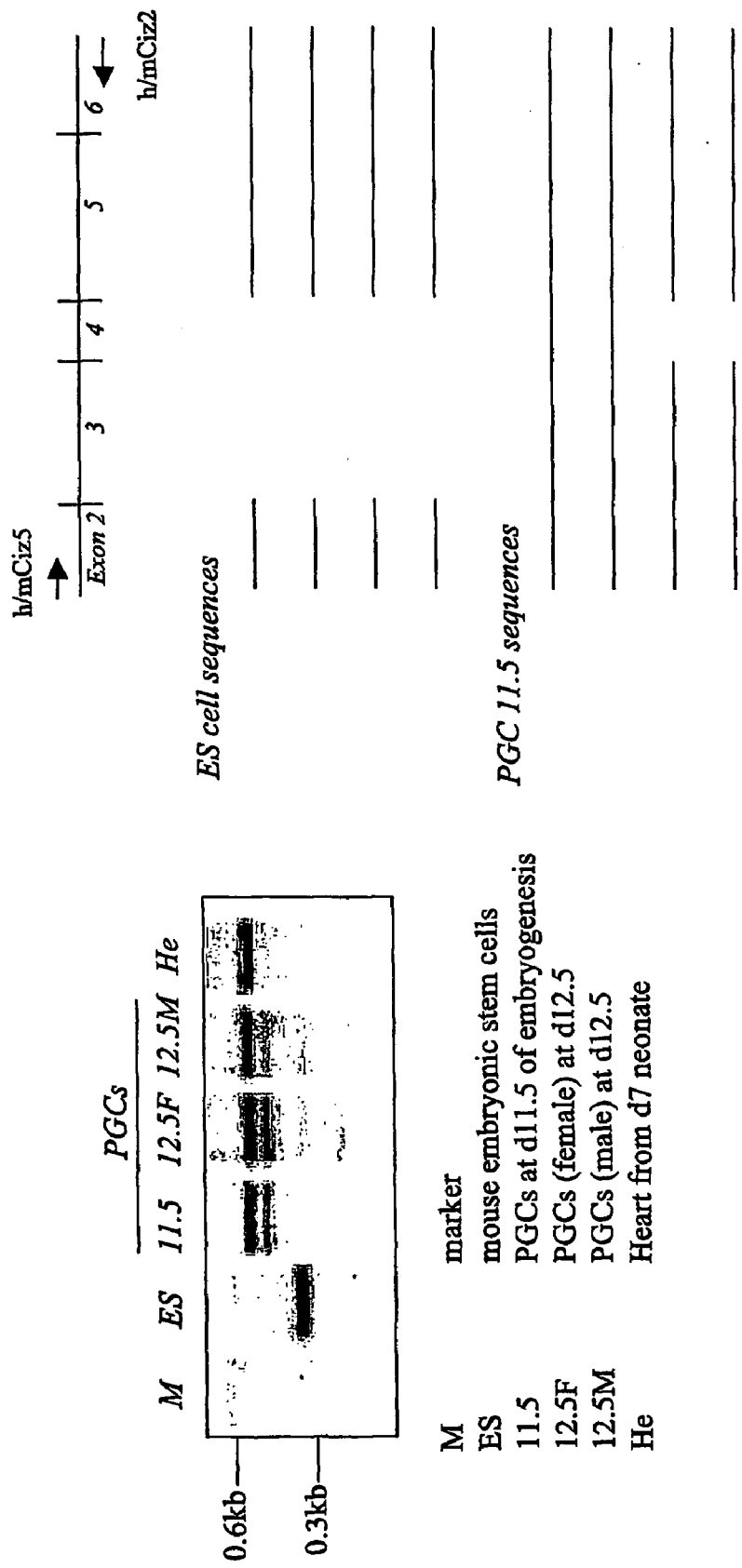
FIG. 7 RT-PCR analysis of Ciz1 exons 3/4 splice variant expression in mouse primordial germ cells and embryonic stem cells. Exons 3 and/or 4 are alternatively spliced in these cell types, but not in neonatal heart. These data are consistent with the hypothesis that full-length Ciz1 is the pre-dominant form in neonatal somatic tissue, and that variants occur with more frequency earlier in development, and in germ line tissues.

A) Translated ESTs from paediatric cancers and adult neural cancers.
B) Translated ESTs from various non-cancer cells and tissues
C) Translated ESTs from leukemias, lymphomas, and from normal haematopoetic and lymphocytic cells
D) Translated ESTs from carcinomas
E) Translated ESTs from a range of other cancers
F) Summary of alternatively spliced regions (SEQ ID NO: 37-44) in human Ciz1 showing conditionally included sequences.

FIG. 12 Ciz1 splice variant expression in Ewings sarcoma family tumour cells lines (ESFT) and neuroblastoma cell lines. A. Whole RNA samples from six independent ESFT cell lines, two neuroblastomas and a control cell line (HEK293 cells) was subject to RT-PCR analysis using 4 different primer sets.

ESFT cell lines are 1) A673, 2) RDES, 3) SKES1, 4) SKNMC, 5) TC3, 6) TTC466. Neuroblastoma cell lines are 1) IMR32, 2) SKNSH.

B. Analysis of Ciz1 Exons 3/4/5 PCR products in ESFTs and neuroblastoma. The products of primers h3 and h4 (spanning potentially variable exons 4 and 6) were analysed in more detail. PCR fragments were purified from agarose gels by standard procedures, subcloned and sequenced to identify the source of fragment size variations. Between one and eleven individual clones for each of the seven cell lines were sequenced and the results are summarised in tabular form. Ciz1 from ESFT cell lines lacks exon 4 in 31% of transcripts overall, and for some ESFT lines this is nearer 50%. DSSSQ (SEQ ID NO:1) is more commonly absent in the two neuroblastoma cell lines tested here.

FIG. 13 Ciz1 isoforms in normal human fibroblasts (Wi38) and metastatic prostate cancer cell lines (PC3 and LNCAP). A. Both prostate cancer cell lines contain an excess of the largest p125 Ciz1 protein variant in the nuclear fraction, compared to the non-cancer cell line. B. Models for the production of p85 (100) from p125 variants by protein processing during initiation of DNA replication.

FIG. 14 illustrates the full length mouse mRNA sequence (SEQ ID NO: 45).

FIG. 15 illustrates the full length human mRNA sequence (SEQ ID NO: 46).

FIG. 16 illustrates the full length mouse protein sequence (SEQ ID NO: 26).

FIG. 17 illustrates the full length human protein sequence (SEQ ID NO: 47).

FIG. 18 illustrates human alternatively spliced protein sequences (SEQ ID NO: 48, 74, 41, 1, 43, 42, 44, 3 and 40, respectively). Sequences shown are absent in the spliced protein sequences.

FIG. 19 illustrates human alternatively spliced mRNA sequences (SEQ ID NO: 49-57, respectively). Sequences shown are absent in the spliced protein sequences.

FIGS. 20 A and B illustrate unique junction sequences created in human Ciz1 proteins by missing exons (SEQ ID NO: 58-61 and 62-65, respectively). Junction sequences represent prime sites of target for therapeutic agents identified by the method of the invention.

FIG. 21A to H illustrate junction sequences created in human Ciz1 mRNA (SEQ ID NO: 66-73, respectively).

DETAILED DESCRIPTION

Identification of Ciz1 We have exploited a polyclonal antibody (antibody V1) that was raised against recombinant human Cdc6 (Coverley et al., 2000; Stoeber et al., 1998; Williams et al., 1998) to identify and study an unknown antigen whose behaviour correlates with initiation of DNA replication in vitro. The antigen has an apparent Mr of 100 kDa (called p85) and is readily detectable in extracts from 3T3 cells (FIG. 1A).

DNA synthesis can be activated in cell-free replication experiments using 'replication competent' late G1 phase nuclei, G1 extracts, and recombinant cyclin A-cdk2. Under these conditions nuclei will incorporate labelled nucleotides into nascent DNA, in a manner strictly dependent on the concentration of active protein kinase (FIG. 1B). Above and below the optimum concentration no initiation of DNA replication takes place. However, other events occur which inversely correlate with initiation (Coverley et al., 2002). Here we use activation of DNA synthesis (FIG. 1B), and Mcm2 phosphorylation (which results in increased mobility, FIG. 1C), to calibrate the effects of recombinant cyclin A-cdk2 in cell-free replication experiments, and correlate the behaviour of p85 with activation of DNA synthesis.

In G1 nuclei that are re-isolated from reactions containing initiation-inducing concentrations of cyclin A-cdk2, p85 antigen is more prevalent compared to nuclei exposed to lower or higher concentrations of kinase (FIG. 1D). This suggests that p85 is regulated at some level by cyclin A-cdk2, in a manner that is co-incident with activation of DNA synthesis. No other antigens correlate so closely with this stage in the cell-free initiation process, therefore we used antibody V1 to clone the gene for mouse p85.

When applied to a cDNA expression library derived from 11-day mouse embryos antibody V1 picked out two clones that survived multiple rounds of screening (see methods). One encoded mouse Cdc6, while the other encoded 716 amino acids of the murine homologue of human Ciz1 (Mitsui et al., 1999). Full-length human and mouse Ciz1 have approximately 70% overall homology at the amino-acid level, with greatest (>80%) homology in the N and C terminal regions. Ciz1 is conserved among vertebrates as homologues exist in rat and fugu, but no proteins with a high degree of homology or similar domain structure could be identified in lower eukaryotes, raising the possibility that Ciz1 evolved to perform a specialised role in vertebrate development.

A previous publication on human Ciz1 (Mitsui et al 1999) demonstrated interaction with the cell-cycle protein p21-CIP1, leading to investigation of a proposed role as a transcription factor, not a DNA replication factor. A second paper (Warder and Keherly 2003) published after the priority date of this patent application suggests a role for Ciz1 in tumorigenesis, but does not demonstrate a role in DNA replication or recognise the importance of Ciz1 splice variant expression.

Multiple Ciz1 isoforms The predicted mouse Ciz1 open reading frame and a cDNA derived from a mouse mammary tumour library (BC018483) contain three regions that are not present in our embryonic clone (AJ575057), hereafter referred to as ECiz1 (FIG. 2A; SEQ ID NO: 27). The three variable regions in ECiz1 appear to be the result of alternative splicing of exons 2/3, 6 and 8 (FIG. 2B). Mouse melanoma clone AK089986 lacks two of the same three regions as ECiz1 (FIG. 2A), while the third encodes an N-terminal polyglutamine stretch that is also absent from human medulloblastoma derived clones. A fourth sequence block derived from exons 3/4 is absent from Ciz1 transcripts derived from mouse ES cells, and from exon 4 in mouse primordial germ cells (FIG. 7). Human Ciz1 is also alternatively spliced at the RNA level to yield transcripts that exclude combinations of the same four sequence blocks as mouse Ciz1 (see below). In fact, all known variations in mouse Ciz1 cDNAs have close human parallels, some of which are identical at the amino-acid level. This suggests that the different Ciz1 isoforms have functional significance. A fifth variable regions (not yet observed in the mouse) is alternatively spliced in human Ciz1 transcripts derived mainly from carcinomas.

The data suggest that shorter forms of Ciz1 (lacking the alternatively spliced exons) are most prevalent early in development and in cell lineages that give rise to the germ line. In the analysis shown in FIG. 7, only Ciz1 from fully developed neonatal heart shows no alternative splicing, while all embryonic cell types contain alternatively spliced forms. Furthermore, the only complete Ciz1 cDNAs in public databases (human or mouse) are derived from non-embryonic cell types, and the only ones derived from embryonic sources are alternatively spliced. Therefore, Ciz1 splice variant expression appears to occur preferentially in cell types that are not yet fully differentiated.

Notably, Ciz1 cDNAs from paediatric cancers are also alternatively spliced (see below). This lead us to the hypothesis that failure to express the appropriate Ciz1 isoform at the right point in development leads to inappropriately regulated Ciz1 activity. This could contribute to unscheduled proliferation and cellular transformation.

ECiz1 stimulates DNA replication in vitro Upon exposure to cytosolic extract from S phase cells, late G1 phase nuclei initiate DNA replication and begin synthesizing nascent DNA (Krude et al., 1997). We used this cell-free assay to test the effect of ECiz1, and derived recombinant fragments, on DNA synthesis (FIG. 3). Full-length ECiz1 protein consistently increased the number of nuclei that replicated in vitro, from 30% (+/−0.9%) to 46% (+/−5.5%), which suggests that Ciz1 is limiting for initiation in S phase extracts (FIG. 3A). Only two other classes of protein (cyclin-dependent kinases, Coverley et al., 2002; Krude et al., 1997; Laman et al., 2001, and the Cdc6 protein, Coverley et al., 2002; Stoeber et al., 1998) have been previously found to stimulate cell-free initiation. Thus, ECiz1 is the first protein to have this property that was not already known to be involved in the replication process. The positive effect of recombinant ECiz1 on cell-free initiation argues that endogenous Ciz1 plays a positive role in DNA replication in mammalian cells.

Stimulation of cell-free initiation is concentration-dependent with peak activity in S phase extract at around 1 nM ECiz1 (FIG. 3B). This echoes previous cell-free analyses with other recombinant proteins (Coverley et al., 2002; Krude et al., 1997), where stimulation of initiation typically peaks and then falls back to the un-stimulated level at high concentrations. For ECiz1, the reason for the drop in activity at high concentrations is not yet clear. However, mutagenesis studies (see below) suggest that the restraining mechanism is likely to be active and specific rather than due to a general imbalance in the composition of higher order protein complexes.

Down regulation of ECiz1 involves threonines 191/192 Ciz 1 is likely to be a phospho-protein in vivo since it contains numerous putative phosphorylation sites, and it displays altered mobility when 3T3 cell extracts are treated with lambda phosphatase (not shown). Murine Ciz1 contains two RXL cyclin binding motifs and five putative cdk-phosphorylation sites, which are present in all known variants. Four of these are located in the N-terminal fragment of ECiz1 that contains in vitro replication activity (see below), and one is adjacent to the site at which exon 6 is alternatively spliced to exclude a short DSSSQ (SEQ ID NO: 1) sequence motif (FIGS. 2A, C). As this motif is 100% identical and alternatively spliced in both mouse and man we reasoned that conditional inclusion might serve to regulate Ciz1 activity, identifying this region of the protein as potentially important. We therefore chose to focus on the cdk site that is four residues upstream and which is also conserved in mouse and man, by combining a genetic approach with cell-free replication assays. Starting with ECiz1, two threonines at 191 and 192 were changed to two alanines, generating ECiz1T(191/2)A (FIG. 2D). When tested in vitro for DNA replication activity, ECiz1T(191/2)A stimulated initiation in late G1 nuclei to a similar extent as ECiz1 (FIG. 3C). However unlike ECiz1, stimulation of initiation was maintained over a broad range of concentrations that extended over at least three orders of magnitude. Therefore, a mechanism to restrict the activity of excess ECiz 1 exists and operates in a cell-free environment. In a separate construct, the threonine at position 293 was also changed to alanine generating ECiz1T(293)A (FIG. 2D), but this alteration had little effect on ECiz1 activity assayed in vitro (FIG. 3D).

These results demonstrate that down-regulation of ECiz1 activity involves threonine 191/2, and is probably caused by cyclin-dependent kinase mediated phosphorylation at this site. This links Ciz1 activity to the cdk-dependent pathways that control all major cell-cycle events, including initiation of DNA replication.

Most pre-replication complex proteins and many replication fork proteins are phosphorylated in vivo, often by cyclin-dependent kinases (Bell and Dutta, 2002; Fujita, 1999). Our data suggests that nuclear accumulation of p85-Ciz1 antigen is regulated (directly or indirectly) by cyclin A-cdk2, and it shows that a specific consensus cdk phosphorylation site at threonine 191/192 is involved in controlling Ciz1 activity. When this site is made unphosphorylatable Ciz1 activity is maintained over a broader range of concentrations in cell-free assays. Therefore, Ciz1 activity is normally down regulated by modification at this site. The functions of the other conserved cdk phosphorylation sites, and the effect of conditional inclusion of an RXL cyclin-binding motif in the alternatively spliced N-terminal portion of Ciz1, remain to be determined. Thus, the simple negative relationship between Ciz1 activity and cdk-dependent phosphorylation that has been uncovered here, is unlikely to be the whole story. However, our analysis so far links Ciz1 with the cdk-dependent pathways that control all major cell-cycle transitions, and is therefore consistent with our main conclusion that Ciz1 is involved in initiation of DNA replication.

In vitro replication activity resides in the N-terminus Ciz1 possesses several C-terminal features that may anchor the protein within the nucleus. The matrin 3 domain suggests interaction with the nuclear matrix and the three zinc-fingers imply interaction with nucleic acids. Indeed, recent evidence suggests that human Ciz1 binds DNA in a weakly sequence specific manner (Warder and Keherley, 2003). To determine whether C-terminal domains are important for ECiz 1 replication activity we divided the protein into two fragments (FIG. 2D). Nterm442 (which contains the NLS, two conserved cdk sites, one zinc finger and all known sites where variable splicing has been observed) stimulates initiation to a similar extent and at the same concentration as ECiz1 (FIG. 3E). In contrast, the C-terminal portion (Cterm274) contains no residual replication activity (FIG. 3F). Therefore, the matrin 3 domain, one of the cyclin-dependent kinase phosphorylation sites and two of the zinc-fingers are not required for the DNA replication activity of ECiz1, when assayed in vitro. It should be noted however that this analysis measures ECiz1 activity in trans under conditions where the consequences of mis-localisation are unlikely to be detected. Therefore, it remains possible that the matrin 3 domain and zinc fingers act in vivo to direct Ciz1 activity to specific sites in the nucleus and thus limit the scope of Ciz1 activity.

Endogenous Ciz1 Antibody V1 recognises Cdc6 as well as p85-Ciz1 (FIG. 1A), so it is not suitable for immuno-fluorescence experiments aimed at visualizing the sub-cellular localization of endogenous Ciz1. We therefore generated two new rabbit polyclonal anti-sera against recombinant ECiz1 fragment Nterm442, designated anti-Ciz1 1793 and 1794. As expected, purified Nterm442 is recognised by anti-Ciz1 antibodies 1793 and 1794 in western blots, but it is also recognised by antibody V1 (FIG. 4A), supporting the conclusion that p85(p100) is indeed Ciz1.

When applied to protein extracts derived from growing 3T3 cells anti-Ciz 1 1793 recognised two antigens, with Mr of 125 and 100 kDa (FIG. 4B), whose relative proportions vary from preparation to preparation. The 100 kDa band co-migrates with the cyclin-A responsive antigen that is recognized by antibody V1 (FIGS. 1 and 4B), which suggests that both antibodies recognise the same protein in vivo. We confirmed that the p100-Ciz 1 bands recognised by antibody V1 and 1793 are the same protein by immuno-precipitation (FIG. 4C). Antibody V1 precipitated a 100 kDa band that was recognised in western blots by 1793, and vice versa. Furthermore, in the same experiment 1793, and to a lesser extent antibody V1, precipitated a 125 kDa antigen, that was recognised in western blots by 1793. Taken together our observations show that the 100 kDa band is indeed Ciz1 (previously known as p85), and they suggest that Ciz1 protein exists in at least two forms in cycling cells.

In addition to the immuno-precipitation evidence described above, several other observations lead to the conclusion that p125 is also a form of Ciz1. First, both of our anti-Ciz1 antibodies (1793 and 1794) have this band in common. Both antibodies produce the same pattern of nuclear staining in immuno-fluorescence experiments, and this is disrupted in cells treated with Ciz1 siRNA (see below). Second, the relative proportions of p100 and p125 vary from preparation to preparation, and could therefore be the result of proteolytic cleavage. Thirdly, our results are strikingly similar to those of Mitsui et al (1999) whose anti-human Ciz1 monoclonal antibody detected two antigens with apparent Mr of 120 and 95 kDa in HEK293 cells. They proposed that the 120 kDa form of human Ciz1 protein is processed to produce the 95 kDa form and our results are consistent with this proposal.

The 125 kDa band recognized by antibody 1793 in mouse and human cells resolves into three Ciz1-related bands during high-resolution electrophoresis of material derived from non-transformed human cells (Wi38-see later), and mouse cells (NIH3T3-not shown). This may be the result of post-translational modification of the Ciz1 protein or of alternative splicing of the Ciz1 transcript.

Sub-cellular distribution of Ciz1 Anti-Ciz1 1793 was used to visualise the sub-cellular distribution of Ciz1 protein (p85 and p125) in 3T3 cells (FIG. 5A), and in HeLa cells (not shown). In both cell types 1793 reacted with a nuclear-specific antigen, and this was blocked by inclusion of recombinant Nterm442 fragment (FIG. 5B). Unlike Cdc6, which is shown for comparison (FIG. 5A), Ciz1 is clearly detectable in all 3T3 cells in this cycling population. Therefore Ciz1 is present in the nucleus throughout interphase, although minor variations in quantity, or isoform would not be detected by this method. After detergent treatment overall nuclear Ciz1 staining was reduced in all nuclei, which suggests that Ciz1 is present in the nucleus as both a soluble fraction and also bound to insoluble nuclear structures.

When soluble protein is washed away, the insoluble, immobilised antigen resolves into a punctate sub-nuclear speckled pattern at high magnification (FIGS. 5C, D). Ciz1 speckles show a similar size range and distribution as replication 'foci' or 'factories', the sites at which DNA synthesis takes place in S phase. To ask whether Ciz1 is coincident with sites of replication factories, we compared the position of Ciz1 speckles to the position of PCNA, a component of replication complexes in S phase cells (FIG. 5C). In confocal section, PCNA foci are less abundant than Ciz1 foci, but they are almost all co-incident with Ciz1 (FIGS. 5D, E, F). This is particularly striking for foci in the medium size range. In merged images, overlap between the positions of PCNA and Ciz1 foci results in yellow spots, while the remaining Ciz1 foci that are not co-incident with PCNA are red. Green (PCNA alone) foci are virtually absent, which suggests that Ciz1 is present at all sites where DNA replication factories have formed.

Ciz1 is also present at sites that don't contain PCNA (FIG. 5D), and unlike PCNA, Ciz1 foci persist throughout interphase (FIG. 5A). One interpretation of these observations is that Ciz1 marks the positions in the nucleus at which PCNA-containing replication factories are able to form in S phase, but that not all of these sites are used at the same time. It remains to be determined whether different Ciz1 foci become active at sites of DNA replication at different times in S phase, or whether other nuclear activities also occur at sites where Ciz1 is bound. Indeed, at this stage it also remains possible that the 100 kDa form and the 125 kDa variants of Ciz1 have different activities, and that they reside at nuclear sites with different functions.

Ciz1 is essential for cell proliferation So far we have shown that the behaviour of p85 (p100)-Ciz1 correlates with initiation of DNA replication in cell-free assays, that recombinant Ciz1 stimulates the frequency of initiation, and that Ciz1 resides at the same nuclear sites as the DNA replication machinery. However, these data do not show that Ciz1 has an essential function in proliferating cells. In order to test this we used RNA interference (RNAi) to selectively reduce Ciz1 transcript levels in NIH3T3 cells. Four target sequences within Ciz1 were chosen (see FIG. 2A) and short interfering (si) RNA molecules were produced in vitro. When applied to cells, all four Ciz1 siRNA's restricted growth (FIG. 6A) and caused a visible reduction in the level of Ciz1 protein after 48 hours (FIG. 6B). The effect of Ciz1 depletion on proliferation becomes apparent between 23 and 40 hours post-transfection, which suggests that the first cell cycle without Ciz 1 RNA is relatively unaffected. By 40 hours, controls and Ciz1 siRNA treated cells diverged significantly with no further proliferation in the Ciz1 depleted population. To verify the specificity of Ciz1 depletion, transcript levels were monitored at 24 hours, before proliferation is significantly inhibited (FIG. 6C). At this point Ciz1 transcripts were reduced to 42% of the level in control cells treated with GAPDH siRNA. These experiments show that Ciz1 is required for cell proliferation and are consistent with a primary function in DNA replication.

To test this further, cells were pulse-labelled with BrdU 48 hours after siRNA treatment to determine the fraction of cells engaged in DNA synthesis (FIG. 6D). When Ciz1 levels were reduced the BrdU labelled fraction was also reduced, suggesting that DNA synthesis is inhibited under these conditions. Furthermore, cells in the Ciz1 depleted population that did incorporate BrdU (approximately 15% of the population) were less intensely labelled. Therefore, in some Ciz1 siRNA treated cells S phase is slowed down rather than inhibited completely, possibly due to incomplete depletion.

Inhibition of DNA synthesis by Ciz1 siRNAs could be a secondary consequence of a general disruption of nuclear function. Therefore, we looked in more detail at a range of other replication proteins whose levels are regulated in a cell cycle dependant manner, to ask whether depleted cells arrest randomly, or accumulate at a particular point.

During initiation of eukaryotic DNA replication Mcm complex proteins assemble at replication origins in late G1, in a Cdc6-dependent manner. Sometime later, DNA polymerases and their accessory factors (including PCNA) become bound to chromatin and origins are activated. This is associated with nuclear export and proteolysis of the majority of Cdc6 and, as DNA synthesis proceeds, gradual displacement of the Mcm complex from chromatin (Bell and Dutta, 2002). In order to identify the point of action of Ciz1 we used immuno-fluorescence to monitor Mcm3 and PCNA. In Ciz1 depleted cells (FIGS. 6E, F) both proteins were detectable within the nucleus bound to detergent resistant nuclear structures. Therefore, these factors are unlikely to bind directly to Ciz1, or to be dependent upon Ciz1 for their assembly. In fact, in four independent experiments the average number of cells with detergent-resistant chromatin-bound Mcm3 actually increased from 31% (+/−6%) to 51% (+/−5%) (FIG. 6E). Increased Mcm3 indicates that the Ciz1 dependent step occurs after pre-replication complex assembly (but before completion of S phase). In the same cell populations the PCNA positive fraction also increased, from 32% (+/−5%) to 49% (+/−6%) (FIG. 6F), narrowing the point of Ciz1 action to after PCNA assembly. Thus, Ciz1 most likely acts to facilitate DNA replication during a late stage in the initiation process, while failure to act inhibits progression through S phase, leaving Mcm3 and PCNA in place.

Taken together, our cell-free and cell-based investigations paint a consistent picture about the primary function of Ciz1. They suggest that Ciz1 is a novel component of DNA replication factories, and they show that Ciz1 plays a positive role in the mammalian cell-cycle, acting to promote initiation of DNA replication.

Three of our lines of investigation suggest that Ciz1 is required during a late stage in the initiation process after pre-replication complex formation. First, p85 (p100)-Ciz1 antigen accumulates in nuclei exposed to cyclin A-cdk2 concentrations that activate DNA synthesis, implying that Ciz1 functions during this step rather than during earlier replication complex assembly steps (Coverley et al., 2002). Second, functional studies with late G1 nuclei show that recombinant ECiz1 increases the number of nuclei that incorporate labeled nucleotides in vitro. Therefore, Ciz1 must be active in a step that converts nuclei that are poised to begin DNA synthesis into ones that are actively synthesizing DNA. Third, RNA interference studies point to a Ciz1-dependent step after Mcm complex formation and after PCNA has become assembled onto DNA, but before these proteins are displaced. These distinct lines of investigation lead to strikingly similar conclusions about the point of action of Ciz1 placing it in the later stages of initiation.

Anti-Ciz1 siRNA as a therapeutic strategy Our analysis shows that Ciz1 is essential for cell proliferation, and that targeting Ciz1 is a viable strategy to restrain proliferation. The alternatively spliced forms of Ciz1 that we observe in various cancers (see below) means that Ciz1 could be targeted in a selective way to restrain proliferation in a subset of cells within a population.

By way of example, this could be done by targeting siRNA's to the junction sequence created in Ciz1 transcripts when the C-terminal sequence GTTGAGGAGGAACTCTGCAAGCAG (SEQ ID NO:2) is missing, in small cell lung carcinoma cells, or by using Ciz1 protein lacking the corresponding VEEELCKQ (SEQ ID NO: 3) sequence to select specific chemical inhibitors.

Accordingly the present invention also provides for the use of junction sequences created in Ciz1 transcripts and proteins when alternatively spliced sequences are not present, as a diagnostic marker, prognostic indicator or therapeutic target.

Figure 8E:
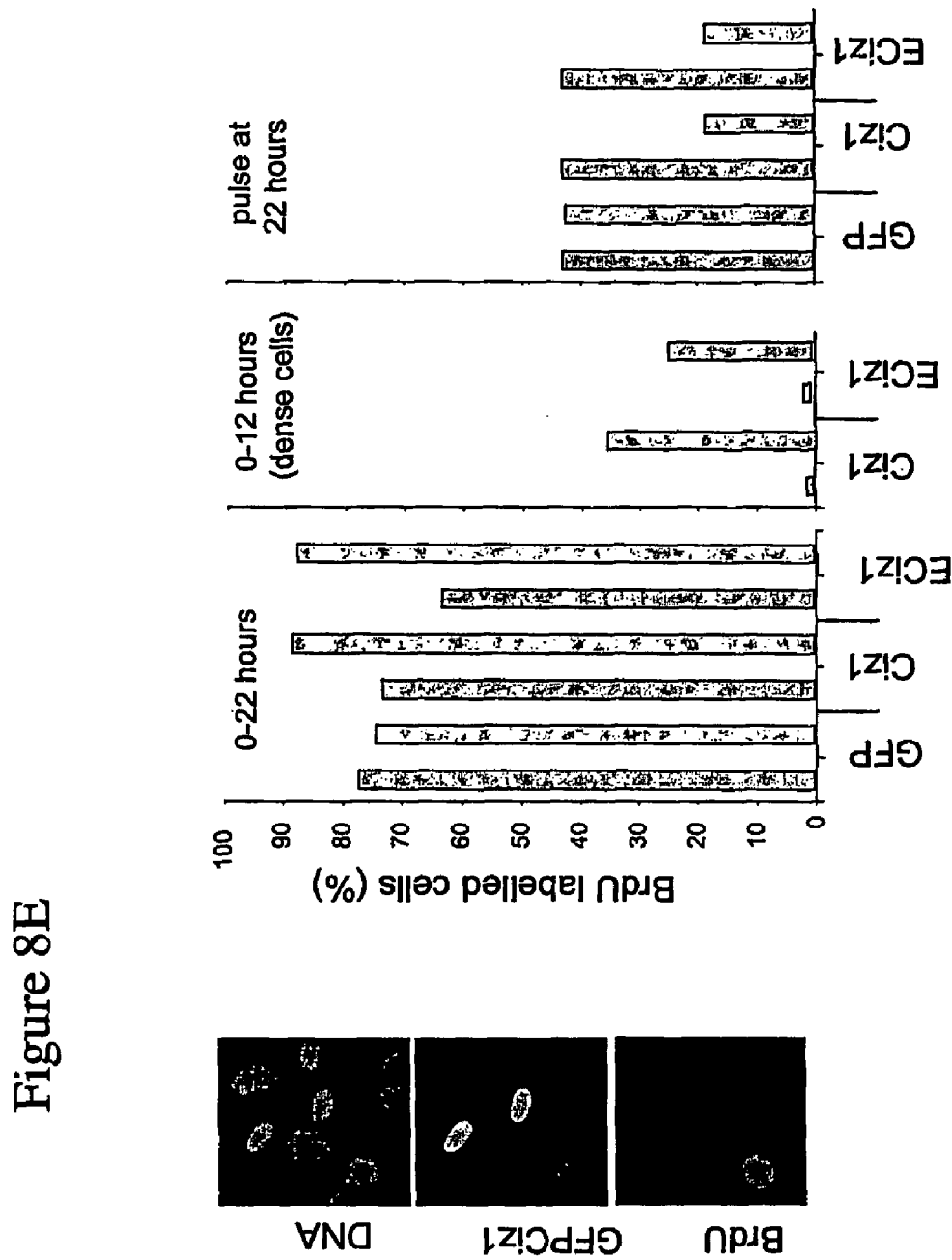
FIG. 8 Transient transfection of mouse 3T3 cells. A. GFP-tagged Ciz1 constructs were transfected into NIH3T3 cells or B. microinjected into the male pro-nucleus of fertilized mouse eggs at the one cell stage. By 24 hours Ciz1 and ECiz1 became localized to the nucleus forming a subnuclear spotty pattern, while GFP alone was present in both the nucleus and the cytoplasm. C. High magnification images of live 3T3 cell nuclei 24 hours after transfection showing the subnuclear organisation of EGFP tagged Ciz1 and ECiz1 and derived fragments with the C-terminal fragment (equivalent to Cterm274) removed. In the absence of C-terminal domains GFP-ECiz1 is diffusely localised in the nucleus 24 hours after transfection, while GFP-Ciz1 aggregates to form one or two large blobs within the nucleus. D. The Cterminal 274 domain alone is cytoplasmic until after cells have passed through mitosis (most likely due to lack of nuclear localisation sequences and passive entry to the nucleus), but once inside binds to nuclear structures and condenses with chromosomes. E. Representative images of GFP-Ciz1 (green), BrdU (red) and total nuclei (blue) in a population labelled with BrdU for the first 12 hours after transfection are shown. Histograms show the proportion of transfected (green) cells that incorporated BrdU compared to the number of untransfected (grey) cells for three separate labelling windows. During 0-22 hours after transfection rapidly cycling cells registered a consistent increase in the BrdU labelled fraction when transfected with either Ciz1 or ECiz1. Similar results were obtained with dense cultures in which most cells had exited the cell cycle and entered quiescence. However, when rapidly cycling cells were exposed to BrDu for a short (20 minute) pulse 22 hours after transfection the number of cells engaged in DNA synthesis was reduced in the Ciz1 and ECiz1 transfected populations, compared to untransfected controls and cells transfected with GFP alone. This indicates that by 22 hours DNA synthesis had ceased in Ciz1 expressing cells.

Embryonic form Ciz1 is localized to the nucleus RT-PCR analysis across potentially variable exons suggest that 3T3 cells predominantly express full-length Ciz1, so our immuno-localization work on endogenous Ciz1 (FIG. 5) does not necessarily reflect the behavior of ECiz1, which lacks several sequence blocks and possibly therefore information that is used to localize the protein. To directly compare the localization of ECiz1 and full-length Ciz1, enhanced GFP tagged constructs were transfected into 3T3 cells (FIG. 8A), and microinjected into mouse pro-nuclei (FIG. 8B). In all cases tagged Ciz1 and ECiz1 were exclusively nuclear, while a control construct expressing GFP alone was present in the nucleus and the cytoplasm. GFP-Ciz1 and GFP-ECiz1 were both visible in live cells as sub-nuclear foci, similar to replication foci seen in fixed cells by immuno-fluorescence. Thus, the three sequence blocks that are absent from ECiz1 do not appear to contribute to the nuclear localization of Ciz1.

Over the three day period following transfection no cell division was observed in the GFP-Ciz1 and GFP-ECiz1 transfected cells. These data suggest that overexpression of functional Ciz1 has an inhibitory effect on the cell cycle (in cells that have their regulatory pathways intact).

Coalescence When GFP-tagged constructs in which the C-terminal one third of Ciz1 had been removed were transfected into 3T3 cells, differences between ECiz1 and full length Ciz1 were observed (FIG. 8C). By 48 hours FL Ciz1 N-term(442 equivalent) had coalesced into large intranuclear blobs which only became apparent in the ECiz1 N-term442 transfected population by day 3 or later. Before this time ECiz1 N-term442 was localised as a nuclear specific but diffuse pattern. Thus ability to coalesce is quantifiably different between Ciz1 and ECiz1, and is therefore affected by one of the three alternatively spliced exons (2/3, 6 or 8).

Like cells transfected with full length Ciz1 and ECiz1, cells transfected with constructs in which the C terminal one third was removed were not seen to multiply during the three day monitoring period.

C-terminal domains anchor Ciz1 to nuclear structures As described above, the difference between Ciz1 and ECiz 1 N-term is masked when C-terminal domains are also present (FIG. 8A). Furthermore the C-terminal fragment alone directs GFP tag to chromatin, forming an irregular pattern that is not as spotty (focal) as Ciz1 or ECiz1, but which remains attached to chromosomes during mitosis (FIG. 8D). This suggests that C-terminal domains are involved in immobilizing Ciz1 on a structural framework in the nucleus. Notably, cells transiently transfected with C-terminal fragment continued to divide resulting in gradual dilution of green fluorescence.

Ectopic Ciz1 promotes premature entry to S phase We looked at events occurring during the first day after transfection. The S phase fraction in transfected cells (green) was compared to the S phase fraction in untransfected cells, by labelling with BrdU at various intervals. During long labelling windows including 0-22 hours (FIG. 8E), 0-12 hours and 0-7 hours (not shown), consistently more of the Ciz1 and ECiz1 transfected cells were engaged in DNA synthesis, compared to untransfected cells. This suggests that Ciz1 and ECiz1 have a positive effect on the G1-S transition, promoting unscheduled entry to S phase. Similar results were obtained with 3T3 cell populations that were densely plated before transfection. This was done in order to minimise the fraction in the untransfected population that was engaged in S phase as part of the normal cell cycle. Under these conditions the difference between the transfected and untransfected population was maximised, clearly demonstrating the effect of ectopic Ciz1 on initiation of DNA replication.

Conversely, when cells were labelled with BrdU during a short pulse administered at 22 hours (FIG. 8E), or at 10 hours or 12 hours post-transfection (not shown), the labelled fraction was consistently reduced in the Ciz1 and ECiz1 transfected populations. This suggests that the S phase that is induced by ectopic Ciz1 or ECiz1 is abnormal, with slow or aborted DNA synthesis that is not sufficient to label cells during short windows of exposure to BrdU.

Therefore, ectopic Ciz1 and ECiz 1 have two effects on S phase in cultured cells. They promote DNA replication, but this results in slow or aborted DNA synthesis.

Figure 9A:
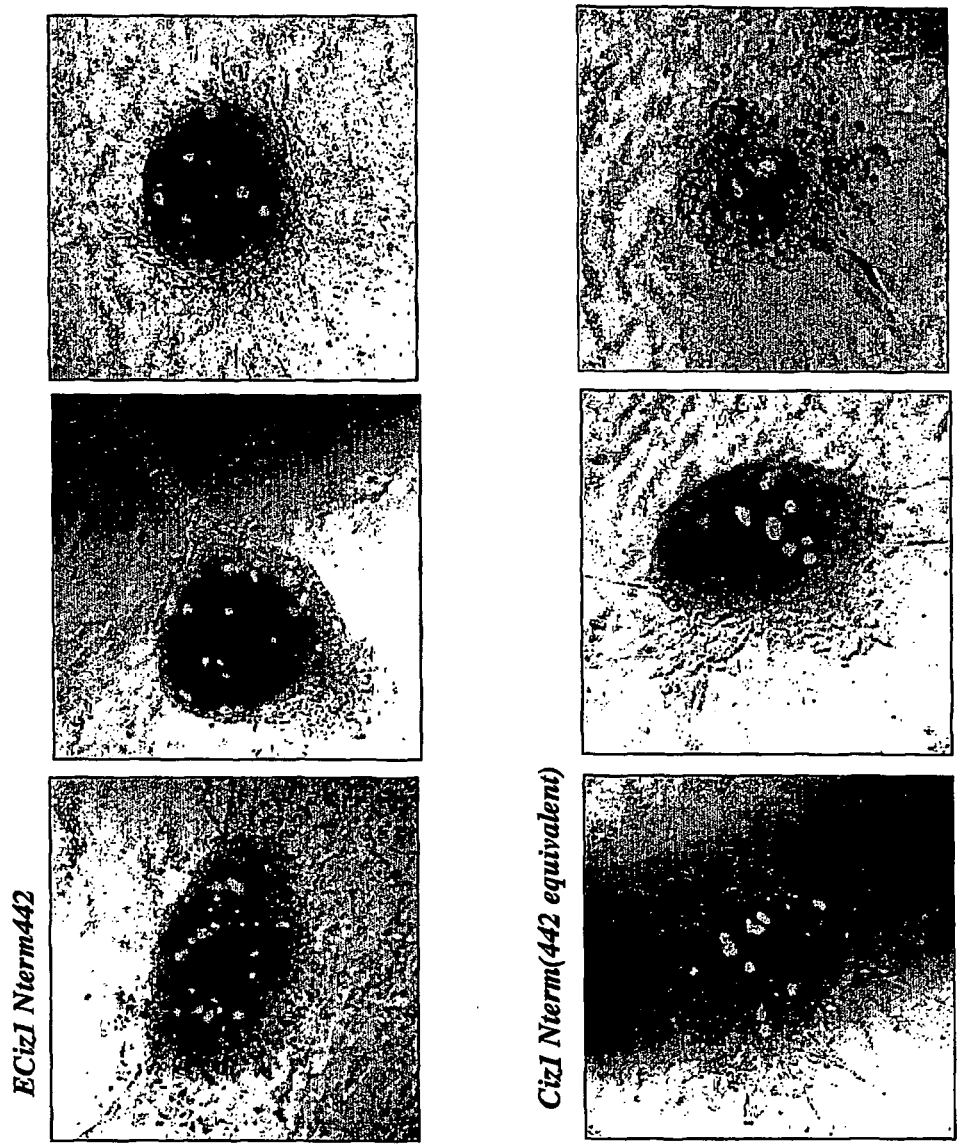
FIG. 9 Altered proliferation potential and cell morphology in transfected populations. Cell clusters arising in transfected 3T3 cell populations. A. Cells were transfected with the N-terminal two thirds of Ciz1 or ECiz1 (N-term442) tagged with GFP, and maintained under selection with 50 µg/ml G418. After three weeks under selection, cell aggregates were visible with GFP positive cells within.

Clones with altered proliferation potential We also monitored transfected populations of 3T3 cells over a three week time period. In cells transfected with the GFP-Nterm442 or the non-alternatively spliced equivalent and maintained under selection with G418, large foci containing hundreds of cells were observed (FIG. 9A). These clusters contained large numbers of GFP expressing cells, demonstrating that overexpression of the N-terminal portion of ECiz1 (in which replication activity resides) is not lethal, and suggesting that over-expression leads to altered proliferation phenotype, compared to untransfected cells, including loss of contact inhibition and failure to form a monolayer. This Ciz1-dependent altered behaviour could contribute to tumour formation. A similar truncated version of mouse Ciz 1, lacking putative chromatin interaction domains was previously isolated from a mouse melanoma (FIG. 2).

Human Ciz1 and Cancer

Figure 10:
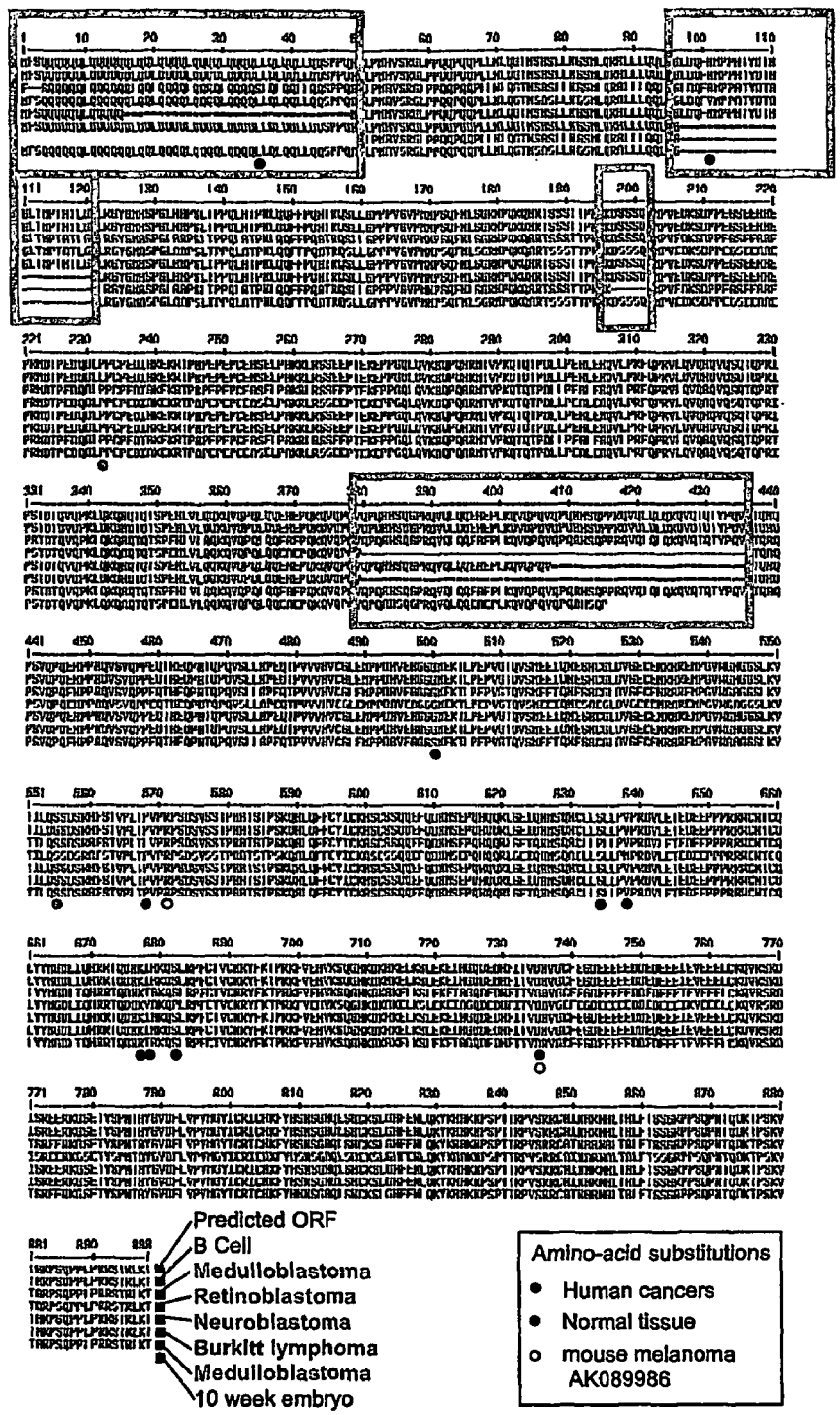
FIG. 10 Human Ciz1 splice variants (SEQ ID NO: 29-36, respectively) in paediatric cancers. There are seven human Ciz1 cDNAs in public databases, but only one is derived from normal adult tissue (B cells) and it contains all predicted exons. The other six are derived from embryonic cells or paediatric cancers. Five of these are alternatively spliced with variability in exons 2, 3, 6, and 8 (like mouse ECiz1), and also in exon 4 (like mouse ES cells, primordial germ cells and testis). The sixth (AF159025) lacks the first methionine and contains single-nucleotide polymorphisms that give rise to amino-acid substitutions. All differences from the predicted sequence (AB030835) are marked.

Ciz1 cDNAs in public databases As mentioned above human Ciz1 is alternatively spliced at the RNA level to yield transcripts that lack three of the same exons as mouse embryonic Ciz1. Seven human Ciz1 cDNAs have been recorded in public databases (FIG. 10), submitted by Mitsui et al (1999), Warder and Keherly (2003) and large-scale genome analysis projects (NIH-MGC project, NEDO human cDNA sequencing project). Only one is derived from normal adult tissue, and this contains all predicted exons (AB030835). The rest are derived from embryonic cells (AK027287), or notably from four different types of paediatric cancer (medulloblastoma, AF159025, AF0234161, retinoblastoma, AK023978, neuroblastoma, BC004119 and burkitt lymphoma, BC021163). The embryonic form and the cancer derived forms lack sequence blocks from the same three regions as our embryonic mouse clone, and from a fourth region which corresponds to exon 4. Therefore, the limited data suggests that alternatively spliced forms are more prevalent early in development. This correlation has not previously been noted in the scientific literature. The presence of alternatively spliced Ciz1 in paediatric cancers raises the possibility that Ciz1 mis-splicing might be linked to inappropriate cell proliferation.

For example, one of the variable exons encodes a short conserved DSSSQ (SEQ ID NO:1) sequence motif that is absent in mouse ECiz1 and in a human medulloblastoma. This is directly adjacent to the consensus cdk phosphorylation site that we have shown to be involved in regulation of ECiz1 function. Conditional inclusion of the DSSSQ (SEQ ID NO:1) sequence might make Ciz1 the subject of regulation by the ATM/ATR family of protein kinases, which phosphorylate proteins at SQ sequences, thereby restraining Ciz1 initiation function in response to DNA damage.

Analysis of expressed sequence tags. The presence of alternatively spliced Ciz1 in paediatric cancers prompted a detailed analysis of Ciz1 ESTs. There are 567 expressed sequence tags (ESTs) included in NCBI unigene cluster Hs.23476 (human Ciz1). These are derived from a wide range of normal and diseased tissues and cell lines. Sequences have been translated and mapped against the predicted full-length amino-acid sequence of human Ciz1. Sequence alterations that give rise to amino-acid substitutions, deletions, frameshifts and premature termination of translation have been recorded.

Alternatively spliced Ciz1 variants were also seen in this EST data set and are recorded here. The four sequence blocks that we previously reported to be alternatively spliced in human and mouse Ciz1 (FIG. 2) were observed in the EST sequences, as well as a previously undetected variant that lacks the exon 14 derived sequence VEEELCKQ (SEQ ID NO: 3). All of these recurrently variant sequence blocks are bounded by appropriate splice sites. A sixth variable sequence block was identified in one carcinoma derived library, caused by inclusion of (SEQ ID NO: 4)
GCCACCCACACCACGAAGAGATGTGTTTGCCCACGTTCCAGTGCAGGGGT

GGAGCACAGCCCGGCTTGTTACAGATAT.

Figure 11A:
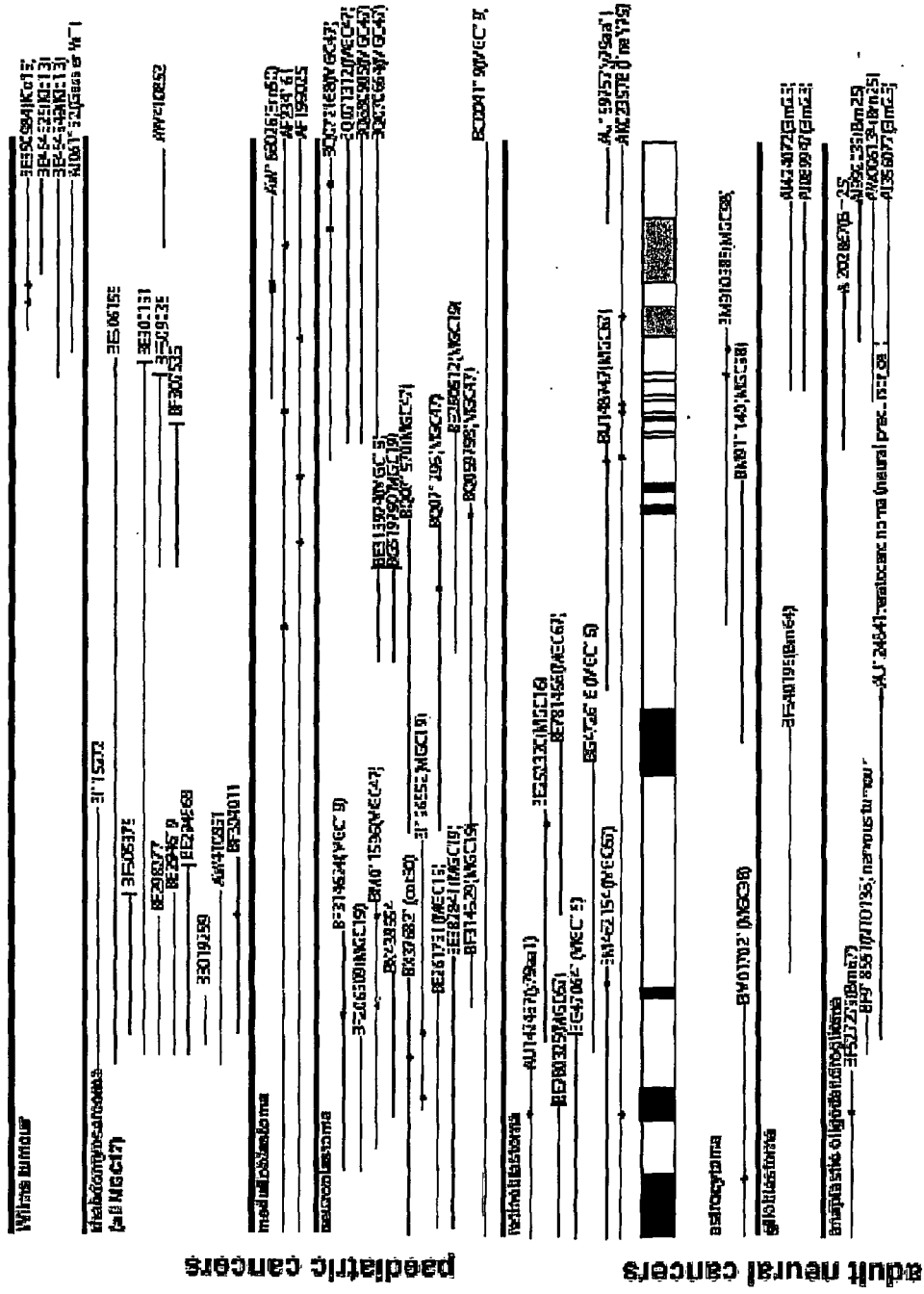
FIG. 11 EST sequence analysis. On each map a schematic representation of the Ciz1 protein is included for reference, showing the positions of alternatively spliced exons (black), putative chromatin interaction domains (grey) and predicted zinc fingers (black vertical lines). All EST sequences are accompanied by their Genbank accession number with the library from which they were derived indicted in parentheses. Sequences absent from Ciz1 ESTs due to alternative splicing are shown in yellow, frame-shifts in red and putative deletions in grey. Single nucleotide polymorphisms that give rise to amino-acid substitutions are indicated by black dots and some of these occur in a consensus cdk phosphorylation site which we have shown to be important for the regulation of Ciz1 activity (blue dots). Position of the inserted sequence in the carcinoma cell line MGC102 is indicated by a triangle.
Figure 11B:
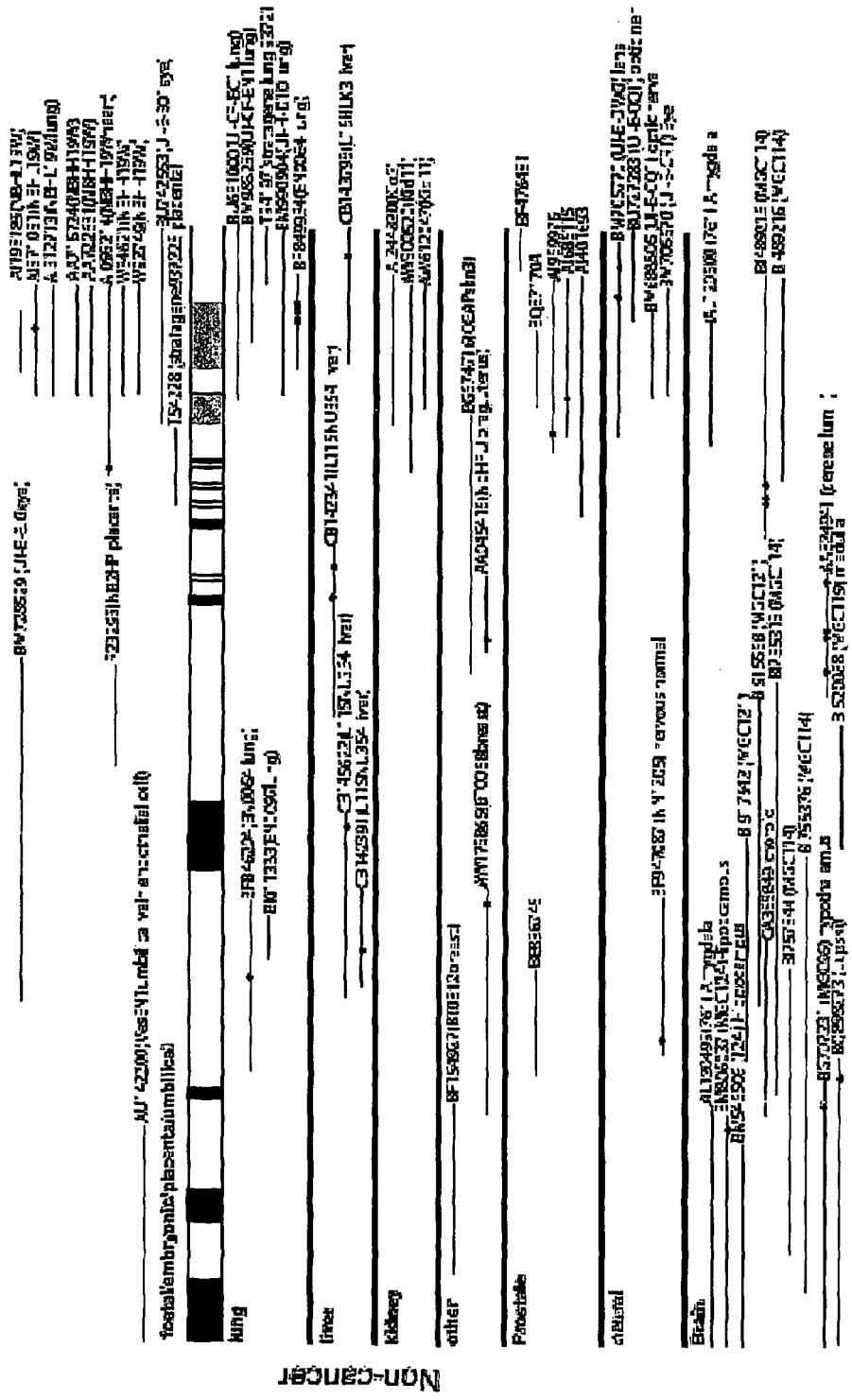
Figure 11C:
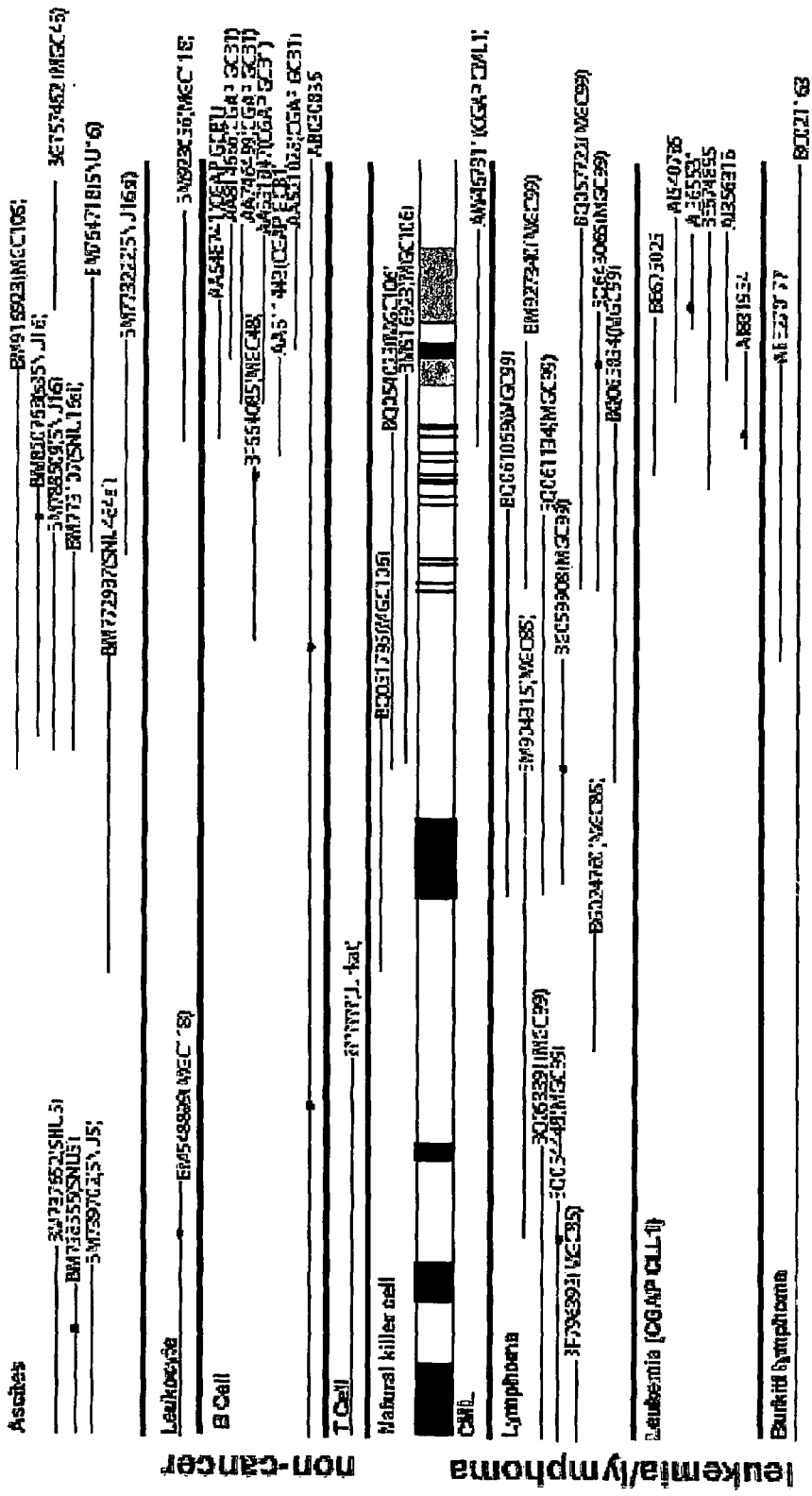
Figure 11D:
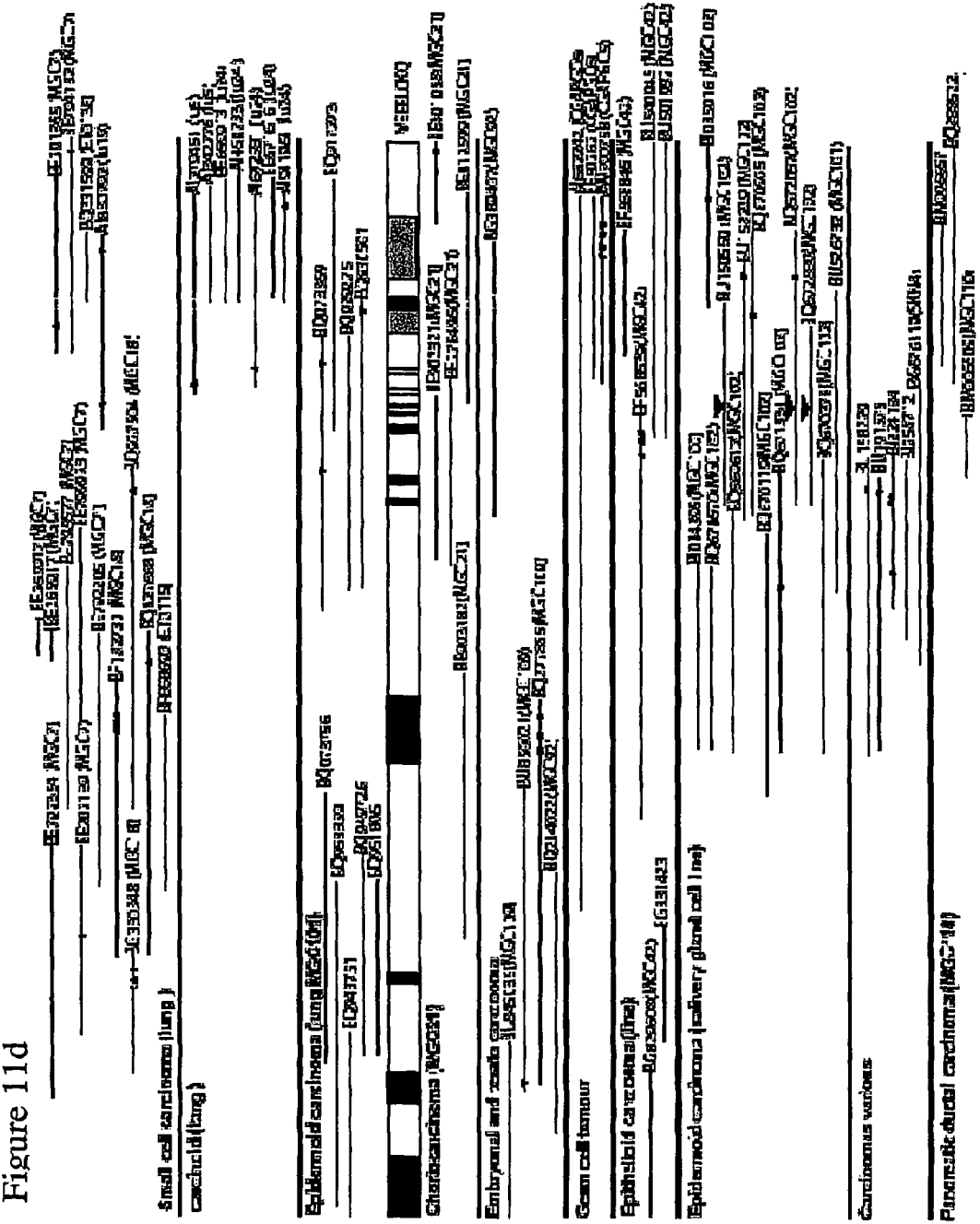
Figure 11E:
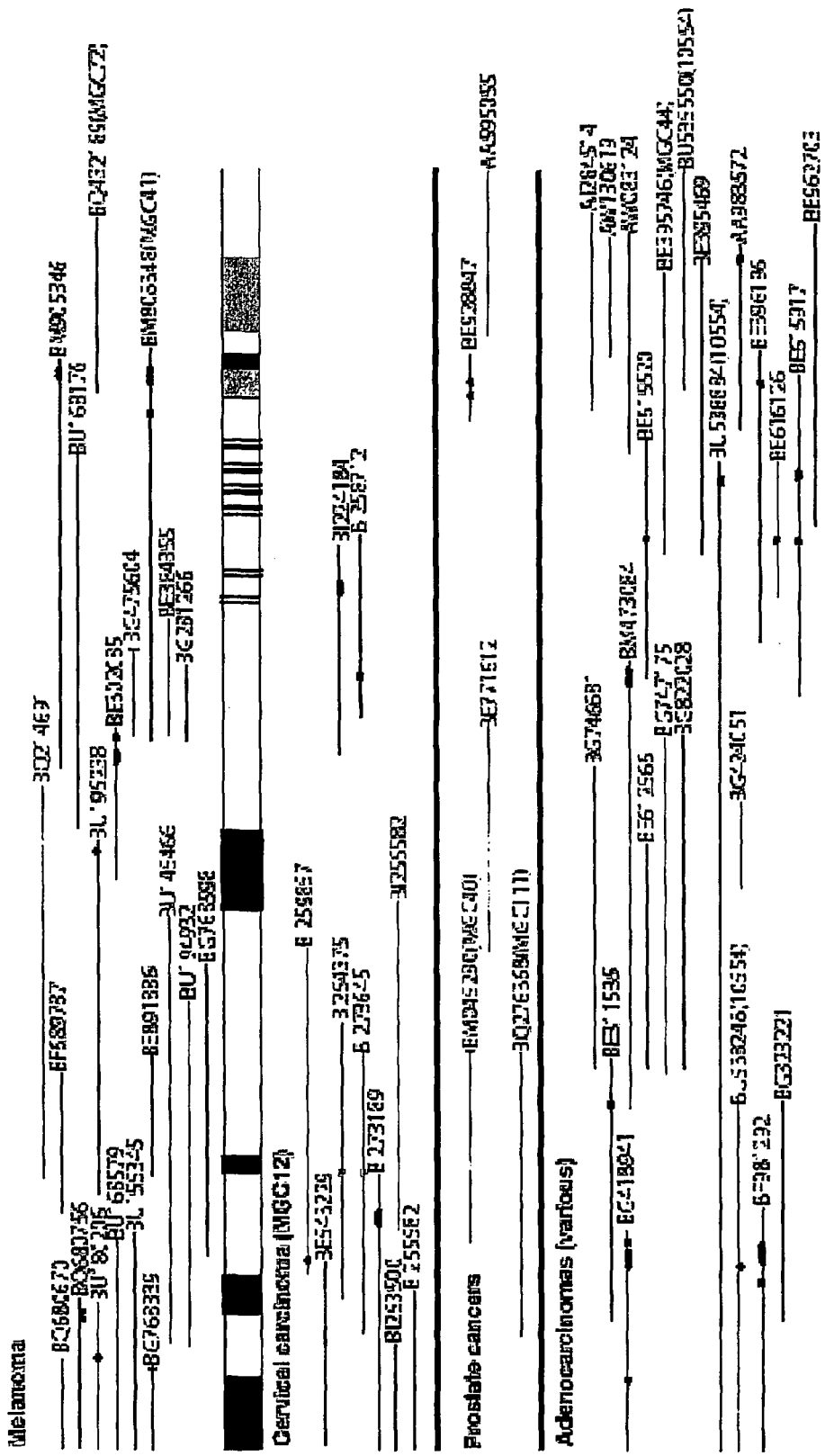
Figure 11F:
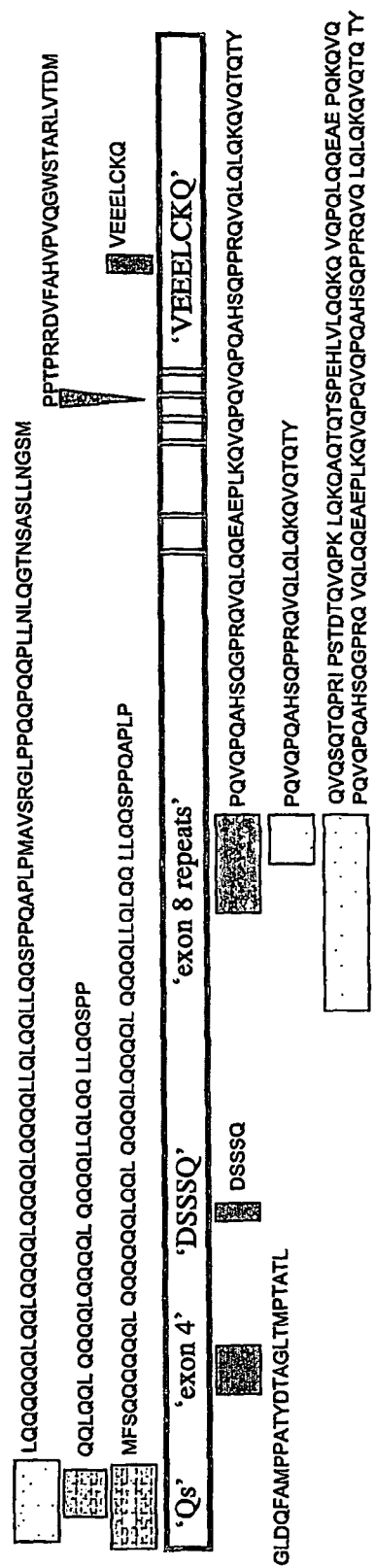

ESTs are grouped according to the cell type from which they were derived with the primary divisions occurring between neoplastic cells of adult, childhood or embryonic origin. ESTs from normal tissue of embryonic or adult origin are included for comparison. EST-derived Ciz1 protein maps are shown in FIGS. 11A-E and the alternatively spliced exons summarized in FIG. 11F.

Three sequence blocks in the N-terminal end of human Ciz1 are absent in transcripts from medulloblastomas and neuroblastoma (FIG. 11A), and occasionally absent from Ciz1 transcripts from other cancers. We also found similar alternative splicing in a third paediatric cancer, Ewings sarcoma (see below). Paediatric cancer-associated alternatively spliced sequences are from exons 2/3 (at least two versions), exon 4 and exon 6.

Exon 8 variants in which one or more copies of a Q-rich degenerate repeat are absent have been noted in transcripts derived from normal cells (of embryonic or adult neural origin) and from various cancers. Alternative splicing in this region could produce Ciz1 with inappropriate activity, therefore exon 8 variant expression, or occurance of point mutations which influence splicing in this region, might be useful as diagnostic or prognostic markers in cancer. The alternatively spliced degenerate repeats in exon 8 are detailed below and summarised in FIG. 11F.

In the C-terminal half of the human Ciz1 protein two sequence blocks are variably spliced. One of these is missing from transcripts derived from three out of five lung carcinoma and lung carcinoid libraries, and from three other carcinoma libraries (but very rarely from transcripts from other cell types).

The second variant sequence block is due to inappropriate inclusion of extra sequence in transcripts from the epidermoid carcinoma library (MGC102).

These sequences and the junction sequences formed in Ciz1 proteins, and Ciz1 transcripts when these segments are excluded or included, are potential targets for selective inhibition of cell proliferation in a wide range of different cancers. The remaining non-variant sequences are potential targets for non-selective inhibition of cell proliferation.

In addition to splicing variations, other non-typical Ciz1 transcripts were found to preferentially occur in some cancers. In Rhabdomyosarcomas Ciz1 is prematurely terminated leading to a predicted protein that lacks C-terminal nuclear binding domains. This could lead to inappropriate DNA replication and might therefore be a therapeutic target or marker in this type of cancer.

Several transcripts contain point mutations that lead to amino-acid substitutions in putative cyclin-dependent kinase (cdk) phosphorylation sites. In the cervical carcinoma library MGC12, this occurs twice. We have shown that two cdk phosphorylation sites are involved in restraining Ciz 1 activity (FIGS. 3C and D), implicating these mutations in the deregulation of proliferation in cancer cells. One of these is the same as the carcinoma-derived mutant mentioned above (FIG. 11E). Cancer-derived transcripts with point mutations in Ciz1 could also be targeted by RNA interference, or have value as diagnostic or prognostic indicators.

Investigation of Ciz1 Variant Expression in Paediatric Cancers

Figure 12A:
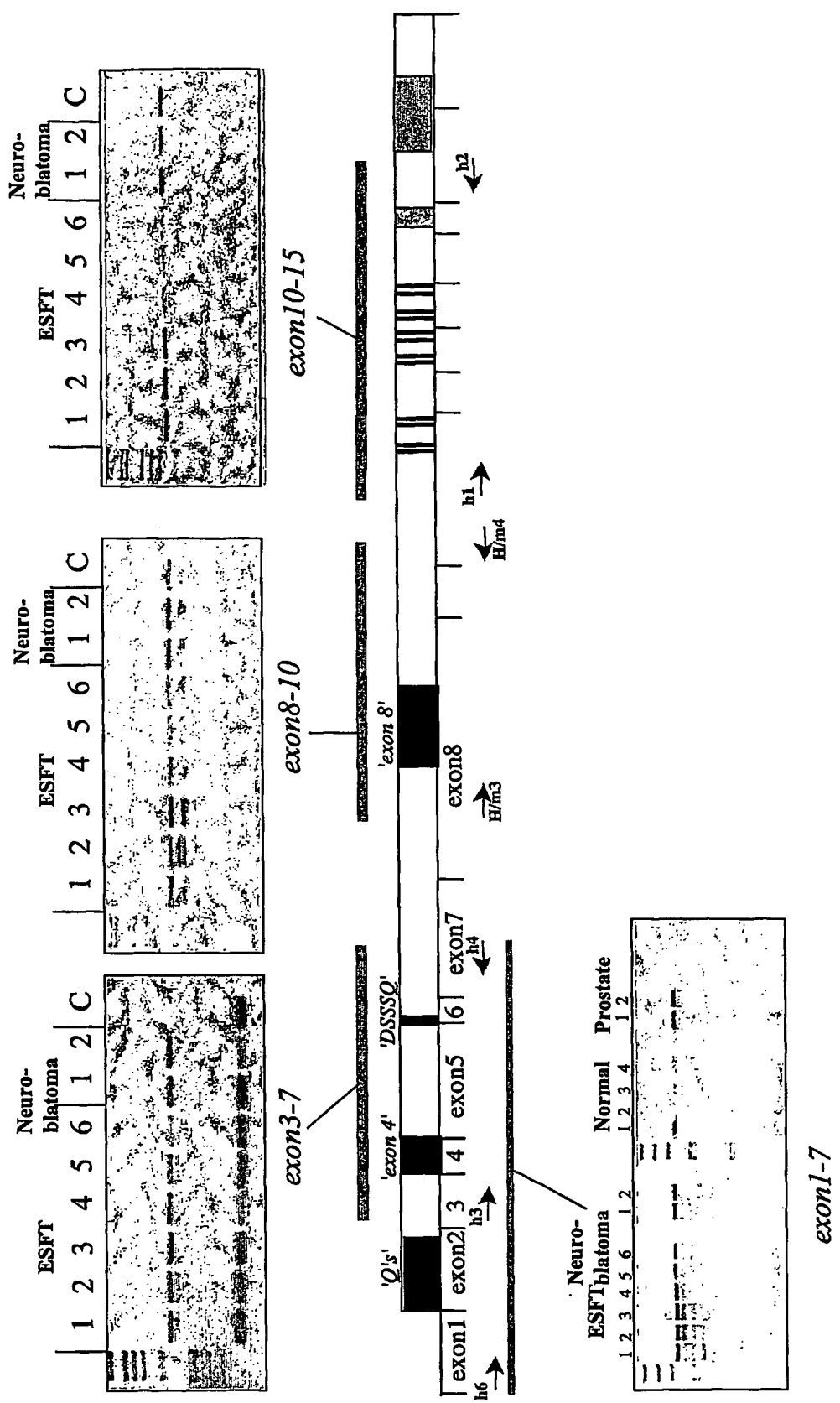

Ciz1 variant expression was investigated in 6 Ewings Sarcoma family tumour cell lines (ESFTs) and two neuroblastoma cell lines, using RTPCR with primer sets that span three regions of known Ciz1 variability (FIG. 12A). This analysis showed that the pattern of Ciz1 variant expression is different in ESFT cells compared to neuroblastoma cells compared to non-transformed cells, but apparently very similar within sets of cell lines from the same tumour. Therefore, Ciz1 variant expression could have prognostic or diagnostic potential for these cancers. Minor variations within a set of lines from the same tumour type could have prognostic value.

By subcloning and sequencing amplified transcripts we found that all six ESFT lines tested express an exon 4 minus form of Ciz1. As Ciz1 is essential for cell proliferation (see below), this offers a possible route for selective restraint of ESFT cells. Transcripts from the two neuroblastoma cell lines tested rarely lack exon 4 but frequently lack sequences the DSSSQ (SEQ ID NO:1) motif encoded by exon 6 (FIG. 12B).

This experimental analysis confirms that paediatric cancers express forms of Ciz1 with variable inclusion of exons 4, 6 and probably exons 2/3.

Two versions of the sequence encompassing exon 8 and one form of the sequence encompassing the VEEELCKQ-coding sequence were detected in ESFTs, neuroblastomas and control suggesting that these regions do not contribute to deregulation of Ciz1 in these paediatric cancers.

In all cases, Ciz1 RT-PCR products were most abundant in reactions carried out with RNA samples from cancer cell lines, compared to controls (Wi38, HEK293, NIH3T3 cells, and primary human osteoblasts). This is consistent with increased expression of Ciz1 variants in tumours.

Analysis of Ciz1 Protein Expression in Prostate Cancer Cell Lines

Figure 13A:
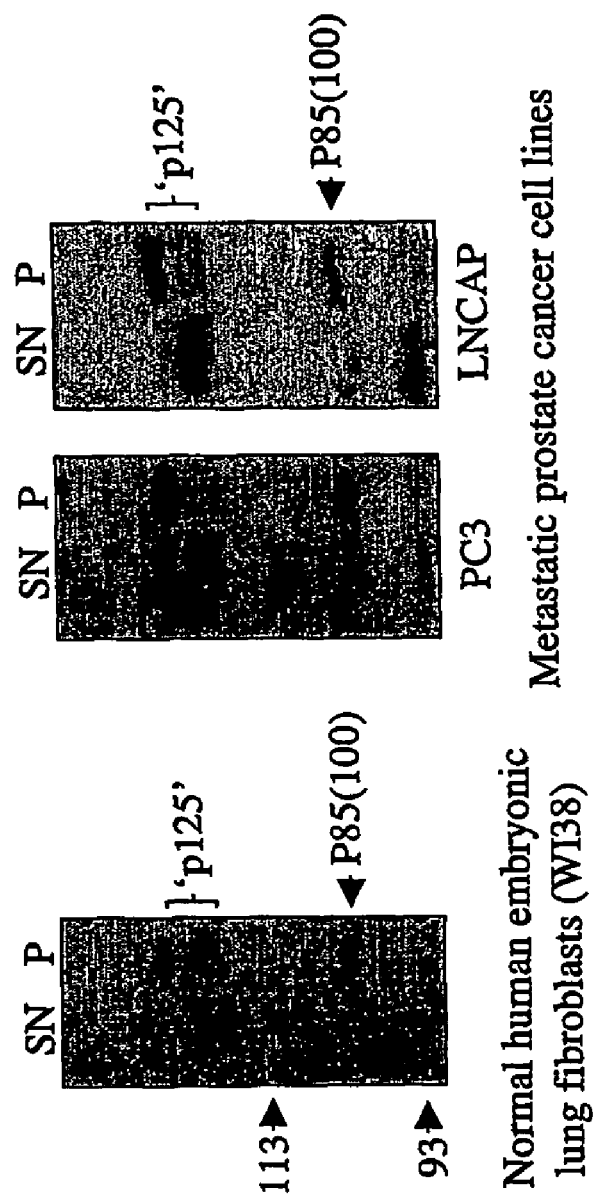

Normal, non-transformed human lung fibroblasts (and mouse NIH3T3 cells) express two major forms of Ciz1 that are detected by anti-Ciz1 polyclonal antibody 1793 in western blots (FIG. 13A). The larger (approximately 125 kDa) band resolves into three distinct bands that are present in equal proportions in Wi38 cells, but grossly uneven proportions in prostate cancer cell lines PC3 and LNCAP (and ESFT cell lines—not shown). We postulate that these protein isoforms are generated by expression of variably spliced exons. Both tumour cell lines also contain more Ciz1 antigen than Wi38 cells, consistent with over-expression of Ciz1 in these cancer cell lines.

Taken together our results (experimental and bioinformatics analysis of genome data) support the conclusion that Ciz1 is mis-regulated in a wide range of human cancers. We have shown that the Ciz1 protein plays a positive role in the DNA replication process, therefore mutant Ciz1 could contribute to cellular transformation, rather than be a consequence of it. If deregulation of Ciz1 is a common step in this process it represents a very attractive target for development of therapeutic agents.

We have also associated particular changes with specific cancers, making it a real possibility that Ciz1 could be useful as a diagnostic or prognostic marker.

These include:—
  Alternative splicing in the N-terminal part of the protein (that contains replication activity in vitro) in paediatric cancers.
  Point mutations in cyclin-dependent kinase phosphorylation sites known to be involved in restraining Ciz1 replication activity.

Non-typical expression and nuclear binding properties of Ciz1-p125 forms in prostate carcinoma cell lines, possibly due to mis-regulated splicing of the degenerate repeats in exon 8, or other exons.

Conditional exclusion of a discrete motif (VEEELCKQ) in the C-terminal end of Ciz1 (probably involved in localization of Ciz1 protein within the nucleus) in small cell carcinoma of the lung and other carcinomas.

Increased levels of Ciz1 protein and RNA (detected by Western blot and by RT-PCR) in all cancer derived cells lines tested so far, compared to Wi38 normal embryonic lung fibroblast, human osteoblast RNA and mouse NIH3T3 fibroblasts.

The sequences shown in FIGS. 14 to 21 are of use for the development of therapeutic, diagnostic, or prognostic reagents.

Materials and Methods

Cloning. A lamba triplEx 5'-stretch, full length enriched cDNA expression library derived from 11 Day old mouse embryos (Clonetech ML5015t) was used to infect E. coli X11blue according to the recommended protocol (Clonetech). Plaques were lifted onto 0.45 micron nitrocellulose filters pre-soaked in 10 mM IPTG (Sigma). Affinity purified antibody V1 was applied to approximately $3 \times 10^6$ plaques at 1/1000 dilution in PBS, 10% non-fat milk powder, 0.4% Tween20, after blocking for 30 minutes in the absence of antibody. After two hours filters were washed three times with the same buffer and reactive plaques were visualized with anti-rabbit secondary antibody conjugated to horse-radish peroxidase (Sigma), and enhanced chemi-luminescence (ECL, Amersham) according to standard procedures. 43 independent plaques were picked but only two strains of phage survived a further three rounds of screening. These were converted to pTriplEx by transforming into BM25.8 and sequenced. One codes for mouse Cdc6 (clone P) and the other (clone L) for an unknown mouse protein that is homologous to human Ciz1. We refer to this as embryonic Ciz1 (ECiz1) and it was submitted to EMBL under the accession number AJ575057.

Bacterial expression pGEX based bacterial expression constructs (Amersham) were used to produce ECiz1 proteins for in vitro analysis. pGEX-ECiz1 was generated by inserting a 2.3 kb SmaI-XbaI (blunt ended) fragment from clone L into the SmaI site of pGEX-6P-3. pGEX-Nterm442 was generated by inserting the 1.35 kb XmaI-XhoI fragment into XmaI-XhoI digested pGEX-6P-3, and pGEX-Cterm274 by inserting the 0.95 kb XhoI fragment into XhoI digested pGEX-6P-3. pGEX-T(191/2)A was generated from pGEX-ECiz1 by site directed mutagenesis (Stratagene Quikchange) using primers AACCCCCTCTTCCGCCGCCCCCAATCG-CAAGA (SEQ ID NO: 5) and TCTTGCGATTGGGGGCG-GCGGAAGAGGGGGTT (SEQ ID NO: 6). pGEX-T(293)A was generated from pGEX-ECiz1 using primers AAGCA-GACACAGGCCCCGGATCGGCTGCCT (SEQ ID NO: 7) and AGGCAGCCGATCCGGGGCCTGTGTCTGCTT (SEQ ID NO: 8). Integrity and reading frame of all clones were sequence verified.

Recombinant Ciz1, Ciz1 fragments and point mutants were produced in BL21-pLysS (Stratagene) as glutathione S-transferase-tagged protein. This was purified from sonicated and cleared bacterial lysates by binding to glutathione sepharose 4B (Amersham). Recombinant protein was eluted by cleavage from the GST tag using precision protease (as recommended by the manufacturer, Amersham), into buffer (50 mM Tris-HC pH 7.0, 150 mM NaCl, 1 mM DTT). This yielded protein preparations between 0.2 and 2.0 mg/ml. For replication assays serial dilutions were made in 100 mM Hepes pH 7.8, 1 mM DTT, 50% glycerol so that not more than 1 ml of protein solution was added to 10 ml replication assays, yielding the concentrations shown. Consistent with previous observations (Mitsui et al., 1999; Warder and Keherly, 2003) recombinant Ciz1, and derived fragment N-term442 migrated through SDS-PAGE with anomalously high molecular weight. Cyclin A-cdk2 was produced in bacteria as previously described (Coverley et al., 2002).

Anti-Ciz1 antibodies Rabbit polyclonal antibody V1 (Coverley et al., 2000; Stoeber et al., 1998; Williams et al., 1998) was raised against an internal fragment of bacterially expressed human Cdc6 corresponding to amino-acids 145-360, and affinity purified by standard procedures (Harlow and Lane, 1988). This antibody reacts strongly with endogenous p100-Ciz1 and also with ECiz1 Nterm442 fragment. Alignment of Nterm442 with Cdc6 amino-acids 145-360 suggest that the shared epitope could be at 294-298 or 304-312 in mouse Ciz1. Recombinant Nterm442 was used to generate two Ciz1-specific polyclonal anti-sera designated 1793 and 1794 (Abcam). 1793 has been used routinely in the experiments described here. Its specificity was verified by reciprocal immuno-precipitation and western blot analysis with antibody V, by inclusion of Nterm 442 (25 µg/ml in antibody buffer, 10 mg/ml BSA, 0.02% SDS, 0.1% Triton X100 in PBS), which blocked reactivity with endogenous epitopes, and by siRNA-mediated depletion of Ciz1 that specifically reduced 1793 nuclear staining.

Immunoprecipitation Asynchronousy growing 3T3 cells were washed in PBS, rinsed in extraction buffer (20 mM Hepes pH7.8, 5 mM potassium acetate, 0.5 mM magnesium chloride) supplemented with EDTA-free protease inhibitor cocktail (Roche) and scrape harvested as for replication extracts. Cells were lysed with 0.1% Triton X 100 and the detergent resistant pellet fraction extracted with 0.3M NaCl in extraction buffer. 5 µl of 1793 or 2 µl of antibody V were used per 100 µl of extract and incubated for 1 hour at 4° C. Antigen-antibody complexes were extracted with 100 µl of protein G-sepharose (Sigma) and beads were washed five times with 50 mM Tris pH 7.8, 1 mM EDTA, 0.1% NP40, 150 mM NaCl. Complexes were boiled in loading buffer (100 mM DTT, 2% SDS, 60 mM Tris pH6.8, 0.001% bromophenol blue) and resolved by 6.5% SDS-polyacrylamide gel electrophoresis.

Immuno-fluorescence Cells were grown on coverslips and fixed in 4% paraformaldehyde, with or without brief pre-exposure to 0.05% Triton X100 in PBS. Endogenous Ciz1 was detected with 1793 serum diluted 1/2000 in antibody buffer following standard procedures. Mcm3 was detected with monoclonal antibody sc9850 (1/1000), Cdc6 with monoclonal sc9964 (1/100) and PCNA with monoclonal antibody PC10 (1/100, all Santa Cruz Biotechnology). Co-localisation analysis of dual stained fluorescent confocal images was carried out as described (Rubbi and Milner, 2000; van Steensel et al., 1996).

Cell synchrony Mouse 3T3 cells were synchronized by release from quiescence as previously described (Coverley et al., 2002). Nuclei prepared from cells harvested 17 hours after release (referred to as 'late-G1') were used in all cell-free replication experiments described here. This yielded populations containing S phase nuclei, replication competent late G1 nuclei and unresponsive early G1/G0 nuclei, in varying proportions. Recipient, mid-G1 3T3 extracts were prepared at 15 hours (these typically contain approximately 5% S phase cells). The series of cell-free replication experiments described here required large amounts of standardized extract, therefore HeLa cells were used because they are easily synchronized in bulk. S phase HeLa extracts were prepared from cells released for two hours from two sequential thymidine-induced S phase blocks, as described (Krude et al., 1997).

Cell-free DNA replication DNA replication assays were performed as described (Coverley et al., 2002; Krude et al., 1997). Briefly, 10 µl of mid G1 or S phase extract (supplemented with energy regenerating system, nucleotides and biotinylated dUTP), and $5 \times 10^4$ late G1 phase nuclei were incubated for 60 mins at 37° C. Reactions were supplemented with baculovirus lysate containing cyclin A-cdk2 (FIGS. 1B and C), where 0.1 µl of lysate has the same specific activity as 1 nM purified kinase (Coverley et al., 2002). All recombinant proteins were serially diluted in 100 mM Hepes pH 7.8, 1 mM DTT, 50% glycerol, so that not more than 1 µl was added to 10 µl replication assays, generating the concentrations indicated. Reactions were stopped with 50 µl of 0.5% Triton X100 and fixed by the addition of 50 µl of 8% paraformaldehyde, for 5 minutes. After transfer to coverslips nuclei were stained with streptavidin-FITC (Amersham) and counterstained with Toto-3-iodide (Molecular Probes). The proportion of labelled nuclei was quantified by inspection at 1000× magnification, and all nuclei with fluorescent foci or intense uniform labelling were scored positive. Images of in vitro replicating nuclei were generated by confocal microscopy at 600× magnifications, of samples counterstained with propidium iodide. For analysis of nuclear proteins, nuclei were re-isolated after 15 minutes exposure to initiating conditions, by diluting reactions two fold with cold PBS and gentle centrifugation.

Data analysis and presentation Prior to use in initiation assays each preparation of synchronized G1 phase nuclei is tested so that the proportion of nuclei that are already in S phase is established ('% S'). To do this nuclei are incubated in an extract that is incapable of inducing initiation of DNA synthesis (from mid-G1 phase cells harvested 15 hours after release from quiescence), but that will efficiently support elongation DNA synthesis from origins that were initiated in vivo. The elongating fraction of nuclei incorporates labeled nucleotides efficiently during in vitro initiation assays but is uninformative. Routinely this fraction is pre-established and subtracted from the raw data. Synchronized populations in which 20% or less are in S phase are used for initiation assays.

When 3T3 cells are released from quiescence by the protocol used here no more than 70% of the total population enters S phase (Coverley et al., 2002). However, the highest observed replication frequency in vitro is nearer 50%; usually obtained by incubation with ECiz1. For the G1 population of 3T3 nuclei used here 17% were in S phase (% S) and the maximum number that replicated in any assay in vitro was 51% (% replication). Therefore, 34% of this population is competent to initiate replication in vitro (% C). Thus, for each data point in FIGS. 3B-F, % initiation=(% replication–% S) % C×100.

RNA interference Endogenous Ciz1 was targeted in proliferating NIH3T3 cells using in vitro transcribed siRNAs (Ambion Silencer kit), directed against four regions of mouse Ciz1. Oligonucleotide sequences that were used to generate siRNAs are AAGCACAGTCACAGGAGCAGACCTGT (SEQ ID NO: 9) CTC and AATCTGCTCCTGTGACTGTGCCCTGTCTC (SEQ ID NO: 10) for siRNA 4, AATCTGTCACAAGTTCTACGACCTGTCTC (SEQ ID NO: 11) and AATCGTAGAACTTGTGACAGACCTGTCTC (SEQ ID NO: 12) for siRNA 8, AATCGCAAGGATTCTTCTTCTCCTGTCTC (SEQ ID NO: 13) and AAAGAAGAAGAATCCTTGCGACCTGTCTC (SEQ ID NO: 14) for siRNA 9, and AATCTGCAGCAGTTCTTTCCCCCTGTCTC (SEQ ID NO: 15) and AAGGGAAAGAACTGCTGCAGACCT-GTCTC (SEQ ID NO: 16) for siRNA 11. Target sequences that are distributed throughout the Ciz1 transcript were chosen based on low secondary structure predictions and on location within exons that are consistently expressed in all known forms of Ciz1 (sequences 4, 8, 11), with the exception of one (siRNA 9) that is known to be alternatively spliced. Negative controls were untreated, mock treated (transfection reagents but no siRNA) and cells treated with GAPDH siRNA (Ambion). Cy3 labelled siRNAs (Ambion) were used to estimate transfection efficiency, which was found to be greater than 95%. RNA interference experiments were performed in 24 well format starting with $2 \times 10^4$ cells per well in 500 µl of medium (DMEM with glutamax supplemented with 4% FCS). siRNA's were added 12 hours after plating using oligofectamine reagent for delivery (Invitrogen). Unless stated otherwise, siRNAs were used in pairs (at 2 nM total concentration in medium), as two doses with the second dose delivered in fresh medium 24 hours after the first. Results were assessed at 48 hours after first exposure, by counting cell number, S phase labelling, and immuno-staining. Northern blots were performed on RNAs isolated from cells treated for 24 hours with a single dose of siRNA, in reactions that were scaled up 5 fold. RNA was prepared using Trizol Reagent (Invitrogen) and samples were electrophoresed through 1% agarose, transferred onto Hybond N+ nylon membrane (Amersham), and sequentially hybridised at 50° C. with cDNA probes using NorthernMax kit reagents (Ambion), following manufacturers instructions. The membrane was stripped between each hybridisation using 0.5% SDS solution at 90° C., allowed to cool slowly to room temperature. Probes were [$^{32}$P]-dCTP labelled using Random Primers DNA labelling system (Gibco BRL), and used in the following order: i. A 1.35 kb Xma1-Xho1 fragment derived from ECiz1. ii. Human β-actin cDNA (Clontech) and iii. Mouse GAPDH cDNA (RNWAY laboratories). The membrane was washed twice in 2×SSC 0.2% SDS for 30-60 mins each, followed by one wash in 0.2×SSC 0.2% SDS for 30 mins, at 55-65° C., depending on probe used. Hybridisation signals were quantified using an Amersham Biosciences Typhoon 9410 variable mode imager, and Image Quant TL software (v2002). Band intensities are expressed in arbitrary units (in parentheses), and results for Ciz1 and GAPDH were normalised against those for β-actin, and expressed as a %.

S phase labelling The fraction of nuclei undergoing DNA synthesis in vivo was monitored by supplementing culture medium with 20 µM bromodeoxyuridine (BrdU, Sigma) for 20 minutes. Incorporated BrdU was visualized after acid treatment with FITC-conjugated anti-BrdU monoclonal antibody (Alexis Biochemicals) according to manufacturers instructions. Nuclei were counterstained with Hoescht 33258 and scored under high (1000×) magnification.

Green Fluorescent Protein Tagged Ciz1

Full-length mouse Ciz1 cDNA was obtained from UK HGMP Resource Centre (MGC clone 27988) and the sequence fully verified. A 2.8 kb SmaI-XbaI (blunt ended) full length Ciz1 fragment from this clone, and a 2.3 kb SmaI-XbaI (blunt ended) ECiz 1 fragment from pTriplEx-clone L were ligated in frame with enhanced green fluorescent protein (EGFP) into the SmaI site of pEGFP-C3 (Clontech). pEGFP-C3 with no insert was used as a control. Constructs were transfected into NIH3T3 cells using TransIT-293 (Mirus), following manufacturers instructions or microinjected into the male pro-nucleus of fertilized mouse eggs at the one cell stage. Growing 3T3 cells transfected with full length EGFP-Ciz1, or EGFP-ECiz1 were analysed by live cell fluorescence microscopy up to three days after transfection. DNA synthesis was monitored during the first 24 hours after transfection, by including the nucleotide analogue BrdU in cell culture medium for various time periods as indicated in figure legends. As described above any cells undergoing DNA synthesis while exposed to BrdU stain with anti-BrdU monoclonal antibody generating red nuclei.

Ciz1 transfected cells were also maintained under selection with 50 µg/ml G418, in standard culture medium (DMEM Glutamax plus 10% fetal calf serum) for up to a month, yielding cell populations with altered morphology.

EST Sequence Analysis

Individual expressed sequence tags (ESTs) mapping to NCBI unigene cluster Hs.23476 (human Ciz1) were translated using Genejockey and the predicted amino-acid sequence compared to the predicted sequence for full length Ciz1, with the aim of identifying recurrent changes in cancer cells. In order to exclude errors that reflect poor quality DNA sequence such as that which occurs at the end of long sequencing runs, only those changes positioned more than 8 amino-acids from the end of uninterrupted sequence are included in this analysis. Frame-shifts that are restored by a second alteration later in the read, and frame-shifts that are followed by a stop codon are only included if followed by uninterrupted sequence. Thus the majority of sequencing errors are excluded from this analysis. However, it is expected that many of the point mutations that remain (including frame-shifts and stops) reflect errors introduced during sequencing. Therefore, this analysis is aimed at uncovering trends, with weight being given to point mutations only if they appear more than once.

Of 567 sequences, that map to Ciz1 unigene cluster we have analysed most (all paediatric cancers, prostate and lung carcinomas, leukemias and lymphomas and a wide range of non-diseased tissues). Some were not mapped because they are extremely short reads or yielded very short amino-acid sequences upon translation, and for a small number we detected no homology to the Ciz1 coding sequence. A small number of ESTs were excluded from the analysis because of multiple frameshifts that produced stretches of homology in all three frames, with no indication of the reading frame used in vivo. These were all from cancer derived material, usually adenocarcinomas.

RT-PCR analysis of Ciz1 isoform expression RNA was isolated using trizol reagent following recommended procedures, DNAse treated and reverse transcribed using random hexamers and superscript II, then amplified with Ciz1 specific primers:—

```
                                              (SEQ ID NO: 17)
h/m5       CAGTCCCCACCACAGGCC, (SEQ ID NO: 18)
h/m2       GGCTTCCTCAGACCCCTCTG.

(SEQ ID NO: 19)
H/m3       ACACAGACCTCTCCAGAGCACTTAG (SEQ ID NO: 20)
H/m4       ATGGTGACCTTCAGGGAGC (SEQ ID NO: 21)
H4         TCCTTGGCGA TGTCCTCTGG GCAGG (SEQ ID NO: 22)
H3         TCCCTCCTCA ACGGCTCCAT GCTGC (SEQ ID NO: 23)
H6         CG TGGGGGCGAC TTGAGCGTTG AGG (SEQ ID NO: 24)
H1         GATGCCAGGGGT ATGGGGCGCC GGG (SEQ ID NO: 25)
H2         TCCGAGCCCT TCCACTCCTC TCTGG.
```

Analysis of Ciz1 Protein Isoforms in Cancer Cell Lines

Cells were grown in DMEM with 10% FCS until sub-confluent, rinsed in cold hepes buffered saline supplemented with EDTA free protease inhibitor cocktail (Roche) then scrape harvested and supplemented with 0.1% Triton X100. Detergent-insoluble material (including nuclei) was pelleted by gentle centrifugation to yield supernatant (SN) and pellet fractions (P). These were boiled in reducing SDS-PAGE sample buffer and proteins resolved by electrophoresis through 8% SDS-PAGE. After transfer to nitrocellulose, Ciz1 isoforms were detected with anti-Ciz1 antibody 1793). All methods used in this analysis are well documented elsewhere.

REFERENCES

Bell, S. P. and Dutta, A. (2002). DNA replication in eukaryotic cells. *Annu Rev Biochem* 71, 333-74.

Cook, P. R. (1999). The organization of replication and transcription. *Science* 284, 1790-5.

Corpet, F. (1998). Multiple sequence alignment with hierarchical clustering. *Nucl. Acids Res.* 16, 10881-10890.

Coverley, D., Laman, H. and Laskey, R. A. (2002). Distinct roles for cyclins E and A during DNA replication complex assembly and activation. *Nat Cell Biol* 4, 523-8.

Coverley, D., Pelizon, C., Trewick, S, and Laskey, R. A. (2000). Chromatin bound Cdc6 persists in S and G2 phases in human cells, while soluble Cdc6 is destroyed in a cyclin A-cdk2 dependent process. *J. Cell Sci.* 113, 1929-1938.

Fujita, M. (1999). Cell cycle regulation of DNA replication initiation proteins in mammalian cells. *Front Biosci* 4, D816-23.

Hanahan, D. and Weinberg, R. A. (2000). The Hallmarks of Cancer. *Cell* 100, 57-70.

Harlow, E. and Lane, D. (1988). Antibodies: A laboratory manual. New York: Cold Spring Harbour Laboratory Press.

Jones, D. L., Alani, R. M. and Munger, K. (1997). The human papillomavirus E7 oncoprotein can uncouple cellular differentiation and proliferation in human keratinocytes by abrogating p21Cip1-mediated inhibition of cdk2. *Genes Dev.* 11, 2101-2111.

Krude, T. (2000). Initiation of human DNA replication in vitro using nuclei from cells arrested at an initiation-competent state. *J. Biol. Chem.* 275, 13699-13707.

Krude, T., Jackman, M., Pines, J. and Laskey, R. A. (1997). Cyclin/Cdk-dependent initiation of DNA replication in a human cell-free system. *Cell* 88, 109-119.

Laman, H., Coverley, D., Krude, T. K., Laskey, R. A. and Jones, N. (2001). Viral cyclin/cdk6 complexes initiate nuclear DNA replication. *Mol. Cell. Biol.* 2, 624-635.

Mercatante, D. R. and Kole, R. (2002). Control of alternative splicing by antisense oligonucleotides as a potential chemotherapy: effects on gene expression. *Biochim Biophys Acta* 1587, 126-32.

Mitsui, K., Matsumoto, A., Ohtsuka, S., Ohtsubo, M. and Yoshimura, A. (1999). Cloning and characterization of a novel p21cip1/waf1-interacting zinc finger protein, Ciz1. *Biochem. Biophys. Res. Com.* 264, 457-464.

Nakayasu, H. and Berezney, R. (1991). Nuclear matrins: identification of the major nuclear matrix proteins. *Proc Natl Acad Sci USA* 88, 10312-6.

Ohnuma, S., Philpott, A. and Harris, W. A. (2001). Cell cycle and cell fate in the nervous system. *Curr Opin Neurobiol* 11, 66-73.

Parker, S. B., Eichele, G., Zhang, P., Rawls, A., Sands, A. T., Bradley, A., Olson, E. N., Harper, J. W. and Elledge, S. J. (1995). p53-independent expression of p21Cip1 in muscle and other terminally differentiating cells. *Science* 267, 1024-7.

Rubbi, C. P. and Milner, J. (2000). Non-activated p53 co-localizes with sites of transcription within both the nucleoplasm and the nucleolus. *Oncogene* 19, 85-96.

Sherr, C. J. and Roberts, J. M. (1999). CDK inhibitors: positive and negative regulators of G1-phase progression. *Genes Dev.* 13, 1501-1512.

Stoeber, K., Mills, A. D., Kubota, Y., Krude, T., Romanowski, P., Marheineke, K., Laskey, R. A. and Williams, G. H. (1998). Cdc6 protein causes premature entry into S phase in a mammalian cell-free system. *EMBO J.* 17, 7219-7229.

van Steensel, B., van Binnendijk, E. P., Hornsby, C. D., van der Voort, H. T., Krozowski, Z. S., de Kloet, E. R. and van Driel, R. (1996). Partial colocalization of glucocorticoid and mineralocorticoid receptors in discrete compartments in nuclei of rat hippocampus neurons. *J Cell Sci* 109 (Pt 4), 787-92.

Warder, D. E. and Keherly, M. J. (2003). Ciz1, Cip1 interacting zinc finger protein 1 binds the consensus DNA sequence AYSR(0-2)YYAC. *J Biomed Sci* 10, 406-17.

Williams, G. H., Romanowski, P., Morris, L., Madine, M., Mills, A. D., Stoeber, K., Marr, J., Laskey, R. A. and Coleman, N. (1998). Improved cervical smear assessment using antibodies against proteins that regulate DNA replication. *Proc. Natl. Acad. Sci. USA* 95, 14932-14937.

Zezula, J., Casaccia-Bonnefil, P., Ezhevsky, S. A., Osterhout, D. J., Levine, J. M., Dowdy, S. F., Chao, M. V. and Koff, A. (2001). p21cip1 is required for the differentiation of oligodendrocytes independently of cell cycle withdrawal. *EMBO Rep* 2, 27-34.

---

The invention claimed is:

1. A diagnostic method for the identification of a cancer comprising detecting the presence or expression of the Ciz 1 gene, Ciz1 splice variants and or mutations in the genomic sequence thereof, wherein the presence or expression of the Ciz 1 gene, Ciz1 splice variants or mutations in the genomic sequence thereof is indicative of the presence of cancer.

2. The diagnostic method according to claim 1 wherein said method comprises one or more of the following steps:
   (i) contacting a sample isolated from a subject to be tested with an agent which specifically binds a nucleic acid molecule comprising a nucleic acid sequence as represented by SEQ ID NO: 45, 46, 66, 67, 68, 69, 70, 71, 72 or 73 and encoding a polypeptide with DNA initiation activity, and
   detecting or measuring the binding of the agent on said nucleic acid molecule in said sample;
   (ii) measuring expression levels of Ciz1 and Ciz1 isform using reverse-transcribed PCR or real-time PCR;
   (iii) measuring the presence of nucleic acid mutations based on altered conformational properties of the Ciz1 molecule; and
   (iv) sequence determination.

3. A kit comprising nucleotide primers selected from the group consisting of SEQ ID NO: 17-25 which bind to Ciz1 alternate splice variants.

4. The method according to claim 2 wherein the cancer is a pediatric cancer selected from the group consisting of: retinoblastoma, neuroblastoma, Burkett lymphoma, medulloblastoma, and Ewings Sarcoma family tumors.

5. The method according to claim 2 wherein the cancer is carcinoma, adenocarcinoma, lymphoma or leukemia.

6. The method according to claim 2 wherein the cancer is liver, lung or skin cancer.

* * * * *